US012606626B2

(12) United States Patent     (10) Patent No.: US 12,606,626 B2
Løset et al.     (45) Date of Patent:    Apr. 21, 2026

(54) ANTIGEN BINDING PROTEINS WHICH BIND TO THE pMHC HLA-DQ2.5:DQ2.5 PRESENTING A GLIADIN PEPTIDE

(71) Applicant: UNIVERSITETET I OSLO, Oslo (NO)

(72) Inventors: Geir Åge Løset, Drøbak (NO); Lene Støkken Høydahl, Asker (NO); Inger Sandlie, Oslo (NO); Ludvig Magne Sollid, Bekkestua (NO); Rahel Frick, Oslo (NO)

(73) Assignee: Universitetet I Oslo, Oslo (NO)

( * ) Notice: Subject to any disclaimer, the term of this patent is extended or adjusted under 35 U.S.C. 154(b) by 430 days.

(21) Appl. No.: 16/969,679

(22) PCT Filed: Feb. 13, 2019

(86) PCT No.: PCT/EP2019/053580
§ 371 (c)(1),
(2) Date: Aug. 13, 2020

(87) PCT Pub. No.: WO2019/158602
PCT Pub. Date: Aug. 22, 2019

(65) Prior Publication Data
US 2021/0147552 A1    May 20, 2021

(30) Foreign Application Priority Data

Feb. 13, 2018    (GB) ...................................... 1802338

(51) Int. Cl.
| | |
|---|---|
| *A61K 39/00* | (2006.01) |
| *C07H 21/04* | (2006.01) |
| *C07K 16/16* | (2006.01) |
| *C07K 16/28* | (2006.01) |
| *C12N 5/10* | (2006.01) |
| *G01N 33/564* | (2006.01) |
| *C12N 5/0783* | (2010.01) |

(52) U.S. Cl.
CPC .......... *C07K 16/2833* (2013.01); *C07K 16/16* (2013.01); *G01N 33/564* (2013.01); *C07K 2317/32* (2013.01); *C07K 2317/565* (2013.01); *C07K 2317/622* (2013.01); *C07K 2317/73* (2013.01); *C07K 2317/92* (2013.01); *G01N 2333/415* (2013.01); *G01N 2333/70539* (2013.01); *G01N 2800/06* (2013.01); *G01N 2800/24* (2013.01)

(58) Field of Classification Search
None
See application file for complete search history.

(56) References Cited

U.S. PATENT DOCUMENTS

| | | |
|---|---|---|
| 5,591,828 A | 1/1997 | Bosslet et al. |
| 6,992,176 B2 | 1/2006 | Reiter et al. |
| 7,399,838 B2 | 7/2008 | Reiter et al. |
| 7,993,869 B2 | 8/2011 | Drijfhout et al. |
| 8,354,066 B2 | 1/2013 | Sivan et al. |
| 8,361,473 B2 | 1/2013 | Makler et al. |
| 8,409,819 B1 | 4/2013 | Barken |
| 8,747,855 B2 | 6/2014 | Reiter et al. |
| 2008/0200652 A1 | 8/2008 | Cherkasky |

FOREIGN PATENT DOCUMENTS

| | | |
|---|---|---|
| EP | 0404097 | 9/1996 |
| EP | 2072045 | 8/2012 |
| EP | 1763365 | 8/2016 |
| WO | 9010457 | 9/1990 |
| WO | 1991009619 | 7/1991 |
| WO | 9311161 | 6/1993 |
| WO | 1998027999 | 7/1998 |
| WO | 02083722 | 10/2002 |
| WO | 2006004394 | 1/2006 |
| WO | 2006136892 | 12/2006 |
| WO | 2011157806 | 12/2011 |
| WO | 2012056407 | 5/2012 |
| WO | 2014191839 A2 | 12/2014 |
| WO | 2016174652 | 11/2016 |
| WO | 2017118745 | 7/2017 |
| WO | 2018155692 A1 | 8/2018 |
| WO | 2019069993 A1 | 4/2019 |

OTHER PUBLICATIONS

Frick et al (bioRxiv. Nov. 15, 2019:840561, pp. 1-40) (Year: 2019).*
Maude, Shannon L., et al. "CD19-targeted chimeric antigen receptor T-cell therapy for acute lymphoblastic leukemia." Blood, The Journal of the American Society of Hematology 125.26 (2015): 4017-4023.
Akbarzadeh, Abolfazl, et al. "Liposome: classification, preparation, and applications." Nanoscale research letters 8.102 (2013): 1-9.
Reulen, Sanne WA, et al. "Protein—liposome conjugates using cysteine-lipids and native chemical ligation." Bioconjugate chemistry 18.2 (2007): 590-596.
Kung, Viola T., and Carl T. Redemann. "Synthesis of carboxyacyl derivatives of phosphatidylethanolamine and use as an efficient method for conjugation of protein to liposomes." Biochimica et Biophysica Acta (BBA)—Biomembranes 862.2 (1986): 435-439.

(Continued)

*Primary Examiner* — Michael Szperka
*Assistant Examiner* — Marianne Dibrino
(74) *Attorney, Agent, or Firm* — Meunier Carlin & Curfman LLC

(57) ABSTRACT

The present invention relates generally to the field of antigen binding proteins such as antibodies, in particular those which bind to HLA-DQ2.5:DQ2.5-glia-α1a, or which bind to HLA-DQ2.5:DQ2.5-glia-α2. The invention further relates to compositions and immunoconjugates comprising such antibodies and to methods of producing such antibodies. The invention also relates to methods and uses which employ such antibodies, for example in the treatment of celiac disease.

Figure 1B:
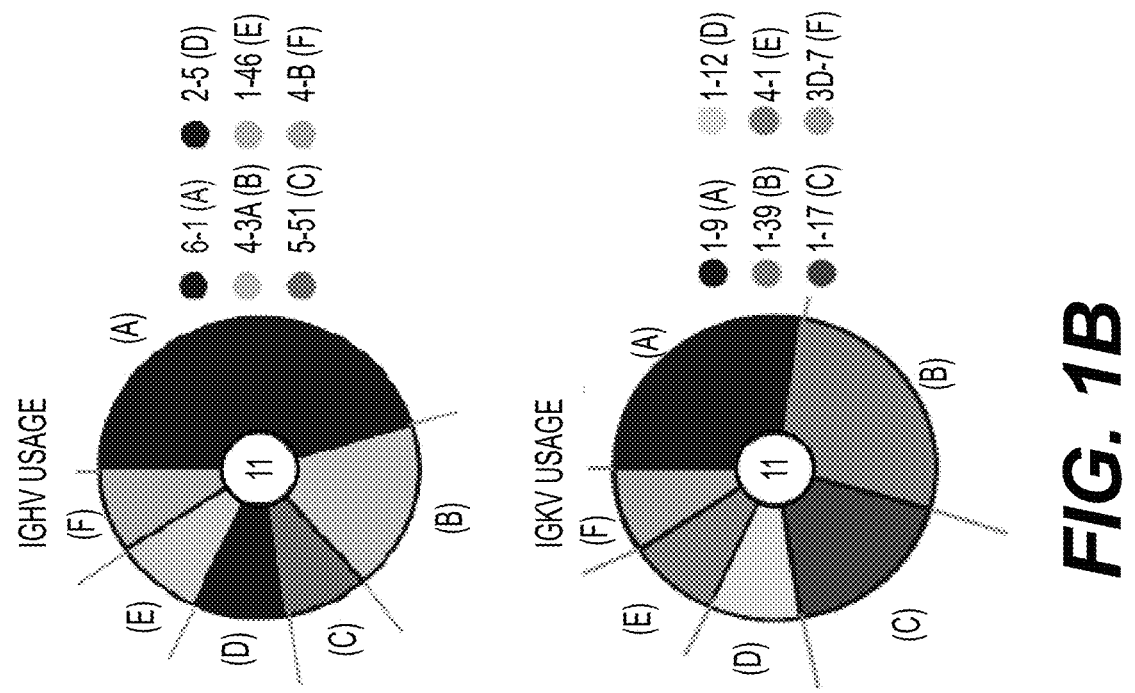

10 Claims, 36 Drawing Sheets
Specification includes a Sequence Listing.

(56)                    References Cited

OTHER PUBLICATIONS

Weitzner, Brian D., et al. "Blind prediction performance of RosettaAntibody 3.0: grafting, relaxation, kinematic loop modeling, and full CDR optimization." Proteins: Structure, Function, and Bioinformatics 82.8 (2014): 1611-1623.

Løset, Geir Åge, et al. "Construction, evaluation and refinement of a large human antibody phage library based on the IgD and IgM variable gene repertoire." Journal of immunological methods 299. 1-2 (2005): 47-62.

Holst, Jeff, et al. "Rapid analysis of T-cell selection in vivo using T cell-receptor retrogenic mice." Nature methods 3.3 (2006): 191-197.

Petersen, Jan, et al. "T-cell receptor recognition of HLA-DQ2-gliadin complexes associated with celiac disease." Nature structural & molecular biology 21.5 (2014): 480-488.

Fallang, Lars-Egil, et al. "Complexes of two cohorts of CLIP peptides and HLA-DQ2 of the autoimmune DR3-DQ2 haplotype are poor substrates for HLA-DM." The Journal of Immunology 181.8 (2008): 5451-5461.

Viken, Helge D., et al. "Characterization of an HLA-DQ2-specific monoclonal antibody: Influence of amino acid substitutions in DQβ 1* 0202." Human immunology 42.4 (1995): 319-327.

Zahnd, Christian, Casim A. Sarkar, and Andreas Plückthun. "Computational analysis of off-rate selection experiments to optimize affinity maturation by directed evolution." Protein Engineering, Design & Selection 23.4 (2010): 175-184.

Marks, James D., et al. "By-passing immunization: human antibodies from V-gene libraries displayed on phage." Journal of molecular biology 222.3 (1991): 581-597.

Koch, Joachim, Frank Breitling, and Stefan Dübel. "Rapid titration of multiple samples of filamentous bacteriophage (M13) on nitrocellulose filters." BioTechniques 29.6 (2000): 1196-1202.

Gunnarsen, Kristin S., et al. "Periplasmic expression of soluble single chain T cell receptors is rescued by the chaperone FkpA." BMC biotechnology 10.1 (2010): 1-13. DOI: 10.1186/1472-6750-10-8.

Norderhaug, Lars, et al. "Versatile vectors for transient and stable expression of recombinant antibody molecules in mammalian cells." Journal of immunological methods 204.1 (1997): 77-87.

Neuberger, Michael S. "Expression and regulation of immunoglobulin heavy chain gene transfected into lymphoid cells." The EMBO Journal 2.8 (1983): 1373-1378.

Mach, Nicolas, et al. "Differences in dendritic cells stimulated in vivo by tumors engineered to secrete granulocyte-macrophage colony-stimulating factor or Flt3-ligand." Cancer research 60.12 (2000): 3239-3246.

Qiao, Shuo-Wang, et al. "Dependence of antibody-mediated presentation of antigen on FcRn." Proceedings of the National Academy of Sciences 105.27 (2008): 9337-9342.

Qiao, Shuo-Wang, et al. "Antigen presentation to celiac lesion-derived T cells of a 33-mer gliadin peptide naturally formed by gastrointestinal digestion." The Journal of Immunology 173.3 (2004): 1757-1762.

Weitzner, Brian D., et al. "Modeling and docking of antibody structures with Rosetta." Nature protocols 12.2 (2017): 401-416.

Marze, Nicholas A., Sergey Lyskov, and Jeffrey J. Gray. "Improved prediction of antibody VL-VH orientation." Protein Engineering, Design and Selection 29.10 (2016): 409-418.

Weitzner, Brian D., and Jeffrey J. Gray. "Accurate structure prediction of CDR H3 loops enabled by a novel structure-based C-terminal constraint." The Journal of Immunology 198.1 (2017): 505-515.

Sircar, Aroop, and Jeffrey J. Gray. "SnugDock: paratope structural optimization during antibody-antigen docking compensates for errors in antibody homology models." PloS computational biology 6.1 (2010): e1000644.

Conway, Patrick, et al. "Relaxation of backbone bond geometry improves protein energy landscape modeling." Protein Science 23.1 (2014): 47-55.

Chaudhury, Sidhartha, and Jeffrey J. Gray. "Conformer selection and induced fit in flexible backbone protein-protein docking using computational and NMR ensembles." Journal of molecular biology 381.4 (2008): 1068-1087.

Application: Celiac Disease. Presentation (single slide) 2017. Boston.1 page.

Loset, Engineered T cell receptors as tools for the study of peptide—MHC interactions, Presentation 2015, Lisbon. 34 pages.

Sharon, Eilon, et al. "Genetic variation in MHC proteins is associated with T cell receptor expression biases." Nature genetics 48.9 (2016): 995-1002.

Dahan, Rony, et al. "Antigen-specific immunomodulation for type 1 diabetes by novel recombinant antibodies directed against diabetes-associates auto-reactive T cell epitope." Journal of autoimmunity 47 (2013): 83-93.

Dørum, Siri, et al. "HLA-DQ molecules as affinity matrix for identification of gluten T cell epitopes." The Journal of Immunology 193.9 (2014): 4497-4506. doi: 10.4049/jimmunol.1301466.

Garcia, K. Christopher, et al. "The molecular basis of TCR germline bias for MHC is surprisingly simple." Nature immunology 10.2 (2009): 143-147.

Gunnarsen, Kristin Støen, et al. "A TCRα framework-centered codon shapes a biased T cell repertoire through direct MHC and CDR3β interactions." JCI insight 2.17 (2017). ://doi.org/10.1172/jci.insight.95193.

Høydahl, Lene Støkken, et al. "Plasma cells are the most abundant gluten peptide MHC-expressing cells in inflamed intestinal tissues from patients with celiac disease." Gastroenterology 156.5 (2019): 1428-1439. ://doi.org/10.1053/j.gastro.2018.12.013.

Kim, Chu-Young, et al. "Structural basis for HLA-DQ2-mediated presentation of gluten epitopes in celiac disease." Proceedings of the National Academy of Sciences 101.12 (2004): 4175-4179.

Quarsten, Hanne, et al. "Staining of celiac disease-relevant T cells by peptide-DQ2 multimers." The Journal of Immunology 167.9 (2001): 4861-4868.

Rudikoff, Stuart, et al. "Single amino acid substitution altering antigen-binding specificity." Proceedings of the National Academy of Sciences 79.6 (1982): 1979-1983.

Sánchez-León, Susana, et al. "Low-gluten, nontransgenic wheat engineered with CRISPR/Cas9." Plant Biotechnology Journal 16.4 (2018): 902-910.

Shan, Lu, et al. "Structural basis for gluten intolerance in celiac sprue." Science 297.5590 (2002): 2275-2279.

Sollid, Ludvig M., et al. "Nomenclature and listing of celiac disease relevant gluten T-cell epitopes restricted by HLA-DQ molecules." Immunogenetics 64.6 (2012): 455-460.

Stryhn, Anette, et al. "Shared fine specificity between T-cell receptors and an antibody recognizing a peptide/major histocompatibility class I complex." Proceedings of the National Academy of Sciences 93.19 (1996): 10338-10342.

Tollefsen, Stig, et al. "HLA-DQ2 and -DQ8 signatures of gluten T cell epitopes in celiac disease." The Journal of clinical investigation 116.8 (2006): 2226-2236.

Tye-Din, Jason A., et al. "Comprehensive, quantitative mapping of T cell epitopes in gluten in celiac disease." Science translational medicine 2.41 (2010): 41ra51-41ra51.

Zhang, Li, et al. "Monoclonal antibody blocking the recognition of an insulin peptide—MHC complex modulates type 1 diabetes." Proceedings of the National Academy of Sciences 111.7 (2014): 2656-2661.

Arentz-Hansen, Helene, et al. "The intestinal T cell response to α-gliadin in adult celiac disease is focused on a single deamidated glutamine targeted by tissue transglutaminase." The Journal of experimental medicine 191.4 (2000): 603-612.

Van den Broeck, Hetty C., et al. "Removing celiac disease-related gluten proteins from bread wheat while retaining technological properties: a study with Chinese Spring deletion lines." BMC plant biology 9.1 (2009): 1-12.

Mitea, Cristina, et al. "Fine specificity of monoclonal antibodies against celiac disease-inducing peptides in the gluteome." The American journal of clinical nutrition 88.4 (2008): 1057-1066.

(56) References Cited

OTHER PUBLICATIONS

Spaenij-Dekking, E. H. A., et al. "A novel and sensitive method for the detection of T cell stimulatory epitopes of $\alpha/\beta$ -and $\gamma$-gliadin." Gut 53.9 (2004): 1267-1273.

Landsverk, Ole JB, et al. "Antibody-secreting plasma cells persist for decades in human intestine." Journal of Experimental Medicine 214.2 (2017): 309-317.

Ludvigsson, Jonas F., et al. "Diagnosis and management of adult coeliac disease: guidelines from the British Society of Gastroenterology." Gut 63.8 (2014): 1210-1228.

Bentley, Gordon, et al. "High-resolution, high-throughput HLA genotyping by next-generation sequencing." Tissue antigens 74.5 (2009): 393-403.

Gunnarsen, Kristin Støen, et al. "Soluble T-cell receptor design influences functional yield in an *E. coli* chaperone-assisted expression system." Plos one 13.4 (2018): e0195868.

Ina Hodnebrug—Thesis for the Master's Degree in Molecular Biosciences. "Construction and evaluation of an scFv library for affinity maturation." Oct. 2016, 84 pages.

International Search Report and Written Opinion in PCT/EP2019/053580. Mailed Jun. 3, 2019. 19 pages.

Qiao et al. Posttranslational Modification of Gluten Shapes TCR Usage in Celiac Disease. J Immunol 2011; 187:3064-3071; Prepublished online Aug. 17, 2011.

Nicole Hartwig Petersen et al: Fast and efficient characterization of an anti-gliadin monoclonal antibody epitope related to celiac disease using resin-bound peptides, J Immunol Methods 365 (2011) 174-182.

Panka et al.; "Variable region framework differences result in decreased or increased affinity of variant anti-digoxin antibodies"; Proc. Nati. Acad. Sci. USA vol. 85, pp. 3080-3084; 5 pages.

* cited by examiner

DQ2.5-GLIA-α1A: PFPQPELPY (SEQ ID NO: 472)

DQ2.5-GLIA-ω1: PFPQPEQPF (SEQ ID NO: 477)

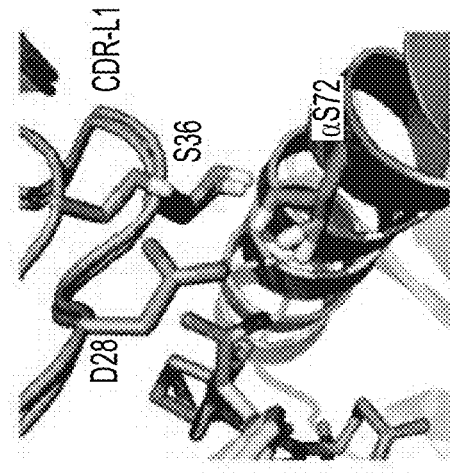
FIG. 3G
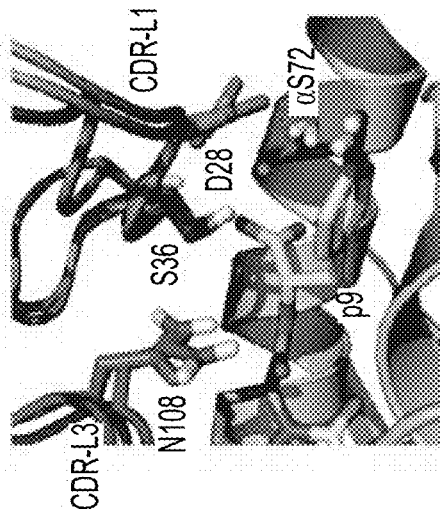
FIG. 3F
FIG. 3E

DQ2.5-GLIA-α1A: PFPQPELPY (SEQ ID NO: 472)

CLIP2: PLLMQALPM (SEQ ID NO: 489)

DQ2.5-GLIA-α1A: PFPQPELPY (SEQ ID NO: 472)

DQ2.5-GLIA-α2: PQPELPYPQ (SEQ ID NO: 473)

Figure 11A:
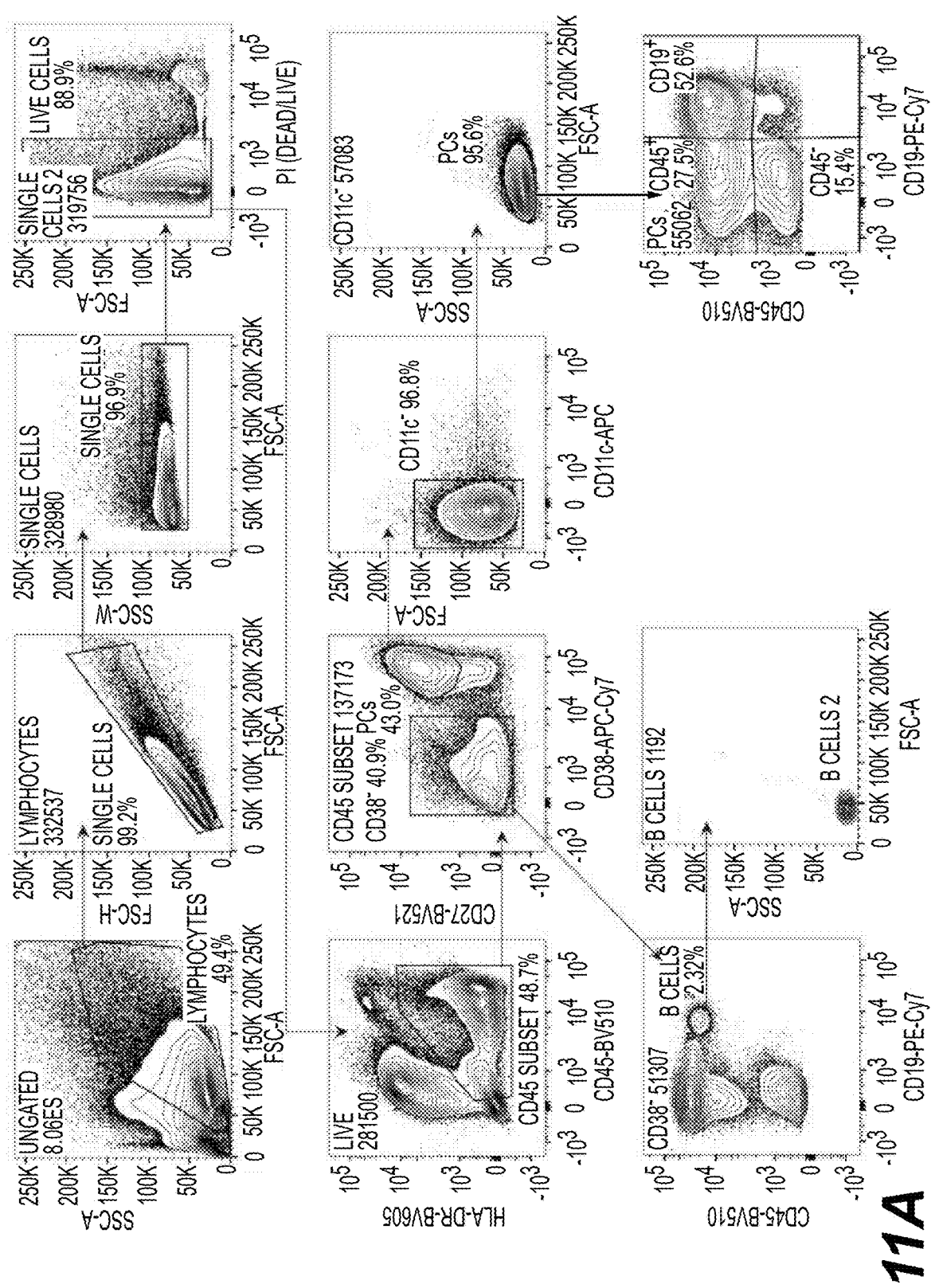
Figures 11B, 12:
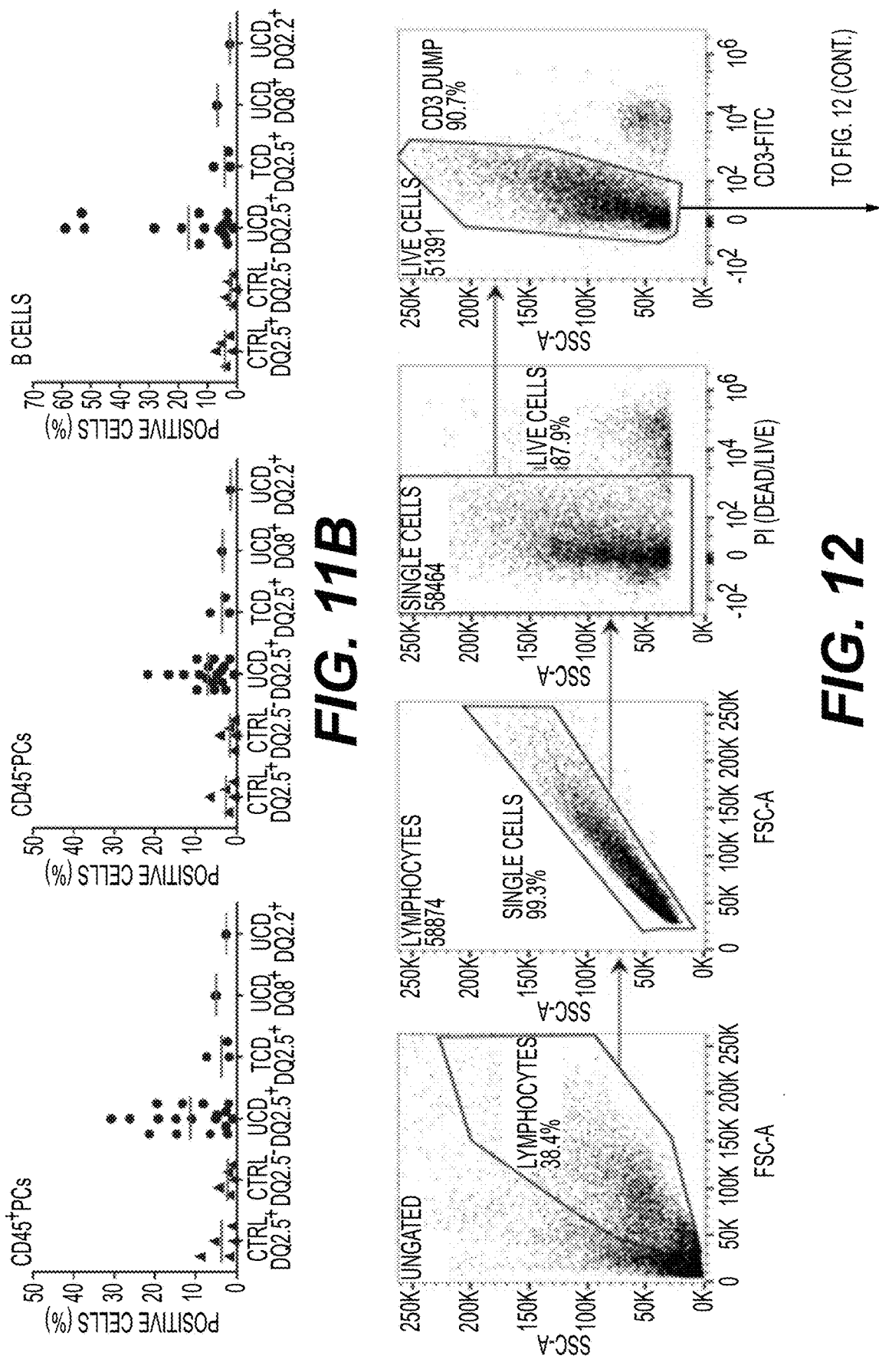
Figure 12:
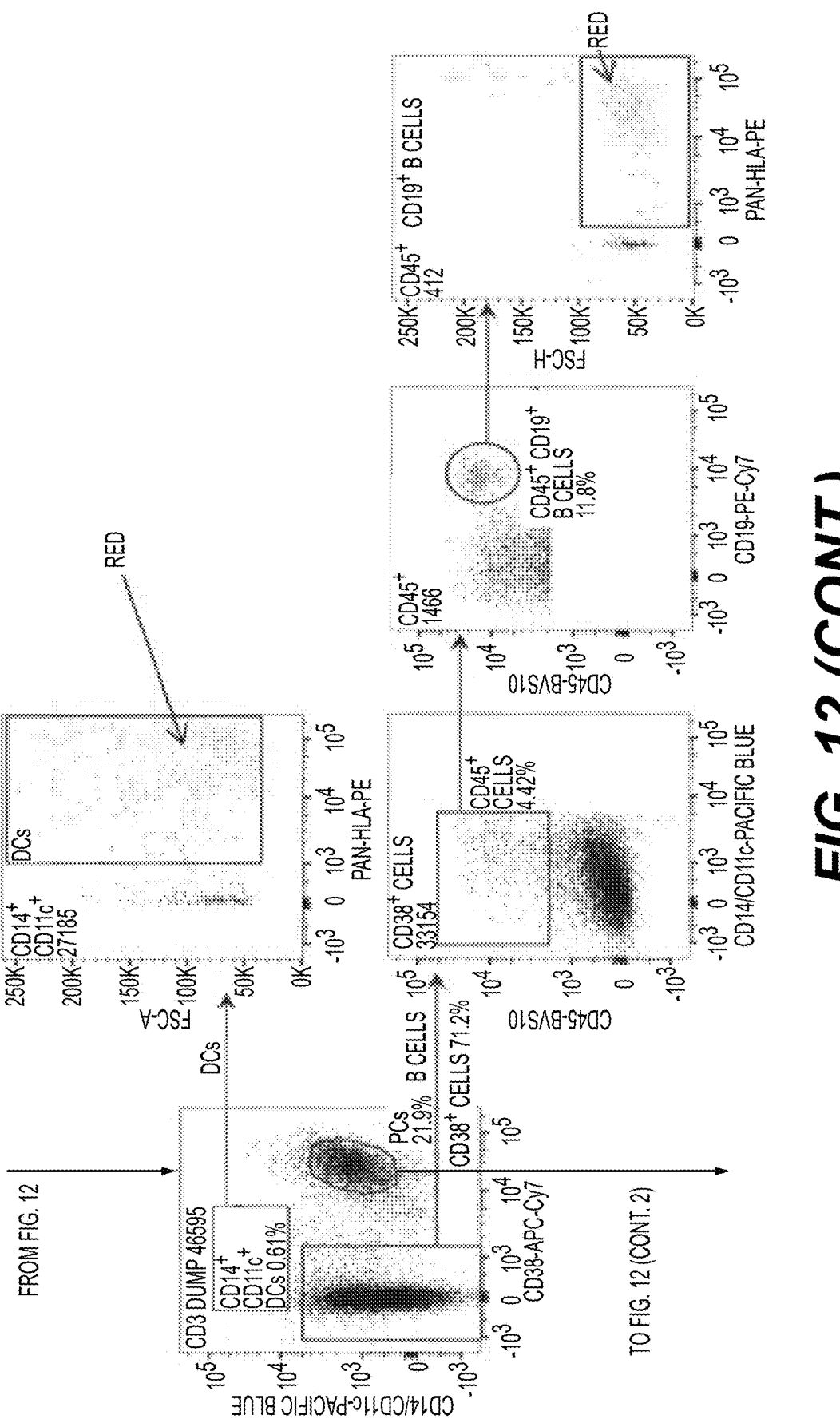

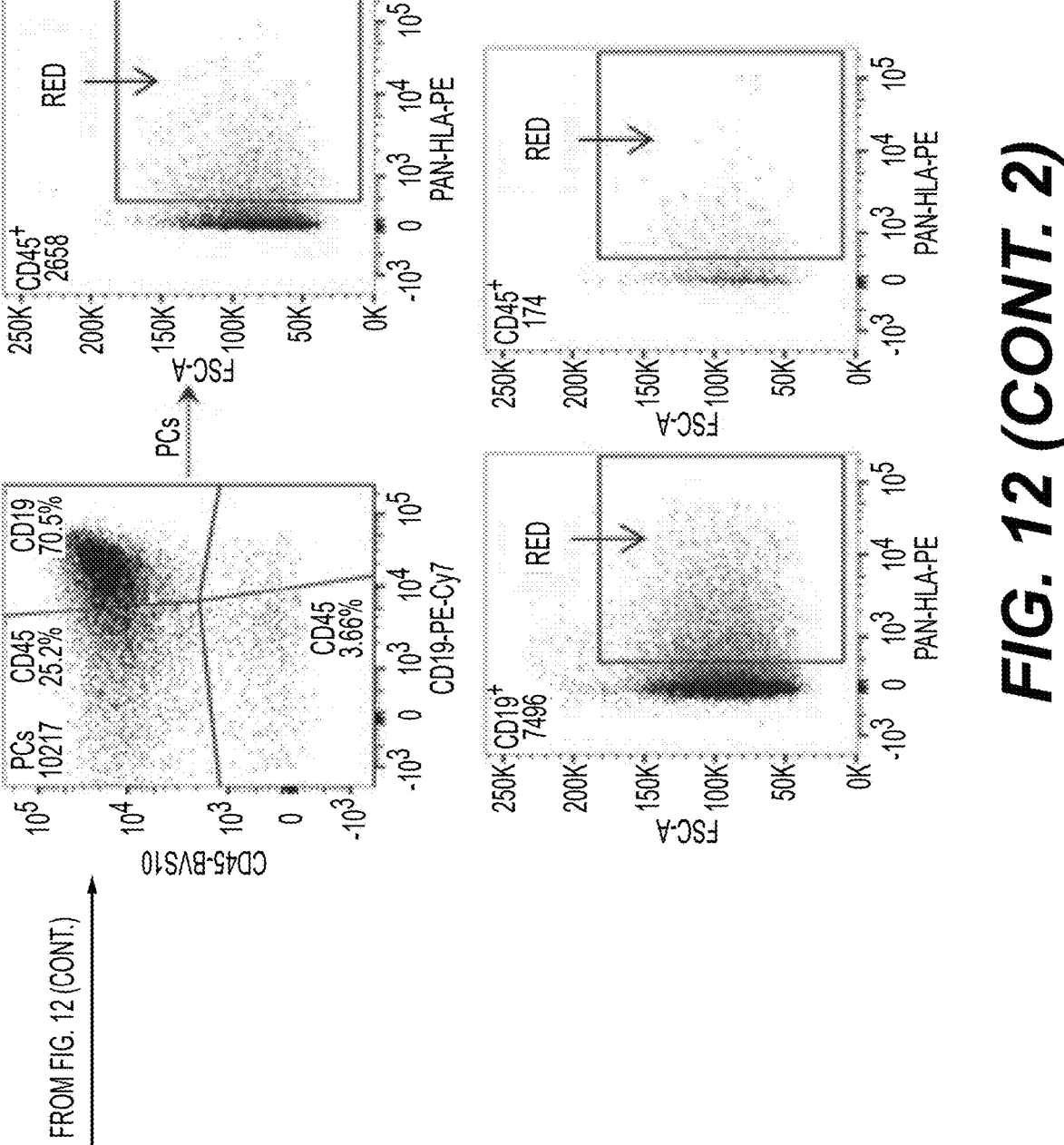
*FIG. 12 (CONT. 2)*

SKW3-364 DOSE-RESPONSE USING PEPTIDE LOADED RAJI APC $EC_{50} \sim 117$ nM $R^2 \sim 0.999$

N-PQPELPYPQPE-C
(SEQ ID NO: 475)

SKW3-380 T CELL INHIBITION ASSAY OF DQ2.5:DQ2.5-GLIA-α1A
PEPTIDE-PULSED RAJI AS APC AND 1 μM mAB AS INHIBITOR

SEQUENCE LISTING

<160> NUMBER OF SEQ ID NOS: 524

<210> SEQ ID NO 1
<211> LENGTH: 375
<212> TYPE: DNA
<213> ORGANISM: Human

<400> SEQUENCE: 1

```
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
```

-continued

```
cagtccccat cgagaggcct tgagtggctg ggaaggacat actacaggtc caagtggtat        180
aatgattatg cagtatctgt gaaaagtcga ataaccatca acccagacac atccaagaac        240
cagttctccc tgcagctgaa ctctgtgact cccgaggaca cggctgtgta ttactgtgca        300
agagatagca gcagtggctg gcatccttac ggtatggacg tctggggcca agggaccacg        360
gtcaccgtct cctca                                                          375
```

<210> SEQ ID NO 2
<211> LENGTH: 324
<212> TYPE: DNA
<213> ORGANISM: Human

<400> SEQUENCE: 2

```
gacatccagg tgacccagtc tccatccttc ctgtctgcat ctgtaggaga cagagtcacc         60
atcacttgcc gggccagtca cgacattagc agttatttag cctggtatca acacaaacca        120
gggaaagccc ccaaactcct gatccatgct gcatccattt tgcaaagtgg ggtcccatca        180
aggttcagcg gaagtggatc tgggacagaa ttcactctca caatcagcag cctgcagcct        240
gaagattttg caacgtacta ctgtcaacag cttaatagtt accctctgct cactttcggc        300
ggagggacca aagtggatat caaa                                               324
```

<210> SEQ ID NO 3
<211> LENGTH: 125
<212> TYPE: PRT
<213> ORGANISM: Human

<400> SEQUENCE: 3

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
                100                 105                 110

Asp Val Trp Gly Gln Gly Thr Thr Val Thr Val Ser Ser
            115                 120                 125
```

<210> SEQ ID NO 4
<211> LENGTH: 108
<212> TYPE: PRT
<213> ORGANISM: Human

<400> SEQUENCE: 4

```
Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Gly Lys Ala Pro Lys Leu Leu Ile
        35                  40                  45
```

```
His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Leu Thr Phe Gly Gly Gly Thr Lys Val Asp Ile Lys
                100                 105

<210> SEQ ID NO 5
<211> LENGTH: 10
<212> TYPE: PRT
<213> ORGANISM: Human

<400> SEQUENCE: 5

Gly Asp Ser Val Ser Ser Asn Ser Ala Ala
1               5                   10

<210> SEQ ID NO 6
<211> LENGTH: 9
<212> TYPE: PRT
<213> ORGANISM: Human

<400> SEQUENCE: 6

Thr Tyr Tyr Arg Ser Lys Trp Tyr Asn
1               5

<210> SEQ ID NO 7
<211> LENGTH: 15
<212> TYPE: PRT
<213> ORGANISM: Human

<400> SEQUENCE: 7

Ala Arg Asp Ser Ser Ser Gly Trp His Pro Tyr Gly Met Asp Val
1               5                   10                  15

<210> SEQ ID NO 8
<211> LENGTH: 6
<212> TYPE: PRT
<213> ORGANISM: Human

<400> SEQUENCE: 8

His Asp Ile Ser Ser Tyr
1               5

<210> SEQ ID NO 9
<211> LENGTH: 3
<212> TYPE: PRT
<213> ORGANISM: Human

<400> SEQUENCE: 9

Ala Ala Ser
1

<210> SEQ ID NO 10
<211> LENGTH: 10
<212> TYPE: PRT
<213> ORGANISM: Human

<400> SEQUENCE: 10

Gln Gln Leu Asn Ser Tyr Pro Leu Leu Thr
1               5                   10
```

```
<210> SEQ ID NO 11
<211> LENGTH: 25
<212> TYPE: PRT
<213> ORGANISM: Human

<400> SEQUENCE: 11

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 12
<211> LENGTH: 17
<212> TYPE: PRT
<213> ORGANISM: Human

<400> SEQUENCE: 12

Trp Asn Trp Ile Arg Gln Ser Pro Ser Arg Gly Leu Glu Trp Leu Gly
1               5                   10                  15

Arg

<210> SEQ ID NO 13
<211> LENGTH: 38
<212> TYPE: PRT
<213> ORGANISM: Human

<400> SEQUENCE: 13

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 14
<211> LENGTH: 11
<212> TYPE: PRT
<213> ORGANISM: Human

<400> SEQUENCE: 14

Trp Gly Gln Gly Thr Thr Val Thr Val Ser Ser
1               5                   10

<210> SEQ ID NO 15
<211> LENGTH: 26
<212> TYPE: PRT
<213> ORGANISM: Human

<400> SEQUENCE: 15

Asp Ile Gln Val Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 16
<211> LENGTH: 17
<212> TYPE: PRT
<213> ORGANISM: Human

<400> SEQUENCE: 16

Leu Ala Trp Tyr Gln His Lys Pro Gly Lys Ala Pro Lys Leu Leu Ile
1               5                   10                  15
```

His

<210> SEQ ID NO 17
<211> LENGTH: 36
<212> TYPE: PRT
<213> ORGANISM: Human

<400> SEQUENCE: 17

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 18
<211> LENGTH: 10
<212> TYPE: PRT
<213> ORGANISM: Human

<400> SEQUENCE: 18

Phe Gly Gly Gly Thr Lys Val Asp Ile Lys
1               5                   10

<210> SEQ ID NO 19
<211> LENGTH: 375
<212> TYPE: DNA
<213> ORGANISM: Human

<400> SEQUENCE: 19
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagca gcagtggctg gcatccttac ggtatggacg tctggggcca agggaccacg     360
gtcaccgtct cctca                                                      375

<210> SEQ ID NO 20
<211> LENGTH: 318
<212> TYPE: DNA
<213> ORGANISM: Human

<400> SEQUENCE: 20
gacatccagg tgacccagtc tccatccttc ctgtctgcat ctgtaggaga cagagtcacc      60
atcacttgcc gggccagtca cgacattagc agttatttag cctggtatca acacaaacca     120
gggaaagccc ccaaactcct gatccatgct gcatccattt tgcaaagtgg ggtcccatca     180
aggttcagcg gaagtggatc tgggacagaa ttcactctca caatcagcag cctgcagcct     240
gaagattttg caacgtacta ctgtcaagat ctcaatagtt atcctctctt cggccaaggg     300
acacgactgg agattaaa                                                    318

<210> SEQ ID NO 21
<211> LENGTH: 125
<212> TYPE: PRT
<213> ORGANISM: Human

<400> SEQUENCE: 21

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

Asp Val Trp Gly Gln Gly Thr Thr Val Thr Val Ser Ser
        115                 120                 125

<210> SEQ ID NO 22
<211> LENGTH: 106
<212> TYPE: PRT
<213> ORGANISM: Human

<400> SEQUENCE: 22

Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Gly Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys
            100                 105

<210> SEQ ID NO 23
<211> LENGTH: 10
<212> TYPE: PRT
<213> ORGANISM: Human

<400> SEQUENCE: 23

Gly Asp Ser Val Ser Ser Asn Ser Ala Ala
1               5                   10

<210> SEQ ID NO 24
<211> LENGTH: 9
<212> TYPE: PRT
<213> ORGANISM: Human

<400> SEQUENCE: 24

Thr Tyr Tyr Arg Ser Lys Trp Tyr Asn
1               5

<210> SEQ ID NO 25
<211> LENGTH: 15
```

```
<212> TYPE: PRT
<213> ORGANISM: Human

<400> SEQUENCE: 25

Ala Arg Asp Ser Ser Ser Gly Trp His Pro Tyr Gly Met Asp Val
1               5                   10                  15

<210> SEQ ID NO 26
<211> LENGTH: 6
<212> TYPE: PRT
<213> ORGANISM: Human

<400> SEQUENCE: 26

His Asp Ile Ser Ser Tyr
1               5

<210> SEQ ID NO 27
<211> LENGTH: 3
<212> TYPE: PRT
<213> ORGANISM: Human

<400> SEQUENCE: 27

Ala Ala Ser
1

<210> SEQ ID NO 28
<211> LENGTH: 8
<212> TYPE: PRT
<213> ORGANISM: Human

<400> SEQUENCE: 28

Gln Asp Leu Asn Ser Tyr Pro Leu
1               5

<210> SEQ ID NO 29
<211> LENGTH: 25
<212> TYPE: PRT
<213> ORGANISM: Human

<400> SEQUENCE: 29

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 30
<211> LENGTH: 17
<212> TYPE: PRT
<213> ORGANISM: Human

<400> SEQUENCE: 30

Trp Asn Trp Ile Arg Gln Ser Pro Ser Arg Gly Leu Glu Trp Leu Gly
1               5                   10                  15

Arg

<210> SEQ ID NO 31
<211> LENGTH: 38
<212> TYPE: PRT
<213> ORGANISM: Human

<400> SEQUENCE: 31

Asp Tyr Ala Val Ser Val Lys Ser Arg Ile Thr Ile Asn Pro Asp Thr
1               5                   10                  15
```

-continued

```
Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 32
<211> LENGTH: 11
<212> TYPE: PRT
<213> ORGANISM: Human

<400> SEQUENCE: 32

Trp Gly Gln Gly Thr Thr Val Thr Val Ser Ser
1               5                  10

<210> SEQ ID NO 33
<211> LENGTH: 26
<212> TYPE: PRT
<213> ORGANISM: Human

<400> SEQUENCE: 33

Asp Ile Gln Val Thr Gln Ser Pro Ser Phe Leu Ser Ala Ser Val Gly
1               5                  10                  15

Asp Arg Val Thr Ile Thr Cys Arg Ala Ser
            20                  25

<210> SEQ ID NO 34
<211> LENGTH: 17
<212> TYPE: PRT
<213> ORGANISM: Human

<400> SEQUENCE: 34

Leu Ala Trp Tyr Gln His Lys Pro Gly Lys Ala Pro Lys Leu Leu Ile
1               5                  10                  15

His

<210> SEQ ID NO 35
<211> LENGTH: 36
<212> TYPE: PRT
<213> ORGANISM: Human

<400> SEQUENCE: 35

Ile Leu Gln Ser Gly Val Pro Ser Arg Phe Ser Gly Ser Gly Ser Gly
1               5                  10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 36
<211> LENGTH: 10
<212> TYPE: PRT
<213> ORGANISM: Human

<400> SEQUENCE: 36

Phe Gly Gln Gly Thr Arg Leu Glu Ile Lys
1               5                  10

<210> SEQ ID NO 37
<211> LENGTH: 375
<212> TYPE: DNA
<213> ORGANISM: Human

<400> SEQUENCE: 37
```

-continued

```
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagca gcagtggctg gcatccttac ggtatggacg tctggggcca agggaccacg     360
gtcaccgtct cctca                                                      375
```

```
<210> SEQ ID NO 38
<211> LENGTH: 318
<212> TYPE: DNA
<213> ORGANISM: Human

<400> SEQUENCE: 38
```

```
gacatccagg tgacccagtc tccatccttc ctgtctgcat ctgtaggaga cagagtcacc      60
atcacttgcc gggccagtca cgacattagc agttatttag cctggtatca acacaaacca     120
tggaaagccc ccaaactcct gatccatgct gcatccattt tgcaaagtgg ggtcccatca     180
aggttcagcg gaagtggatc tgggacagaa ttcactctca caatcagcag cctgcagcct     240
gaagattttg caacgtacta ctgtcaagat ctcaatagtt atcctctctt cggccaaggg     300
acacgactgg agattaaa                                                   318
```

```
<210> SEQ ID NO 39
<211> LENGTH: 125
<212> TYPE: PRT
<213> ORGANISM: Human

<400> SEQUENCE: 39
```

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
                100                 105                 110

Asp Val Trp Gly Gln Gly Thr Thr Val Thr Val Ser Ser
        115                 120                 125
```

```
<210> SEQ ID NO 40
<211> LENGTH: 106
<212> TYPE: PRT
<213> ORGANISM: Human

<400> SEQUENCE: 40
```

```
Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
```

-continued

```
              20              25              30

Leu Ala Trp Tyr Gln His Lys Pro Trp Lys Ala Pro Lys Leu Leu Ile
         35              40              45

His Ala Ala Ser Ile Leu Gln Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Gln Asp Leu Asn Ser Tyr Pro Leu
                 85              90              95

Phe Gly Gln Gly Thr Arg Leu Glu Ile Lys
             100             105

<210> SEQ ID NO 41
<211> LENGTH: 10
<212> TYPE: PRT
<213> ORGANISM: Human

<400> SEQUENCE: 41

Gly Asp Ser Val Ser Ser Asn Ser Ala Ala
1               5               10

<210> SEQ ID NO 42
<211> LENGTH: 9
<212> TYPE: PRT
<213> ORGANISM: Human

<400> SEQUENCE: 42

Thr Tyr Tyr Arg Ser Lys Trp Tyr Asn
1               5

<210> SEQ ID NO 43
<211> LENGTH: 15
<212> TYPE: PRT
<213> ORGANISM: Human

<400> SEQUENCE: 43

Ala Arg Asp Ser Ser Ser Gly Trp His Pro Tyr Gly Met Asp Val
1               5               10              15

<210> SEQ ID NO 44
<211> LENGTH: 6
<212> TYPE: PRT
<213> ORGANISM: Human

<400> SEQUENCE: 44

His Asp Ile Ser Ser Tyr
1               5

<210> SEQ ID NO 45
<211> LENGTH: 3
<212> TYPE: PRT
<213> ORGANISM: Human

<400> SEQUENCE: 45

Ala Ala Ser
1

<210> SEQ ID NO 46
<211> LENGTH: 8
<212> TYPE: PRT
<213> ORGANISM: Human

<400> SEQUENCE: 46
```

-continued

```
Gln Asp Leu Asn Ser Tyr Pro Leu
1               5

<210> SEQ ID NO 47
<211> LENGTH: 25
<212> TYPE: PRT
<213> ORGANISM: Human

<400> SEQUENCE: 47

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 48
<211> LENGTH: 17
<212> TYPE: PRT
<213> ORGANISM: Human

<400> SEQUENCE: 48

Trp Asn Trp Ile Arg Gln Ser Pro Ser Arg Gly Leu Glu Trp Leu Gly
1               5                   10                  15

Arg

<210> SEQ ID NO 49
<211> LENGTH: 38
<212> TYPE: PRT
<213> ORGANISM: Human

<400> SEQUENCE: 49

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 50
<211> LENGTH: 11
<212> TYPE: PRT
<213> ORGANISM: Human

<400> SEQUENCE: 50

Trp Gly Gln Gly Thr Thr Val Thr Val Ser Ser
1               5                   10

<210> SEQ ID NO 51
<211> LENGTH: 26
<212> TYPE: PRT
<213> ORGANISM: Human

<400> SEQUENCE: 51

Asp Ile Gln Val Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 52
<211> LENGTH: 17
<212> TYPE: PRT
<213> ORGANISM: Human
```

<400> SEQUENCE: 52

Leu Ala Trp Tyr Gln His Lys Pro Trp Lys Ala Pro Lys Leu Leu Ile
1               5                   10                  15

His

<210> SEQ ID NO 53
<211> LENGTH: 36
<212> TYPE: PRT
<213> ORGANISM: Human

<400> SEQUENCE: 53

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
                20                  25                  30

Thr Tyr Tyr Cys
        35

<210> SEQ ID NO 54
<211> LENGTH: 10
<212> TYPE: PRT
<213> ORGANISM: Human

<400> SEQUENCE: 54

Phe Gly Gln Gly Thr Arg Leu Glu Ile Lys
1               5                   10

<210> SEQ ID NO 55
<211> LENGTH: 375
<212> TYPE: DNA
<213> ORGANISM: Human

<400> SEQUENCE: 55
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagattcta ctactgggtg gaatgcttac ggtatggacg tctggggcca agggaccacg     360
gtcaccgtct cctca                                                       375

<210> SEQ ID NO 56
<211> LENGTH: 318
<212> TYPE: DNA
<213> ORGANISM: Human

<400> SEQUENCE: 56
gacatccagg tgacccagtc tccatccttc ctgtctgcat ctgtaggaga cagagtcacc      60
atcacttgcc gggccagtca cgacattagc agttatttag cctggtatca acacaaaccg     120
tggaaagccc ccaaactcct gatccatgct gcatccattt tgcaaagtgg ggtcccatca     180
aggttcagcg gaagtggatc tgggacagaa ttcactctca caatcagcag cctgcagcct     240
gaagattttg caacgtacta ctgtcaagat tcaatagtt atcctctctt cggccaaggg      300
acacgactgg agattaaa                                                     318

<210> SEQ ID NO 57

-continued

<211> LENGTH: 125
<212> TYPE: PRT
<213> ORGANISM: Human

<400> SEQUENCE: 57

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Thr Thr Gly Trp Asn Ala Tyr Gly Met
            100                 105                 110

Asp Val Trp Gly Gln Gly Thr Thr Val Thr Val Ser Ser
        115                 120                 125
```

<210> SEQ ID NO 58
<211> LENGTH: 106
<212> TYPE: PRT
<213> ORGANISM: Human
<400> SEQUENCE: 58

```
Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
            35                  40                  45

His Ala Ala Ser Ile Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys
            100                 105
```

<210> SEQ ID NO 59
<211> LENGTH: 10
<212> TYPE: PRT
<213> ORGANISM: Human
<400> SEQUENCE: 59

```
Gly Asp Ser Val Ser Ser Asn Ser Ala Ala
1               5                   10
```

<210> SEQ ID NO 60
<211> LENGTH: 9
<212> TYPE: PRT
<213> ORGANISM: Human
<400> SEQUENCE: 60

```
Thr Tyr Tyr Arg Ser Lys Trp Tyr Asn
```

```
1               5

<210> SEQ ID NO 61
<211> LENGTH: 15
<212> TYPE: PRT
<213> ORGANISM: Human

<400> SEQUENCE: 61

Ala Arg Asp Ser Thr Thr Gly Trp Asn Ala Tyr Gly Met Asp Val
1               5                   10                  15

<210> SEQ ID NO 62
<211> LENGTH: 6
<212> TYPE: PRT
<213> ORGANISM: Human

<400> SEQUENCE: 62

His Asp Ile Ser Ser Tyr
1               5

<210> SEQ ID NO 63
<211> LENGTH: 3
<212> TYPE: PRT
<213> ORGANISM: Human

<400> SEQUENCE: 63

Ala Ala Ser
1

<210> SEQ ID NO 64
<211> LENGTH: 8
<212> TYPE: PRT
<213> ORGANISM: Human

<400> SEQUENCE: 64

Gln Asp Leu Asn Ser Tyr Pro Leu
1               5

<210> SEQ ID NO 65
<211> LENGTH: 25
<212> TYPE: PRT
<213> ORGANISM: Human

<400> SEQUENCE: 65

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 66
<211> LENGTH: 17
<212> TYPE: PRT
<213> ORGANISM: Human

<400> SEQUENCE: 66

Trp Asn Trp Ile Arg Gln Ser Pro Ser Arg Gly Leu Glu Trp Leu Gly
1               5                   10                  15

Arg

<210> SEQ ID NO 67
<211> LENGTH: 38
<212> TYPE: PRT
<213> ORGANISM: Human
```

-continued

<400> SEQUENCE: 67

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 68
<211> LENGTH: 11
<212> TYPE: PRT
<213> ORGANISM: Human

<400> SEQUENCE: 68

Trp Gly Gln Gly Thr Thr Val Thr Val Ser Ser
1               5                   10

<210> SEQ ID NO 69
<211> LENGTH: 26
<212> TYPE: PRT
<213> ORGANISM: Human

<400> SEQUENCE: 69

Asp Ile Gln Val Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 70
<211> LENGTH: 17
<212> TYPE: PRT
<213> ORGANISM: Human

<400> SEQUENCE: 70

Leu Ala Trp Tyr Gln His Lys Pro Trp Lys Ala Pro Lys Leu Leu Ile
1               5                   10                  15

His

<210> SEQ ID NO 71
<211> LENGTH: 36
<212> TYPE: PRT
<213> ORGANISM: Human

<400> SEQUENCE: 71

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 72
<211> LENGTH: 10
<212> TYPE: PRT
<213> ORGANISM: Human

<400> SEQUENCE: 72

Phe Gly Gln Gly Thr Arg Leu Glu Ile Lys
1               5                   10

<210> SEQ ID NO 73

<211> LENGTH: 375
<212> TYPE: DNA
<213> ORGANISM: Human

<400> SEQUENCE: 73
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagattcta cgagtgggtg gcatccttac ggtatggacg tctggggcca agggaccacg     360
gtcaccgtct cctca                                                     375

<210> SEQ ID NO 74
<211> LENGTH: 318
<212> TYPE: DNA
<213> ORGANISM: Human

<400> SEQUENCE: 74
gacatccagg tgacccagtc tccatccttc ctgtctgcat ctgtaggaga cagagtcacc      60
atcacttgcc gggccagtca cgacattagc agttatttag cctggtatca acacaaaccg     120
tggaaagccc ccaaactcct gatccatgct gcatccattt tgcaaagtgg ggtcccatca     180
aggttcagcg gaagtggatc tgggacagaa ttcactctca caatcagcag cctgcagcct     240
gaagattttg caacgtacta ctgtcaagat ctcaatagtt atcctctctt cggccaaggg     300
acacgactgg agattaaa                                                  318

<210> SEQ ID NO 75
<211> LENGTH: 125
<212> TYPE: PRT
<213> ORGANISM: Human

<400> SEQUENCE: 75

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Thr Ser Gly Trp His Pro Tyr Gly Met
            100                 105                 110

Asp Val Trp Gly Gln Gly Thr Thr Val Thr Val Ser Ser
        115                 120                 125

<210> SEQ ID NO 76
<211> LENGTH: 106
<212> TYPE: PRT
<213> ORGANISM: Human

<400> SEQUENCE: 76

-continued

```
Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys
            100                 105
```

<210> SEQ ID NO 77
<211> LENGTH: 10
<212> TYPE: PRT
<213> ORGANISM: Human

<400> SEQUENCE: 77

```
Gly Asp Ser Val Ser Ser Asn Ser Ala Ala
1               5                   10
```

<210> SEQ ID NO 78
<211> LENGTH: 9
<212> TYPE: PRT
<213> ORGANISM: Human

<400> SEQUENCE: 78

```
Thr Tyr Tyr Arg Ser Lys Trp Tyr Asn
1               5
```

<210> SEQ ID NO 79
<211> LENGTH: 15
<212> TYPE: PRT
<213> ORGANISM: Human

<400> SEQUENCE: 79

```
Ala Arg Asp Ser Thr Ser Gly Trp His Pro Tyr Gly Met Asp Val
1               5                   10                  15
```

<210> SEQ ID NO 80
<211> LENGTH: 6
<212> TYPE: PRT
<213> ORGANISM: Human

<400> SEQUENCE: 80

```
His Asp Ile Ser Ser Tyr
1               5
```

<210> SEQ ID NO 81
<211> LENGTH: 3
<212> TYPE: PRT
<213> ORGANISM: Human

<400> SEQUENCE: 81

```
Ala Ala Ser
1
```

<210> SEQ ID NO 82

```
<211> LENGTH: 8
<212> TYPE: PRT
<213> ORGANISM: Human

<400> SEQUENCE: 82

Gln Asp Leu Asn Ser Tyr Pro Leu
1               5

<210> SEQ ID NO 83
<211> LENGTH: 25
<212> TYPE: PRT
<213> ORGANISM: Human

<400> SEQUENCE: 83

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 84
<211> LENGTH: 17
<212> TYPE: PRT
<213> ORGANISM: Human

<400> SEQUENCE: 84

Trp Asn Trp Ile Arg Gln Ser Pro Ser Arg Gly Leu Glu Trp Leu Gly
1               5                   10                  15

Arg

<210> SEQ ID NO 85
<211> LENGTH: 38
<212> TYPE: PRT
<213> ORGANISM: Human

<400> SEQUENCE: 85

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
            35

<210> SEQ ID NO 86
<211> LENGTH: 11
<212> TYPE: PRT
<213> ORGANISM: Human

<400> SEQUENCE: 86

Trp Gly Gln Gly Thr Thr Val Thr Val Ser Ser
1               5                   10

<210> SEQ ID NO 87
<211> LENGTH: 26
<212> TYPE: PRT
<213> ORGANISM: Human

<400> SEQUENCE: 87

Asp Ile Gln Val Thr Gln Ser Pro Ser Phe Leu Ser Ala Ser Val Gly
1               5                   10                  15

Asp Arg Val Thr Ile Thr Cys Arg Ala Ser
            20                  25
```

<210> SEQ ID NO 88
<211> LENGTH: 17
<212> TYPE: PRT
<213> ORGANISM: Human

<400> SEQUENCE: 88

Leu Ala Trp Tyr Gln His Lys Pro Trp Lys Ala Pro Lys Leu Leu Ile
1               5                   10                  15

His

<210> SEQ ID NO 89
<211> LENGTH: 36
<212> TYPE: PRT
<213> ORGANISM: Human

<400> SEQUENCE: 89

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
            35

<210> SEQ ID NO 90
<211> LENGTH: 10
<212> TYPE: PRT
<213> ORGANISM: Human

<400> SEQUENCE: 90

Phe Gly Gln Gly Thr Arg Leu Glu Ile Lys
1               5                   10

<210> SEQ ID NO 91
<211> LENGTH: 375
<212> TYPE: DNA
<213> ORGANISM: Human

<400> SEQUENCE: 91
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacaggtc caagtggtat    180
aatgattatg cagtatctgt gaaaagtcga ataaccatca acccagacac atccaagaac    240
cagttctccc tgcagctgaa ctctgtgact cccgaggaca cggctgtgta ttactgtgca    300
agagattcga ctacggggtg gggtgcgtac ggtatggacg tctggggcca agggaccacg    360
gtcaccgtct cctca                                                     375

<210> SEQ ID NO 92
<211> LENGTH: 318
<212> TYPE: DNA
<213> ORGANISM: Human

<400> SEQUENCE: 92
gacatccagg tgacccagtc tccatccttc ctgtctgcat ctgtaggaga cagagtcacc     60
atcacttgcc gggccagtca cgacattagc agttatttag cctggtatca acacaaaccg    120
tggaaagccc ccaaactcct gatccatgct gcatccattt gcaaagtggg gtcccatca    180 aggttcagcg gaagtggatc tgggacagaa ttcactctca caatcagcag cctgcagcct    240
gaagattttg caacgtacta ctgtcaagat ctcaatagtt atcctctctt cggccaaggg    300

-continued acacgactgg agattaaa                                                                    318

```
<210> SEQ ID NO 93
<211> LENGTH: 125
<212> TYPE: PRT
<213> ORGANISM: Human

<400> SEQUENCE: 93

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Ser Thr Thr Gly Trp Gly Ala Tyr Gly Met
            100                 105                 110

Asp Val Trp Gly Gln Gly Thr Thr Val Thr Val Ser Ser
        115                 120                 125

<210> SEQ ID NO 94
<211> LENGTH: 106
<212> TYPE: PRT
<213> ORGANISM: Human

<400> SEQUENCE: 94

Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
            85                  90                  95

Phe Gly Gln Gly Thr Arg Leu Glu Ile Lys
            100                 105

<210> SEQ ID NO 95
<211> LENGTH: 10
<212> TYPE: PRT
<213> ORGANISM: Human

<400> SEQUENCE: 95

Gly Asp Ser Val Ser Ser Asn Ser Ala Ala
1               5                   10

<210> SEQ ID NO 96
<211> LENGTH: 9
<212> TYPE: PRT
```

<213> ORGANISM: Human

<400> SEQUENCE: 96

Thr Tyr Tyr Arg Ser Lys Trp Tyr Asn
1               5

<210> SEQ ID NO 97
<211> LENGTH: 15
<212> TYPE: PRT
<213> ORGANISM: Human

<400> SEQUENCE: 97

Ala Arg Asp Ser Thr Thr Gly Trp Gly Ala Tyr Gly Met Asp Val
1               5                   10                  15

<210> SEQ ID NO 98
<211> LENGTH: 6
<212> TYPE: PRT
<213> ORGANISM: Human

<400> SEQUENCE: 98

His Asp Ile Ser Ser Tyr
1               5

<210> SEQ ID NO 99
<211> LENGTH: 3
<212> TYPE: PRT
<213> ORGANISM: Human

<400> SEQUENCE: 99

Ala Ala Ser
1

<210> SEQ ID NO 100
<211> LENGTH: 8
<212> TYPE: PRT
<213> ORGANISM: Human

<400> SEQUENCE: 100

Gln Asp Leu Asn Ser Tyr Pro Leu
1               5

<210> SEQ ID NO 101
<211> LENGTH: 25
<212> TYPE: PRT
<213> ORGANISM: Human

<400> SEQUENCE: 101

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 102
<211> LENGTH: 17
<212> TYPE: PRT
<213> ORGANISM: Human

<400> SEQUENCE: 102

Trp Asn Trp Ile Arg Gln Ser Pro Ser Arg Gly Leu Glu Trp Leu Gly
1               5                   10                  15

Arg

-continued

```
<210> SEQ ID NO 103
<211> LENGTH: 38
<212> TYPE: PRT
<213> ORGANISM: Human

<400> SEQUENCE: 103

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
            35

<210> SEQ ID NO 104
<211> LENGTH: 11
<212> TYPE: PRT
<213> ORGANISM: Human

<400> SEQUENCE: 104

Trp Gly Gln Gly Thr Thr Val Thr Val Ser Ser
1               5                   10

<210> SEQ ID NO 105
<211> LENGTH: 26
<212> TYPE: PRT
<213> ORGANISM: Human

<400> SEQUENCE: 105

Asp Ile Gln Val Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 106
<211> LENGTH: 17
<212> TYPE: PRT
<213> ORGANISM: Human

<400> SEQUENCE: 106

Leu Ala Trp Tyr Gln His Lys Pro Trp Lys Ala Pro Lys Leu Leu Ile
1               5                   10                  15

His

<210> SEQ ID NO 107
<211> LENGTH: 36
<212> TYPE: PRT
<213> ORGANISM: Human

<400> SEQUENCE: 107

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
            35

<210> SEQ ID NO 108
<211> LENGTH: 10
<212> TYPE: PRT
<213> ORGANISM: Human

<400> SEQUENCE: 108
```

```
Phe Gly Gln Gly Thr Arg Leu Glu Ile Lys
1               5                   10
```

```
<210> SEQ ID NO 109
<211> LENGTH: 375
<212> TYPE: DNA
<213> ORGANISM: Human

<400> SEQUENCE: 109
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagga ctactgggtg gcatccgtac ggtatggacg tctggggcca agggaccacg     360
gtcaccgtct cctca                                                      375
```

```
<210> SEQ ID NO 110
<211> LENGTH: 318
<212> TYPE: DNA
<213> ORGANISM: Human

<400> SEQUENCE: 110
gacatccagg tgacccagtc tccatccttc ctgtctgcat ctgtaggaga cagagtcacc      60
atcacttgcc gggccagtca cgacattagc agttatttag cctggtatca acacaaaccg     120
tggaaagccc ccaaactcct gatccatgct gcatccattt tgcaaagtgg ggtcccatca     180
aggttcagcg gaagtggatc tgggacagaa ttcactctca caatcagcag cctgcagcct     240
gaagattttg caacgtacta ctgtcaagat ctcaatagtt atcctctctt cggccaaggg     300
acacgactgg agattaaa                                                   318
```

```
<210> SEQ ID NO 111
<211> LENGTH: 125
<212> TYPE: PRT
<213> ORGANISM: Human

<400> SEQUENCE: 111

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Thr Thr Gly Trp His Pro Tyr Gly Met
                100                 105                 110

Asp Val Trp Gly Gln Gly Thr Thr Val Thr Val Ser Ser
            115                 120                 125
```

```
<210> SEQ ID NO 112
```

```
<211> LENGTH: 106
<212> TYPE: PRT
<213> ORGANISM: Human

<400> SEQUENCE: 112

Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys
            100                 105

<210> SEQ ID NO 113
<211> LENGTH: 10
<212> TYPE: PRT
<213> ORGANISM: Human

<400> SEQUENCE: 113

Gly Asp Ser Val Ser Ser Asn Ser Ala Ala
1               5                   10

<210> SEQ ID NO 114
<211> LENGTH: 9
<212> TYPE: PRT
<213> ORGANISM: Human

<400> SEQUENCE: 114

Thr Tyr Tyr Arg Ser Lys Trp Tyr Asn
1               5

<210> SEQ ID NO 115
<211> LENGTH: 15
<212> TYPE: PRT
<213> ORGANISM: Human

<400> SEQUENCE: 115

Ala Arg Asp Arg Thr Thr Gly Trp His Pro Tyr Gly Met Asp Val
1               5                   10                  15

<210> SEQ ID NO 116
<211> LENGTH: 6
<212> TYPE: PRT
<213> ORGANISM: Human

<400> SEQUENCE: 116

His Asp Ile Ser Ser Tyr
1               5

<210> SEQ ID NO 117
<211> LENGTH: 3
<212> TYPE: PRT
<213> ORGANISM: Human

<400> SEQUENCE: 117
```

```
Ala Ala Ser
1

<210> SEQ ID NO 118
<211> LENGTH: 8
<212> TYPE: PRT
<213> ORGANISM: Human

<400> SEQUENCE: 118

Gln Asp Leu Asn Ser Tyr Pro Leu
1               5

<210> SEQ ID NO 119
<211> LENGTH: 25
<212> TYPE: PRT
<213> ORGANISM: Human

<400> SEQUENCE: 119

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 120
<211> LENGTH: 17
<212> TYPE: PRT
<213> ORGANISM: Human

<400> SEQUENCE: 120

Trp Asn Trp Ile Arg Gln Ser Pro Ser Arg Gly Leu Glu Trp Leu Gly
1               5                   10                  15

Arg

<210> SEQ ID NO 121
<211> LENGTH: 38
<212> TYPE: PRT
<213> ORGANISM: Human

<400> SEQUENCE: 121

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 122
<211> LENGTH: 11
<212> TYPE: PRT
<213> ORGANISM: Human

<400> SEQUENCE: 122

Trp Gly Gln Gly Thr Thr Val Thr Val Ser Ser
1               5                   10

<210> SEQ ID NO 123
<211> LENGTH: 26
<212> TYPE: PRT
<213> ORGANISM: Human

<400> SEQUENCE: 123

Asp Ile Gln Val Thr Gln Ser Pro Ser Phe Leu Ser Ala Ser Val Gly
1               5                   10                  15
```

Asp Arg Val Thr Ile Thr Cys Arg Ala Ser
            20                          25

<210> SEQ ID NO 124
<211> LENGTH: 17
<212> TYPE: PRT
<213> ORGANISM: Human

<400> SEQUENCE: 124

Leu Ala Trp Tyr Gln His Lys Pro Trp Lys Ala Pro Lys Leu Leu Ile
1               5                   10                  15

His

<210> SEQ ID NO 125
<211> LENGTH: 36
<212> TYPE: PRT
<213> ORGANISM: Human

<400> SEQUENCE: 125

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 126
<211> LENGTH: 10
<212> TYPE: PRT
<213> ORGANISM: Human

<400> SEQUENCE: 126

Phe Gly Gln Gly Thr Arg Leu Glu Ile Lys
1               5                   10

<210> SEQ ID NO 127
<211> LENGTH: 375
<212> TYPE: DNA
<213> ORGANISM: Human

<400> SEQUENCE: 127
caggtacagc tgcagcagtc aggtccagga ctggtgaagc cctcgcagac cctctcactc      60
acctgtgcca tctccgggga cagtgtctct agcagcagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagca gcagtggctg gcatccttac ggtatggacg tctggggcca agggaccacg     360
gtcaccgtct cctca                                                       375

<210> SEQ ID NO 128
<211> LENGTH: 318
<212> TYPE: DNA
<213> ORGANISM: Human

<400> SEQUENCE: 128
gacgtccagg tgacccagtc tccatccttc ctgtctgcat ctgtaggaga cagagtcacc      60
atcacttgcc gggccagtca cgacattagc agttatttag cctggtatca acacaaaccg     120

```
tggaaagccc ccaaactcct gatccatgct gcatccgttt tgcaaagtgg ggtcccatca     180
aggttcagcg gaagtggatc tgggacagaa ttcactctca caatcagcag cctgcagcct     240
gaagattttg caacgtacta ctgtcaaaat ctcaatagtt atcctctctt cggccaaggg     300
acacgactgg agattaaa                                                   318
```

<210> SEQ ID NO 129
<211> LENGTH: 125
<212> TYPE: PRT
<213> ORGANISM: Human

<400> SEQUENCE: 129

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

Asp Val Trp Gly Gln Gly Thr Thr Val Thr Val Ser Ser
        115                 120                 125
```

<210> SEQ ID NO 130
<211> LENGTH: 106
<212> TYPE: PRT
<213> ORGANISM: Human

<400> SEQUENCE: 130

```
Asp Val Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Val Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asn Leu Asn Ser Tyr Pro Leu
                85                  90                  95

Phe Gly Gln Gly Thr Arg Leu Glu Ile Lys
            100                 105
```

<210> SEQ ID NO 131
<211> LENGTH: 10
<212> TYPE: PRT
<213> ORGANISM: Human

<400> SEQUENCE: 131

```
Gly Asp Ser Val Ser Ser Ser Ser Ala Ala
1               5                   10
```

-continued

```
<210> SEQ ID NO 132
<211> LENGTH: 9
<212> TYPE: PRT
<213> ORGANISM: Human

<400> SEQUENCE: 132

Thr Tyr Tyr Arg Ser Lys Trp Tyr Asn
1               5

<210> SEQ ID NO 133
<211> LENGTH: 15
<212> TYPE: PRT
<213> ORGANISM: Human

<400> SEQUENCE: 133

Ala Arg Asp Ser Ser Ser Gly Trp His Pro Tyr Gly Met Asp Val
1               5               10              15

<210> SEQ ID NO 134
<211> LENGTH: 6
<212> TYPE: PRT
<213> ORGANISM: Human

<400> SEQUENCE: 134

His Asp Ile Ser Ser Tyr
1               5

<210> SEQ ID NO 135
<211> LENGTH: 3
<212> TYPE: PRT
<213> ORGANISM: Human

<400> SEQUENCE: 135

Ala Ala Ser
1

<210> SEQ ID NO 136
<211> LENGTH: 8
<212> TYPE: PRT
<213> ORGANISM: Human

<400> SEQUENCE: 136

Gln Asn Leu Asn Ser Tyr Pro Leu
1               5

<210> SEQ ID NO 137
<211> LENGTH: 25
<212> TYPE: PRT
<213> ORGANISM: Human

<400> SEQUENCE: 137

Gln Val Gln Leu Gln Gln Ser Gly Pro Gly Leu Val Lys Pro Ser Gln
1               5               10              15

Thr Leu Ser Leu Thr Cys Ala Ile Ser
            20              25

<210> SEQ ID NO 138
<211> LENGTH: 17
<212> TYPE: PRT
<213> ORGANISM: Human

<400> SEQUENCE: 138

Trp Asn Trp Ile Arg Gln Ser Pro Ser Arg Gly Leu Glu Trp Leu Gly
```

```
1               5               10              15

Arg

<210> SEQ ID NO 139
<211> LENGTH: 38
<212> TYPE: PRT
<213> ORGANISM: Human

<400> SEQUENCE: 139

Asp Tyr Ala Val Ser Val Lys Ser Arg Ile Thr Ile Asn Pro Asp Thr
1               5               10              15

Ser Lys Asn Gln Phe Ser Leu Gln Leu Asn Ser Val Thr Pro Glu Asp
            20              25              30

Thr Ala Val Tyr Tyr Cys
        35

<210> SEQ ID NO 140
<211> LENGTH: 11
<212> TYPE: PRT
<213> ORGANISM: Human

<400> SEQUENCE: 140

Trp Gly Gln Gly Thr Thr Val Thr Val Ser Ser
1               5               10

<210> SEQ ID NO 141
<211> LENGTH: 26
<212> TYPE: PRT
<213> ORGANISM: Human

<400> SEQUENCE: 141

Asp Val Gln Val Thr Gln Ser Pro Ser Phe Leu Ser Ala Ser Val Gly
1               5               10              15

Asp Arg Val Thr Ile Thr Cys Arg Ala Ser
            20              25

<210> SEQ ID NO 142
<211> LENGTH: 17
<212> TYPE: PRT
<213> ORGANISM: Human

<400> SEQUENCE: 142

Leu Ala Trp Tyr Gln His Lys Pro Trp Lys Ala Pro Lys Leu Leu Ile
1               5               10              15

His

<210> SEQ ID NO 143
<211> LENGTH: 36
<212> TYPE: PRT
<213> ORGANISM: Human

<400> SEQUENCE: 143

Val Leu Gln Ser Gly Val Pro Ser Arg Phe Ser Gly Ser Gly Ser Gly
1               5               10              15

Thr Glu Phe Thr Leu Thr Ile Ser Ser Leu Gln Pro Glu Asp Phe Ala
            20              25              30

Thr Tyr Tyr Cys
        35

<210> SEQ ID NO 144
<211> LENGTH: 10
```

<212> TYPE: PRT
<213> ORGANISM: Human

<400> SEQUENCE: 144

Phe Gly Gln Gly Thr Arg Leu Glu Ile Lys
1               5                   10

<210> SEQ ID NO 145
<211> LENGTH: 375
<212> TYPE: DNA
<213> ORGANISM: Human

<400> SEQUENCE: 145
caggtacagc tgcagcagtc aggtccagaa ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagca gcagtggctg gcatccttac ggtatggacg tctggggcca agggaccacg     360
gtcaccgtct cctca                                                       375

<210> SEQ ID NO 146
<211> LENGTH: 318
<212> TYPE: DNA
<213> ORGANISM: Human

<400> SEQUENCE: 146
gacatccggg tgacccagtc tccatccttc ctgtctgcat ctgtaggaga cagagtcacc      60
atcacttgcc ggaccagtca cgacattagc agttatttag cctggtatca acacaaaccg     120
tggaaagccc ccaaactcct gatccatgct gcatccattt gcaaagtggg ggtcccatca     180
aggttcagcg gaagtggatc tgggacagaa ttcactctca caatcagcag cctgcagcct     240
gaagattttg caacgtacta ctgtcaagat ctcaatagtt atcctctctt cggccaaggg     300
acacgactgg agattaaa                                                    318

<210> SEQ ID NO 147
<211> LENGTH: 125
<212> TYPE: PRT
<213> ORGANISM: Human

<400> SEQUENCE: 147

Gln Val Gln Leu Gln Gln Ser Gly Pro Glu Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

```
Asp Val Trp Gly Gln Gly Thr Thr Val Thr Val Ser Ser
        115                 120                 125

<210> SEQ ID NO 148
<211> LENGTH: 106
<212> TYPE: PRT
<213> ORGANISM: Human

<400> SEQUENCE: 148

Asp Ile Arg Val Thr Gln Ser Pro Ser Phe Leu Ser Ala Ser Val Gly
1               5                   10                  15

Asp Arg Val Thr Ile Thr Cys Arg Thr Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys
            100                 105

<210> SEQ ID NO 149
<211> LENGTH: 10
<212> TYPE: PRT
<213> ORGANISM: Human

<400> SEQUENCE: 149

Gly Asp Ser Val Ser Ser Asn Ser Ala Ala
1               5                   10

<210> SEQ ID NO 150
<211> LENGTH: 9
<212> TYPE: PRT
<213> ORGANISM: Human

<400> SEQUENCE: 150

Thr Tyr Tyr Arg Ser Lys Trp Tyr Asn
1               5

<210> SEQ ID NO 151
<211> LENGTH: 15
<212> TYPE: PRT
<213> ORGANISM: Human

<400> SEQUENCE: 151

Ala Arg Asp Ser Ser Ser Gly Trp His Pro Tyr Gly Met Asp Val
1               5                   10                  15

<210> SEQ ID NO 152
<211> LENGTH: 6
<212> TYPE: PRT
<213> ORGANISM: Human

<400> SEQUENCE: 152

His Asp Ile Ser Ser Tyr
1               5

<210> SEQ ID NO 153
<211> LENGTH: 3
```

<212> TYPE: PRT
<213> ORGANISM: Human

<400> SEQUENCE: 153

Ala Ala Ser
1

<210> SEQ ID NO 154
<211> LENGTH: 8
<212> TYPE: PRT
<213> ORGANISM: Human

<400> SEQUENCE: 154

Gln Asp Leu Asn Ser Tyr Pro Leu
1               5

<210> SEQ ID NO 155
<211> LENGTH: 25
<212> TYPE: PRT
<213> ORGANISM: Human

<400> SEQUENCE: 155

Gln Val Gln Leu Gln Gln Ser Gly Pro Glu Leu Val Lys Pro Ser Gln
1               5                   10                  15

Thr Leu Ser Leu Thr Cys Ala Ile Ser
            20                  25

<210> SEQ ID NO 156
<211> LENGTH: 17
<212> TYPE: PRT
<213> ORGANISM: Human

<400> SEQUENCE: 156

Trp Asn Trp Ile Arg Gln Ser Pro Ser Arg Gly Leu Glu Trp Leu Gly
1               5                   10                  15

Arg

<210> SEQ ID NO 157
<211> LENGTH: 38
<212> TYPE: PRT
<213> ORGANISM: Human

<400> SEQUENCE: 157

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
            35

<210> SEQ ID NO 158
<211> LENGTH: 11
<212> TYPE: PRT
<213> ORGANISM: Human

<400> SEQUENCE: 158

Trp Gly Gln Gly Thr Thr Val Thr Val Ser Ser
1               5                   10

<210> SEQ ID NO 159
<211> LENGTH: 26
<212> TYPE: PRT
<213> ORGANISM: Human

<400> SEQUENCE: 159

Asp Ile Arg Val Thr Gln Ser Pro Ser Phe Leu Ser Ala Ser Val Gly
1               5                   10                  15

Asp Arg Val Thr Ile Thr Cys Arg Thr Ser
            20                  25

<210> SEQ ID NO 160
<211> LENGTH: 17
<212> TYPE: PRT
<213> ORGANISM: Human

<400> SEQUENCE: 160

Leu Ala Trp Tyr Gln His Lys Pro Trp Lys Ala Pro Lys Leu Leu Ile
1               5                   10                  15

His

<210> SEQ ID NO 161
<211> LENGTH: 36
<212> TYPE: PRT
<213> ORGANISM: Human

<400> SEQUENCE: 161

Ile Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 162
<211> LENGTH: 10
<212> TYPE: PRT
<213> ORGANISM: Human

<400> SEQUENCE: 162

Phe Gly Gln Gly Thr Arg Leu Glu Ile Lys
1               5                   10

<210> SEQ ID NO 163
<211> LENGTH: 354
<212> TYPE: DNA
<213> ORGANISM: Human

<400> SEQUENCE: 163
caggtccagc ttgtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagacgta    300
cagaggatgg ggatggacgt ctggggccaa gggaccacgg tcaccgtctc ctca          354

<210> SEQ ID NO 164
<211> LENGTH: 321
<212> TYPE: DNA
<213> ORGANISM: Human

<400> SEQUENCE: 164
gacatccaga tgacccagtc tccttcttcc gtctctacat ctgtaggaga cagagtcacc     60

-continued

```
atcacttgtc gggcgagtca ggatattagt aactggttag cctggtatca gcagaaacca      120
ggaaaagccc ctaagctcct gatctatgat tcatccactt tgcaaagtgg ggtcccatca      180
aggttcagcg gcagtggatc tgggacagat ttcactctca ccatcagcac cctgcagcct      240
gaggattttg caacttatta ctgtcaacag tttaatagtt atccccctca tttcggcgga      300
gggaccaaag tggatatcaa a                                                321
```

<210> SEQ ID NO 165
<211> LENGTH: 118
<212> TYPE: PRT
<213> ORGANISM: Human

<400> SEQUENCE: 165

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gln Arg Met Gly Met Asp Val Trp Gly Gln Gly Thr
            100                 105                 110

Thr Val Thr Val Ser Ser
        115
```

<210> SEQ ID NO 166
<211> LENGTH: 107
<212> TYPE: PRT
<213> ORGANISM: Human

<400> SEQUENCE: 166

```
Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105
```

<210> SEQ ID NO 167
<211> LENGTH: 8
<212> TYPE: PRT
<213> ORGANISM: Human

<400> SEQUENCE: 167

Gly Gly Thr Phe Ser Ser Tyr Ala
1               5

<210> SEQ ID NO 168
<211> LENGTH: 8
<212> TYPE: PRT
<213> ORGANISM: Human

<400> SEQUENCE: 168

Ile Ile Pro Ile Phe Gly Thr Ala
1               5

<210> SEQ ID NO 169
<211> LENGTH: 11
<212> TYPE: PRT
<213> ORGANISM: Human

<400> SEQUENCE: 169

Ala Arg Asp Val Gln Arg Met Gly Met Asp Val
1               5               10

<210> SEQ ID NO 170
<211> LENGTH: 6
<212> TYPE: PRT
<213> ORGANISM: Human

<400> SEQUENCE: 170

Gln Asp Ile Ser Asn Trp
1               5

<210> SEQ ID NO 171
<211> LENGTH: 3
<212> TYPE: PRT
<213> ORGANISM: Human

<400> SEQUENCE: 171

Asp Ser Ser
1

<210> SEQ ID NO 172
<211> LENGTH: 9
<212> TYPE: PRT
<213> ORGANISM: Human

<400> SEQUENCE: 172

Gln Gln Phe Asn Ser Tyr Pro Leu Thr
1               5

<210> SEQ ID NO 173
<211> LENGTH: 25
<212> TYPE: PRT
<213> ORGANISM: Human

<400> SEQUENCE: 173

Gln Val Gln Leu Val Gln Ser Gly Ala Glu Val Lys Lys Pro Gly Ser
1               5               10              15

Ser Val Lys Val Ser Cys Lys Ala Ser
            20              25

<210> SEQ ID NO 174
<211> LENGTH: 17
<212> TYPE: PRT
<213> ORGANISM: Human

<400> SEQUENCE: 174

Ile Ser Trp Val Arg Gln Ala Pro Gly Gln Gly Leu Glu Trp Met Gly
1               5                   10                  15

Gly

<210> SEQ ID NO 175
<211> LENGTH: 38
<212> TYPE: PRT
<213> ORGANISM: Human

<400> SEQUENCE: 175

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
                20                  25                  30

Thr Ala Val Tyr Tyr Cys
        35

<210> SEQ ID NO 176
<211> LENGTH: 11
<212> TYPE: PRT
<213> ORGANISM: Human

<400> SEQUENCE: 176

Trp Gly Gln Gly Thr Thr Val Thr Val Ser Ser
1               5                   10

<210> SEQ ID NO 177
<211> LENGTH: 26
<212> TYPE: PRT
<213> ORGANISM: Human

<400> SEQUENCE: 177

Asp Ile Gln Met Thr Gln Ser Pro Ser Ser Val Ser Thr Ser Val Gly
1               5                   10                  15

Asp Arg Val Thr Ile Thr Cys Arg Ala Ser
                20                  25

<210> SEQ ID NO 178
<211> LENGTH: 17
<212> TYPE: PRT
<213> ORGANISM: Human

<400> SEQUENCE: 178

Leu Ala Trp Tyr Gln Gln Lys Pro Gly Lys Ala Pro Lys Leu Leu Ile
1               5                   10                  15

Tyr

<210> SEQ ID NO 179
<211> LENGTH: 36
<212> TYPE: PRT
<213> ORGANISM: Human

<400> SEQUENCE: 179

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
                20                  25                  30

Thr Tyr Tyr Cys
        35

```
<210> SEQ ID NO 180
<211> LENGTH: 10
<212> TYPE: PRT
<213> ORGANISM: Human

<400> SEQUENCE: 180

Phe Gly Gly Gly Thr Lys Val Asp Ile Lys
1               5                   10

<210> SEQ ID NO 181
<211> LENGTH: 363
<212> TYPE: DNA
<213> ORGANISM: Human

<400> SEQUENCE: 181
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggggct     300
attggcgtat tctcgggcta ctttgactac tggggccagg gaaccctggt caccgtctcc     360
tca                                                                    363

<210> SEQ ID NO 182
<211> LENGTH: 339
<212> TYPE: DNA
<213> ORGANISM: Human

<400> SEQUENCE: 182
gatattgtgc tgacgcagac tccagactcc ctggctgtgt ctccgggcga gagggccacc      60
atcaactgca gtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtgtattact gtcagcaata ttatgatacc     300
cctctcactt tcggcggagg gaccaaggtg gagatcaaa                             339

<210> SEQ ID NO 183
<211> LENGTH: 121
<212> TYPE: PRT
<213> ORGANISM: Human

<400> SEQUENCE: 183

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Gly Ala Ile Gly Val Phe Ser Gly Tyr Phe Asp Tyr Trp Gly
            100                 105                 110

Gln Gly Thr Leu Val Thr Val Ser Ser
        115                 120

<210> SEQ ID NO 184
<211> LENGTH: 113
<212> TYPE: PRT
<213> ORGANISM: Human

<400> SEQUENCE: 184

Asp Ile Val Leu Thr Gln Thr Pro Asp Ser Leu Ala Val Ser Pro Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asp Thr Pro Leu Thr Phe Gly Gly Gly Thr Lys Val Glu Ile
            100                 105                 110

Lys

<210> SEQ ID NO 185
<211> LENGTH: 8
<212> TYPE: PRT
<213> ORGANISM: Human

<400> SEQUENCE: 185

Gly Gly Thr Phe Ser Ser Tyr Ala
1               5

<210> SEQ ID NO 186
<211> LENGTH: 8
<212> TYPE: PRT
<213> ORGANISM: Human

<400> SEQUENCE: 186

Ile Ile Pro Ile Phe Gly Thr Ala
1               5

<210> SEQ ID NO 187
<211> LENGTH: 14
<212> TYPE: PRT
<213> ORGANISM: Human

<400> SEQUENCE: 187

Ala Arg Gly Ala Ile Gly Val Phe Ser Gly Tyr Phe Asp Tyr
1               5                   10

<210> SEQ ID NO 188
<211> LENGTH: 11
<212> TYPE: PRT
<213> ORGANISM: Human

<400> SEQUENCE: 188

Gln Ser Val Leu Tyr Ser Ser Asn Asn Lys Asn
```

-continued

```
1               5               10

<210> SEQ ID NO 189
<211> LENGTH: 3
<212> TYPE: PRT
<213> ORGANISM: Human

<400> SEQUENCE: 189

Trp Ala Ser
1

<210> SEQ ID NO 190
<211> LENGTH: 9
<212> TYPE: PRT
<213> ORGANISM: Human

<400> SEQUENCE: 190

Gln Gln Tyr Tyr Asp Thr Pro Leu Thr
1               5

<210> SEQ ID NO 191
<211> LENGTH: 25
<212> TYPE: PRT
<213> ORGANISM: Human

<400> SEQUENCE: 191

Gln Val Gln Leu Val Gln Ser Gly Ala Glu Val Lys Lys Pro Gly Ser
1               5               10              15

Ser Val Lys Val Ser Cys Lys Ala Ser
            20              25

<210> SEQ ID NO 192
<211> LENGTH: 17
<212> TYPE: PRT
<213> ORGANISM: Human

<400> SEQUENCE: 192

Ile Ser Trp Val Arg Gln Ala Pro Gly Gln Gly Leu Glu Trp Met Gly
1               5               10              15

Gly

<210> SEQ ID NO 193
<211> LENGTH: 38
<212> TYPE: PRT
<213> ORGANISM: Human

<400> SEQUENCE: 193

Asn Tyr Ala Gln Lys Phe Gln Gly Arg Val Thr Ile Thr Ala Asp Glu
1               5               10              15

Ser Thr Ser Thr Ala Tyr Met Glu Leu Ser Ser Leu Arg Ser Glu Asp
            20              25              30

Thr Ala Val Tyr Tyr Cys
        35

<210> SEQ ID NO 194
<211> LENGTH: 11
<212> TYPE: PRT
<213> ORGANISM: Human

<400> SEQUENCE: 194

Trp Gly Gln Gly Thr Leu Val Thr Val Ser Ser
1               5               10
```

-continued

<210> SEQ ID NO 195
<211> LENGTH: 26
<212> TYPE: PRT
<213> ORGANISM: Human

<400> SEQUENCE: 195

Asp Ile Val Leu Thr Gln Thr Pro Asp Ser Leu Ala Val Ser Pro Gly
1               5                   10                  15

Glu Arg Ala Thr Ile Asn Cys Lys Ser Ser
            20                  25

<210> SEQ ID NO 196
<211> LENGTH: 17
<212> TYPE: PRT
<213> ORGANISM: Human

<400> SEQUENCE: 196

Leu Ala Trp Tyr Gln Gln Lys Pro Gly Gln Pro Pro Lys Leu Leu Ile
1               5                   10                  15

Tyr

<210> SEQ ID NO 197
<211> LENGTH: 36
<212> TYPE: PRT
<213> ORGANISM: Human

<400> SEQUENCE: 197

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 198
<211> LENGTH: 10
<212> TYPE: PRT
<213> ORGANISM: Human

<400> SEQUENCE: 198

Phe Gly Gly Gly Thr Lys Val Glu Ile Lys
1               5                   10

<210> SEQ ID NO 199
<211> LENGTH: 360
<212> TYPE: DNA
<213> ORGANISM: Human

<400> SEQUENCE: 199
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagggtat     300
tactatgata gcagtgccct ggactactgg ggccagggaa ccctggtcac cgtctcctca     360

<210> SEQ ID NO 200
<211> LENGTH: 330
<212> TYPE: DNA

<213> ORGANISM: Human

<400> SEQUENCE: 200
cagtctgctc tgattcagcc tgcctccgtg tctgggtctc ctggacagtc gatcaccatc          60
tcctgcactg gaaccagcag tgacgttggt ggttatggct atgtctcctg gtaccaacac         120
cacccaggca aagcccccaa actcatcatt tatgatgtct ccaatcggcc ctcagggtt          180 tctgatcgct tctctggctc caagtctgcc aacacggcct ccctgaccat ctctgggctc         240
cagactgagg acgaggctga ttattactgc agctcatata caagcagcgg cactgtgctc         300
ttcggcggag ggaccaagct caccgtccta                                          330

<210> SEQ ID NO 201
<211> LENGTH: 120
<212> TYPE: PRT
<213> ORGANISM: Human

<400> SEQUENCE: 201

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Tyr Asp Ser Ser Ala Leu Asp Tyr Trp Gly Gln
            100                 105                 110

Gly Thr Leu Val Thr Val Ser Ser
        115                 120

<210> SEQ ID NO 202
<211> LENGTH: 110
<212> TYPE: PRT
<213> ORGANISM: Human

<400> SEQUENCE: 202

Gln Ser Ala Leu Ile Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Gly Tyr Val Ser Trp Tyr Gln His Pro Gly Lys Ala Pro Lys Leu
        35                  40                  45

Ile Ile Tyr Asp Val Ser Asn Arg Pro Ser Gly Val Ser Asp Arg Phe
    50                  55                  60

Ser Gly Ser Lys Ser Ala Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Gly Thr Val Leu Phe Gly Gly Gly Thr Lys Leu Thr Val Leu
            100                 105                 110

<210> SEQ ID NO 203

-continued

```
<211> LENGTH: 8
<212> TYPE: PRT
<213> ORGANISM: Human

<400> SEQUENCE: 203

Gly Gly Thr Phe Ser Ser Tyr Ala
1               5

<210> SEQ ID NO 204
<211> LENGTH: 8
<212> TYPE: PRT
<213> ORGANISM: Human

<400> SEQUENCE: 204

Ile Ile Pro Ile Phe Gly Thr Ala
1               5

<210> SEQ ID NO 205
<211> LENGTH: 13
<212> TYPE: PRT
<213> ORGANISM: Human

<400> SEQUENCE: 205

Ala Arg Gly Tyr Tyr Tyr Asp Ser Ser Ala Leu Asp Tyr
1               5                   10

<210> SEQ ID NO 206
<211> LENGTH: 10
<212> TYPE: PRT
<213> ORGANISM: Human

<400> SEQUENCE: 206

Gly Thr Ser Ser Asp Val Gly Gly Tyr Gly
1               5                   10

<210> SEQ ID NO 207
<211> LENGTH: 3
<212> TYPE: PRT
<213> ORGANISM: Human

<400> SEQUENCE: 207

Asp Val Ser
1

<210> SEQ ID NO 208
<211> LENGTH: 10
<212> TYPE: PRT
<213> ORGANISM: Human

<400> SEQUENCE: 208

Ser Ser Tyr Thr Ser Ser Gly Thr Val Leu
1               5                   10

<210> SEQ ID NO 209
<211> LENGTH: 25
<212> TYPE: PRT
<213> ORGANISM: Human

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

-continued

```
<210> SEQ ID NO 210
<211> LENGTH: 17
<212> TYPE: PRT
<213> ORGANISM: Human

<400> SEQUENCE: 210

Ile Ser Trp Val Arg Gln Ala Pro Gly Gln Gly Leu Glu Trp Met Gly
1               5                   10                  15

Gly

<210> SEQ ID NO 211
<211> LENGTH: 38
<212> TYPE: PRT
<213> ORGANISM: Human

<400> SEQUENCE: 211

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 212
<211> LENGTH: 11
<212> TYPE: PRT
<213> ORGANISM: Human

<400> SEQUENCE: 212

Trp Gly Gln Gly Thr Leu Val Thr Val Ser Ser
1               5                   10

<210> SEQ ID NO 213
<211> LENGTH: 23
<212> TYPE: PRT
<213> ORGANISM: Human

<400> SEQUENCE: 213

Gln Ser Ala Leu Ile Gln Pro Ala Ser Val Ser Gly Ser Pro Gly Gln
1               5                   10                  15

Ser Ile Thr Ile Ser Cys Thr
            20

<210> SEQ ID NO 214
<211> LENGTH: 17
<212> TYPE: PRT
<213> ORGANISM: Human

<400> SEQUENCE: 214

Val Ser Trp Tyr Gln His His Pro Gly Lys Ala Pro Lys Leu Ile Ile
1               5                   10                  15

Tyr

<210> SEQ ID NO 215
<211> LENGTH: 36
<212> TYPE: PRT
<213> ORGANISM: Human

<400> SEQUENCE: 215

Asn Arg Pro Ser Gly Val Ser Asp Arg Phe Ser Gly Ser Lys Ser Ala
1               5                   10                  15

Asn Thr Ala Ser Leu Thr Ile Ser Gly Leu Gln Thr Glu Asp Glu Ala
```

-continued

```
              20              25              30

Asp Tyr Tyr Cys
        35

<210> SEQ ID NO 216
<211> LENGTH: 10
<212> TYPE: PRT
<213> ORGANISM: Human

<400> SEQUENCE: 216

Phe Gly Gly Gly Thr Lys Leu Thr Val Leu
1               5               10

<210> SEQ ID NO 217
<211> LENGTH: 381
<212> TYPE: DNA
<213> ORGANISM: Human

<400> SEQUENCE: 217
caggtgcagc tggtggaatc tgggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agccacgatt accgcggacg aatccacgag cacagcctac    240
atggagctga gcagcctgag atctgaggac acggccgtgt attactgtgc gagaggccga    300
aatacctatt gtagtggtgg tagctgctac tccccgcact ttgactactg gggccaggga    360
accctggtca ccgtctcctc a                                              381

<210> SEQ ID NO 218
<211> LENGTH: 318
<212> TYPE: DNA
<213> ORGANISM: Human

<400> SEQUENCE: 218
gacatccagg tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg aagtggatc tgggacagat tttactttca ccatcagcag cctgcagcct    240
gaagatattg caacatatta ctgtcaacag tatgataatc tcccaacttt cggcggaggg    300
accaaggtgg agatcaaa                                                  318

<210> SEQ ID NO 219
<211> LENGTH: 127
<212> TYPE: PRT
<213> ORGANISM: Human

<400> SEQUENCE: 219

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Ala Thr Ile Thr Ala Asp Glu Ser Thr Ser Thr Ala Tyr
```

-continued

```
65              70              75              80

Met Glu Leu Ser Ser Leu Arg Ser Glu Asp Thr Ala Val Tyr Tyr Cys
                85              90              95

Ala Arg Gly Arg Asn Thr Tyr Cys Ser Gly Gly Ser Cys Tyr Ser Pro
            100             105             110

His Phe Asp Tyr Trp Gly Gln Gly Thr Leu Val Thr Val Ser Ser
            115             120             125
```

<210> SEQ ID NO 220
<211> LENGTH: 106
<212> TYPE: PRT
<213> ORGANISM: Human

<400> SEQUENCE: 220

```
Asp Ile Gln Val Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
            20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
        50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Tyr Asp Asn Leu Pro Thr
                85              90              95

Phe Gly Gly Gly Thr Lys Val Glu Ile Lys
            100             105
```

<210> SEQ ID NO 221
<211> LENGTH: 8
<212> TYPE: PRT
<213> ORGANISM: Human

<400> SEQUENCE: 221

```
Gly Gly Thr Phe Ser Ser Tyr Ala
1               5
```

<210> SEQ ID NO 222
<211> LENGTH: 8
<212> TYPE: PRT
<213> ORGANISM: Human

<400> SEQUENCE: 222

```
Ile Ile Pro Ile Phe Gly Thr Ala
1               5
```

<210> SEQ ID NO 223
<211> LENGTH: 20
<212> TYPE: PRT
<213> ORGANISM: Human

<400> SEQUENCE: 223

```
Ala Arg Gly Arg Asn Thr Tyr Cys Ser Gly Gly Ser Cys Tyr Ser Pro
1               5               10              15

His Phe Asp Tyr
            20
```

<210> SEQ ID NO 224
<211> LENGTH: 6

```
<212> TYPE: PRT
<213> ORGANISM: Human

<400> SEQUENCE: 224

Gln Asp Ile Ser Asn Tyr
1               5

<210> SEQ ID NO 225
<211> LENGTH: 3
<212> TYPE: PRT
<213> ORGANISM: Human

<400> SEQUENCE: 225

Asp Ala Ser
1

<210> SEQ ID NO 226
<211> LENGTH: 8
<212> TYPE: PRT
<213> ORGANISM: Human

<400> SEQUENCE: 226

Gln Gln Tyr Asp Asn Leu Pro Thr
1               5

<210> SEQ ID NO 227
<211> LENGTH: 25
<212> TYPE: PRT
<213> ORGANISM: Human

<400> SEQUENCE: 227

Gln Val Gln Leu Val Glu Ser Gly Ala Glu Val Lys Lys Pro Gly Ser
1               5                   10                  15

Ser Val Lys Val Ser Cys Lys Ala Ser
            20                  25

<210> SEQ ID NO 228
<211> LENGTH: 17
<212> TYPE: PRT
<213> ORGANISM: Human

<400> SEQUENCE: 228

Ile Ser Trp Val Arg Gln Ala Pro Gly Gln Gly Leu Glu Trp Met Gly
1               5                   10                  15

Gly

<210> SEQ ID NO 229
<211> LENGTH: 38
<212> TYPE: PRT
<213> ORGANISM: Human

<400> SEQUENCE: 229

Asn Tyr Ala Gln Lys Phe Gln Gly Arg Ala Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
            35

<210> SEQ ID NO 230
<211> LENGTH: 11
<212> TYPE: PRT
<213> ORGANISM: Human
```

<400> SEQUENCE: 230

Trp Gly Gln Gly Thr Leu Val Thr Val Ser Ser
1               5                   10

<210> SEQ ID NO 231
<211> LENGTH: 26
<212> TYPE: PRT
<213> ORGANISM: Human

<400> SEQUENCE: 231

Asp Ile Gln Val Thr Gln Ser Pro Ser Ser Leu Ser Ala Ser Val Gly
1               5                   10                  15

Asp Arg Val Thr Ile Thr Cys Gln Ala Ser
            20                  25

<210> SEQ ID NO 232
<211> LENGTH: 17
<212> TYPE: PRT
<213> ORGANISM: Human

<400> SEQUENCE: 232

Leu Asn Trp Tyr Gln Gln Lys Pro Gly Lys Ala Pro Lys Leu Leu Ile
1               5                   10                  15

Tyr

<210> SEQ ID NO 233
<211> LENGTH: 36
<212> TYPE: PRT
<213> ORGANISM: Human

<400> SEQUENCE: 233

Asn Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
            20                  25                  30

Thr Tyr Tyr Cys
        35

<210> SEQ ID NO 234
<211> LENGTH: 10
<212> TYPE: PRT
<213> ORGANISM: Human

<400> SEQUENCE: 234

Phe Gly Gly Gly Thr Lys Val Glu Ile Lys
1               5                   10

<210> SEQ ID NO 235
<211> LENGTH: 375
<212> TYPE: DNA
<213> ORGANISM: Human

<400> SEQUENCE: 235
caggtgcagc tggtggaatc tgggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggagtg     300

```
ccgtccgggt atagcagtgg ctggtttttac tactttgact actggggcca gggaaccctg          360
gtcaccgtct cctca                                                            375
```

<210> SEQ ID NO 236
<211> LENGTH: 321
<212> TYPE: DNA
<213> ORGANISM: Human

<400> SEQUENCE: 236

```
gaaattgtga tgacacagtc tccatcctcc ctgtctgcat ctgtaggaga cagagccacc           60
ctctcctgca gggccagtca gagtgttaac accaacttag cctggtacca gcagaaacct          120
ggccaggctc ccaggctcct catctatggt gcatctacca gggccactgg tagcccagcc          180
aggttcagtg gcagtgggtc tgggacagag ttcactctca ccatcagcag cctgcagcct          240
ggtgattttg caacttatta ctgccaacag tatgataatt atcccctgac gttcggccaa          300
gggaccaagg tggaaatcaa a                                                    321
```

<210> SEQ ID NO 237
<211> LENGTH: 125
<212> TYPE: PRT
<213> ORGANISM: Human

<400> SEQUENCE: 237

```
Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Pro Ser Gly Tyr Ser Ser Gly Trp Phe Tyr Tyr Phe
            100                 105                 110

Asp Tyr Trp Gly Gln Gly Thr Leu Val Thr Val Ser Ser
        115                 120                 125
```

<210> SEQ ID NO 238
<211> LENGTH: 107
<212> TYPE: PRT
<213> ORGANISM: Human

<400> SEQUENCE: 238

```
Glu Ile Val Met Thr Gln Ser Pro Ser Ser Leu Ser Ala Ser Val Gly
1               5                   10                  15

Asp Arg Ala Thr Leu Ser Cys Arg Ala Ser Gln Ser Val Asn Thr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ser Pro Ala Arg Phe Ser Gly
    50                  55                  60

Ser Gly Ser Gly Thr Glu Phe Thr Leu Thr Ile Ser Ser Leu Gln Pro
65                  70                  75                  80
```

-continued

```
Gly Asp Phe Ala Thr Tyr Tyr Cys Gln Gln Tyr Asp Asn Tyr Pro Leu
                85                  90                  95

Thr Phe Gly Gln Gly Thr Lys Val Glu Ile Lys
            100                 105

<210> SEQ ID NO 239
<211> LENGTH: 8
<212> TYPE: PRT
<213> ORGANISM: Human

<400> SEQUENCE: 239

Gly Gly Thr Phe Ser Ser Tyr Ala
1               5

<210> SEQ ID NO 240
<211> LENGTH: 8
<212> TYPE: PRT
<213> ORGANISM: Human

<400> SEQUENCE: 240

Ile Ile Pro Ile Phe Gly Thr Ala
1               5

<210> SEQ ID NO 241
<211> LENGTH: 18
<212> TYPE: PRT
<213> ORGANISM: Human

<400> SEQUENCE: 241

Ala Arg Gly Val Pro Ser Gly Tyr Ser Ser Gly Trp Phe Tyr Tyr Phe
1               5                   10                  15

Asp Tyr

<210> SEQ ID NO 242
<211> LENGTH: 6
<212> TYPE: PRT
<213> ORGANISM: Human

<400> SEQUENCE: 242

Gln Ser Val Asn Thr Asn
1               5

<210> SEQ ID NO 243
<211> LENGTH: 3
<212> TYPE: PRT
<213> ORGANISM: Human

<400> SEQUENCE: 243

Gly Ala Ser
1

<210> SEQ ID NO 244
<211> LENGTH: 9
<212> TYPE: PRT
<213> ORGANISM: Human

<400> SEQUENCE: 244

Gln Gln Tyr Asp Asn Tyr Pro Leu Thr
1               5

<210> SEQ ID NO 245
<211> LENGTH: 25
<212> TYPE: PRT
<213> ORGANISM: Human
```

<400> SEQUENCE: 245

Gln Val Gln Leu Val Glu Ser Gly Ala Glu Val Lys Lys Pro Gly Ser
1                   5                   10                  15

Ser Val Lys Val Ser Cys Lys Ala Ser
            20                  25

<210> SEQ ID NO 246
<211> LENGTH: 17
<212> TYPE: PRT
<213> ORGANISM: Human

<400> SEQUENCE: 246

Ile Ser Trp Val Arg Gln Ala Pro Gly Gln Gly Leu Glu Trp Met Gly
1                   5                   10                  15

Gly

<210> SEQ ID NO 247
<211> LENGTH: 38
<212> TYPE: PRT
<213> ORGANISM: Human

<400> SEQUENCE: 247

Asn Tyr Ala Gln Lys Phe Gln Gly Arg Val Thr Ile Thr Ala Asp Glu
1                   5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 248
<211> LENGTH: 11
<212> TYPE: PRT
<213> ORGANISM: Human

<400> SEQUENCE: 248

Trp Gly Gln Gly Thr Leu Val Thr Val Ser Ser
1                   5                   10

<210> SEQ ID NO 249
<211> LENGTH: 26
<212> TYPE: PRT
<213> ORGANISM: Human

<400> SEQUENCE: 249

Glu Ile Val Met Thr Gln Ser Pro Ser Ser Leu Ser Ala Ser Val Gly
1                   5                   10                  15

Asp Arg Ala Thr Leu Ser Cys Arg Ala Ser
            20                  25

<210> SEQ ID NO 250
<211> LENGTH: 17
<212> TYPE: PRT
<213> ORGANISM: Human

<400> SEQUENCE: 250

Leu Ala Trp Tyr Gln Gln Lys Pro Gly Gln Ala Pro Arg Leu Leu Ile
1                   5                   10                  15

Tyr

<210> SEQ ID NO 251

```
<211> LENGTH: 36
<212> TYPE: PRT
<213> ORGANISM: Human

<400> SEQUENCE: 251

Thr Arg Ala Thr Gly Ser Pro Ala Arg Phe Ser Gly Ser Gly Ser Gly
1               5                   10                  15

Thr Glu Phe Thr Leu Thr Ile Ser Ser Leu Gln Pro Gly Asp Phe Ala
            20                  25                  30

Thr Tyr Tyr Cys
        35

<210> SEQ ID NO 252
<211> LENGTH: 10
<212> TYPE: PRT
<213> ORGANISM: Human

<400> SEQUENCE: 252

Phe Gly Gln Gly Thr Lys Val Glu Ile Lys
1               5                   10

<210> SEQ ID NO 253
<211> LENGTH: 369
<212> TYPE: DNA
<213> ORGANISM: Human

<400> SEQUENCE: 253
caggtccagc tggtacagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agtaaactac     180
gcacagaagt tccagggcag agtcacgatt accgcggacg aatccacgag cacagcctac     240
atggagctga gcagcctgag atctgaggac acggccgtgt attactgtgc gagagtcgcg     300
gttattcccc cggactacta ctacggtatg gacgtctggg gccaagggac cacggtcacc     360
gtctcctca                                                             369

<210> SEQ ID NO 254
<211> LENGTH: 327
<212> TYPE: DNA
<213> ORGANISM: Human

<400> SEQUENCE: 254
gaaacgacac tcacgcagtc tccagccacc ctgtctgtgt ctccagggga aagagccacc      60
ctctcctgca gggccagtca gagtgttagc agcaacttag cctggtacca gcagagacct     120
ggccaggctc ccaggctcct catctatggt gcatccacca gggccgctgg tatcccagtc     180
aggttcagtg gcagtgggtc tgggacagag ttcactctca ccatcagcag cctgcagtct     240
gaagattttg cagtttatta ctgtcagcac tatgataact ggcctccgcg attcactttc     300
ggccctggga ccaaagtgga tattaaa                                         327

<210> SEQ ID NO 255
<211> LENGTH: 123
<212> TYPE: PRT
<213> ORGANISM: Human

<400> SEQUENCE: 255

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
        20              25                  30

Ala Ile Ser Trp Val Arg Gln Ala Pro Gly Gln Gly Leu Glu Trp Met
        35              40                  45

Gly Gly Ile Ile Pro Ile Phe Gly Thr Val Asn Tyr Ala Gln Lys Phe
    50              55              60

Gln Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
                85              90                  95

Ala Arg Val Ala Val Ile Pro Pro Asp Tyr Tyr Tyr Gly Met Asp Val
            100             105             110

Trp Gly Gln Gly Thr Thr Val Thr Val Ser Ser
        115             120
```

```
<210> SEQ ID NO 256
<211> LENGTH: 109
<212> TYPE: PRT
<213> ORGANISM: Human

<400> SEQUENCE: 256

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
        20              25                  30

Leu Ala Trp Tyr Gln Gln Arg Pro Gly Gln Ala Pro Arg Leu Leu Ile
        35              40                  45

Tyr Gly Ala Ser Thr Arg Ala Ala Gly Ile Pro Val Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln His Tyr Asp Asn Trp Pro Pro
                85              90                  95

Arg Phe Thr Phe Gly Pro Gly Thr Lys Val Asp Ile Lys
            100             105
```

```
<210> SEQ ID NO 257
<211> LENGTH: 8
<212> TYPE: PRT
<213> ORGANISM: Human

<400> SEQUENCE: 257

Gly Gly Thr Phe Ser Ser Tyr Ala
1               5
```

```
<210> SEQ ID NO 258
<211> LENGTH: 8
<212> TYPE: PRT
<213> ORGANISM: Human

<400> SEQUENCE: 258

Ile Ile Pro Ile Phe Gly Thr Val
1               5
```

```
<210> SEQ ID NO 259
<211> LENGTH: 16
<212> TYPE: PRT
<213> ORGANISM: Human

<400> SEQUENCE: 259
```

```
Ala Arg Val Ala Val Ile Pro Pro Asp Tyr Tyr Tyr Gly Met Asp Val
1               5                   10                  15

<210> SEQ ID NO 260
<211> LENGTH: 6
<212> TYPE: PRT
<213> ORGANISM: Human

<400> SEQUENCE: 260

Gln Ser Val Ser Ser Asn
1               5

<210> SEQ ID NO 261
<211> LENGTH: 3
<212> TYPE: PRT
<213> ORGANISM: Human

<400> SEQUENCE: 261

Gly Ala Ser
1

<210> SEQ ID NO 262
<211> LENGTH: 11
<212> TYPE: PRT
<213> ORGANISM: Human

<400> SEQUENCE: 262

Gln His Tyr Asp Asn Trp Pro Pro Arg Phe Thr
1               5                   10

<210> SEQ ID NO 263
<211> LENGTH: 25
<212> TYPE: PRT
<213> ORGANISM: Human

<400> SEQUENCE: 263

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 264
<211> LENGTH: 17
<212> TYPE: PRT
<213> ORGANISM: Human

<400> SEQUENCE: 264

Ile Ser Trp Val Arg Gln Ala Pro Gly Gln Gly Leu Glu Trp Met Gly
1               5                   10                  15

Gly

<210> SEQ ID NO 265
<211> LENGTH: 38
<212> TYPE: PRT
<213> ORGANISM: Human

<400> SEQUENCE: 265

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
```

-continued

35

<210> SEQ ID NO 266
<211> LENGTH: 11
<212> TYPE: PRT
<213> ORGANISM: Human

<400> SEQUENCE: 266

Trp Gly Gln Gly Thr Thr Val Thr Val Ser Ser
1               5                   10

<210> SEQ ID NO 267
<211> LENGTH: 26
<212> TYPE: PRT
<213> ORGANISM: Human

<400> SEQUENCE: 267

Glu Thr Thr Leu Thr Gln Ser Pro Ala Thr Leu Ser Val Ser Pro Gly
1               5                   10                  15

Glu Arg Ala Thr Leu Ser Cys Arg Ala Ser
            20                  25

<210> SEQ ID NO 268
<211> LENGTH: 17
<212> TYPE: PRT
<213> ORGANISM: Human

<400> SEQUENCE: 268

Leu Ala Trp Tyr Gln Gln Arg Pro Gly Gln Ala Pro Arg Leu Leu Ile
1               5                   10                  15

Tyr

<210> SEQ ID NO 269
<211> LENGTH: 36
<212> TYPE: PRT
<213> ORGANISM: Human

<400> SEQUENCE: 269

Thr Arg Ala Ala Gly Ile Pro Val Arg Phe Ser Gly Ser Gly Ser Gly
1               5                   10                  15

Thr Glu Phe Thr Leu Thr Ile Ser Ser Leu Gln Ser Glu Asp Phe Ala
            20                  25                  30

Val Tyr Tyr Cys
        35

<210> SEQ ID NO 270
<211> LENGTH: 10
<212> TYPE: PRT
<213> ORGANISM: Human

<400> SEQUENCE: 270

Phe Gly Pro Gly Thr Lys Val Asp Ile Lys
1               5                   10

<210> SEQ ID NO 271
<211> LENGTH: 372
<212> TYPE: DNA
<213> ORGANISM: Human

<400> SEQUENCE: 271
caggtccagc tggtgcagtc tggggctgag gtgaagaagc ctgggtcctc ggtgaaggtc      60
tcatgcaagg cttctggagg caccttcagc agctatgcta tcagctgggt gcgacaggcc     120

-continued

```
cctggacaag ggcttgagtg gatgggaggg atcatccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagggggagcc     300 ggcccgttat ggttcaggga gttagtgtac ttccagcact ggggccaggg aaccctggtc      360
accgtctcct ca                                                          372

<210> SEQ ID NO 272
<211> LENGTH: 318
<212> TYPE: DNA
<213> ORGANISM: Human

<400> SEQUENCE: 272
gaaattgtga tgacgcagtc tccagccact ctgtctgtgt ctccagggga gagggccacc       60
ctctcctgca gggtcagtca gaatataata aaaaacttag cctggtacca acagaaacct      120
ggccaggctc ccaggctcct catttatgat gcctccacca gggccactgg tatcccagcc      180
aggttcactg gcagtgggtc tgggacagag ttcactctca ccatcgacga cctgcagtct      240
gaagattctg cagtttattt ctgtcagcag tacaattggt ggcctcgttt cggccctggg      300
accaaagtgg atatcaaa                                                    318

<210> SEQ ID NO 273
<211> LENGTH: 124
<212> TYPE: PRT
<213> ORGANISM: Human

<400> SEQUENCE: 273

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Pro Leu Trp Phe Arg Glu Leu Val Tyr Phe Gln
            100                 105                 110

His Trp Gly Gln Gly Thr Leu Val Thr Val Ser Ser
        115                 120

<210> SEQ ID NO 274
<211> LENGTH: 106
<212> TYPE: PRT
<213> ORGANISM: Human

<400> SEQUENCE: 274

Glu Ile Val Met Thr Gln Ser Pro Ala Thr Leu Ser Val Ser Pro Gly
1               5                   10                  15

Glu Arg Ala Thr Leu Ser Cys Arg Val Ser Gln Asn Ile Ile Lys Asn
            20                  25                  30

Leu Ala Trp Tyr Gln Gln Lys Pro Gly Gln Ala Pro Arg Leu Leu Ile
        35                  40                  45
```

-continued

```
Tyr Asp Ala Ser Thr Arg Ala Thr Gly Ile Pro Ala Arg Phe Thr Gly
    50                  55                  60

Ser Gly Ser Gly Thr Glu Phe Thr Leu Thr Ile Asp Asp Leu Gln Ser
65                  70                  75                  80

Glu Asp Ser Ala Val Tyr Phe Cys Gln Gln Tyr Asn Trp Trp Pro Arg
                85                  90                  95

Phe Gly Pro Gly Thr Lys Val Asp Ile Lys
            100                 105
```

```
<210> SEQ ID NO 275
<211> LENGTH: 8
<212> TYPE: PRT
<213> ORGANISM: Human

<400> SEQUENCE: 275

Gly Gly Thr Phe Ser Ser Tyr Ala
1               5
```

```
<210> SEQ ID NO 276
<211> LENGTH: 8
<212> TYPE: PRT
<213> ORGANISM: Human

<400> SEQUENCE: 276

Ile Ile Pro Ile Phe Gly Thr Ala
1               5
```

```
<210> SEQ ID NO 277
<211> LENGTH: 17
<212> TYPE: PRT
<213> ORGANISM: Human

<400> SEQUENCE: 277

Ala Arg Gly Ala Gly Pro Leu Trp Phe Arg Glu Leu Val Tyr Phe Gln
1               5                   10                  15

His
```

```
<210> SEQ ID NO 278
<211> LENGTH: 6
<212> TYPE: PRT
<213> ORGANISM: Human

<400> SEQUENCE: 278

Gln Asn Ile Ile Lys Asn
1               5
```

```
<210> SEQ ID NO 279
<211> LENGTH: 3
<212> TYPE: PRT
<213> ORGANISM: Human

<400> SEQUENCE: 279

Asp Ala Ser
1
```

```
<210> SEQ ID NO 280
<211> LENGTH: 8
<212> TYPE: PRT
<213> ORGANISM: Human

<400> SEQUENCE: 280

Gln Gln Tyr Asn Trp Trp Pro Arg
```

-continued

```
1               5
```

<210> SEQ ID NO 281
<211> LENGTH: 25
<212> TYPE: PRT
<213> ORGANISM: Human

<400> SEQUENCE: 281

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 282
<211> LENGTH: 17
<212> TYPE: PRT
<213> ORGANISM: Human

<400> SEQUENCE: 282

```
Ile Ser Trp Val Arg Gln Ala Pro Gly Gln Gly Leu Glu Trp Met Gly
1               5                   10                  15

Gly
```

<210> SEQ ID NO 283
<211> LENGTH: 38
<212> TYPE: PRT
<213> ORGANISM: Human

<400> SEQUENCE: 283

```
Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
            35
```

<210> SEQ ID NO 284
<211> LENGTH: 11
<212> TYPE: PRT
<213> ORGANISM: Human

<400> SEQUENCE: 284

```
Trp Gly Gln Gly Thr Leu Val Thr Val Ser Ser
1               5                   10
```

<210> SEQ ID NO 285
<211> LENGTH: 26
<212> TYPE: PRT
<213> ORGANISM: Human

<400> SEQUENCE: 285

```
Glu Ile Val Met Thr Gln Ser Pro Ala Thr Leu Ser Val Ser Pro Gly
1               5                   10                  15

Glu Arg Ala Thr Leu Ser Cys Arg Val Ser
            20                  25
```

<210> SEQ ID NO 286
<211> LENGTH: 17
<212> TYPE: PRT
<213> ORGANISM: Human

<400> SEQUENCE: 286

Leu Ala Trp Tyr Gln Gln Lys Pro Gly Gln Ala Pro Arg Leu Leu Ile
1               5                   10                  15

Tyr

<210> SEQ ID NO 287
<211> LENGTH: 36
<212> TYPE: PRT
<213> ORGANISM: Human

<400> SEQUENCE: 287

Thr Arg Ala Thr Gly Ile Pro Ala Arg Phe Thr Gly Ser Gly Ser Gly
1               5                   10                  15

Thr Glu Phe Thr Leu Thr Ile Asp Asp Leu Gln Ser Glu Asp Ser Ala
            20                  25                  30

Val Tyr Phe Cys
        35

<210> SEQ ID NO 288
<211> LENGTH: 10
<212> TYPE: PRT
<213> ORGANISM: Human

<400> SEQUENCE: 288

Phe Gly Pro Gly Thr Lys Val Asp Ile Lys
1               5                   10

<210> SEQ ID NO 289
<211> LENGTH: 369
<212> TYPE: DNA
<213> ORGANISM: Human

<400> SEQUENCE: 289
caggtgcagc tggtgcaatc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggccag     300
gttttgatct ggacgtacta ctacggtatg gacgtctggg gccaagggac cacggtcacc     360
gtctcctca                                                             369

<210> SEQ ID NO 290
<211> LENGTH: 321
<212> TYPE: DNA
<213> ORGANISM: Human

<400> SEQUENCE: 290
gacatccggt tgacccagtc tccatcctcc ctgtctgcat ctgtaggaga tagagtcacc      60
atcacttgcc aggcgagtca ggacattagc aactatttaa attggtatca gcagaaacca     120
gggaaagccc ctaagctcct gatctacgat gcatccaatt tagaaacagg ggtcccatca     180
aggttcagtg gaagtggatc tgggacagat tttactttca tcatcagcag cctgcagcct     240
gaagatattg caacatatta ctgtcaacag tatgataatc tcccgctcac tttcggtgga     300
gggaccaagc tggagatcaa a                                              321

<210> SEQ ID NO 291
<211> LENGTH: 123
<212> TYPE: PRT

<213> ORGANISM: Human

<400> SEQUENCE: 291

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Val Leu Ile Trp Thr Tyr Tyr Tyr Gly Met Asp Val
            100                 105                 110

Trp Gly Gln Gly Thr Thr Val Thr Val Ser Ser
        115                 120

<210> SEQ ID NO 292
<211> LENGTH: 107
<212> TYPE: PRT
<213> ORGANISM: Human

<400> SEQUENCE: 292

Asp Ile Arg Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Ile Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Leu Glu Ile Lys
            100                 105

<210> SEQ ID NO 293
<211> LENGTH: 8
<212> TYPE: PRT
<213> ORGANISM: Human

<400> SEQUENCE: 293

Gly Gly Thr Phe Ser Ser Tyr Ala
1               5

<210> SEQ ID NO 294
<211> LENGTH: 8
<212> TYPE: PRT
<213> ORGANISM: Human

<400> SEQUENCE: 294

Ile Ile Pro Ile Phe Gly Thr Ala
1               5

-continued

```
<210> SEQ ID NO 295
<211> LENGTH: 16
<212> TYPE: PRT
<213> ORGANISM: Human

<400> SEQUENCE: 295

Ala Arg Gly Gln Val Leu Ile Trp Thr Tyr Tyr Gly Met Asp Val
1               5                   10                  15

<210> SEQ ID NO 296
<211> LENGTH: 6
<212> TYPE: PRT
<213> ORGANISM: Human

<400> SEQUENCE: 296

Gln Asp Ile Ser Asn Tyr
1               5

<210> SEQ ID NO 297
<211> LENGTH: 3
<212> TYPE: PRT
<213> ORGANISM: Human

<400> SEQUENCE: 297

Asp Ala Ser
1

<210> SEQ ID NO 298
<211> LENGTH: 9
<212> TYPE: PRT
<213> ORGANISM: Human

<400> SEQUENCE: 298

Gln Gln Tyr Asp Asn Leu Pro Leu Thr
1               5

<210> SEQ ID NO 299
<211> LENGTH: 25
<212> TYPE: PRT
<213> ORGANISM: Human

<400> SEQUENCE: 299

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 300
<211> LENGTH: 17
<212> TYPE: PRT
<213> ORGANISM: Human

<400> SEQUENCE: 300

Ile Ser Trp Val Arg Gln Ala Pro Gly Gln Gly Leu Glu Trp Met Gly
1               5                   10                  15

Gly

<210> SEQ ID NO 301
<211> LENGTH: 38
<212> TYPE: PRT
<213> ORGANISM: Human

<400> SEQUENCE: 301
```

```
Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
                20                  25                  30

Thr Ala Val Tyr Tyr Cys
        35

<210> SEQ ID NO 302
<211> LENGTH: 11
<212> TYPE: PRT
<213> ORGANISM: Human

<400> SEQUENCE: 302

Trp Gly Gln Gly Thr Thr Val Thr Val Ser Ser
1               5                   10

<210> SEQ ID NO 303
<211> LENGTH: 26
<212> TYPE: PRT
<213> ORGANISM: Human

<400> SEQUENCE: 303

Asp Ile Arg Leu Thr Gln Ser Pro Ser Ser Leu Ser Ala Ser Val Gly
1               5                   10                  15

Asp Arg Val Thr Ile Thr Cys Gln Ala Ser
            20                  25

<210> SEQ ID NO 304
<211> LENGTH: 17
<212> TYPE: PRT
<213> ORGANISM: Human

<400> SEQUENCE: 304

Leu Asn Trp Tyr Gln Gln Lys Pro Gly Lys Ala Pro Lys Leu Leu Ile
1               5                   10                  15

Tyr

<210> SEQ ID NO 305
<211> LENGTH: 36
<212> TYPE: PRT
<213> ORGANISM: Human

<400> SEQUENCE: 305

Asn Leu Glu Thr Gly Val Pro Ser Arg Phe Ser Gly Ser Gly Ser Gly
1               5                   10                  15

Thr Asp Phe Thr Phe Ile Ile Ser Ser Leu Gln Pro Glu Asp Ile Ala
                20                  25                  30

Thr Tyr Tyr Cys
        35

<210> SEQ ID NO 306
<211> LENGTH: 10
<212> TYPE: PRT
<213> ORGANISM: Human

<400> SEQUENCE: 306

Phe Gly Gly Gly Thr Lys Leu Glu Ile Lys
1               5                   10

<210> SEQ ID NO 307
<211> LENGTH: 360
<212> TYPE: DNA
```

<213> ORGANISM: Human

<400> SEQUENCE: 307

```
caggtccagc ttgtgcagtc tgggggctgag gtgaagaagc ctgggtcctc ggtgaaggtc          60
tcctgcaagg cttctggagg cacctctacg ggttttattg gtgctatcag ctgggtgcga         120
caggcccctg gacaagggct tgagtggatg ggagggatca tccctatctt tggtacagca         180
aactacgcac agaagttcca gggcagagtc acgattaccg cggacgaatc cacgagcaca         240
gcctacatgg agctgagcag cctgagatct gaggacacgg ccgtgtatta ctgtgcgaga         300
gacgtacaga ggatgggggat ggacgtctgg ggccaaggga ccacggtcac cgtctcctca         360
```

<210> SEQ ID NO 308
<211> LENGTH: 321
<212> TYPE: DNA
<213> ORGANISM: Human

<400> SEQUENCE: 308

```
gacatccaga tgacccagtc tccttcttcc gtctctacat ctgtaggaga cagagtcacc          60
atcacttgtc gggcgagtca ggatattagt aactggttag cctggtatca gcagaaacca         120
ggaaaagccc ctaagctcct gatctatgat tcatccactt tgcaaagtgg ggtcccatca         180
aggttcagcg gcagtggatc tgggacagat ttcactctca ccatcagcac cctgcagcct         240
gaggattttg caacttatta ctgtcaacag tttaatagtt atcccctcac tttcggcgga         300
gggaccaaag tggatatcaa a                                                    321
```

<210> SEQ ID NO 309
<211> LENGTH: 120
<212> TYPE: PRT
<213> ORGANISM: Human

<400> SEQUENCE: 309

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Thr Gly Phe
            20                  25                  30

Ile Gly Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Val Gln Arg Met Gly Met Asp Val Trp Gly Gln
            100                 105                 110

Gly Thr Thr Val Thr Val Ser Ser
        115                 120
```

<210> SEQ ID NO 310
<211> LENGTH: 107
<212> TYPE: PRT
<213> ORGANISM: Human

<400> SEQUENCE: 310

```
Asp Ile Gln Met Thr Gln Ser Pro Ser Ser Val Ser Thr Ser Val Gly
1               5                   10                  15
```

-continued

Asp Arg Val Thr Ile Thr Cys Arg Ala Ser Gln Asp Ile Ser Asn Trp
                20                      25                      30

Leu Ala Trp Tyr Gln Gln Lys Pro Gly Lys Ala Pro Lys Leu Leu Ile
            35                      40                      45

Tyr Asp Ser Ser Thr Leu Gln Ser Gly Val Pro Ser Arg Phe Ser Gly
        50                      55                      60

Ser Gly Ser Gly Thr Asp Phe Thr Leu Thr Ile Ser Thr Leu Gln Pro
65                      70                      75                      80

Glu Asp Phe Ala Thr Tyr Tyr Cys Gln Gln Phe Asn Ser Tyr Pro Leu
                85                      90                      95

Thr Phe Gly Gly Gly Thr Lys Val Asp Ile Lys
                100                     105

<210> SEQ ID NO 311
<211> LENGTH: 10
<212> TYPE: PRT
<213> ORGANISM: Human

<400> SEQUENCE: 311

Gly Gly Thr Ser Thr Gly Phe Ile Gly Ala
1               5                       10

<210> SEQ ID NO 312
<211> LENGTH: 8
<212> TYPE: PRT
<213> ORGANISM: Human

<400> SEQUENCE: 312

Ile Ile Pro Ile Phe Gly Thr Ala
1               5

<210> SEQ ID NO 313
<211> LENGTH: 11
<212> TYPE: PRT
<213> ORGANISM: Human

<400> SEQUENCE: 313

Ala Arg Asp Val Gln Arg Met Gly Met Asp Val
1               5                       10

<210> SEQ ID NO 314
<211> LENGTH: 6
<212> TYPE: PRT
<213> ORGANISM: Human

<400> SEQUENCE: 314

Gln Asp Ile Ser Asn Trp
1               5

<210> SEQ ID NO 315
<211> LENGTH: 3
<212> TYPE: PRT
<213> ORGANISM: Human

<400> SEQUENCE: 315

Asp Ser Ser
1

<210> SEQ ID NO 316
<211> LENGTH: 9
<212> TYPE: PRT
<213> ORGANISM: Human

<400> SEQUENCE: 316

Gln Gln Phe Asn Ser Tyr Pro Leu Thr
1               5

<210> SEQ ID NO 317
<211> LENGTH: 25
<212> TYPE: PRT
<213> ORGANISM: Human

<400> SEQUENCE: 317

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 318
<211> LENGTH: 17
<212> TYPE: PRT
<213> ORGANISM: Human

<400> SEQUENCE: 318

Ile Ser Trp Val Arg Gln Ala Pro Gly Gln Gly Leu Glu Trp Met Gly
1               5                   10                  15

Gly

<210> SEQ ID NO 319
<211> LENGTH: 38
<212> TYPE: PRT
<213> ORGANISM: Human

<400> SEQUENCE: 319

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 320
<211> LENGTH: 11
<212> TYPE: PRT
<213> ORGANISM: Human

<400> SEQUENCE: 320

Trp Gly Gln Gly Thr Thr Val Thr Val Ser Ser
1               5                   10

<210> SEQ ID NO 321
<211> LENGTH: 26
<212> TYPE: PRT
<213> ORGANISM: Human

<400> SEQUENCE: 321

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25

<210> SEQ ID NO 322
<211> LENGTH: 17
<212> TYPE: PRT
<213> ORGANISM: Human

-continued

```
<400> SEQUENCE: 322

Leu Ala Trp Tyr Gln Gln Lys Pro Gly Lys Ala Pro Lys Leu Leu Ile
1               5                   10                  15

Tyr

<210> SEQ ID NO 323
<211> LENGTH: 36
<212> TYPE: PRT
<213> ORGANISM: Human

<400> SEQUENCE: 323

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
        35

<210> SEQ ID NO 324
<211> LENGTH: 10
<212> TYPE: PRT
<213> ORGANISM: Human

<400> SEQUENCE: 324

Phe Gly Gly Gly Thr Lys Val Asp Ile Lys
1               5                   10

<210> SEQ ID NO 325
<211> LENGTH: 360
<212> TYPE: DNA
<213> ORGANISM: Human

<400> SEQUENCE: 325
caggtccagc ttgtgcagtc tgggggtgag gtgaagaagc ctgggtcctc ggtgaaggtc      60
tcctgcaagg cttctggagg cacctttcag tcttattatg gggctatcag ctgggtgcga     120
caggcccctg gacaagggct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcgaga     300
gacgtacaga ggatggggat ggacgtctgg ggccaaggga ccacggtcac cgtctcctca     360

<210> SEQ ID NO 326
<211> LENGTH: 321
<212> TYPE: DNA
<213> ORGANISM: Human

<400> SEQUENCE: 326
gacatccaga tgacccagtc tccttcttcc gtctctacat ctgtaggaga cagagtcacc      60
atcacttgtc gggcgagtca ggatattagt aactggttag cctggtatca gcagaaacca     120
ggaaaagccc ctaagctcct gatctatgat tcatccactt tgcaaagtgg ggtcccatca     180
aggttcagcg gcagtggatc tgggacagat ttcactctca ccatcagcac cctgcagcct     240
gaggattttg caacttatta ctgtcaacag tttaatagtt atcccctcac tttcggcgga     300
gggaccaaag tggatatcaa a                                               321

<210> SEQ ID NO 327
<211> LENGTH: 120
```

<212> TYPE: PRT
<213> ORGANISM: Human

<400> SEQUENCE: 327

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gln Ser Tyr
            20                  25                  30

Tyr Gly Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Val Gln Arg Met Gly Met Asp Val Trp Gly Gln
            100                 105                 110

Gly Thr Thr Val Thr Val Ser Ser
        115                 120

<210> SEQ ID NO 328
<211> LENGTH: 107
<212> TYPE: PRT
<213> ORGANISM: Human

<400> SEQUENCE: 328

Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 329
<211> LENGTH: 10
<212> TYPE: PRT
<213> ORGANISM: Human

<400> SEQUENCE: 329

Gly Gly Thr Phe Gln Ser Tyr Tyr Gly Ala
1               5                   10

<210> SEQ ID NO 330
<211> LENGTH: 8
<212> TYPE: PRT
<213> ORGANISM: Human

<400> SEQUENCE: 330

Ile Ile Pro Ile Phe Gly Thr Ala
1               5

```
<210> SEQ ID NO 331
<211> LENGTH: 11
<212> TYPE: PRT
<213> ORGANISM: Human

<400> SEQUENCE: 331

Ala Arg Asp Val Gln Arg Met Gly Met Asp Val
1               5               10

<210> SEQ ID NO 332
<211> LENGTH: 6
<212> TYPE: PRT
<213> ORGANISM: Human

<400> SEQUENCE: 332

Gln Asp Ile Ser Asn Trp
1               5

<210> SEQ ID NO 333
<211> LENGTH: 3
<212> TYPE: PRT
<213> ORGANISM: Human

<400> SEQUENCE: 333

Asp Ser Ser
1

<210> SEQ ID NO 334
<211> LENGTH: 9
<212> TYPE: PRT
<213> ORGANISM: Human

<400> SEQUENCE: 334

Gln Gln Phe Asn Ser Tyr Pro Leu Thr
1               5

<210> SEQ ID NO 335
<211> LENGTH: 25
<212> TYPE: PRT
<213> ORGANISM: Human

<400> SEQUENCE: 335

Gln Val Gln Leu Val Gln Ser Gly Ala Glu Val Lys Lys Pro Gly Ser
1               5               10              15

Ser Val Lys Val Ser Cys Lys Ala Ser
            20              25

<210> SEQ ID NO 336
<211> LENGTH: 17
<212> TYPE: PRT
<213> ORGANISM: Human

<400> SEQUENCE: 336

Ile Ser Trp Val Arg Gln Ala Pro Gly Gln Gly Leu Glu Trp Met Gly
1               5               10              15

Gly

<210> SEQ ID NO 337
<211> LENGTH: 38
<212> TYPE: PRT
<213> ORGANISM: Human

<400> SEQUENCE: 337
```

-continued

```
Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 338
<211> LENGTH: 11
<212> TYPE: PRT
<213> ORGANISM: Human

<400> SEQUENCE: 338

Trp Gly Gln Gly Thr Thr Val Thr Val Ser Ser
1               5                   10

<210> SEQ ID NO 339
<211> LENGTH: 26
<212> TYPE: PRT
<213> ORGANISM: Human

<400> SEQUENCE: 339

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25

<210> SEQ ID NO 340
<211> LENGTH: 17
<212> TYPE: PRT
<213> ORGANISM: Human

<400> SEQUENCE: 340

Leu Ala Trp Tyr Gln Gln Lys Pro Gly Lys Ala Pro Lys Leu Leu Ile
1               5                   10                  15

Tyr

<210> SEQ ID NO 341
<211> LENGTH: 36
<212> TYPE: PRT
<213> ORGANISM: Human

<400> SEQUENCE: 341

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
        35

<210> SEQ ID NO 342
<211> LENGTH: 10
<212> TYPE: PRT
<213> ORGANISM: Human

<400> SEQUENCE: 342

Phe Gly Gly Gly Thr Lys Val Asp Ile Lys
1               5                   10

<210> SEQ ID NO 343
<211> LENGTH: 363
```

```
<212> TYPE: DNA
<213> ORGANISM: Human

<400> SEQUENCE: 343
caggtccagc ttgtgcagtc tggggctgag gtgaagaagc ctgggtcctc ggtgaaggtc      60
tcctgcaagg cttctggagg caccaatttg atggggtatt atggtgctat cagctgggtg     120
cgacaggccc ctggacaagg gcttgagtgg atgggaggga tcatccctat ctttggtaca     180
gcaaactacg cacagaagtt ccagggcaga gtcacgatta ccgcggacga atccacgagc     240
acagcctaca tggagctgag cagcctgaga tctgaggaca cggccgtgta ttactgtgcg     300
agagacgtac agaggatggg gatggacgtc tggggccaag ggaccacggt caccgtctcc     360
tca                                                                    363

<210> SEQ ID NO 344
<211> LENGTH: 321
<212> TYPE: DNA
<213> ORGANISM: Human

<400> SEQUENCE: 344
gacatccaga tgacccagtc tccttcttcc gtctctacat ctgtaggaga cagagtcacc      60
atcacttgtc gggcgagtca ggatattagt aactggttag cctggtatca gcagaaacca     120
ggaaaagccc ctaagctcct gatctatgat tcatccactt tgcaaagtgg ggtcccatca     180
aggttcagcg gcagtggatc tgggacagat ttcactctca ccatcagcac cctgcagcct     240
gaggattttg caacttatta ctgtcaacag tttaatagtt atcccctcac tttcggcgga     300
gggaccaaag tggatatcaa a                                                321

<210> SEQ ID NO 345
<211> LENGTH: 121
<212> TYPE: PRT
<213> ORGANISM: Human

<400> SEQUENCE: 345

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Asn Leu Met Gly
            20                  25                  30

Tyr Tyr Gly Ala Ile Ser Trp Val Arg Gln Ala Pro Gly Gln Gly Leu
        35                  40                  45

Glu Trp Met Gly Gly Ile Ile Pro Ile Phe Gly Thr Ala Asn Tyr Ala
    50                  55                  60

Gln Lys Phe Gln Gly Arg Val Thr Ile Thr Ala Asp Glu Ser Thr Ser
65                  70                  75                  80

Thr Ala Tyr Met Glu Leu Ser Ser Leu Arg Ser Glu Asp Thr Ala Val
                85                  90                  95

Tyr Tyr Cys Ala Arg Asp Val Gln Arg Met Gly Met Asp Val Trp Gly
            100                 105                 110

Gln Gly Thr Thr Val Thr Val Ser Ser
        115                 120

<210> SEQ ID NO 346
<211> LENGTH: 107
<212> TYPE: PRT
<213> ORGANISM: Human

<400> SEQUENCE: 346
```

-continued

```
Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
        50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 347
<211> LENGTH: 11
<212> TYPE: PRT
<213> ORGANISM: Human

<400> SEQUENCE: 347

Gly Gly Thr Asn Leu Met Gly Tyr Tyr Gly Ala
1               5                   10

<210> SEQ ID NO 348
<211> LENGTH: 8
<212> TYPE: PRT
<213> ORGANISM: Human

<400> SEQUENCE: 348

Ile Ile Pro Ile Phe Gly Thr Ala
1               5

<210> SEQ ID NO 349
<211> LENGTH: 11
<212> TYPE: PRT
<213> ORGANISM: Human

<400> SEQUENCE: 349

Ala Arg Asp Val Gln Arg Met Gly Met Asp Val
1               5                   10

<210> SEQ ID NO 350
<211> LENGTH: 6
<212> TYPE: PRT
<213> ORGANISM: Human

<400> SEQUENCE: 350

Gln Asp Ile Ser Asn Trp
1               5

<210> SEQ ID NO 351
<211> LENGTH: 3
<212> TYPE: PRT
<213> ORGANISM: Human

<400> SEQUENCE: 351

Asp Ser Ser
1

<210> SEQ ID NO 352
<211> LENGTH: 9
```

<212> TYPE: PRT
<213> ORGANISM: Human

<400> SEQUENCE: 352

Gln Gln Phe Asn Ser Tyr Pro Leu Thr
1               5

<210> SEQ ID NO 353
<211> LENGTH: 25
<212> TYPE: PRT
<213> ORGANISM: Human

<400> SEQUENCE: 353

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 354
<211> LENGTH: 17
<212> TYPE: PRT
<213> ORGANISM: Human

<400> SEQUENCE: 354

Ile Ser Trp Val Arg Gln Ala Pro Gly Gln Gly Leu Glu Trp Met Gly
1               5                   10                  15

Gly

<210> SEQ ID NO 355
<211> LENGTH: 38
<212> TYPE: PRT
<213> ORGANISM: Human

<400> SEQUENCE: 355

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 356
<211> LENGTH: 11
<212> TYPE: PRT
<213> ORGANISM: Human

<400> SEQUENCE: 356

Trp Gly Gln Gly Thr Thr Val Thr Val Ser Ser
1               5                   10

<210> SEQ ID NO 357
<211> LENGTH: 26
<212> TYPE: PRT
<213> ORGANISM: Human

<400> SEQUENCE: 357

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25

<210> SEQ ID NO 358

-continued

```
<211> LENGTH: 17
<212> TYPE: PRT
<213> ORGANISM: Human

<400> SEQUENCE: 358

Leu Ala Trp Tyr Gln Gln Lys Pro Gly Lys Ala Pro Lys Leu Leu Ile
1               5                   10                  15

Tyr

<210> SEQ ID NO 359
<211> LENGTH: 36
<212> TYPE: PRT
<213> ORGANISM: Human

<400> SEQUENCE: 359

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
        35

<210> SEQ ID NO 360
<211> LENGTH: 10
<212> TYPE: PRT
<213> ORGANISM: Human

<400> SEQUENCE: 360

Phe Gly Gly Gly Thr Lys Val Asp Ile Lys
1               5                   10

<210> SEQ ID NO 361
<211> LENGTH: 360
<212> TYPE: DNA
<213> ORGANISM: Human

<400> SEQUENCE: 361
caggtccagc ttgtgcagtc tgggggctgag gtgaagaagc ctgggtcctc ggtgaaggtc      60
tcctgcaagg cttctggagg caccgttagg tctagggttc atgctatcag ctgggtgcga     120
caggcccctg gacaagggct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcgaga     300
gacgtacaga ggatggggat ggacgtctgg ggccaaggga ccacggtcac cgtctcctca     360

<210> SEQ ID NO 362
<211> LENGTH: 321
<212> TYPE: DNA
<213> ORGANISM: Human

<400> SEQUENCE: 362
gacatccaga tgacccagtc tccttcttcc gtctctacat ctgtaggaga cagagtcacc      60
atcacttgtc gggcgagtca ggatattagt aactggttag cctggtatca gcagaaacca     120
ggaaaagccc ctaagctcct gatctatgat tcatccactt tgcaaagtgg ggtcccatca     180
aggttcagcg gcagtggatc tgggacagat ttcactctca ccatcagcac cctgcagcct     240
gaggattttg caacttatta ctgtcaacag tttaatagtt atcccctcac tttcggcgga     300
gggaccaaag tggatatcaa a                                              321
```

-continued

<210> SEQ ID NO 363
<211> LENGTH: 120
<212> TYPE: PRT
<213> ORGANISM: Human

<400> SEQUENCE: 363

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Val Arg Ser Arg
                20                  25                  30

Val His Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln
        50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Val Gln Arg Met Gly Met Asp Val Trp Gly Gln
            100                 105                 110

Gly Thr Thr Val Thr Val Ser Ser
        115                 120

<210> SEQ ID NO 364
<211> LENGTH: 107
<212> TYPE: PRT
<213> ORGANISM: Human

<400> SEQUENCE: 364

Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
                20                  25                  30

Leu Ala Trp Tyr Gln Gln Lys Pro Gly Lys Ala Pro Lys Leu Leu Ile
            35                  40                  45

Tyr Asp Ser Ser Thr Leu Gln Ser Gly Val Pro Ser Arg Phe Ser Gly
        50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 365
<211> LENGTH: 10
<212> TYPE: PRT
<213> ORGANISM: Human

<400> SEQUENCE: 365

Gly Gly Thr Val Arg Ser Arg Val His Ala
1               5                   10

<210> SEQ ID NO 366
<211> LENGTH: 8
<212> TYPE: PRT
<213> ORGANISM: Human

<400> SEQUENCE: 366

```
Ile Ile Pro Ile Phe Gly Thr Ala
1               5

<210> SEQ ID NO 367
<211> LENGTH: 11
<212> TYPE: PRT
<213> ORGANISM: Human

<400> SEQUENCE: 367

Ala Arg Asp Val Gln Arg Met Gly Met Asp Val
1               5                   10

<210> SEQ ID NO 368
<211> LENGTH: 6
<212> TYPE: PRT
<213> ORGANISM: Human

<400> SEQUENCE: 368

Gln Asp Ile Ser Asn Trp
1               5

<210> SEQ ID NO 369
<211> LENGTH: 3
<212> TYPE: PRT
<213> ORGANISM: Human

<400> SEQUENCE: 369

Asp Ser Ser
1

<210> SEQ ID NO 370
<211> LENGTH: 9
<212> TYPE: PRT
<213> ORGANISM: Human

<400> SEQUENCE: 370

Gln Gln Phe Asn Ser Tyr Pro Leu Thr
1               5

<210> SEQ ID NO 371
<211> LENGTH: 25
<212> TYPE: PRT
<213> ORGANISM: Human

<400> SEQUENCE: 371

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 372
<211> LENGTH: 17
<212> TYPE: PRT
<213> ORGANISM: Human

<400> SEQUENCE: 372

Ile Ser Trp Val Arg Gln Ala Pro Gly Gln Gly Leu Glu Trp Met Gly
1               5                   10                  15

Gly

<210> SEQ ID NO 373
<211> LENGTH: 38
<212> TYPE: PRT
```

-continued

```
<213> ORGANISM: Human

<400> SEQUENCE: 373

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 374
<211> LENGTH: 11
<212> TYPE: PRT
<213> ORGANISM: Human

<400> SEQUENCE: 374

Trp Gly Gln Gly Thr Thr Val Thr Val Ser Ser
1               5                   10

<210> SEQ ID NO 375
<211> LENGTH: 26
<212> TYPE: PRT
<213> ORGANISM: Human

<400> SEQUENCE: 375

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25

<210> SEQ ID NO 376
<211> LENGTH: 17
<212> TYPE: PRT
<213> ORGANISM: Human

<400> SEQUENCE: 376

Leu Ala Trp Tyr Gln Gln Lys Pro Gly Lys Ala Pro Lys Leu Leu Ile
1               5                   10                  15

Tyr

<210> SEQ ID NO 377
<211> LENGTH: 36
<212> TYPE: PRT
<213> ORGANISM: Human

<400> SEQUENCE: 377

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
        35

<210> SEQ ID NO 378
<211> LENGTH: 10
<212> TYPE: PRT
<213> ORGANISM: Human

<400> SEQUENCE: 378

Phe Gly Gly Gly Thr Lys Val Asp Ile Lys
1               5                   10
```

<210> SEQ ID NO 379
<211> LENGTH: 360
<212> TYPE: DNA
<213> ORGANISM: Human

<400> SEQUENCE: 379
caggtccagc ttgtgcagtc tggggctgag gtgaagaagc ctgggtcctc ggtgaaggtc      60
tcctgcaagg cttctggagg caccgggtcg gagtttatgg gtgctatcag ctgggtgcga     120
caggcccctg gacaagggct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcgaga     300
gacgtacaga ggatgggggat ggacgtctgg ggccaaggga ccacggtcac cgtctcctca     360

<210> SEQ ID NO 380
<211> LENGTH: 321
<212> TYPE: DNA
<213> ORGANISM: Human

<400> SEQUENCE: 380
gacatccaga tgacccagtc tccttcttcc gtctctacat ctgtaggaga cagagtcacc      60
atcacttgtc gggcgagtca ggatattagt aactggttag cctggtatca gcagaaacca     120
ggaaaagccc ctaagctcct gatctatgat tcatccactt tgcaaagtgg ggtcccatca     180
aggttcagcg gcagtggatc tgggacagat ttcactctca ccatcagcac cctgcagcct     240
gaggattttg caacttatta ctgtcaacag tttaatagtt atcccctcac tttcggcgga     300
gggaccaaag tggatatcaa a                                               321

<210> SEQ ID NO 381
<211> LENGTH: 120
<212> TYPE: PRT
<213> ORGANISM: Human

<400> SEQUENCE: 381

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Gly Ser Glu Phe
            20                  25                  30

Met Gly Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Val Gln Arg Met Gly Met Asp Val Trp Gly Gln
            100                 105                 110

Gly Thr Thr Val Thr Val Ser Ser
        115                 120

<210> SEQ ID NO 382
<211> LENGTH: 107
<212> TYPE: PRT
<213> ORGANISM: Human

<400> SEQUENCE: 382

-continued

```
Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 383
<211> LENGTH: 10
<212> TYPE: PRT
<213> ORGANISM: Human

<400> SEQUENCE: 383

Gly Gly Thr Gly Ser Glu Phe Met Gly Ala
1               5                   10

<210> SEQ ID NO 384
<211> LENGTH: 8
<212> TYPE: PRT
<213> ORGANISM: Human

<400> SEQUENCE: 384

Ile Ile Pro Ile Phe Gly Thr Ala
1               5

<210> SEQ ID NO 385
<211> LENGTH: 11
<212> TYPE: PRT
<213> ORGANISM: Human

<400> SEQUENCE: 385

Ala Arg Asp Val Gln Arg Met Gly Met Asp Val
1               5                   10

<210> SEQ ID NO 386
<211> LENGTH: 6
<212> TYPE: PRT
<213> ORGANISM: Human

<400> SEQUENCE: 386

Gln Asp Ile Ser Asn Trp
1               5

<210> SEQ ID NO 387
<211> LENGTH: 3
<212> TYPE: PRT
<213> ORGANISM: Human

<400> SEQUENCE: 387

Asp Ser Ser
1

<210> SEQ ID NO 388
```

-continued

```
<211> LENGTH: 9
<212> TYPE: PRT
<213> ORGANISM: Human

<400> SEQUENCE: 388

Gln Gln Phe Asn Ser Tyr Pro Leu Thr
1               5

<210> SEQ ID NO 389
<211> LENGTH: 25
<212> TYPE: PRT
<213> ORGANISM: Human

<400> SEQUENCE: 389

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 390
<211> LENGTH: 17
<212> TYPE: PRT
<213> ORGANISM: Human

<400> SEQUENCE: 390

Ile Ser Trp Val Arg Gln Ala Pro Gly Gln Gly Leu Glu Trp Met Gly
1               5                   10                  15

Gly

<210> SEQ ID NO 391
<211> LENGTH: 38
<212> TYPE: PRT
<213> ORGANISM: Human

<400> SEQUENCE: 391

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 392
<211> LENGTH: 11
<212> TYPE: PRT
<213> ORGANISM: Human

<400> SEQUENCE: 392

Trp Gly Gln Gly Thr Thr Val Thr Val Ser Ser
1               5                   10

<210> SEQ ID NO 393
<211> LENGTH: 26
<212> TYPE: PRT
<213> ORGANISM: Human

<400> SEQUENCE: 393

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25
```

-continued

```
<210> SEQ ID NO 394
<211> LENGTH: 17
<212> TYPE: PRT
<213> ORGANISM: Human

<400> SEQUENCE: 394

Leu Ala Trp Tyr Gln Gln Lys Pro Gly Lys Ala Pro Lys Leu Leu Ile
1               5                   10                  15

Tyr

<210> SEQ ID NO 395
<211> LENGTH: 36
<212> TYPE: PRT
<213> ORGANISM: Human

<400> SEQUENCE: 395

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
            35

<210> SEQ ID NO 396
<211> LENGTH: 10
<212> TYPE: PRT
<213> ORGANISM: Human

<400> SEQUENCE: 396

Phe Gly Gly Gly Thr Lys Val Asp Ile Lys
1               5                   10

<210> SEQ ID NO 397
<211> LENGTH: 360
<212> TYPE: DNA
<213> ORGANISM: Human

<400> SEQUENCE: 397
caggtccagc ttgtgcagtc tgggggctgag gtgaagaagc ctgggtcctc ggtgaaggtc      60
tcctgcaagg cttctggagg cacctataat ccgggtgtgt ctgctatcag ctgggtgcga     120
caggcccctg gacaagggct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcgaga     300
gacgtacaga ggatggggat ggacgtctgg ggccaaggga ccacggtcac cgtctcctca     360

<210> SEQ ID NO 398
<211> LENGTH: 321
<212> TYPE: DNA
<213> ORGANISM: Human

<400> SEQUENCE: 398
gacatccaga tgacccagtc tccttcttcc gtctctacat ctgtaggaga cagagtcacc      60
atcacttgtc gggcgagtca ggatattagt aactggttag cctggtatca gcagaaacca     120
ggaaaagccc ctaagctcct gatctatgat tcatccactt gcaaagtggg gtcccatca      180 aggttcagcg gcagtggatc tgggacagat ttcactctca ccatcagcac cctgcagcct     240
gaggattttg caacttatta ctgtcaacag tttaatagtt atcccctcac tttcggcgga     300
gggaccaaag tggatatcaa a                                              321
```

```
<210> SEQ ID NO 399
<211> LENGTH: 120
<212> TYPE: PRT
<213> ORGANISM: Human

<400> SEQUENCE: 399

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Tyr Asn Pro Gly
            20                  25                  30

Val Ser Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Val Gln Arg Met Gly Met Asp Val Trp Gly Gln
            100                 105                 110

Gly Thr Thr Val Thr Val Ser Ser
        115                 120

<210> SEQ ID NO 400
<211> LENGTH: 107
<212> TYPE: PRT
<213> ORGANISM: Human

<400> SEQUENCE: 400

Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 401
<211> LENGTH: 10
<212> TYPE: PRT
<213> ORGANISM: Human

<400> SEQUENCE: 401

Gly Gly Thr Tyr Asn Pro Gly Val Ser Ala
1               5                   10

<210> SEQ ID NO 402
<211> LENGTH: 8
<212> TYPE: PRT
<213> ORGANISM: Human
```

-continued

```
<400> SEQUENCE: 402

Ile Ile Pro Ile Phe Gly Thr Ala
1               5

<210> SEQ ID NO 403
<211> LENGTH: 11
<212> TYPE: PRT
<213> ORGANISM: Human

<400> SEQUENCE: 403

Ala Arg Asp Val Gln Arg Met Gly Met Asp Val
1               5               10

<210> SEQ ID NO 404
<211> LENGTH: 6
<212> TYPE: PRT
<213> ORGANISM: Human

<400> SEQUENCE: 404

Gln Asp Ile Ser Asn Trp
1               5

<210> SEQ ID NO 405
<211> LENGTH: 3
<212> TYPE: PRT
<213> ORGANISM: Human

<400> SEQUENCE: 405

Asp Ser Ser
1

<210> SEQ ID NO 406
<211> LENGTH: 9
<212> TYPE: PRT
<213> ORGANISM: Human

<400> SEQUENCE: 406

Gln Gln Phe Asn Ser Tyr Pro Leu Thr
1               5

<210> SEQ ID NO 407
<211> LENGTH: 25
<212> TYPE: PRT
<213> ORGANISM: Human

<400> SEQUENCE: 407

Gln Val Gln Leu Val Gln Ser Gly Ala Glu Val Lys Lys Pro Gly Ser
1               5               10              15

Ser Val Lys Val Ser Cys Lys Ala Ser
            20              25

<210> SEQ ID NO 408
<211> LENGTH: 17
<212> TYPE: PRT
<213> ORGANISM: Human

<400> SEQUENCE: 408

Ile Ser Trp Val Arg Gln Ala Pro Gly Gln Gly Leu Glu Trp Met Gly
1               5               10              15

Gly

<210> SEQ ID NO 409
<211> LENGTH: 38
```

-continued

<212> TYPE: PRT
<213> ORGANISM: Human

<400> SEQUENCE: 409

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 410
<211> LENGTH: 11
<212> TYPE: PRT
<213> ORGANISM: Human

<400> SEQUENCE: 410

Trp Gly Gln Gly Thr Thr Val Thr Val Ser Ser
1               5                   10

<210> SEQ ID NO 411
<211> LENGTH: 26
<212> TYPE: PRT
<213> ORGANISM: Human

<400> SEQUENCE: 411

Asp Ile Gln Met Thr Gln Ser Pro Ser Ser Val Ser Thr Ser Val Gly
1               5                   10                  15

Asp Arg Val Thr Ile Thr Cys Arg Ala Ser
            20                  25

<210> SEQ ID NO 412
<211> LENGTH: 17
<212> TYPE: PRT
<213> ORGANISM: Human

<400> SEQUENCE: 412

Leu Ala Trp Tyr Gln Gln Lys Pro Gly Lys Ala Pro Lys Leu Leu Ile
1               5                   10                  15

Tyr

<210> SEQ ID NO 413
<211> LENGTH: 36
<212> TYPE: PRT
<213> ORGANISM: Human

<400> SEQUENCE: 413

Thr Leu Gln Ser Gly Val Pro Ser Arg Phe Ser Gly Ser Gly Ser Gly
1               5                   10                  15

Thr Asp Phe Thr Leu Thr Ile Ser Thr Leu Gln Pro Glu Asp Phe Ala
            20                  25                  30

Thr Tyr Tyr Cys
        35

<210> SEQ ID NO 414
<211> LENGTH: 10
<212> TYPE: PRT
<213> ORGANISM: Human

<400> SEQUENCE: 414

Phe Gly Gly Gly Thr Lys Val Asp Ile Lys
1               5                   10

```
<210> SEQ ID NO 415
<211> LENGTH: 10
<212> TYPE: PRT
<213> ORGANISM: Artificial Sequence
<220> FEATURE:
<223> OTHER INFORMATION: VL CDR3 consensus sequence relating to all the
      specifically described HLA-DQ2.5-gliadin-alpha1a antigen binding
      proteins described herein (in Tables A-I and AA)
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (9)..(9)
<223> OTHER INFORMATION: any amino acid or no amino acid
<220> FEATURE:
<221> NAME/KEY: MISC_FEATURE
<222> LOCATION: (10)..(10)
<223> OTHER INFORMATION: any amino acid or no amino acid

<400> SEQUENCE: 415

Gln Xaa Leu Asn Ser Tyr Pro Leu Xaa Xaa
1               5                   10

<210> SEQ ID NO 416
<211> LENGTH: 10
<212> TYPE: PRT
<213> ORGANISM: Artificial Sequence
<220> FEATURE:
<223> OTHER INFORMATION: VL CDR3 consensus sequence relating to certain
      of the specifically described HLA-DQ2.5-gliadin-alpha1a antigen
      binding proteins described herein  (in Tables A-G and I)
<220> FEATURE:
<221> NAME/KEY: MISC_FEATURE
<222> LOCATION: (2)..(2)
<223> OTHER INFORMATION: Q or D
<220> FEATURE:
<221> NAME/KEY: MISC_FEATURE
<222> LOCATION: (9)..(9)
<223> OTHER INFORMATION: no amino acid or L
<220> FEATURE:
<221> NAME/KEY: MISC_FEATURE
<222> LOCATION: (10)..(10)
<223> OTHER INFORMATION: no amino acid or T

<400> SEQUENCE: 416

Gln Xaa Leu Asn Ser Tyr Pro Leu Xaa Xaa
1               5                   10

<210> SEQ ID NO 417
<211> LENGTH: 15
<212> TYPE: PRT
<213> ORGANISM: Artificial Sequence
<220> FEATURE:
<223> OTHER INFORMATION: VH CDR3 consensus sequence relating to all the
      specifically described HLA-DQ2.5-gliadin-alpha1a antigen binding
      proteins described herein (Tables A-I and AA)
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (9)..(9)
```

```
<223> OTHER INFORMATION: any amino acid
<220> FEATURE:
<221> NAME/KEY: MISC_FEATURE
<222> LOCATION: (10)..(10)
<223> OTHER INFORMATION: any amino acid

<400> SEQUENCE: 417

Ala Arg Asp Xaa Xaa Xaa Gly Trp Xaa Xaa Tyr Gly Met Asp Val
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: VH CDR3 consensus sequence relating to all the
      specifically described HLA-DQ2.5-gliadin-alpha1a antigen binding
      proteins described herein (Tables A-I and AA)
<220> FEATURE:
<221> NAME/KEY: MISC_FEATURE
<222> LOCATION: (4)..(4)
<223> OTHER INFORMATION: S or R
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (9)..(9)
<223> OTHER INFORMATION: H or N or G
<220> FEATURE:
<221> NAME/KEY: MISC_FEATURE
<222> LOCATION: (10)..(10)
<223> OTHER INFORMATION: P or A

<400> SEQUENCE: 418

Ala Arg Asp Xaa Xaa Xaa Gly Trp Xaa Xaa Tyr Gly Met Asp Val
1               5                   10                  15

<210> SEQ ID NO 419
<211> LENGTH: 12
<212> TYPE: PRT
<213> ORGANISM: Artificial Sequence
<220> FEATURE:
<223> OTHER INFORMATION: VL CDR1 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: Q or G
<220> FEATURE:
<221> NAME/KEY: MISC_FEATURE
<222> LOCATION: (2)..(2)
<223> OTHER INFORMATION: D or S or T or N
<220> FEATURE:
<221> NAME/KEY: MISC_FEATURE
<222> LOCATION: (3)..(3)
<223> OTHER INFORMATION: I or V or S
<220> FEATURE:
<221> NAME/KEY: MISC_FEATURE
<222> LOCATION: (4)..(4)
<223> OTHER INFORMATION: S or L or N or I
<220> FEATURE:
<221> NAME/KEY: MISC_FEATURE
<222> LOCATION: (5)..(5)
<223> OTHER INFORMATION: N or S or Y or D or T or K
<220> FEATURE:
<221> NAME/KEY: MISC_FEATURE
<222> LOCATION: (6)..(6)
<223> OTHER INFORMATION: W or N or S or V or Y
```

```
<220> FEATURE:
<221> NAME/KEY: MISC_FEATURE
<222> LOCATION: (7)..(7)
<223> OTHER INFORMATION: no amino acid or any amino acid
<220> FEATURE:
<221> NAME/KEY: MISC_FEATURE
<222> LOCATION: (8)..(8)
<223> OTHER INFORMATION: no amino acid or any amino acid
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid
<220> FEATURE:
<221> NAME/KEY: MISC_FEATURE
<222> LOCATION: (12)..(12)
<223> OTHER INFORMATION: no amino acid or any amino acid

<400> SEQUENCE: 419

Xaa Xaa Xaa Xaa Xaa Xaa Xaa Xaa Xaa Xaa Xaa Xaa
1               5                   10

<210> SEQ ID NO 420
<211> LENGTH: 12
<212> TYPE: PRT
<213> ORGANISM: Artificial Sequence
<220> FEATURE:
<223> OTHER INFORMATION: VL CDR1 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: Q or G
<220> FEATURE:
<221> NAME/KEY: MISC_FEATURE
<222> LOCATION: (2)..(2)
<223> OTHER INFORMATION: D or S or T or N
<220> FEATURE:
<221> NAME/KEY: MISC_FEATURE
<222> LOCATION: (3)..(3)
<223> OTHER INFORMATION: I or V or S
<220> FEATURE:
<221> NAME/KEY: MISC_FEATURE
<222> LOCATION: (4)..(4)
<223> OTHER INFORMATION: S or L or N or I
<220> FEATURE:
<221> NAME/KEY: MISC_FEATURE
<222> LOCATION: (5)..(5)
<223> OTHER INFORMATION: N or S or Y or D or T or K
<220> FEATURE:
<221> NAME/KEY: MISC_FEATURE
<222> LOCATION: (6)..(6)
<223> OTHER INFORMATION: W or N or S or V or Y
<220> FEATURE:
<221> NAME/KEY: MISC_FEATURE
<222> LOCATION: (7)..(7)
<223> OTHER INFORMATION: no amino acid or S or G
<220> FEATURE:
<221> NAME/KEY: MISC_FEATURE
<222> LOCATION: (8)..(8)
<223> OTHER INFORMATION: no amino acid or N or G
<220> FEATURE:
<221> NAME/KEY: MISC_FEATURE
<222> LOCATION: (9)..(9)
<223> OTHER INFORMATION: no amino acid or N or Y
<220> FEATURE:
<221> NAME/KEY: MISC_FEATURE
<222> LOCATION: (10)..(10)
<223> OTHER INFORMATION: no amino acid or K or G
```

```
<220> FEATURE:
<221> NAME/KEY: MISC_FEATURE
<222> LOCATION: (11)..(11)
<223> OTHER INFORMATION: no amino acid or N or Y
<220> FEATURE:
<221> NAME/KEY: MISC_FEATURE
<222> LOCATION: (12)..(12)
<223> OTHER INFORMATION: no amino acid or Y

<400> SEQUENCE: 420

Xaa Xaa Xaa Xaa Xaa Xaa Xaa Xaa Xaa Xaa Xaa Xaa
1               5                   10

<210> SEQ ID NO 421
<211> LENGTH: 3
<212> TYPE: PRT
<213> ORGANISM: Artificial Sequence
<220> FEATURE:
<223> OTHER INFORMATION: VL CDR2 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (2)..(2)
<223> OTHER INFORMATION: any amino acid

<400> SEQUENCE: 421

Xaa Xaa Ser
1

<210> SEQ ID NO 422
<211> LENGTH: 3
<212> TYPE: PRT
<213> ORGANISM: Artificial Sequence
<220> FEATURE:
<223> OTHER INFORMATION: VL CDR2 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: D or G or W
<220> FEATURE:
<221> NAME/KEY: MISC_FEATURE
<222> LOCATION: (2)..(2)
<223> OTHER INFORMATION: S or A or V

<400> SEQUENCE: 422

Xaa Xaa Ser
1

<210> SEQ ID NO 423
<211> LENGTH: 11
<212> TYPE: PRT
<213> ORGANISM: Artificial Sequence
<220> FEATURE:
<223> OTHER INFORMATION: VL CDR3 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: Q or S
<220> FEATURE:
<221> NAME/KEY: MISC_FEATURE
<222> LOCATION: (2)..(2)
<223> OTHER INFORMATION: Q or S or H
<220> FEATURE:
<221> NAME/KEY: MISC_FEATURE
```

-continued

```
<222> LOCATION: (3)..(3)
<223> OTHER INFORMATION: F or Y
<220> FEATURE:
<221> NAME/KEY: MISC_FEATURE
<222> LOCATION: (4)..(4)
<223> OTHER INFORMATION: N or Y or D or T
<220> FEATURE:
<221> NAME/KEY: MISC_FEATURE
<222> LOCATION: (5)..(5)
<223> OTHER INFORMATION: S or N or D or W
<220> FEATURE:
<221> NAME/KEY: MISC_FEATURE
<222> LOCATION: (6)..(6)
<223> OTHER INFORMATION: Y or W or T or S or L
<220> FEATURE:
<221> NAME/KEY: MISC_FEATURE
<222> LOCATION: (7)..(7)
<223> OTHER INFORMATION: P or G
<220> FEATURE:
<221> NAME/KEY: MISC_FEATURE
<222> LOCATION: (8)..(8)
<223> OTHER INFORMATION: L or T or P or R
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid

<400> SEQUENCE: 423

Xaa Xaa Xaa Xaa Xaa Xaa Xaa Xaa Xaa Xaa Xaa
1               5                   10

<210> SEQ ID NO 424
<211> LENGTH: 11
<212> TYPE: PRT
<213> ORGANISM: Artificial Sequence
<220> FEATURE:
<223> OTHER INFORMATION: VL CDR3 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (1)..(1)
<223> OTHER INFORMATION: Q or S
<220> FEATURE:
<221> NAME/KEY: MISC_FEATURE
<222> LOCATION: (2)..(2)
<223> OTHER INFORMATION: Q or S or H
<220> FEATURE:
<221> NAME/KEY: MISC_FEATURE
<222> LOCATION: (3)..(3)
<223> OTHER INFORMATION: F or Y
<220> FEATURE:
<221> NAME/KEY: MISC_FEATURE
<222> LOCATION: (4)..(4)
<223> OTHER INFORMATION: N or Y or D or T
<220> FEATURE:
<221> NAME/KEY: MISC_FEATURE
<222> LOCATION: (5)..(5)
<223> OTHER INFORMATION: S or N or D or W
<220> FEATURE:
<221> NAME/KEY: MISC_FEATURE
<222> LOCATION: (6)..(6)
<223> OTHER INFORMATION: Y or W or T or S or L
<220> FEATURE:
<221> NAME/KEY: MISC_FEATURE
<222> LOCATION: (7)..(7)
<223> OTHER INFORMATION: P or G
<220> FEATURE:
<221> NAME/KEY: MISC_FEATURE
```

```
<222> LOCATION: (8)..(8)
<223> OTHER INFORMATION: L or T or P or R
<220> FEATURE:
<221> NAME/KEY: MISC_FEATURE
<222> LOCATION: (9)..(9)
<223> OTHER INFORMATION: no amino acid or T or V or R
<220> FEATURE:
<221> NAME/KEY: MISC_FEATURE
<222> LOCATION: (10)..(10)
<223> OTHER INFORMATION: no amino acid or L or F
<220> FEATURE:
<221> NAME/KEY: MISC_FEATURE
<222> LOCATION: (11)..(11)
<223> OTHER INFORMATION: no amino acid or T

<400> SEQUENCE: 424

Xaa Xaa Xaa Xaa Xaa Xaa Xaa Xaa Xaa Xaa Xaa
1               5                   10

<210> SEQ ID NO 425
<211> LENGTH: 11
<212> TYPE: PRT
<213> ORGANISM: Artificial Sequence
<220> FEATURE:
<223> OTHER INFORMATION: VH CDR1 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (4)..(4)
<223> OTHER INFORMATION: F or S or N or V or G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: Y or F or G or R
<220> FEATURE:
<221> NAME/KEY: MISC_FEATURE
<222> LOCATION: (8)..(8)
<223> OTHER INFORMATION: A or G or I or Y or V or M
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid

<400> SEQUENCE: 425

Gly Gly Thr Xaa Xaa Xaa Xaa Xaa Xaa Xaa Xaa
1               5                   10

<210> SEQ ID NO 426
<211> LENGTH: 11
<212> TYPE: PRT
<213> ORGANISM: Artificial Sequence
<220> FEATURE:
<223> OTHER INFORMATION: VH CDR1 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (4)..(4)
```

```
<223> OTHER INFORMATION: F or S or N or V or G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: Y or F or G or R
<220> FEATURE:
<221> NAME/KEY: MISC_FEATURE
<222> LOCATION: (8)..(8)
<223> OTHER INFORMATION: A or G or I or Y or V or M
<220> FEATURE:
<221> NAME/KEY: MISC_FEATURE
<222> LOCATION: (9)..(9)
<223> OTHER INFORMATION: no amino acid or G or Y or H or S
<220> FEATURE:
<221> NAME/KEY: MISC_FEATURE
<222> LOCATION: (10)..(10)
<223> OTHER INFORMATION: no amino acid or A or G
<220> FEATURE:
<221> NAME/KEY: MISC_FEATURE
<222> LOCATION: (11)..(11)
<223> OTHER INFORMATION: no amino acid or A

<400> SEQUENCE: 426

Gly Gly Thr Xaa Xaa Xaa Xaa Xaa Xaa Xaa Xaa
1               5                   10

<210> SEQ ID NO 427
<211> LENGTH: 8
<212> TYPE: PRT
<213> ORGANISM: Artificial Sequence
<220> FEATURE:
<223> OTHER INFORMATION: VH CDR2 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (8)..(8)
<223> OTHER INFORMATION: any amino acid

<400> SEQUENCE: 427

Ile Ile Pro Ile Phe Gly Thr Xaa
1               5

<210> SEQ ID NO 428
<211> LENGTH: 8
<212> TYPE: PRT
<213> ORGANISM: Artificial Sequence
<220> FEATURE:
<223> OTHER INFORMATION: VH CDR2 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (8)..(8)
<223> OTHER INFORMATION: A or V

<400> SEQUENCE: 428

Ile Ile Pro Ile Phe Gly Thr Xaa
1               5

<210> SEQ ID NO 429
<211> LENGTH: 20
<212> TYPE: PRT
<213> ORGANISM: Artificial Sequence
<220> FEATURE:
```

-continued

<223> OTHER INFORMATION: VH CDR3 consensus sequence relating to all the
       specifically described HLA-DQ2.5-gliadin-alpha2 antigen binding
       proteins described herein (Tables J-W)
<220> FEATURE:
<221> NAME/KEY: MISC_FEATURE
<222> LOCATION: (3)..(3)
<223> OTHER INFORMATION: D or V or G
<220> FEATURE:
<221> NAME/KEY: MISC_FEATURE
<222> LOCATION: (4)..(4)
<223> OTHER INFORMATION: V or A or Y or R or Q
<220> FEATURE:
<221> NAME/KEY: MISC_FEATURE
<222> LOCATION: (5)..(5)
<223> OTHER INFORMATION: Q or I or Y or N or P or V or G
<220> FEATURE:
<221> NAME/KEY: MISC_FEATURE
<222> LOCATION: (6)..(6)
<223> OTHER INFORMATION: R or G or Y or T or S or I or P or L
<220> FEATURE:
<221> NAME/KEY: MISC_FEATURE
<222> LOCATION: (7)..(7)
<223> OTHER INFORMATION: M or G or V or D or Y or P or L or I
<220> FEATURE:
<221> NAME/KEY: MISC_FEATURE
<222> LOCATION: (8)..(8)
<223> OTHER INFORMATION: G or F or S or C or Y or P or W
<220> FEATURE:
<221> NAME/KEY: MISC_FEATURE
<222> LOCATION: (9)..(9)
<223> OTHER INFORMATION: M or F or S or D or T
<220> FEATURE:
<221> NAME/KEY: MISC_FEATURE
<222> LOCATION: (10)..(10)
<223> OTHER INFORMATION: D or G or A or S or Y or R
<220> FEATURE:
<221> NAME/KEY: MISC_FEATURE
<222> LOCATION: (11)..(11)
<223> OTHER INFORMATION: V or Y or L or G or E
<220> FEATURE:
<221> NAME/KEY: MISC_FEATURE
<222> LOCATION: (12)..(12)
<223> OTHER INFORMATION: no amino acid or any amino acid
<220> FEATURE:
<221> NAME/KEY: MISC_FEATURE
<222> LOCATION: (13)..(13)
<223> OTHER INFORMATION: no amino acid or any amino acid
<220> FEATURE:
<221> NAME/KEY: MISC_FEATURE
<222> LOCATION: (14)..(14)
<223> OTHER INFORMATION: no amino acid or any amino acid
<220> FEATURE:
<221> NAME/KEY: MISC_FEATURE
<222> LOCATION: (15)..(15)
<223> OTHER INFORMATION: no amino acid or any amino acid
<220> FEATURE:
<221> NAME/KEY: MISC_FEATURE
<222> LOCATION: (16)..(16)
<223> OTHER INFORMATION: no amino acid or any amino acid
<220> FEATURE:
<221> NAME/KEY: MISC_FEATURE
<222> LOCATION: (17)..(17)
<223> OTHER INFORMATION: no amino acid or any amino acid
<220> FEATURE:
<221> NAME/KEY: MISC_FEATURE
<222> LOCATION: (18)..(18)
<223> OTHER INFORMATION: no amino acid or any amino acid
<220> FEATURE:
<221> NAME/KEY: MISC_FEATURE
<222> LOCATION: (19)..(19)
<223> OTHER INFORMATION: no amino acid or any amino acid
<220> FEATURE:
<221> NAME/KEY: MISC_FEATURE
<222> LOCATION: (20)..(20)
<223> OTHER INFORMATION: no amino acid or any amino acid

<400> SEQUENCE: 429

Ala Arg Xaa Xaa Xaa Xaa Xaa Xaa Xaa Xaa Xaa Xaa Xaa Xaa Xaa Xaa

-continued

```
1               5               10              15

Xaa Xaa Xaa Xaa
            20

<210> SEQ ID NO 430
<211> LENGTH: 20
<212> TYPE: PRT
<213> ORGANISM: Artificial Sequence
<220> FEATURE:
<223> OTHER INFORMATION: VH CDR3 consensus sequence relating to all the
      specifically described HLA-DQ2.5-gliadin-alpha2 antigen binding
      proteins described herein (Tables J-W)
<220> FEATURE:
<221> NAME/KEY: MISC_FEATURE
<222> LOCATION: (3)..(3)
<223> OTHER INFORMATION: D or V or G
<220> FEATURE:
<221> NAME/KEY: MISC_FEATURE
<222> LOCATION: (4)..(4)
<223> OTHER INFORMATION: V or A or Y or R or Q
<220> FEATURE:
<221> NAME/KEY: MISC_FEATURE
<222> LOCATION: (5)..(5)
<223> OTHER INFORMATION: Q or I or Y or N or P or V or G
<220> FEATURE:
<221> NAME/KEY: MISC_FEATURE
<222> LOCATION: (6)..(6)
<223> OTHER INFORMATION: R or G or Y or T or S or I or P or L
<220> FEATURE:
<221> NAME/KEY: MISC_FEATURE
<222> LOCATION: (7)..(7)
<223> OTHER INFORMATION: M or G or V or D or Y or P or L or I
<220> FEATURE:
<221> NAME/KEY: MISC_FEATURE
<222> LOCATION: (8)..(8)
<223> OTHER INFORMATION: G or F or S or C or Y or P or W
<220> FEATURE:
<221> NAME/KEY: MISC_FEATURE
<222> LOCATION: (9)..(9)
<223> OTHER INFORMATION: M or F or S or D or T
<220> FEATURE:
<221> NAME/KEY: MISC_FEATURE
<222> LOCATION: (10)..(10)
<223> OTHER INFORMATION: D or G or A or S or Y or R
<220> FEATURE:
<221> NAME/KEY: MISC_FEATURE
<222> LOCATION: (11)..(11)
<223> OTHER INFORMATION: V or Y or L or G or E
<220> FEATURE:
<221> NAME/KEY: MISC_FEATURE
<222> LOCATION: (12)..(12)
<223> OTHER INFORMATION: no amino acid or F or D or S or W or Y or L
<220> FEATURE:
<221> NAME/KEY: MISC_FEATURE
<222> LOCATION: (13)..(13)
<223> OTHER INFORMATION: no amino acid or D or Y or C or F or G or V
<220> FEATURE:
<221> NAME/KEY: MISC_FEATURE
<222> LOCATION: (14)..(14)
<223> OTHER INFORMATION: no amino acid or Y or M
<220> FEATURE:
<221> NAME/KEY: MISC_FEATURE
<222> LOCATION: (15)..(15)
<223> OTHER INFORMATION: no amino acid or S or Y or D or F
<220> FEATURE:
<221> NAME/KEY: MISC_FEATURE
<222> LOCATION: (16)..(16)
<223> OTHER INFORMATION: no amino acid or P or F or V or Q
<220> FEATURE:
<221> NAME/KEY: MISC_FEATURE
<222> LOCATION: (17)..(17)
<223> OTHER INFORMATION: no amino acid or H or D
<220> FEATURE:
<221> NAME/KEY: MISC_FEATURE
<222> LOCATION: (18)..(18)
<223> OTHER INFORMATION: no amino acid or F or Y
<220> FEATURE:
```

```
<221> NAME/KEY: MISC_FEATURE
<222> LOCATION: (19)..(19)
<223> OTHER INFORMATION: no amino acid or D
<220> FEATURE:
<221> NAME/KEY: MISC_FEATURE
<222> LOCATION: (20)..(20)
<223> OTHER INFORMATION: no amino acid or Y

<400> SEQUENCE: 430

Ala Arg Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 431
<211> LENGTH: 15
<212> TYPE: PRT
<213> ORGANISM: Artificial Sequence
<220> FEATURE:
<223> OTHER INFORMATION: VH CDR3 consensus sequence relating to the
      HLA-DQ2.5-gliadin-alpha1a antibody 107 described herein and the
      specifically described affinity matured variants thereof
      described herein (Tables C-I and AA)
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (9)..(9)
<223> OTHER INFORMATION: any amino acid
<220> FEATURE:
<221> NAME/KEY: MISC_FEATURE
<222> LOCATION: (10)..(10)
<223> OTHER INFORMATION: any amino acid

<400> SEQUENCE: 431

Ala Arg Asp Xaa Xaa Xaa Gly Trp Xaa Xaa Tyr Gly Met Asp Val
1               5                   10                  15

<210> SEQ ID NO 432
<211> LENGTH: 15
<212> TYPE: PRT
<213> ORGANISM: Artificial Sequence
<220> FEATURE:
<223> OTHER INFORMATION: VH CDR3 consensus sequence relating to the
      HLA-DQ2.5-gliadin-alpha1a antibody 107 described herein and the
      specifically described affinity matured variants thereof
      described herein (Tables C-I and AA)
<220> FEATURE:
<221> NAME/KEY: MISC_FEATURE
<222> LOCATION: (4)..(4)
<223> OTHER INFORMATION: S or R
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (9)..(9)
<223> OTHER INFORMATION: H or N or G
<220> FEATURE:
```

```
<221> NAME/KEY: MISC_FEATURE
<222> LOCATION: (10)..(10)
<223> OTHER INFORMATION: P or A

<400> SEQUENCE: 432

Ala Arg Asp Xaa Xaa Xaa Gly Trp Xaa Xaa Tyr Gly Met Asp Val
1               5                   10                  15

<210> SEQ ID NO 433
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha2 antibody 206 described herein and the
      specifically described affinity matured variants thereof
      described herein (Tables J and R-W)
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid

<400> SEQUENCE: 433

Gly Gly Thr Xaa Xaa Xaa Xaa Xaa Xaa Xaa Xaa
1               5                   10

<210> SEQ ID NO 434
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha2 antibody 206 described herein and the
      specifically described affinity matured variants thereof
      described herein (Tables J and R-W)
<220> FEATURE:
<221> NAME/KEY: MISC_FEATURE
<222> LOCATION: (4)..(4)
<223> OTHER INFORMATION: F or S or N or V or G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
```

```
<220> FEATURE:
<221> NAME/KEY: MISC_FEATURE
<222> LOCATION: (7)..(7)
<223> OTHER INFORMATION: Y or F or R or G
<220> FEATURE:
<221> NAME/KEY: MISC_FEATURE
<222> LOCATION: (8)..(8)
<223> OTHER INFORMATION: A or I or Y or V or M
<220> FEATURE:
<221> NAME/KEY: MISC_FEATURE
<222> LOCATION: (9)..(9)
<223> OTHER INFORMATION: no amino acid or G or Y or H or S
<220> FEATURE:
<221> NAME/KEY: MISC_FEATURE
<222> LOCATION: (10)..(10)
<223> OTHER INFORMATION: no amino acid or A or G
<220> FEATURE:
<221> NAME/KEY: MISC_FEATURE
<222> LOCATION: (11)..(11)
<223> OTHER INFORMATION: no amino acid or A

<400> SEQUENCE: 434

Gly Gly Thr Xaa Xaa Xaa Xaa Xaa Xaa Xaa Xaa
1               5                   10

<210> SEQ ID NO 435
<211> LENGTH: 6
<212> TYPE: PRT
<213> ORGANISM: Artificial Sequence
<220> FEATURE:
<223> OTHER INFORMATION: VL CDR1 consensus sequence relating to the
      HLA-DQ2.5-gliadin-alpha1a antibody 107 described herein, the
      HLA-DQ2.5-gliadin-alpha2 antibody 206 described herein and the
      affinity matured variants thereof described herein
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid

<400> SEQUENCE: 435

Xaa Asp Ile Ser Xaa Xaa
1               5

<210> SEQ ID NO 436
<211> LENGTH: 6
<212> TYPE: PRT
<213> ORGANISM: Artificial Sequence
<220> FEATURE:
<223> OTHER INFORMATION: VL CDR1 consensus sequence relating to the
      HLA-DQ2.5-gliadin-alpha1a antibody 107 described herein, the
      HLA-DQ2.5-gliadin-alpha2 antibody 206 described herein and the
      affinity matured variants thereof described herein
<220> FEATURE:
<221> NAME/KEY: MISC_FEATURE
<222> LOCATION: (1)..(1)
<223> OTHER INFORMATION: H or Q
<220> FEATURE:
<221> NAME/KEY: MISC_FEATURE
<222> LOCATION: (5)..(5)
<223> OTHER INFORMATION: S or N
<220> FEATURE:
<221> NAME/KEY: MISC_FEATURE
<222> LOCATION: (6)..(6)
<223> OTHER INFORMATION: Y or W

<400> SEQUENCE: 436
```

Xaa Asp Ile Ser Xaa Xaa
1               5

<210> SEQ ID NO 437
<211> LENGTH: 3
<212> TYPE: PRT
<213> ORGANISM: Artificial Sequence
<220> FEATURE:
<223> OTHER INFORMATION: VL CDR2 consensus sequence relating to the
      HLA-DQ2.5-gliadin-alpha1a antibody 107 described herein, the
      HLA-DQ2.5-gliadin-alpha2 antibody 206 described herein and the
      affinity matured variants thereof described herein
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (2)..(2)
<223> OTHER INFORMATION: any amino acid

<400> SEQUENCE: 437

Xaa Xaa Ser
1

<210> SEQ ID NO 438
<211> LENGTH: 3
<212> TYPE: PRT
<213> ORGANISM: Artificial Sequence
<220> FEATURE:
<223> OTHER INFORMATION: VL CDR2 consensus sequence relating to the
      HLA-DQ2.5-gliadin-alpha1a antibody 107 described herein, the
      HLA-DQ2.5-gliadin-alpha2 antibody 206 described herein and the
      affinity matured variants thereof described herein
<220> FEATURE:
<221> NAME/KEY: MISC_FEATURE
<222> LOCATION: (1)..(1)
<223> OTHER INFORMATION: A or D
<220> FEATURE:
<221> NAME/KEY: MISC_FEATURE
<222> LOCATION: (2)..(2)
<223> OTHER INFORMATION: A or S

<400> SEQUENCE: 438

Xaa Xaa Ser
1

<210> SEQ ID NO 439
<211> LENGTH: 9
<212> TYPE: PRT
<213> ORGANISM: Artificial Sequence
<220> FEATURE:
<223> OTHER INFORMATION: VL CDR3 consensus sequence relating to the
      HLA-DQ2.5-gliadin-alpha1a antibody 107 described herein, the
      HLA-DQ2.5-gliadin-alpha2 antibody 206 described herein and the
      affinity matured variants thereof described herein
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (9)..(9)
<223> OTHER INFORMATION: no amino acid or any amino acid

<400> SEQUENCE: 439

Gln Xaa Xaa Asn Ser Tyr Pro Leu Xaa
1               5

```
<210> SEQ ID NO 440
<211> LENGTH: 9
<212> TYPE: PRT
<213> ORGANISM: Artificial Sequence
<220> FEATURE:
<223> OTHER INFORMATION: VL CDR3 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: D or Q
<220> FEATURE:
<221> NAME/KEY: MISC_FEATURE
<222> LOCATION: (3)..(3)
<223> OTHER INFORMATION: L or F
<220> FEATURE:
<221> NAME/KEY: MISC_FEATURE
<222> LOCATION: (9)..(9)
<223> OTHER INFORMATION: no amino acid or T

<400> SEQUENCE: 440

Gln Xaa Xaa Asn Ser Tyr Pro Leu Xaa
1               5

<210> SEQ ID NO 441
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: G or D
<220> FEATURE:
<221> NAME/KEY: MISC_FEATURE
<222> LOCATION: (3)..(3)
<223> OTHER INFORMATION: S or T
<220> FEATURE:
<221> NAME/KEY: MISC_FEATURE
<222> LOCATION: (4)..(4)
<223> OTHER INFORMATION: V or F or S or N of G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: N or Y or F or G or R
<220> FEATURE:
<221> NAME/KEY: MISC_FEATURE
<222> LOCATION: (8)..(8)
<223> OTHER INFORMATION: S or A or I or Y or V or M
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid
```

```
<400> SEQUENCE: 441

Gly Xaa Xaa Xaa Xaa Xaa Xaa Xaa Xaa Xaa Xaa
1               5                   10

<210> SEQ ID NO 442
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: G or D
<220> FEATURE:
<221> NAME/KEY: MISC_FEATURE
<222> LOCATION: (3)..(3)
<223> OTHER INFORMATION: S or T
<220> FEATURE:
<221> NAME/KEY: MISC_FEATURE
<222> LOCATION: (4)..(4)
<223> OTHER INFORMATION: V or F or S or N of G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: N or Y or F or G or R
<220> FEATURE:
<221> NAME/KEY: MISC_FEATURE
<222> LOCATION: (8)..(8)
<223> OTHER INFORMATION: S or A or I or Y or V or M
<220> FEATURE:
<221> NAME/KEY: MISC_FEATURE
<222> LOCATION: (9)..(9)
<223> OTHER INFORMATION: no amino acid or A or G or Y or H or S
<220> FEATURE:
<221> NAME/KEY: MISC_FEATURE
<222> LOCATION: (10)..(10)
<223> OTHER INFORMATION: no amino acid or A or G
<220> FEATURE:
<221> NAME/KEY: MISC_FEATURE
<222> LOCATION: (11)..(11)
<223> OTHER INFORMATION: no amino acid or A

<400> SEQUENCE: 442

Gly Xaa Xaa Xaa Xaa Xaa Xaa Xaa Xaa Xaa Xaa
1               5                   10

<210> SEQ ID NO 443
<211> LENGTH: 8
<212> TYPE: PRT
<213> ORGANISM: Artificial Sequence
<220> FEATURE:
<223> OTHER INFORMATION: VH CDR3 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (4)..(4)
<223> OTHER INFORMATION: any amino acid; can be represented as Xn, where
      n is 4, 5, 6, 7, or 8.

<400> SEQUENCE: 443
```

```
Ala Arg Asp Xaa Gly Met Asp Val
1               5

<210> SEQ ID NO 444
<211> LENGTH: 461
<212> TYPE: PRT
<213> ORGANISM: Artificial Sequence
<220> FEATURE:
<223> OTHER INFORMATION: Heavy chain (aa) (variable + constant domain).
      mIgG2b

<400> SEQUENCE: 444

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Gly Trp His Pro Tyr Gly Met
            100                 105                 110

Asp Val Trp Gly Gln Gly Thr Thr Val Thr Val Ser Ser Ala Lys Thr
            115                 120                 125

Thr Pro Pro Ser Val Tyr Pro Leu Ala Pro Gly Cys Gly Asp Thr Thr
        130                 135                 140

Gly Ser Ser Val Thr Leu Gly Cys Leu Val Lys Gly Tyr Phe Pro Glu
145                 150                 155                 160

Ser Val Thr Val Thr Trp Asn Ser Gly Ser Leu Ser Ser Ser Val His
                165                 170                 175

Thr Phe Pro Ala Leu Leu Gln Ser Gly Leu Tyr Thr Met Ser Ser Ser
            180                 185                 190

Val Thr Val Pro Ser Ser Thr Trp Pro Ser Gln Thr Val Thr Cys Ser
        195                 200                 205

Val Ala His Pro Ala Ser Ser Thr Thr Val Asp Lys Lys Leu Glu Pro
    210                 215                 220

Ser Gly Pro Ile Ser Thr Ile Asn Pro Cys Pro Pro Cys Lys Glu Cys
225                 230                 235                 240

His Lys Cys Pro Ala Pro Asn Leu Glu Gly Gly Pro Ser Val Phe Ile
            245                 250                 255

Phe Pro Pro Asn Ile Lys Asp Val Leu Met Ile Ser Leu Thr Pro Lys
            260                 265                 270

Val Thr Cys Val Val Val Asp Val Ser Glu Asp Asp Pro Asp Val Gln
        275                 280                 285

Ile Ser Trp Phe Val Asn Asn Val Glu Val His Thr Ala Gln Thr Gln
    290                 295                 300

Thr His Arg Glu Asp Tyr Ala Ser Thr Ile Arg Val Val Ser Thr Leu
305                 310                 315                 320

Pro Ile Gln His Gln Asp Trp Met Ser Gly Lys Glu Phe Lys Cys Lys
                325                 330                 335

Val Asn Asn Lys Asp Leu Pro Ser Pro Ile Glu Arg Thr Ile Ser Lys
            340                 345                 350
```

-continued

```
Ile Lys Gly Leu Val Arg Ala Pro Gln Val Tyr Ile Leu Pro Pro Pro
        355                 360             365

Ala Glu Gln Leu Ser Arg Lys Asp Val Ser Leu Thr Cys Leu Val Val
        370                 375             380

Gly Phe Asn Pro Gly Asp Ile Ser Val Glu Trp Thr Ser Asn Gly His
385                 390             395             400

Thr Glu Glu Asn Tyr Lys Asp Thr Ala Pro Val Leu Asp Ser Asp Gly
                405             410             415

Ser Tyr Phe Ile Tyr Ser Lys Leu Asn Met Lys Thr Ser Lys Trp Glu
                420             425             430

Lys Thr Asp Ser Phe Ser Cys Asn Val Arg His Glu Gly Leu Lys Asn
        435                 440             445

Tyr Tyr Leu Lys Lys Thr Ile Ser Arg Ser Pro Gly Lys
        450             455             460
```

```
<210> SEQ ID NO 445
<211> LENGTH: 215
<212> TYPE: PRT
<213> ORGANISM: Artificial Sequence
<220> FEATURE:
<223> OTHER INFORMATION: Light chain (aa) (variable + constant domain).
      mIgG2b

<400> SEQUENCE: 445
```

```
Asp Ile Gln Val Thr Gln Ser Pro Ser Phe Leu Ser Ala Ser Val Gly
1               5               10              15

Asp Arg Val Thr Ile Thr Cys Arg Ala Ser His Asp Ile Ser Ser Tyr
                20              25              30

Leu Ala Trp Tyr Gln His Lys Pro Gly Lys Ala Pro Lys Leu Leu Ile
        35              40              45

His Ala Ala Ser Ile Leu Gln Ser Gly Val Pro Ser Arg Phe Ser Gly
        50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Gln Gln Leu Asn Ser Tyr Pro Leu
                85              90              95

Leu Thr Phe Gly Gly Gly Thr Lys Val Asp Ile Lys Arg Ala Asp Ala
                100             105             110

Ala Pro Thr Val Ser Ile Phe Pro Pro Ser Ser Glu Gln Leu Thr Ser
        115             120             125

Gly Gly Ala Ser Val Val Cys Phe Leu Asn Asn Phe Tyr Pro Lys Asp
        130             135             140

Ile Asn Val Lys Trp Lys Ile Asp Gly Ser Glu Arg Gln Asn Gly Val
145             150             155             160

Leu Asn Ser Trp Thr Asp Gln Asp Ser Lys Asp Ser Thr Tyr Ser Met
                165             170             175

Ser Ser Thr Leu Thr Leu Thr Lys Asp Glu Tyr Glu Arg His Asn Ser
        180             185             190

Tyr Thr Cys Glu Ala Thr His Lys Thr Ser Thr Ser Pro Ile Val Lys
        195             200             205

Ser Phe Asn Arg Asn Glu Cys
        210             215
```

```
<210> SEQ ID NO 446
<211> LENGTH: 455
<212> TYPE: PRT
```

<213> ORGANISM: Artificial Sequence
<220> FEATURE:
<223> OTHER INFORMATION: Heavy chain (aa) (variable + constant domain).
      hIgG1

<400> SEQUENCE: 446

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
    370                 375                 380
```

-continued

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

<210> SEQ ID NO 447
<211> LENGTH: 215
<212> TYPE: PRT
<213> ORGANISM: Artificial Sequence
<220> FEATURE:
<223> OTHER INFORMATION: Light chain (aa) (variable + constant domain).
    hIgG1

<400> SEQUENCE: 447

```
Asp Ile Gln Val Thr Gln Ser Pro Ser Phe Leu Ser Ala Ser Val Gly
1                 5                 10                  15

Asp Arg Val Thr Ile Thr Cys Arg Ala Ser His Asp Ile Ser Ser Tyr
                20                  25                  30

Leu Ala Trp Tyr Gln His Lys Pro Gly Lys Ala Pro Lys Leu Leu Ile
            35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```

<210> SEQ ID NO 448
<211> LENGTH: 461
<212> TYPE: PRT
<213> ORGANISM: Artificial Sequence
<220> FEATURE:
<223> OTHER INFORMATION: Heavy chain (aa) (variable +constant domain).
    mIgG2b

<400> SEQUENCE: 448

-continued

```
Gln Val Gln Leu Gln Gln Ser Gly Pro Gly Leu Val Lys Pro Ser Gln
1               5               10              15

Thr Leu Ser Leu Thr Cys Ala Ile Ser Gly Asp Ser Val Ser Ser Asn
            20              25              30

Ser Ala Ala Trp Asn Trp Ile Arg Gln Ser Pro Ser Arg Gly Leu Glu
        35              40              45

Trp Leu Gly Arg Thr Tyr Tyr Arg Ser Lys Trp Tyr Asn Asp Tyr Ala
    50              55              60

Val Ser Val Lys Ser Arg Ile Thr Ile Asn Pro Asp Thr Ser Lys Asn
65              70              75              80

Gln Phe Ser Leu Gln Leu Asn Ser Val Thr Pro Glu Asp Thr Ala Val
            85              90              95

Tyr Tyr Cys Ala Arg Asp Ser Ser Ser Gly Trp His Pro Tyr Gly Met
            100             105             110

Asp Val Trp Gly Gln Gly Thr Thr Val Thr Val Ser Ser Ala Lys Thr
        115             120             125

Thr Pro Pro Ser Val Tyr Pro Leu Ala Pro Gly Cys Gly Asp Thr Thr
    130             135             140

Gly Ser Ser Val Thr Leu Gly Cys Leu Val Lys Gly Tyr Phe Pro Glu
145             150             155             160

Ser Val Thr Val Thr Trp Asn Ser Gly Ser Leu Ser Ser Ser Val His
        165             170             175

Thr Phe Pro Ala Leu Leu Gln Ser Gly Leu Tyr Thr Met Ser Ser Ser
        180             185             190

Val Thr Val Pro Ser Ser Thr Trp Pro Ser Gln Thr Val Thr Cys Ser
        195             200             205

Val Ala His Pro Ala Ser Ser Thr Thr Val Asp Lys Lys Leu Glu Pro
    210             215             220

Ser Gly Pro Ile Ser Thr Ile Asn Pro Cys Pro Pro Cys Lys Glu Cys
225             230             235             240

His Lys Cys Pro Ala Pro Asn Leu Glu Gly Gly Pro Ser Val Phe Ile
            245             250             255

Phe Pro Pro Asn Ile Lys Asp Val Leu Met Ile Ser Leu Thr Pro Lys
            260             265             270

Val Thr Cys Val Val Val Asp Val Ser Glu Asp Asp Pro Asp Val Gln
        275             280             285

Ile Ser Trp Phe Val Asn Asn Val Glu Val His Thr Ala Gln Thr Gln
    290             295             300

Thr His Arg Glu Asp Tyr Ala Ser Thr Ile Arg Val Val Ser Thr Leu
305             310             315             320

Pro Ile Gln His Gln Asp Trp Met Ser Gly Lys Glu Phe Lys Cys Lys
            325             330             335

Val Asn Asn Lys Asp Leu Pro Ser Pro Ile Glu Arg Thr Ile Ser Lys
            340             345             350

Ile Lys Gly Leu Val Arg Ala Pro Gln Val Tyr Ile Leu Pro Pro Pro
            355             360             365

Ala Glu Gln Leu Ser Arg Lys Asp Val Ser Leu Thr Cys Leu Val Val
    370             375             380

Gly Phe Asn Pro Gly Asp Ile Ser Val Glu Trp Thr Ser Asn Gly His
385             390             395             400

Thr Glu Glu Asn Tyr Lys Asp Thr Ala Pro Val Leu Asp Ser Asp Gly
            405             410             415

Ser Tyr Phe Ile Tyr Ser Lys Leu Asn Met Lys Thr Ser Lys Trp Glu
```

-continued

```
                420             425             430
Lys Thr Asp Ser Phe Ser Cys Asn Val Arg His Glu Gly Leu Lys Asn
        435             440             445
Tyr Tyr Leu Lys Lys Thr Ile Ser Arg Ser Pro Gly Lys
    450             455             460
```

<210> SEQ ID NO 449
<211> LENGTH: 213
<212> TYPE: PRT
<213> ORGANISM: Artificial Sequence
<220> FEATURE:
<223> OTHER INFORMATION: Light chain (aa) (variable +constant domain).
      mIgG2b

<400> SEQUENCE: 449

```
Asp Ile Gln Val Thr Gln Ser Pro Ser Phe Leu Ser Ala Ser Val Gly
1               5               10              15

Asp Arg Val Thr Ile Thr Cys Arg Ala Ser His Asp Ile Ser Ser Tyr
            20              25              30

Leu Ala Trp Tyr Gln His Lys Pro Gly Lys Ala Pro Lys Leu Leu Ile
        35              40              45

His Ala Ala Ser Ile Leu Gln Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Gln Asp Leu Asn Ser Tyr Pro Leu
            85              90              95

Phe Gly Gln Gly Thr Arg Leu Glu Ile Lys Arg Ala Asp Ala Ala Pro
            100             105             110

Thr Val Ser Ile Phe Pro Pro Ser Ser Glu Gln Leu Thr Ser Gly Gly
        115             120             125

Ala Ser Val Val Cys Phe Leu Asn Asn Phe Tyr Pro Lys Asp Ile Asn
    130             135             140

Val Lys Trp Lys Ile Asp Gly Ser Glu Arg Gln Asn Gly Val Leu Asn
145             150             155             160

Ser Trp Thr Asp Gln Asp Ser Lys Asp Ser Thr Tyr Ser Met Ser Ser
            165             170             175

Thr Leu Thr Leu Thr Lys Asp Glu Tyr Glu Arg His Asn Ser Tyr Thr
            180             185             190

Cys Glu Ala Thr His Lys Thr Ser Thr Ser Pro Ile Val Lys Ser Phe
        195             200             205

Asn Arg Asn Glu Cys
    210
```

<210> SEQ ID NO 450
<211> LENGTH: 455
<212> TYPE: PRT
<213> ORGANISM: Artificial Sequence
<220> FEATURE:
<223> OTHER INFORMATION: Heavy chain (aa) (variable + constant domain).
      hIgG1

<400> SEQUENCE: 450

```
Gln Val Gln Leu Gln Gln Ser Gly Pro Gly Leu Val Lys Pro Ser Gln
1               5               10              15

Thr Leu Ser Leu Thr Cys Ala Ile Ser Gly Asp Ser Val Ser Ser Asn
            20              25              30

Ser Ala Ala Trp Asn Trp Ile Arg Gln Ser Pro Ser Arg Gly Leu Glu
```

-continued

```
              35                    40                    45
Trp Leu Gly Arg Thr Tyr Tyr Arg Ser Lys Trp Tyr Asn Asp Tyr Ala
    50                    55                    60

Val Ser Val Lys Ser Arg Ile Thr Ile Asn Pro Asp Thr Ser Lys Asn
65                    70                    75                    80

Gln Phe Ser Leu Gln Leu Asn Ser Val Thr Pro Glu Asp Thr Ala Val
                85                    90                    95

Tyr Tyr Cys Ala Arg Asp Ser Ser Ser Gly Trp His Pro Tyr Gly Met
            100                   105                   110

Asp Val Trp Gly Gln Gly Thr Thr Val Thr Val Ser Ser Ala Ser Thr
            115                   120                   125

Lys Gly Pro Ser Val Phe Pro Leu Ala Pro Ser Ser Lys Ser Thr Ser
    130                   135                   140

Gly Gly Thr Ala Ala Leu Gly Cys Leu Val Lys Asp Tyr Phe Pro Glu
145                   150                   155                   160

Pro Val Thr Val Ser Trp Asn Ser Gly Ala Leu Thr Ser Gly Val His
                165                   170                   175

Thr Phe Pro Ala Val Leu Gln Ser Ser Gly Leu Tyr Ser Leu Ser Ser
            180                   185                   190

Val Val Thr Val Pro Ser Ser Ser Leu Gly Thr Gln Thr Tyr Ile Cys
            195                   200                   205

Asn Val Asn His Lys Pro Ser Asn Thr Lys Val Asp Lys Lys Val Glu
    210                   215                   220

Pro Lys Ser Cys Asp Lys Thr His Thr Cys Pro Pro Cys Pro Ala Pro
225                   230                   235                   240

Glu Leu Leu Gly Gly Pro Ser Val Phe Leu Phe Pro Pro Lys Pro Lys
                245                   250                   255

Asp Thr Leu Met Ile Ser Arg Thr Pro Glu Val Thr Cys Val Val Val
            260                   265                   270

Asp Val Ser His Glu Asp Pro Glu Val Lys Phe Asn Trp Tyr Val Asp
            275                   280                   285

Gly Val Glu Val His Asn Ala Lys Thr Lys Pro Arg Glu Glu Gln Tyr
    290                   295                   300

Gly Ser Thr Tyr Arg Val Val Ser Val Leu Thr Val Leu His Gln Asp
305                   310                   315                   320

Trp Leu Asn Gly Lys Glu Tyr Lys Cys Lys Val Ser Asn Lys Ala Leu
                325                   330                   335

Pro Ala Pro Ile Glu Lys Thr Ile Ser Lys Ala Lys Gly Gln Pro Arg
            340                   345                   350

Glu Pro Gln Val Tyr Thr Leu Pro Pro Ser Arg Asp Glu Leu Thr Lys
            355                   360                   365

Asn Gln Val Ser Leu Thr Cys Leu Val Lys Gly Phe Tyr Pro Ser Asp
    370                   375                   380

Ile Ala Val Glu Trp Glu Ser Asn Gly Gln Pro Glu Asn Asn Tyr Lys
385                   390                   395                   400

Thr Thr Pro Pro Val Leu Asp Ser Asp Gly Ser Phe Phe Leu Tyr Ser
                405                   410                   415

Lys Leu Thr Val Asp Lys Ser Arg Trp Gln Gln Gly Asn Val Phe Ser
            420                   425                   430

Cys Ser Val Met His Glu Ala Leu His Asn His Tyr Thr Gln Lys Ser
            435                   440                   445

Leu Ser Leu Ser Pro Gly Lys
    450                   455
```

```
<210> SEQ ID NO 451
<211> LENGTH: 213
<212> TYPE: PRT
<213> ORGANISM: Artificial Sequence
<220> FEATURE:
<223> OTHER INFORMATION: Light chain (aa) (variable + constant domain).
     hIgG1

<400> SEQUENCE: 451

Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Gly Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 452
<211> LENGTH: 461
<212> TYPE: PRT
<213> ORGANISM: Artificial Sequence
<220> FEATURE:
<223> OTHER INFORMATION: Heavy chain (aa) (variable +constant domain).
     mIgG2b

<400> SEQUENCE: 452

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80
```

-continued

```
Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

Asp Val Trp Gly Gln Gly Thr Thr Val Thr Val Ser Ser Ala Lys Thr
            115                 120                 125

Thr Pro Pro Ser Val Tyr Pro Leu Ala Pro Gly Cys Gly Asp Thr Thr
        130                 135                 140

Gly Ser Ser Val Thr Leu Gly Cys Leu Val Lys Gly Tyr Phe Pro Glu
145                 150                 155                 160

Ser Val Thr Val Thr Trp Asn Ser Gly Ser Leu Ser Ser Ser Val His
                165                 170                 175

Thr Phe Pro Ala Leu Leu Gln Ser Gly Leu Tyr Thr Met Ser Ser Ser
            180                 185                 190

Val Thr Val Pro Ser Ser Thr Trp Pro Ser Gln Thr Val Thr Cys Ser
            195                 200                 205

Val Ala His Pro Ala Ser Ser Thr Thr Val Asp Lys Lys Leu Glu Pro
        210                 215                 220

Ser Gly Pro Ile Ser Thr Ile Asn Pro Cys Pro Pro Cys Lys Glu Cys
225                 230                 235                 240

His Lys Cys Pro Ala Pro Asn Leu Glu Gly Gly Pro Ser Val Phe Ile
            245                 250                 255

Phe Pro Pro Asn Ile Lys Asp Val Leu Met Ile Ser Leu Thr Pro Lys
            260                 265                 270

Val Thr Cys Val Val Val Asp Val Ser Glu Asp Asp Pro Asp Val Gln
        275                 280                 285

Ile Ser Trp Phe Val Asn Asn Val Glu Val His Thr Ala Gln Thr Gln
        290                 295                 300

Thr His Arg Glu Asp Tyr Ala Ser Thr Ile Arg Val Val Ser Thr Leu
305                 310                 315                 320

Pro Ile Gln His Gln Asp Trp Met Ser Gly Lys Glu Phe Lys Cys Lys
            325                 330                 335

Val Asn Asn Lys Asp Leu Pro Ser Pro Ile Glu Arg Thr Ile Ser Lys
            340                 345                 350

Ile Lys Gly Leu Val Arg Ala Pro Gln Val Tyr Ile Leu Pro Pro Pro
            355                 360                 365

Ala Glu Gln Leu Ser Arg Lys Asp Val Ser Leu Thr Cys Leu Val Val
        370                 375                 380

Gly Phe Asn Pro Gly Asp Ile Ser Val Glu Trp Thr Ser Asn Gly His
385                 390                 395                 400

Thr Glu Glu Asn Tyr Lys Asp Thr Ala Pro Val Leu Asp Ser Asp Gly
            405                 410                 415

Ser Tyr Phe Ile Tyr Ser Lys Leu Asn Met Lys Thr Ser Lys Trp Glu
            420                 425                 430

Lys Thr Asp Ser Phe Ser Cys Asn Val Arg His Glu Gly Leu Lys Asn
            435                 440                 445

Tyr Tyr Leu Lys Lys Thr Ile Ser Arg Ser Pro Gly Lys
    450                 455                 460
```

<210> SEQ ID NO 453
<211> LENGTH: 213
<212> TYPE: PRT
<213> ORGANISM: Artificial Sequence
<220> FEATURE:

<223> OTHER INFORMATION: Light chain (aa) (variable +constant domain).
      mIgG2b

<400> SEQUENCE: 453

Asp Ile Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asp Leu Asn Ser Tyr Pro Leu
                85                  90                  95

Phe Gly Gln Gly Thr Arg Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 454
<211> LENGTH: 455
<212> TYPE: PRT
<213> ORGANISM: Artificial Sequence
<220> FEATURE:
<223> OTHER INFORMATION: Heavy chain (aa) (variable + constant domain).
      hIgG1

<400> SEQUENCE: 454

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Ser Ser Gly Trp His Pro Tyr Gly Met
            100                 105                 110

```
Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
    450                 455
```

<210> SEQ ID NO 455
<211> LENGTH: 213
<212> TYPE: PRT
<213> ORGANISM: Artificial Sequence
<220> FEATURE:
<223> OTHER INFORMATION: Light chain (aa) (variable + constant domain).
      hIgG1

<400> SEQUENCE: 455

```
Asp Ile Gln Val Thr Gln Ser Pro Ser Phe Leu Ser Ala Ser Val Gly
1                   5                   10                  15
```

```
Asp Arg Val Thr Ile Thr Cys Arg Ala Ser His Asp Ile Ser Ser Tyr
        20              25              30

Leu Ala Trp Tyr Gln His Lys Pro Trp Lys Ala Pro Lys Leu Leu Ile
        35              40              45

His Ala Ala Ser Ile Leu Gln Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Gln Asp Leu Asn Ser Tyr Pro Leu
                85              90              95

Phe Gly Gln Gly Thr Arg Leu Glu Ile Lys Arg Thr Val Ala Ala Pro
            100             105             110

Ser Val Phe Ile Phe Pro Pro Ser Asp Glu Gln Leu Lys Ser Gly Thr
        115             120             125

Ala Ser Val Val Cys Leu Leu Asn Asn Phe Tyr Pro Arg Glu Ala Lys
        130             135             140

Val Gln Trp Lys Val Asp Asn Ala Leu Gln Ser Gly Asn Ser Gln Glu
145             150             155             160

Ser Val Thr Glu Gln Asp Ser Lys Asp Ser Thr Tyr Ser Leu Ser Ser
                165             170             175

Thr Leu Thr Leu Ser Lys Ala Asp Tyr Glu Lys His Lys Val Tyr Ala
            180             185             190

Cys Glu Val Thr His Gln Gly Leu Ser Ser Pro Val Thr Lys Ser Phe
        195             200             205

Asn Arg Gly Glu Cys
    210
```

```
<210> SEQ ID NO 456
<211> LENGTH: 454
<212> TYPE: PRT
<213> ORGANISM: Artificial Sequence
<220> FEATURE:
<223> OTHER INFORMATION: Heavy chain (aa) (variable + constant domain).
     mIgG2b

<400> SEQUENCE: 456
```

```
Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ser Tyr
        20              25              30

Ala Ile Ser Trp Val Arg Gln Ala Pro Gly Gln Gly Leu Glu Trp Met
        35              40              45

Gly Gly Ile Ile Pro Ile Phe Gly Thr Ala Asn Tyr Ala Gln Lys Phe
    50              55              60

Gln Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Asp Val Gln Arg Met Gly Met Asp Val Trp Gly Gln Gly Thr
            100             105             110

Thr Val Thr Val Ser Ser Ala Lys Thr Thr Pro Pro Ser Val Tyr Pro
        115             120             125

Leu Ala Pro Gly Cys Gly Asp Thr Thr Gly Ser Ser Val Thr Leu Gly
        130             135             140

Cys Leu Val Lys Gly Tyr Phe Pro Glu Ser Val Thr Val Thr Trp Asn
```

```
        145                150                155                160

Ser Gly Ser Leu Ser Ser Ser Val His Thr Phe Pro Ala Leu Leu Gln
                    165                170                175

Ser Gly Leu Tyr Thr Met Ser Ser Ser Val Thr Val Pro Ser Ser Thr
                    180                185                190

Trp Pro Ser Gln Thr Val Thr Cys Ser Val Ala His Pro Ala Ser Ser
                    195                200                205

Thr Thr Val Asp Lys Lys Leu Glu Pro Ser Gly Pro Ile Ser Thr Ile
            210                215                220

Asn Pro Cys Pro Pro Cys Lys Glu Cys His Lys Cys Pro Ala Pro Asn
        225                230                235                240

Leu Glu Gly Gly Pro Ser Val Phe Ile Phe Pro Pro Asn Ile Lys Asp
                    245                250                255

Val Leu Met Ile Ser Leu Thr Pro Lys Val Thr Cys Val Val Val Asp
                    260                265                270

Val Ser Glu Asp Asp Pro Asp Val Gln Ile Ser Trp Phe Val Asn Asn
                    275                280                285

Val Glu Val His Thr Ala Gln Thr Gln Thr His Arg Glu Asp Tyr Ala
            290                295                300

Ser Thr Ile Arg Val Val Ser Thr Leu Pro Ile Gln His Gln Asp Trp
        305                310                315                320

Met Ser Gly Lys Glu Phe Lys Cys Lys Val Asn Asn Lys Asp Leu Pro
                    325                330                335

Ser Pro Ile Glu Arg Thr Ile Ser Lys Ile Lys Gly Leu Val Arg Ala
                    340                345                350

Pro Gln Val Tyr Ile Leu Pro Pro Pro Ala Glu Gln Leu Ser Arg Lys
                    355                360                365

Asp Val Ser Leu Thr Cys Leu Val Val Gly Phe Asn Pro Gly Asp Ile
            370                375                380

Ser Val Glu Trp Thr Ser Asn Gly His Thr Glu Glu Asn Tyr Lys Asp
        385                390                395                400

Thr Ala Pro Val Leu Asp Ser Asp Gly Ser Tyr Phe Ile Tyr Ser Lys
                    405                410                415

Leu Asn Met Lys Thr Ser Lys Trp Glu Lys Thr Asp Ser Phe Ser Cys
                    420                425                430

Asn Val Arg His Glu Gly Leu Lys Asn Tyr Tyr Leu Lys Lys Thr Ile
                    435                440                445

Ser Arg Ser Pro Gly Lys
            450

<210> SEQ ID NO 457
<211> LENGTH: 214
<212> TYPE: PRT
<213> ORGANISM: Artificial Sequence
<220> FEATURE:
<223> OTHER INFORMATION: Light chain (aa) (variable + constant domain).
      mIgG2b

<400> SEQUENCE: 457

Asp Ile Gln Met Thr Gln Ser Pro Ser Ser Val Ser Thr Ser Val Gly
        1                5                10                15

Asp Arg Val Thr Ile Thr Cys Arg Ala Ser Gln Asp Ile Ser Asn Trp
                    20                25                30

Leu Ala Trp Tyr Gln Gln Lys Pro Gly Lys Ala Pro Lys Leu Leu Ile
                    35                40                45
```

Tyr Asp Ser Ser Thr Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 458
<211> LENGTH: 448
<212> TYPE: PRT
<213> ORGANISM: Artificial Sequence
<220> FEATURE:
<223> OTHER INFORMATION: Heavy chain (aa) (variable + constant domain).
      hIgG1

<400> SEQUENCE: 458

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gln Arg Met Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

-continued

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Gly Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

<210> SEQ ID NO 459
<211> LENGTH: 214
<212> TYPE: PRT
<213> ORGANISM: Artificial Sequence
<220> FEATURE:
<223> OTHER INFORMATION: Light chain (aa) (variable + constant domain).
     hIgG1

<400> SEQUENCE: 459

```
Asp Ile Gln Met Thr Gln Ser Pro Ser Ser Val Ser Thr Ser Val Gly
1               5                   10                  15

Asp Arg Val Thr Ile Thr Cys Arg Ala Ser Gln Asp Ile Ser Asn Trp
                20                  25                  30

Leu Ala Trp Tyr Gln Gln Lys Pro Gly Lys Ala Pro Lys Leu Leu Ile
        35                  40                  45

Tyr Asp Ser Ser Thr Leu Gln Ser Gly Val Pro Ser Arg Phe Ser Gly
        50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys Arg Thr Val Ala Ala
```

-continued

```
                    100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 460
<211> LENGTH: 463
<212> TYPE: PRT
<213> ORGANISM: Artificial Sequence
<220> FEATURE:
<223> OTHER INFORMATION: Heavy chain (aa) (variable + constant domain).
      mIgG2b

<400> SEQUENCE: 460

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Ala Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Asn Thr Tyr Cys Ser Gly Gly Ser Cys Tyr Ser Pro
            100                 105                 110

His Phe Asp Tyr Trp Gly Gln Gly Thr Leu Val Thr Val Ser Ser Ala
            115                 120                 125

Lys Thr Thr Pro Pro Ser Val Tyr Pro Leu Ala Pro Gly Cys Gly Asp
    130                 135                 140

Thr Thr Gly Ser Ser Val Thr Leu Gly Cys Leu Val Lys Gly Tyr Phe
145                 150                 155                 160

Pro Glu Ser Val Thr Val Thr Trp Asn Ser Gly Ser Leu Ser Ser Ser
                165                 170                 175

Val His Thr Phe Pro Ala Leu Leu Gln Ser Gly Leu Tyr Thr Met Ser
                180                 185                 190

Ser Ser Val Thr Val Pro Ser Ser Thr Trp Pro Ser Gln Thr Val Thr
            195                 200                 205

Cys Ser Val Ala His Pro Ala Ser Ser Thr Thr Val Asp Lys Lys Leu
    210                 215                 220

Glu Pro Ser Gly Pro Ile Ser Thr Ile Asn Pro Cys Pro Pro Cys Lys
225                 230                 235                 240
```

Glu Cys His Lys Cys Pro Ala Pro Asn Leu Glu Gly Gly Pro Ser Val
                245                 250                 255

Phe Ile Phe Pro Pro Asn Ile Lys Asp Val Leu Met Ile Ser Leu Thr
                260                 265                 270

Pro Lys Val Thr Cys Val Val Val Asp Val Ser Glu Asp Asp Pro Asp
                275                 280                 285

Val Gln Ile Ser Trp Phe Val Asn Asn Val Glu Val His Thr Ala Gln
        290                 295                 300

Thr Gln Thr His Arg Glu Asp Tyr Ala Ser Thr Ile Arg Val Val Ser
305                 310                 315                 320

Thr Leu Pro Ile Gln His Gln Asp Trp Met Ser Gly Lys Glu Phe Lys
                325                 330                 335

Cys Lys Val Asn Asn Lys Asp Leu Pro Ser Pro Ile Glu Arg Thr Ile
                340                 345                 350

Ser Lys Ile Lys Gly Leu Val Arg Ala Pro Gln Val Tyr Ile Leu Pro
                355                 360                 365

Pro Pro Ala Glu Gln Leu Ser Arg Lys Asp Val Ser Leu Thr Cys Leu
        370                 375                 380

Val Val Gly Phe Asn Pro Gly Asp Ile Ser Val Glu Trp Thr Ser Asn
385                 390                 395                 400

Gly His Thr Glu Glu Asn Tyr Lys Asp Thr Ala Pro Val Leu Asp Ser
                405                 410                 415

Asp Gly Ser Tyr Phe Ile Tyr Ser Lys Leu Asn Met Lys Thr Ser Lys
                420                 425                 430

Trp Glu Lys Thr Asp Ser Phe Ser Cys Asn Val Arg His Glu Gly Leu
                435                 440                 445

Lys Asn Tyr Tyr Leu Lys Lys Thr Ile Ser Arg Ser Pro Gly Lys
        450                 455                 460

<210> SEQ ID NO 461
<211> LENGTH: 213
<212> TYPE: PRT
<213> ORGANISM: Artificial Sequence
<220> FEATURE:
<223> OTHER INFORMATION: Light chain (aa) (variable + constant domain).
    mIgG2b

<400> SEQUENCE: 461

Asp Ile Gln Val Thr Gln Ser Pro Ser Ser Leu Ser Ala Ser Val Gly
1                 5                 10                 15

Asp Arg Val Thr Ile Thr Cys Gln Ala Ser Gln Asp Ile Ser Asn Tyr
                20                 25                 30

Leu Asn Trp Tyr Gln Gln Lys Pro Gly Lys Ala Pro Lys Leu Leu Ile
        35                 40                 45

Tyr Asp Ala Ser Asn Leu Glu Thr Gly Val Pro Ser Arg Phe Ser Gly
        50                 55                 60

Ser Gly Ser Gly Thr Asp Phe Thr Phe Thr Ile Ser Ser Leu Gln Pro
65                 70                 75                 80

Glu Asp Ile Ala Thr Tyr Tyr Cys Gln Gln Tyr Asp Asn Leu Pro Thr
                85                 90                 95

Phe Gly Gly Gly Thr Lys Val Glu Ile Lys Arg Ala Asp Ala Ala Pro
                100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
        130                 135                 140

-continued

```
Val Lys Trp Lys Ile Asp Gly Ser Glu Arg Gln Asn Gly Val Leu Asn
145             150             155             160

Ser Trp Thr Asp Gln Asp Ser Lys Asp Ser Thr Tyr Ser Met Ser Ser
                165             170             175

Thr Leu Thr Leu Thr Lys Asp Glu Tyr Glu Arg His Asn Ser Tyr Thr
            180             185             190

Cys Glu Ala Thr His Lys Thr Ser Thr Ser Pro Ile Val Lys Ser Phe
        195             200             205

Asn Arg Asn Glu Cys
    210

<210> SEQ ID NO 462
<211> LENGTH: 457
<212> TYPE: PRT
<213> ORGANISM: Artificial Sequence
<220> FEATURE:
<223> OTHER INFORMATION: Heavy chain (aa) (variable + constant domain).
    hIgG1

<400> SEQUENCE: 462

Gln Val Gln Leu Val Glu Ser Gly Ala Glu Val Lys Lys Pro Gly Ser
1               5               10              15

Ser Val Lys Val Ser Cys Lys Ala Ser Gly Gly Thr Phe Ser Ser Tyr
            20              25              30

Ala Ile Ser Trp Val Arg Gln Ala Pro Gly Gln Gly Leu Glu Trp Met
        35              40              45

Gly Gly Ile Ile Pro Ile Phe Gly Thr Ala Asn Tyr Ala Gln Lys Phe
    50              55              60

Gln Gly Arg Ala Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Gly Arg Asn Thr Tyr Cys Ser Gly Gly Ser Cys Tyr Ser Pro
            100             105             110

His Phe Asp Tyr Trp Gly Gln Gly Thr Leu Val Thr Val Ser Ser Ala
        115             120             125

Ser Thr Lys Gly Pro Ser Val Phe Pro Leu Ala Pro Ser Ser Lys Ser
    130             135             140

Thr Ser Gly Gly Thr Ala Ala Leu Gly Cys Leu Val Lys Asp Tyr Phe
145             150             155             160

Pro Glu Pro Val Thr Val Ser Trp Asn Ser Gly Ala Leu Thr Ser Gly
                165             170             175

Val His Thr Phe Pro Ala Val Leu Gln Ser Ser Gly Leu Tyr Ser Leu
            180             185             190

Ser Ser Val Val Thr Val Pro Ser Ser Ser Leu Gly Thr Gln Thr Tyr
            195             200             205

Ile Cys Asn Val Asn His Lys Pro Ser Asn Thr Lys Val Asp Lys Lys
    210             215             220

Val Glu Pro Lys Ser Cys Asp Lys Thr His Thr Cys Pro Pro Cys Pro
225             230             235             240

Ala Pro Glu Leu Leu Gly Gly Pro Ser Val Phe Leu Phe Pro Pro Lys
            245             250             255

Pro Lys Asp Thr Leu Met Ile Ser Arg Thr Pro Glu Val Thr Cys Val
            260             265             270

Val Val Asp Val Ser His Glu Asp Pro Glu Val Lys Phe Asn Trp Tyr
```

-continued

```
              275                 280                 285
Val Asp Gly Val Glu Val His Asn Ala Lys Thr Lys Pro Arg Glu Glu
    290                 295                 300

Gln Tyr Gly Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Asp Glu Leu
                355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
    450                 455

<210> SEQ ID NO 463
<211> LENGTH: 213
<212> TYPE: PRT
<213> ORGANISM: Artificial Sequence
<220> FEATURE:
<223> OTHER INFORMATION: Light chain (aa) (variable + constant domain).
    hIgG1

<400> SEQUENCE: 463

Asp Ile Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 464
<211> LENGTH: 459
<212> TYPE: PRT
<213> ORGANISM: Artificial Sequence
<220> FEATURE:
<223> OTHER INFORMATION: Heavy chain (aa) (variable + constant domain).
      mIgG2b

<400> SEQUENCE: 464
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Val Leu Ile Trp Thr Tyr Tyr Tyr Gly Met Asp Val
        100                 105                 110

Trp Gly Gln Gly Thr Thr Val Thr Val Ser Ser Ala Lys Thr Thr Pro
        115                 120                 125

Pro Ser Val Tyr Pro Leu Ala Pro Gly Cys Gly Asp Thr Thr Gly Ser
        130                 135                 140

Ser Val Thr Leu Gly Cys Leu Val Lys Gly Tyr Phe Pro Glu Ser Val
145                 150                 155                 160

Thr Val Thr Trp Asn Ser Gly Ser Leu Ser Ser Ser Val His Thr Phe
                165                 170                 175

Pro Ala Leu Leu Gln Ser Gly Leu Tyr Thr Met Ser Ser Ser Val Thr
        180                 185                 190

Val Pro Ser Ser Thr Trp Pro Ser Gln Thr Val Thr Cys Ser Val Ala
        195                 200                 205

His Pro Ala Ser Ser Thr Thr Val Asp Lys Lys Leu Glu Pro Ser Gly
        210                 215                 220

Pro Ile Ser Thr Ile Asn Pro Cys Pro Pro Cys Lys Glu Cys His Lys
225                 230                 235                 240

Cys Pro Ala Pro Asn Leu Glu Gly Gly Pro Ser Val Phe Ile Phe Pro
                245                 250                 255

Pro Asn Ile Lys Asp Val Leu Met Ile Ser Leu Thr Pro Lys Val Thr
                260                 265                 270

Cys Val Val Val Asp Val Ser Glu Asp Asp Pro Asp Val Gln Ile Ser
        275                 280                 285

Trp Phe Val Asn Asn Val Glu Val His Thr Ala Gln Thr Gln Thr His
        290                 295                 300

Arg Glu Asp Tyr Ala Ser Thr Ile Arg Val Val Ser Thr Leu Pro Ile
305                 310                 315                 320
```

-continued

```
Gln His Gln Asp Trp Met Ser Gly Lys Glu Phe Lys Cys Lys Val Asn
              325             330             335

Asn Lys Asp Leu Pro Ser Pro Ile Glu Arg Thr Ile Ser Lys Ile Lys
              340             345             350

Gly Leu Val Arg Ala Pro Gln Val Tyr Ile Leu Pro Pro Ala Glu
              355             360             365

Gln Leu Ser Arg Lys Asp Val Ser Leu Thr Cys Leu Val Val Gly Phe
    370             375             380

Asn Pro Gly Asp Ile Ser Val Glu Trp Thr Ser Asn Gly His Thr Glu
385             390             395             400

Glu Asn Tyr Lys Asp Thr Ala Pro Val Leu Asp Ser Asp Gly Ser Tyr
              405             410             415

Phe Ile Tyr Ser Lys Leu Asn Met Lys Thr Ser Lys Trp Glu Lys Thr
              420             425             430

Asp Ser Phe Ser Cys Asn Val Arg His Glu Gly Leu Lys Asn Tyr Tyr
              435             440             445

Leu Lys Lys Thr Ile Ser Arg Ser Pro Gly Lys
    450             455
```

<210> SEQ ID NO 465
<211> LENGTH: 214
<212> TYPE: PRT
<213> ORGANISM: Artificial Sequence
<220> FEATURE:
<223> OTHER INFORMATION: Light chain (aa) (variable + constant domain).
     mIgG2b

<400> SEQUENCE: 465

```
Asp Ile Arg Leu Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
              20              25              30

Leu Asn Trp Tyr Gln Gln Lys Pro Gly Lys Ala Pro Lys Leu Leu Ile
              35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Ile Ile Ser Ser Leu Gln Pro
65              70              75              80

Glu Asp Ile Ala Thr Tyr Tyr Cys Gln Gln Tyr Asp Asn Leu Pro Leu
              85              90              95

Thr Phe Gly Gly Gly Thr Lys Leu Glu Ile Lys Arg Ala Asp Ala Ala
              100             105             110

Pro Thr Val Ser Ile Phe Pro Pro Ser Ser Glu Gln Leu Thr Ser Gly
              115             120             125

Gly Ala Ser Val Val Cys Phe Leu Asn Asn Phe Tyr Pro Lys Asp Ile
    130             135             140

Asn Val Lys Trp Lys Ile Asp Gly Ser Glu Arg Gln Asn Gly Val Leu
145             150             155             160

Asn Ser Trp Thr Asp Gln Asp Ser Lys Asp Ser Thr Tyr Ser Met Ser
              165             170             175

Ser Thr Leu Thr Leu Thr Lys Asp Glu Tyr Glu Arg His Asn Ser Tyr
              180             185             190

Thr Cys Glu Ala Thr His Lys Thr Ser Thr Ser Pro Ile Val Lys Ser
              195             200             205

Phe Asn Arg Asn Glu Cys
```

-continued

210

<210> SEQ ID NO 466
<211> LENGTH: 453
<212> TYPE: PRT
<213> ORGANISM: Artificial Sequence
<220> FEATURE:
<223> OTHER INFORMATION: Heavy chain (aa) (variable + constant domain).
      hIgG1

<400> SEQUENCE: 466

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Val Leu Ile Trp Thr Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

-continued

```
Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro Gly Lys
        450
```

```
<210> SEQ ID NO 467
<211> LENGTH: 214
<212> TYPE: PRT
<213> ORGANISM: Artificial Sequence
<220> FEATURE:
<223> OTHER INFORMATION: Light chain (aa) (variable + constant domain).
      hIgG1

<400> SEQUENCE: 467
```

```
Asp Ile Arg Leu Thr Gln Ser Pro Ser Ser Leu Ser Ala Ser Val Gly
1                   5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Ile Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210
```

```
<210> SEQ ID NO 468
<211> LENGTH: 336
<212> TYPE: PRT
<213> ORGANISM: Mouse
```

407

408

```
<400> SEQUENCE: 468

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
            115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
            165                 170                 175

Gln Thr Gln Thr His Arg Glu Asp Tyr Ala Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
            245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
            325                 330                 335

<210> SEQ ID NO 469
<211> LENGTH: 106
<212> TYPE: PRT
<213> ORGANISM: Mouse

<400> SEQUENCE: 469

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30
```

-continued

```
Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
        50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
                100                 105

<210> SEQ ID NO 470
<211> LENGTH: 330
<212> TYPE: PRT
<213> ORGANISM: Human

<400> SEQUENCE: 470

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
```

```
                290              295              300
Val Phe Ser Cys Ser Val Met His Glu Ala Leu His Asn His Tyr Thr
305                 310              315              320

Gln Lys Ser Leu Ser Leu Ser Pro Gly Lys
                325              330

<210> SEQ ID NO 471
<211> LENGTH: 106
<212> TYPE: PRT
<213> ORGANISM: Human

<400> SEQUENCE: 471

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 472
<211> LENGTH: 9
<212> TYPE: PRT
<213> ORGANISM: Artificial Sequence
<220> FEATURE:
<223> OTHER INFORMATION: DQ2.5-glia-alpha1a

<400> SEQUENCE: 472

Pro Phe Pro Gln Pro Glu Leu Pro Tyr
1               5

<210> SEQ ID NO 473
<211> LENGTH: 9
<212> TYPE: PRT
<213> ORGANISM: Artificial Sequence
<220> FEATURE:
<223> OTHER INFORMATION: DQ2.5-glia-alpha2

<400> SEQUENCE: 473

Pro Gln Pro Glu Leu Pro Tyr Pro Gln
1               5

<210> SEQ ID NO 474
<211> LENGTH: 12
<212> TYPE: PRT
<213> ORGANISM: Artificial Sequence
<220> FEATURE:
<223> OTHER INFORMATION: DQ2.5-glia-alpha1a plus flanking residues

<400> SEQUENCE: 474

Gln Leu Gln Pro Phe Pro Gln Pro Glu Leu Pro Tyr
1               5                   10

<210> SEQ ID NO 475
<211> LENGTH: 11
```

```
<212> TYPE: PRT
<213> ORGANISM: Artificial Sequence
<220> FEATURE:
<223> OTHER INFORMATION: DQ2.5-glia-alpha2 plus flanking residues

<400> SEQUENCE: 475

Pro Gln Pro Glu Leu Pro Tyr Pro Gln Pro Glu
1               5                   10

<210> SEQ ID NO 476
<211> LENGTH: 33
<212> TYPE: PRT
<213> ORGANISM: Artificial Sequence
<220> FEATURE:
<223> OTHER INFORMATION: alpha-gliadin 33-mer peptide

<400> SEQUENCE: 476

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 477
<211> LENGTH: 9
<212> TYPE: PRT
<213> ORGANISM: Artificial Sequence
<220> FEATURE:
<223> OTHER INFORMATION: DQ2.5-glia-omega1

<400> SEQUENCE: 477

Pro Phe Pro Gln Pro Glu Gln Pro Phe
1               5

<210> SEQ ID NO 478
<211> LENGTH: 9
<212> TYPE: PRT
<213> ORGANISM: Artificial Sequence
<220> FEATURE:
<223> OTHER INFORMATION: DQ2.5-glia-omega2

<400> SEQUENCE: 478

Pro Gln Pro Glu Gln Pro Phe Pro Trp
1               5

<210> SEQ ID NO 479
<211> LENGTH: 12
<212> TYPE: PRT
<213> ORGANISM: Artificial Sequence
<220> FEATURE:
<223> OTHER INFORMATION: DQ2.5-glia-omega1 plus flanking sequence

<400> SEQUENCE: 479

Gln Gln Pro Phe Pro Gln Pro Glu Gln Pro Phe Pro
1               5                   10

<210> SEQ ID NO 480
<211> LENGTH: 12
<212> TYPE: PRT
<213> ORGANISM: Artificial Sequence
<220> FEATURE:
<223> OTHER INFORMATION: DQ2.5-glia-omega2 plus flanking sequence

<400> SEQUENCE: 480

Phe Pro Gln Pro Glu Gln Pro Phe Pro Trp Gln Pro
1               5                   10
```

```
<210> SEQ ID NO 481
<211> LENGTH: 9
<212> TYPE: PRT
<213> ORGANISM: Artificial Sequence
<220> FEATURE:
<223> OTHER INFORMATION: DQ2.5-glia-gamma1

<400> SEQUENCE: 481

Pro Gln Gln Ser Phe Pro Glu Gln Glu
1               5

<210> SEQ ID NO 482
<211> LENGTH: 14
<212> TYPE: PRT
<213> ORGANISM: Artificial Sequence
<220> FEATURE:
<223> OTHER INFORMATION: DQ2.5-glia-gamma1 plus flanking sequence

<400> SEQUENCE: 482

Pro Glu Gln Pro Gln Gln Ser Phe Pro Glu Gln Glu Arg Pro
1               5                   10

<210> SEQ ID NO 483
<211> LENGTH: 9
<212> TYPE: PRT
<213> ORGANISM: Artificial Sequence
<220> FEATURE:
<223> OTHER INFORMATION: DQ2.5-glia-gamma2

<400> SEQUENCE: 483

Ile Gln Pro Glu Gln Pro Ala Gln Leu
1               5

<210> SEQ ID NO 484
<211> LENGTH: 12
<212> TYPE: PRT
<213> ORGANISM: Artificial Sequence
<220> FEATURE:
<223> OTHER INFORMATION: DQ2.5-glia-gamma2 plus flanking sequence

<400> SEQUENCE: 484

Gln Gly Ile Ile Gln Pro Glu Gln Pro Ala Gln Leu
1               5                   10

<210> SEQ ID NO 485
<211> LENGTH: 9
<212> TYPE: PRT
<213> ORGANISM: Artificial Sequence
<220> FEATURE:
<223> OTHER INFORMATION: DQ2.5-glia-gamma3

<400> SEQUENCE: 485

Glu Gln Pro Glu Gln Pro Tyr Pro Gln
1               5

<210> SEQ ID NO 486
<211> LENGTH: 11
<212> TYPE: PRT
<213> ORGANISM: Artificial Sequence
<220> FEATURE:
<223> OTHER INFORMATION: DQ2.5-glia-gamma3 plus flanking sequence

<400> SEQUENCE: 486

Thr Glu Gln Pro Glu Gln Pro Tyr Pro Gln Pro
1               5                   10
```

-continued

<210> SEQ ID NO 487
<211> LENGTH: 9
<212> TYPE: PRT
<213> ORGANISM: Artificial Sequence
<220> FEATURE:
<223> OTHER INFORMATION: DQ2.5-glia-gamma4c

<400> SEQUENCE: 487

Glu Gln Pro Glu Gln Pro Phe Pro Gln
1               5

<210> SEQ ID NO 488
<211> LENGTH: 11
<212> TYPE: PRT
<213> ORGANISM: Artificial Sequence
<220> FEATURE:
<223> OTHER INFORMATION: DQ2.5-glia-gamma4c plus flanking sequence

<400> SEQUENCE: 488

Thr Glu Gln Pro Glu Gln Pro Phe Pro Gln Pro
1               5                   10

<210> SEQ ID NO 489
<211> LENGTH: 9
<212> TYPE: PRT
<213> ORGANISM: Artificial Sequence
<220> FEATURE:
<223> OTHER INFORMATION: CLIP2

<400> SEQUENCE: 489

Pro Leu Leu Met Gln Ala Leu Pro Met
1               5

<210> SEQ ID NO 490
<211> LENGTH: 16
<212> TYPE: PRT
<213> ORGANISM: Artificial Sequence
<220> FEATURE:
<223> OTHER INFORMATION: CLIP2 plus flanking sequence

<400> SEQUENCE: 490

Met Ala Thr Pro Leu Leu Met Gln Ala Leu Pro Met Met Gly Ala Leu
1               5                   10                  15

<210> SEQ ID NO 491
<211> LENGTH: 9
<212> TYPE: PRT
<213> ORGANISM: Artificial Sequence
<220> FEATURE:
<223> OTHER INFORMATION: DQ2.5-glia-alpha1a (native form or
      non-deamidated form)

<400> SEQUENCE: 491

Pro Phe Pro Gln Pro Gln Leu Pro Tyr
1               5

<210> SEQ ID NO 492
<211> LENGTH: 9
<212> TYPE: PRT
<213> ORGANISM: Artificial Sequence
<220> FEATURE:
<223> OTHER INFORMATION: DQ2.5-glia-alpha2 (native form or
      non-deamidated form)

<400> SEQUENCE: 492

Pro Gln Pro Gln Leu Pro Tyr Pro Gln
1               5

```
<210> SEQ ID NO 493
<211> LENGTH: 229
<212> TYPE: PRT
<213> ORGANISM: Human

<400> SEQUENCE: 493

Ile Val Ala Asp His Val Ala Ser Tyr Gly Val Asn Leu Tyr Gln Ser
1               5                   10                  15

Tyr Gly Pro Ser Gly Gln Tyr Thr His Glu Phe Asp Gly Asp Glu Gln
                20                  25                  30

Phe Tyr Val Asp Leu Gly Arg Lys Glu Thr Val Trp Cys Leu Pro Val
            35                  40                  45

Leu Arg Gln Phe Arg Phe Asp Pro Gln Phe Ala Leu Thr Asn Ile Ala
        50                  55                  60

Val Leu Lys His Asn Leu Asn Ser Leu Ile Lys Arg Ser Asn Ser Thr
65                  70                  75                  80

Ala Ala Thr Asn Glu Val Pro Glu Val Thr Val Phe Ser Lys Ser Pro
                85                  90                  95

Val Thr Leu Gly Gln Pro Asn Ile Leu Ile Cys Leu Val Asp Asn Ile
            100                 105                 110

Phe Pro Pro Val Val Asn Ile Thr Trp Leu Ser Asn Gly His Ser Val
            115                 120                 125

Thr Glu Gly Val Ser Glu Thr Ser Phe Leu Ser Lys Ser Asp His Ser
        130                 135                 140

Phe Phe Lys Ile Ser Tyr Leu Thr Leu Leu Pro Ser Ala Glu Glu Ser
145                 150                 155                 160

Tyr Asp Cys Lys Val Glu His Trp Gly Leu Asp Lys Pro Leu Leu Lys
                165                 170                 175

His Trp Glu Pro Glu Ile Pro Ala Pro Met Ser Glu Leu Thr Glu Thr
                180                 185                 190

Val Val Cys Ala Leu Gly Leu Ser Val Gly Leu Val Gly Ile Val Val
                195                 200                 205

Gly Thr Val Phe Ile Ile Arg Gly Leu Arg Ser Val Gly Ala Ser Arg
    210                 215                 220

His Gln Gly Pro Leu
225

<210> SEQ ID NO 494
<211> LENGTH: 229
<212> TYPE: PRT
<213> ORGANISM: Human

<400> SEQUENCE: 494

Arg Asp Ser Pro Glu Asp Phe Val Tyr Gln Phe Lys Gly Met Cys Tyr
1               5                   10                  15

Phe Thr Asn Gly Thr Glu Arg Val Arg Leu Val Ser Arg Ser Ile Tyr
                20                  25                  30

Asn Arg Glu Glu Ile Val Arg Phe Asp Ser Asp Val Gly Glu Phe Arg
            35                  40                  45

Ala Val Thr Leu Leu Gly Leu Pro Ala Ala Glu Tyr Trp Asn Ser Gln
        50                  55                  60

Lys Asp Ile Leu Glu Arg Lys Arg Ala Ala Val Asp Arg Val Cys Arg
65                  70                  75                  80

His Asn Tyr Gln Leu Glu Leu Arg Thr Thr Leu Gln Arg Arg Val Glu
                85                  90                  95
```

-continued

```
Pro Thr Val Thr Ile Ser Pro Ser Arg Thr Glu Ala Leu Asn His His
            100             105             110

Asn Leu Leu Val Cys Ser Val Thr Asp Phe Tyr Pro Ala Gln Ile Lys
        115             120             125

Val Arg Trp Phe Arg Asn Asp Gln Glu Glu Thr Ala Gly Val Val Ser
    130             135             140

Thr Pro Leu Ile Arg Asn Gly Asp Trp Thr Phe Gln Ile Leu Val Met
145             150             155             160

Leu Glu Met Thr Pro Gln Arg Gly Asp Val Tyr Thr Cys His Val Glu
            165             170             175

His Pro Ser Leu Gln Ser Pro Ile Thr Val Glu Trp Arg Ala Gln Ser
        180             185             190

Glu Ser Ala Gln Ser Lys Met Leu Ser Gly Ile Gly Gly Phe Val Leu
        195             200             205

Gly Leu Ile Phe Leu Gly Leu Gly Leu Ile Ile His His Arg Ser Gln
    210             215             220

Lys Gly Leu Leu His
225
```

```
<210> SEQ ID NO 495
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha2 specifically described affinity matured
      antibodies described herein (Tables R-W).
<220> FEATURE:
<221> NAME/KEY: MISC_FEATURE
<222> LOCATION: (4)..(4)
<223> OTHER INFORMATION: F or S or N or V or G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: Y or F or R or G
<220> FEATURE:
<221> NAME/KEY: MISC_FEATURE
<222> LOCATION: (8)..(8)
<223> OTHER INFORMATION: I or Y or V or M
<220> FEATURE:
<221> NAME/KEY: MISC_FEATURE
<222> LOCATION: (9)..(9)
<223> OTHER INFORMATION: no amino acid or G  or Y or H or S
<220> FEATURE:
<221> NAME/KEY: MISC_FEATURE
<222> LOCATION: (10)..(10)
<223> OTHER INFORMATION: no amino acid or A or G
<220> FEATURE:
<221> NAME/KEY: MISC_FEATURE
<222> LOCATION: (11)..(11)
<223> OTHER INFORMATION: no amino acid or A

<400> SEQUENCE: 495

Gly Gly Thr Xaa Xaa Xaa Xaa Xaa Xaa Xaa Xaa
1               5                   10

<210> SEQ ID NO 496
<211> LENGTH: 375
<212> TYPE: DNA
```

<213> ORGANISM: Artificial Sequence
<220> FEATURE:
<223> OTHER INFORMATION: RF117 VH domain (nt)

<400> SEQUENCE: 496
caggtacagc tgcagcagtc aggtccagga ctggtgaagc cctcgcagac cctctcactc      60
acctgtgcca tctccgggga cagtgtctct agcagcagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagatagga ctactgggtg gcatccgtat ggtatggacg tctggggcca agggaccacg     360
gtcaccgtct cctca                                                     375

<210> SEQ ID NO 497
<211> LENGTH: 318
<212> TYPE: DNA
<213> ORGANISM: Artificial Sequence
<220> FEATURE:
<223> OTHER INFORMATION: RF117 VL domain (nt)

<400> SEQUENCE: 497
gacgtccagg tgacccagtc tccatccttc ctgtctgcat ctgtaggaga cagagtcacc      60
atcacttgcc gggccagtca cgacattagc agttatttag cctggtatca acacaaaccg     120
tggaaagccc ccaaactcct gatccatgct gcatccgttt tgcaaagtgg ggtcccatca     180
aggttcagcg gaagtggatc tgggacagaa ttcactctca caatcagcag cctgcagcct     240
gaagattttg caacgtacta ctgtcaaaat ctcaatagtt atcctctctt cggccaaggg     300
acacgactgg agattaaa                                                  318

<210> SEQ ID NO 498
<211> LENGTH: 125
<212> TYPE: PRT
<213> ORGANISM: Artificial Sequence
<220> FEATURE:
<223> OTHER INFORMATION: RF117 VH domain (aa)

<400> SEQUENCE: 498

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Thr Thr Gly Trp His Pro Tyr Gly Met
            100                 105                 110

Asp Val Trp Gly Gln Gly Thr Thr Val Thr Val Ser Ser
        115                 120                 125

<210> SEQ ID NO 499
<211> LENGTH: 106

```
<212> TYPE: PRT
<213> ORGANISM: Artificial Sequence
<220> FEATURE:
<223> OTHER INFORMATION: RF117 VL domain (aa)

<400> SEQUENCE: 499

Asp Val Gln Val Thr Gln Ser Pro Ser Phe Leu Ser Ala Ser Val Gly
1               5                   10                  15

Asp Arg Val Thr Ile Thr Cys Arg Ala Ser His Asp Ile Ser Ser Tyr
            20                  25                  30

Leu Ala Trp Tyr Gln His Lys Pro Trp Lys Ala Pro Lys Leu Leu Ile
        35                  40                  45

His Ala Ala Ser Val Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asn Leu Asn Ser Tyr Pro Leu
                85                  90                  95

Phe Gly Gln Gly Thr Arg Leu Glu Ile Lys
            100                 105

<210> SEQ ID NO 500
<211> LENGTH: 10
<212> TYPE: PRT
<213> ORGANISM: Human

<400> SEQUENCE: 500

Gly Asp Ser Val Ser Ser Ser Ser Ala Ala
1               5                   10

<210> SEQ ID NO 501
<211> LENGTH: 9
<212> TYPE: PRT
<213> ORGANISM: Human

<400> SEQUENCE: 501

Thr Tyr Tyr Arg Ser Lys Trp Tyr Asn
1               5

<210> SEQ ID NO 502
<211> LENGTH: 15
<212> TYPE: PRT
<213> ORGANISM: Human

<400> SEQUENCE: 502

Ala Arg Asp Arg Thr Thr Gly Trp His Pro Tyr Gly Met Asp Val
1               5                   10                  15

<210> SEQ ID NO 503
<211> LENGTH: 6
<212> TYPE: PRT
<213> ORGANISM: Human

<400> SEQUENCE: 503

His Asp Ile Ser Ser Tyr
1               5

<210> SEQ ID NO 504
<211> LENGTH: 3
<212> TYPE: PRT
<213> ORGANISM: Human

<400> SEQUENCE: 504
```

Ala Ala Ser
1

<210> SEQ ID NO 505
<211> LENGTH: 8
<212> TYPE: PRT
<213> ORGANISM: Human

<400> SEQUENCE: 505

Gln Asn Leu Asn Ser Tyr Pro Leu
1               5

<210> SEQ ID NO 506
<211> LENGTH: 25
<212> TYPE: PRT
<213> ORGANISM: Human

<400> SEQUENCE: 506

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 507
<211> LENGTH: 17
<212> TYPE: PRT
<213> ORGANISM: Human

<400> SEQUENCE: 507

Trp Asn Trp Ile Arg Gln Ser Pro Ser Arg Gly Leu Glu Trp Leu Gly
1               5                   10                  15

Arg

<210> SEQ ID NO 508
<211> LENGTH: 38
<212> TYPE: PRT
<213> ORGANISM: Human

<400> SEQUENCE: 508

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
            35

<210> SEQ ID NO 509
<211> LENGTH: 11
<212> TYPE: PRT
<213> ORGANISM: Human

<400> SEQUENCE: 509

Trp Gly Gln Gly Thr Thr Val Thr Val Ser Ser
1               5                   10

<210> SEQ ID NO 510
<211> LENGTH: 26
<212> TYPE: PRT
<213> ORGANISM: Human

<400> SEQUENCE: 510

Asp Val Gln Val Thr Gln Ser Pro Ser Phe Leu Ser Ala Ser Val Gly

```
1               5                   10                  15

Asp Arg Val Thr Ile Thr Cys Arg Ala Ser
            20                  25
```

```
<210> SEQ ID NO 511
<211> LENGTH: 17
<212> TYPE: PRT
<213> ORGANISM: Human

<400> SEQUENCE: 511

Leu Ala Trp Tyr Gln His Lys Pro Trp Lys Ala Pro Lys Leu Leu Ile
1               5                   10                  15

His
```

```
<210> SEQ ID NO 512
<211> LENGTH: 36
<212> TYPE: PRT
<213> ORGANISM: Human

<400> SEQUENCE: 512

Val Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35
```

```
<210> SEQ ID NO 513
<211> LENGTH: 10
<212> TYPE: PRT
<213> ORGANISM: Human

<400> SEQUENCE: 513

Phe Gly Gln Gly Thr Arg Leu Glu Ile Lys
1               5                   10
```

```
<210> SEQ ID NO 514
<211> LENGTH: 455
<212> TYPE: PRT
<213> ORGANISM: Artificial Sequence
<220> FEATURE:
<223> OTHER INFORMATION: Heavy chain (aa) (variable + constant domain).
      hIgG1

<400> SEQUENCE: 514

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Thr Thr Gly Trp His Pro Tyr Gly Met
            100                 105                 110

Asp Val Trp Gly Gln Gly Thr Thr Val Thr Val Ser Ser Ala Ser Thr
```

```
              115                 120                 125
Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
    450                 455

<210> SEQ ID NO 515
<211> LENGTH: 213
<212> TYPE: PRT
<213> ORGANISM: Artificial Sequence
<220> FEATURE:
<223> OTHER INFORMATION: Light chain (aa) (variable + constant domain).
      hIgG1

<400> SEQUENCE: 515

Asp Val Gln Val Thr Gln Ser Pro Ser Phe Leu Ser Ala Ser Val Gly
1               5                   10                  15
```

```
Asp Arg Val Thr Ile Thr Cys Arg Ala Ser His Asp Ile Ser Ser Tyr
        20                  25                  30

Leu Ala Trp Tyr Gln His Lys Pro Trp Lys Ala Pro Lys Leu Leu Ile
        35                  40                  45

His Ala Ala Ser Val Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asn Leu Asn Ser Tyr Pro Leu
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 516
<211> LENGTH: 17
<212> TYPE: DNA
<213> ORGANISM: Artificial Sequence
<220> FEATURE:
<223> OTHER INFORMATION: Primer scTCR_fw

<400> SEQUENCE: 516
ctcagccggc catggcc                                              17

<210> SEQ ID NO 517
<211> LENGTH: 18
<212> TYPE: DNA
<213> ORGANISM: Artificial Sequence
<220> FEATURE:
<223> OTHER INFORMATION: Primer scTCR_rv

<400> SEQUENCE: 517
tttggatcca gcggccgc                                            18

<210> SEQ ID NO 518
<211> LENGTH: 10
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibodies described herein (Tables A-I
      and AA).
<220> FEATURE:
<221> NAME/KEY: MISC_FEATURE
<222> LOCATION: (7)..(7)
<223> OTHER INFORMATION: any amino acid

<400> SEQUENCE: 518
```

```
Gly Asp Ser Val Ser Ser Xaa Ser Ala Ala
1               5               10

<210> SEQ ID NO 519
<211> LENGTH: 10
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibodies described herein (Tables A-I
      and AA).
<220> FEATURE:
<221> NAME/KEY: MISC_FEATURE
<222> LOCATION: (7)..(7)
<223> OTHER INFORMATION: N or S

<400> SEQUENCE: 519

Gly Asp Ser Val Ser Ser Xaa Ser Ala Ala
1               5               10

<210> SEQ ID NO 520
<211> LENGTH: 10
<212> TYPE: PRT
<213> ORGANISM: Artificial Sequence
<220> FEATURE:
<223> OTHER INFORMATION: VL CDR3 consensus sequence relating to all the
      specifically described HLA-DQ2.5-gliadin-alpha1a antigen binding
      proteins described herein (Tables A-I and AA)
<220> FEATURE:
<221> NAME/KEY: MISC_FEATURE
<222> LOCATION: (2)..(2)
<223> OTHER INFORMATION: Q or D or N
<220> FEATURE:
<221> NAME/KEY: MISC_FEATURE
<222> LOCATION: (9)..(9)
<223> OTHER INFORMATION: no amino acid or L
<220> FEATURE:
<221> NAME/KEY: MISC_FEATURE
<222> LOCATION: (10)..(10)
<223> OTHER INFORMATION: no amino acid or T

<400> SEQUENCE: 520

Gln Xaa Leu Asn Ser Tyr Pro Leu Xaa Xaa
1               5               10

<210> SEQ ID NO 521
<211> LENGTH: 9
<212> TYPE: PRT
<213> ORGANISM: Artificial Sequence
<220> FEATURE:
<223> OTHER INFORMATION: VL CDR3 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: D or Q or N
<220> FEATURE:
<221> NAME/KEY: MISC_FEATURE
<222> LOCATION: (3)..(3)
<223> OTHER INFORMATION: L or F
<220> FEATURE:
<221> NAME/KEY: MISC_FEATURE
<222> LOCATION: (9)..(9)
<223> OTHER INFORMATION: no amino acid or T

<400> SEQUENCE: 521

Gln Xaa Xaa Asn Ser Tyr Pro Leu Xaa
1               5

<210> SEQ ID NO 522
```

```
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: G or D
<220> FEATURE:
<221> NAME/KEY: MISC_FEATURE
<222> LOCATION: (3)..(3)
<223> OTHER INFORMATION: S or T
<220> FEATURE:
<221> NAME/KEY: MISC_FEATURE
<222> LOCATION: (4)..(4)
<223> OTHER INFORMATION: V or F or S or N of G or Y
<220> FEATURE:
<221> NAME/KEY: MISC_FEATURE
<222> LOCATION: (5)..(5)
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: N or Y or F or G or R or S
<220> FEATURE:
<221> NAME/KEY: MISC_FEATURE
<222> LOCATION: (8)..(8)
<223> OTHER INFORMATION: S or A or I or Y or V or M
<220> FEATURE:
<221> NAME/KEY: MISC_FEATURE
<222> LOCATION: (9)..(9)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: no amino acid or any amino acid
<220> FEATURE:
<221> NAME/KEY: MISC_FEATURE
<222> LOCATION: (11)..(11)
<223> OTHER INFORMATION: no amino acid or any amino acid

<400> SEQUENCE: 522

Gly Xaa Xaa Xaa Xaa Xaa Xaa Xaa Xaa Xaa Xaa
1               5                   10

<210> SEQ ID NO 523
<211> LENGTH: 11
<212> TYPE: PRT
<213> ORGANISM: Artificial Sequence
<220> FEATURE:
<223> OTHER INFORMATION: VH CDR1 consensus sequence relating to the
      HLA-DQ2.5-gliadin-alpha1a antibody 107 described herein, the
      HLA-DQ2.5-gliadin-alpha2 antibody 206 described herein and
      affinity matured variants thereof described herein
<220> FEATURE:
<221> NAME/KEY: MISC_FEATURE
<222> LOCATION: (2)..(2)
<223> OTHER INFORMATION: G or D
<220> FEATURE:
<221> NAME/KEY: MISC_FEATURE
<222> LOCATION: (3)..(3)
<223> OTHER INFORMATION: S or T
<220> FEATURE:
<221> NAME/KEY: MISC_FEATURE
<222> LOCATION: (4)..(4)
<223> OTHER INFORMATION: V or F or S or N or G or Y
<220> FEATURE:
<221> NAME/KEY: MISC_FEATURE
<222> LOCATION: (5)..(5)
```

-continued

```
<223> OTHER INFORMATION: S or T or Q or L or R or N
<220> FEATURE:
<221> NAME/KEY: MISC_FEATURE
<222> LOCATION: (6)..(6)
<223> OTHER INFORMATION: S or G or M or E or P
<220> FEATURE:
<221> NAME/KEY: MISC_FEATURE
<222> LOCATION: (7)..(7)
<223> OTHER INFORMATION: N or Y or F or G or R or S
<220> FEATURE:
<221> NAME/KEY: MISC_FEATURE
<222> LOCATION: (8)..(8)
<223> OTHER INFORMATION: S or A or I or Y or V or M
<220> FEATURE:
<221> NAME/KEY: MISC_FEATURE
<222> LOCATION: (9)..(9)
<223> OTHER INFORMATION: no amino acid or A or G or Y or H or S
<220> FEATURE:
<221> NAME/KEY: MISC_FEATURE
<222> LOCATION: (10)..(10)
<223> OTHER INFORMATION: no amino acid or A or G
<220> FEATURE:
<221> NAME/KEY: MISC_FEATURE
<222> LOCATION: (11)..(11)
<223> OTHER INFORMATION: no amino acid or A

<400> SEQUENCE: 523

Gly Xaa Xaa Xaa Xaa Xaa Xaa Xaa Xaa Xaa Xaa
1               5                   10

<210> SEQ ID NO 524
<211> LENGTH: 12
<212> TYPE: PRT
<213> ORGANISM: Artificial Sequence
<220> FEATURE:
<223> OTHER INFORMATION: 12mer DQ2.5-glia-alpha2

<400> SEQUENCE: 524

Pro Gln Pro Glu Leu Pro Tyr Pro Gln Pro Gln Leu
1               5                   10
```

ANTIGEN BINDING PROTEINS WHICH BIND TO THE pMHC HLA-DQ2.5:DQ2.5 PRESENTING A GLIADIN PEPTIDE

REFERENCE TO SEQUENCE LISTING

The Sequence Listing submitted Sep. 25, 2023, as a text file named "10414-034US1_ST25.txt," created on Sep. 25, 2023, and having a size of 273,635 bytes is hereby incorporated by reference pursuant.

The present invention relates generally to the field of antigen binding proteins, in particular to antibodies which bind to, or bind specifically to, the pMHC (peptide-Major Histocompatibility Complex) HLA-DQ2.5:DQ2.5 presenting a gliadin peptide. More particularly, the invention relates to antigen binding proteins (e.g. antibodies) which bind to, or bind specifically to, HLA-DQ2.5:DQ2.5-glia-α1a, or which bind to, or bind specifically to, HLA-DQ2.5:DQ2.5-glia-α2. The invention further relates to compositions and immunoconjugates comprising such antibodies and to methods of producing such antibodies. The invention also relates to methods and uses which employ such antibodies, for example in the treatment of celiac disease.

Celiac disease (CD) is an autoimmune-like, chronic T cell-mediated inflammatory disorder of the small intestine caused by dietary gluten proteins from wheat, barley and rye. The disease has a strong HLA association with about 90% of the patients expressing HLA-DQ2.5 (DQA1*05-DQB1*02), and most of the remaining HLA-DQ8 (DQA1*03-DQB1*03:02) or HLA-DQ2.2 (DQA1*02:01-DQB1*02). Gluten proteins are resistant to proteolysis due to high proline content, and as a result, long immunogenic peptide fragments remain in the intestine. The T-cell response to wheat gluten is dominated by reactivity to two epitopes of α-gliadin, DQ2.5-glia-α1a (PFPQPELPY) (SEQ ID NO: 472) and DQ2.5-glia-α2 (PQPELPYPQ) (SEQ ID NO: 473), which can be found within a proteolysis resistant α-gliadin 33mer peptide, as well as to two epitopes of ω-gliadin, DQ2.5-glia-ω1 (PFPQPEQPF) (SEQ ID NO: 477) and DQ2.5-glia-ω2 (PQPEQPFPW) (SEQ ID NO: 478). Importantly, the immunogenicity of gluten peptides depends on post-translational modification by the enzyme transglutaminase 2 (TG2), which by deamidation converts certain glutamine residues to glutamate. The introduction of negatively charged anchor residues makes the peptides better suited for HLA-DQ2.5 binding and increase the pMHC (peptide-major histocompatability complex) stability.

Activation of CD4$^+$ T cells by antigen presentation both in the mesenteric lymph nodes and in gut-associated lymphoid tissue is thought to be an initial event in induction of CD pathogenesis. Studies on the characteristics of antigen presenting cells (APC) in the healthy duodenum have identified classical macrophages (CD163$^+$) and DCs (CD11c$^+$) as the main populations, with minor populations of cells with an intermediate DC phenotype (CD11c$^+$ CD163$^+$). The same cell subpopulations are found in active celiac lesions, but with altered density and somewhat altered phenotypes. Although not commonly regarded as APCs, plasma cells (PCs) secreting antibodies against gluten and TG2 are increased in density in the lamina propria of CD patients. It is not clear how these different cell populations contribute to the disease development. In contrast, only scarce populations of B cells can be found.

Although the T-cell receptor (TCR) is the endogenous binding partner for pMHC, the use of recombinant TCRs for the purpose of detecting peptide presentation is challenging.

TCRs have low affinity for pMHC, in the 1-100 μM range, and soluble TCRs are intrinsically unstable and production is demanding. Therefore, monoclonal antibodies (mAbs) with TCR-like specificity are attractive alternatives and generation of mAbs against pMHC has been reported using both hybridoma technology and phage display.

What are needed in the art are new, preferably improved, agents, such as antibodies, that can be used as reagents for the investigation of particular gliadin peptides presented by MHC class II molecules, for example in the context of celiac disease. Such antibodies may also be used in the treatment, prophylaxis and diagnosis of celiac disease.

The present inventors have identified antigen binding proteins, specifically antibodies, which bind to, or bind specifically to, HLA-DQ2.5:DQ2.5-glia-α1a, or which bind specifically to HLA-DQ2.5:DQ2.5-glia-α2. The antibodies generated by the inventors have advantageous properties which make them ideal agents for the above-mentioned uses.

In one aspect, the invention provides an antigen binding protein which binds to, or specifically binds to, HLA-DQ2.5:DQ2.5 presenting a gliadin peptide, said antigen binding protein comprising at least one light chain variable domain and at least one heavy chain variable domain, each domain comprising three complementarity determining regions (CDRs), wherein (a) said antigen binding protein binds to, or specifically binds to, HLA-DQ2.5:DQ2.5-glia-α1a and comprises
  a variable heavy (VH) CDR1 comprising the amino acid sequence of SEQ ID NO:5, or a sequence containing 1, 2 or 3 amino acid substitutions, additions or deletions relative to SEQ ID NO:5;
  a variable heavy (VH) CDR2 comprising the amino acid sequence of SEQ ID NO:6, or a sequence containing 1, 2 or 3 amino acid substitutions, additions or deletions relative to SEQ ID NO:6;
  a variable heavy (VH) CDR3 comprising the amino acid sequence of SEQ ID NO:417;
  a variable light (VL) CDR1 comprising the amino acid sequence of SEQ ID NO:8 or a sequence containing 1, 2 or 3 amino acid substitutions, additions or deletions relative to SEQ ID NO:8;
  a variable light (VL) CDR2 comprising the amino acid sequence of SEQ ID NO:9 or a sequence containing 1 amino acid substitution, addition or deletion relative to SEQ ID NO:9; and
  a variable light (VL) CDR3 comprising the amino acid sequence of SEQ ID NO:415; or wherein
(b) said antigen binding protein binds to, or specifically binds, to HLA-DQ2.5:DQ2.5-glia-α2 and comprises
  a variable heavy (VH) CDR1 comprising the amino acid sequence of SEQ ID NO:425;
  a variable heavy (VH) CDR2 comprising the amino acid sequence of SEQ ID NO:427;
  a variable heavy (VH) CDR3 comprising the amino acid sequence of SEQ ID NO:429;
  a variable light (VL) CDR1 comprising the amino acid sequence of SEQ ID NO:419;
  a variable light (VL) CDR2 comprising the amino acid sequence of SEQ ID NO:421; and
  a variable light (VL) CDR3 comprising the amino acid sequence of SEQ ID NO:423.
In certain embodiments,
(a) said antigen binding protein binds to, or specifically binds to, HLA-DQ2.5:DQ2.5-glia-α1a and comprises
  a variable heavy (VH) CDR1 comprising the amino acid sequence of SEQ ID NO:5, or a sequence containing 1, 2 or 3 amino acid substitutions, additions or deletions relative to SEQ ID NO:5;

a variable heavy (VH) CDR2 comprising the amino acid sequence of SEQ ID NO:6, or a sequence containing 1, 2 or 3 amino acid substitutions, additions or deletions relative to SEQ ID NO:6;

a variable heavy (VH) CDR3 comprising the amino acid sequence of SEQ ID NO:418;

a variable light (VL) CDR1 comprising the amino acid sequence of SEQ ID NO:8 or a sequence containing 1, 2 or 3 amino acid substitutions, additions or deletions relative to SEQ ID NO:8;

a variable light (VL) CDR2 comprising the amino acid sequence of SEQ ID NO:9 or a sequence containing 1 amino acid substitution, addition or deletion relative to SEQ ID NO:9; and a variable light (VL) CDR3 comprising the amino acid sequence of SEQ ID NO:416 or SEQ ID NO:520; or (b) said antigen binding protein binds to, or specifically binds to, HLA-DQ2.5:DQ2.5-glia-α2 and comprises a variable heavy (VH) CDR1 comprising the amino acid sequence of SEQ ID NO:426;

a variable heavy (VH) CDR2 comprising the amino acid sequence of SEQ ID NO:428;

a variable heavy (VH) CDR3 comprising the amino acid sequence of SEQ ID NO:430;

a variable light (VL) CDR1 comprising the amino acid sequence of SEQ ID NO:420;

a variable light (VL) CDR2 comprising the amino acid sequence of SEQ ID NO:422; and a variable light (VL) CDR3 comprising the amino acid sequence of SEQ ID NO:424.

In some embodiments, said antigen binding protein binds to, or specifically binds to, HLA-DQ2.5:DQ2.5-glia-α1a and comprises a variable heavy (VH) CDR1 comprising the amino acid sequence of SEQ ID NO:5, or a sequence containing 1, 2 or 3 amino acid substitutions, additions or deletions relative to SEQ ID NO:5;

a variable heavy (VH) CDR2 comprising the amino acid sequence of SEQ ID NO:6, or a sequence containing 1, 2 or 3 amino acid substitutions, additions or deletions relative to SEQ ID NO:6;

a variable heavy (VH) CDR3 comprising the amino acid sequence of SEQ ID NO:417;

a variable light (VL) CDR1 comprising the amino acid sequence of SEQ ID NO:8 or a sequence containing 1, 2 or 3 amino acid substitutions, additions or deletions relative to SEQ ID NO:8;

a variable light (VL) CDR2 comprising the amino acid sequence of SEQ ID NO:9 or a sequence containing 1 amino acid substitution, addition or deletion relative to SEQ ID NO:9; and a variable light (VL) CDR3 comprising the amino acid sequence of SEQ ID NO:415.

In some embodiments, said antigen binding protein binds to, or specifically binds to, HLA-DQ2.5:DQ2.5-glia-α1a and comprises a variable heavy (VH) CDR1 comprising the amino acid sequence of SEQ ID NO:5, or a sequence containing 1, 2 or 3 amino acid substitutions, additions or deletions relative to SEQ ID NO:5;

a variable heavy (VH) CDR2 comprising the amino acid sequence of SEQ ID NO:6, or a sequence containing 1, 2 or 3 amino acid substitutions, additions or deletions relative to SEQ ID NO:6;

a variable heavy (VH) CDR3 comprising the amino acid sequence of SEQ ID NO:418;

a variable light (VL) CDR1 comprising the amino acid sequence of SEQ ID NO:8 or a sequence containing 1, 2 or 3 amino acid substitutions, additions or deletions relative to SEQ ID NO:8;

a variable light (VL) CDR2 comprising the amino acid sequence of SEQ ID NO:9 or a sequence containing 1 amino acid substitution, addition or deletion relative to SEQ ID NO:9; and a variable light (VL) CDR3 comprising the amino acid sequence of SEQ ID NO:416 or SEQ ID NO:520.

In some embodiments, said antigen binding protein binds to, or specifically binds to, HLA-DQ2.5:DQ2.5-glia-α2 and comprises a variable heavy (VH) CDR1 comprising the amino acid sequence of SEQ ID NO:425;

a variable heavy (VH) CDR2 comprising the amino acid sequence of SEQ ID NO:427;

a variable heavy (VH) CDR3 comprising the amino acid sequence of SEQ ID NO:429;

a variable light (VL) CDR1 comprising the amino acid sequence of SEQ ID NO:419;

a variable light (VL) CDR2 comprising the amino acid sequence of SEQ ID NO:421; and a variable light (VL) CDR3 comprising the amino acid sequence of SEQ ID NO:423.

In some embodiments, said antigen binding protein binds to, or specifically binds to, HLA-DQ2.5:DQ2.5-glia-α2 and comprises a variable heavy (VH) CDR1 comprising the amino acid sequence of SEQ ID NO:426;

a variable heavy (VH) CDR2 comprising the amino acid sequence of SEQ ID NO:428;

a variable heavy (VH) CDR3 comprising the amino acid sequence of SEQ ID NO:430;

a variable light (VL) CDR1 comprising the amino acid sequence of SEQ ID NO:420;

a variable light (VL) CDR2 comprising the amino acid sequence of SEQ ID NO:422; and a variable light (VL) CDR3 comprising the amino acid sequence of SEQ ID NO:424.

In other embodiments of the present invention, the antigen binding protein comprises a light chain variable domain that comprises a variable light (VL) CDR1 comprising the amino acid sequence of SEQ ID NO:435;

a variable light (VL) CDR2 comprising the amino acid sequence of SEQ ID NO:437; and a variable light (VL) CDR3 comprising the amino acid sequence of SEQ ID NO:439.

In other embodiments of the present invention, the antigen binding protein comprises a light chain variable domain that comprises a variable light (VL) CDR1 comprising the amino acid sequence of SEQ ID NO:436;

a variable light (VL) CDR2 comprising the amino acid sequence of SEQ ID NO:438; and a variable light (VL) CDR3 comprising the amino acid sequence of SEQ ID NO:440 or SEQ ID NO:521.

In other embodiments of the present invention, the antigen binding protein comprises a heavy chain variable domain that comprises a variable heavy (VH) CDR1 comprising the amino acid sequence of SEQ ID NO:441 (preferably SEQ ID NO:442) or SEQ ID NO:522 (preferably SEQ ID NO:523);

a variable heavy (VH) CDR2 comprising the amino acid sequence of SEQ ID NO:42 or a sequence containing 1, 2 or 3 amino acid substitutions, additions or deletions relative to SEQ ID NO:42, or SEQ ID NO:168 or a sequence containing 1, 2 or 3 amino acid substitutions, additions or deletions relative to SEQ ID NO:168; and a variable heavy (VH) CDR3 comprising the amino acid sequence of SEQ ID NO:443.

In some such embodiments, an antigen binding protein comprising a variable heavy (VH) CDR2 comprising the amino acid sequence of SEQ ID NO:42 or a sequence containing 1, 2 or 3 amino acid substitutions, additions or deletions relative to SEQ ID NO:42 binds to, or specifically binds to, HLA-DQ2.5:DQ2.5-glia-α1a. In other such embodiments, an antigen binding protein comprising a variable heavy (VH) CDR2 comprising the amino acid sequence of SEQ ID NO:168 or a sequence containing 1, 2 or 3 amino acid substitutions, additions or deletions relative to SEQ ID NO:168 binds to, or specifically binds to, HLA-DQ2.5:DQ2.5-glia-α2.

In other embodiments of the present invention, the antigen binding protein comprises a light chain variable domain that comprises a variable light (VL) CDR1 comprising the amino acid sequence of SEQ ID NO:435, preferably SEQ ID NO:436;

a variable light (VL) CDR2 comprising the amino acid sequence of SEQ ID NO:437, preferably SEQ ID NO:438;

a variable light (VL) CDR3 comprising the amino acid sequence of SEQ ID NO:439, preferably SEQ ID NO:440 or SEQ ID NO:521; and a variable heavy (VH) CDR1 comprising the amino acid sequence of SEQ ID NO:441 (preferably SEQ ID NO:442) or SEQ ID NO: 522 (preferably SEQ ID NO:523);

a variable heavy (VH) CDR2 comprising the amino acid sequence of SEQ ID NO:42 or a sequence containing 1, 2 or 3 amino acid substitutions, additions or deletions relative to SEQ ID NO:42, or SEQ ID NO:168 or a sequence containing 1, 2 or 3 amino acid substitutions, additions or deletions relative to SEQ ID NO:168; and a variable heavy (VH) CDR3 comprising the amino acid sequence of SEQ ID NO:443.

In other embodiments, said antigen binding protein binds to, or specifically binds to, HLA-DQ2.5:DQ2.5-glia-α1a and comprises a variable heavy (VH) CDR1 comprising the amino acid sequence of SEQ ID NO:41, or a sequence containing 1, 2 or 3 amino acid substitutions, additions or deletions relative to SEQ ID NO:41;

a variable heavy (VH) CDR2 comprising the amino acid sequence of SEQ ID NO:42, or a sequence containing 1, 2 or 3 amino acid substitutions, additions or deletions relative to SEQ ID NO:42;

a variable heavy (VH) CDR3 comprising the amino acid sequence of SEQ ID NO:431, preferably SEQ ID NO:432;

a variable light (VL) CDR1 comprising the amino acid sequence of SEQ ID NO:44 or a sequence containing 1, 2 or 3 amino acid substitutions, additions or deletions relative to SEQ ID NO:44;

a variable light (VL) CDR2 comprising the amino acid sequence of SEQ ID NO:45 or a sequence containing 1 amino acid substitution, addition or deletion relative to SEQ ID NO:45; and a variable light (VL) CDR3 comprising the amino acid sequence of SEQ ID NO:46.

In one aspect (and in certain embodiments), the invention provides an antigen binding protein which binds to, or specifically binds to, HLA-DQ2.5:DQ2.5 presenting a gliadin peptide, said antigen binding protein comprising at least one light chain variable domain and at least one heavy chain variable domain, each domain comprising three complementarity determining regions (CDRs), wherein said antigen binding protein binds to, or specifically binds to, HLA-DQ2.5:DQ2.5-glia-α1a and comprises a variable heavy (VH) CDR1 comprising the amino acid sequence of SEQ ID NO:518, preferably 519;

a variable heavy (VH) CDR2 comprising the amino acid sequence of SEQ ID NO:6, or a sequence containing 1, 2 or 3 amino acid substitutions, additions or deletions relative to SEQ ID NO:6;

a variable heavy (VH) CDR3 comprising the amino acid sequence of SEQ ID NO:417, preferably SEQ ID NO:418;

a variable light (VL) CDR1 comprising the amino acid sequence of SEQ ID NO:8 or a sequence containing 1, 2 or 3 amino acid substitutions, additions or deletions relative to SEQ ID NO:8;

a variable light (VL) CDR2 comprising the amino acid sequence of SEQ ID NO:9 or a sequence containing 1 amino acid substitution, addition or deletion relative to SEQ ID NO:9; and a variable light (VL) CDR3 comprising the amino acid sequence of SEQ ID NO:415, preferably SEQ ID NO:416 or SEQ ID NO:520, more preferably SEQ ID NO:521.

Other features and properties of other aspects and embodiments of the invention apply, mutatis mutandis, to this aspect of the invention.

In some embodiments, said antigen binding protein binds to, or specifically binds to, HLA-DQ2.5:DQ2.5-glia-α2 and comprises a variable heavy (VH) CDR1 comprising the amino acid sequence of SEQ ID NO:433, preferably 434;

a variable heavy (VH) CDR2 comprising the amino acid sequence of SEQ ID NO:168 or a sequence containing 1, 2 or 3 amino acid substitutions, additions or deletions relative to SEQ ID NO:168;

a variable heavy (VH) CDR3 comprising the amino acid sequence of SEQ ID NO:169 or a sequence containing 1, 2 or 3 amino acid substitutions, additions or deletions relative to SEQ ID NO:169;

a variable light (VL) CDR1 comprising the amino acid sequence of SEQ ID NO:170 or a sequence containing 1, 2 or 3 amino acid substitutions, additions or deletions relative to SEQ ID NO:170;

a variable light (VL) CDR2 comprising the amino acid sequence of SEQ ID NO:171 or a sequence containing 1 amino acid substitution, addition or deletion relative to SEQ ID NO:171; and a variable light (VL) CDR3 comprising the amino acid sequence of SEQ ID NO:172 or a sequence containing 1, 2 or 3 amino acid substitutions, additions or deletions relative to SEQ ID NO:172.

In some embodiments, said antigen binding protein binds to, or specifically binds to, HLA-DQ2.5:DQ2.5-glia-α2 and comprises a variable heavy (VH) CDR1 comprising the amino acid sequence of SEQ ID NO:495;

a variable heavy (VH) CDR2 comprising the amino acid sequence of SEQ ID NO:168 or a sequence containing 1, 2 or 3 amino acid substitutions, additions or deletions relative to SEQ ID NO:168;

a variable heavy (VH) CDR3 comprising the amino acid sequence of SEQ ID NO:169 or a sequence containing 1, 2 or 3 amino acid substitutions, additions or deletions relative to SEQ ID NO:169;

a variable light (VL) CDR1 comprising the amino acid sequence of SEQ ID NO:170 or a sequence containing 1, 2 or 3 amino acid substitutions, additions or deletions relative to SEQ ID NO:170;

a variable light (VL) CDR2 comprising the amino acid sequence of SEQ ID NO:171 or a sequence containing 1 amino acid substitution, addition or deletion relative to SEQ ID NO:171; and a variable light (VL) CDR3 comprising the amino acid sequence of SEQ ID NO:172 or a sequence containing 1, 2 or 3 amino acid substitutions, additions or deletions relative to SEQ ID NO:172.

In a preferred aspect, and in preferred embodiments, the antigen binding protein binds to, or specifically binds to, HLA-DQ2.5:DQ2.5-glia-α1a and comprises at least one light chain variable domain having a VL CDR1, VL CDR2 and VL CDR3 amino acid sequence as set forth in any one of Tables A-I or Table AA herein and/or (preferably "and") at least one heavy chain variable domain having a VH CDR1, VH CDR2 and VH CDR3 amino acid sequence as set forth in any one of Tables A-I or Table AA herein. Tables A-I herein set forth sequences of the R2A1-8E, R3A2-9F, R4A1-3A (also referred to as 107), 107-4.5D, 107-4.6D, 107-4.6C, 107-4.7C, 107-5.6A and 107-15.6A antibodies. Table AA herein sets forth sequences of the RF117 antibody. Thus, preferred antigen binding proteins are those comprising (or based on) these antibody sequences.

In one aspect, and in certain embodiments, the antigen binding protein binds to, or specifically binds to, HLA-DQ2.5:DQ2.5-glia-α1a and comprises at least one light chain variable domain having a VL CDR1, VL CDR2 and VL CDR3 amino acid sequence as set forth in any one of Tables D-I or Table AA herein and/or (preferably "and") at least one heavy chain variable domain having a VH CDR1, VH CDR2 and VH CDR3 amino acid sequence as set forth in any one of Tables D-I or Table AA herein. Tables D-I herein set forth sequences of the 107-4.5D, 107-4.6D, 107-4.6C, 107-4.7C, 107-5.6A and 107-15.6A antibodies. Table AA herein sets forth sequences of the RF117 antibody. Thus, preferred antigen binding proteins are those comprising (or based on) these antibody sequences.

In a one aspect, and in certain embodiments, the antigen binding protein binds to, or specifically binds to, HLA-DQ2.5:DQ2.5-glia-α2 and comprises at least one light chain variable domain having a VL CDR1, VL CDR2 and VL CDR3 amino acid sequence as set forth in any one of Tables J-W herein and/or (preferably "and") at least one heavy chain variable domain having a VH CDR1, VH CDR2 and VH CDR3 amino acid sequence as set forth in any one of Tables J-W herein. Tables J-W herein set forth sequences of the 206, 217, 218, 220, 221, 223, 226, 228, 206-2.B11, 206-3. D8, 206-3.C7, 206-3.C11, 206-3.F6 and 206-12.F6 antibodies. Thus, preferred antigen binding proteins are those comprising (or based on) these antibody sequences.

In a one aspect, and in certain embodiments, the antigen binding protein binds to, or specifically binds to, HLA-DQ2.5:DQ2.5-glia-α2 and has at least one light chain variable domain comprising a VL CDR1, VL CDR2 and VL CDR3 amino acid sequence as set forth in any one of Tables R-W herein and/or (preferably "and") at least one heavy chain variable domain having a VH CDR1, VH CDR2 and VH CDR3 amino acid sequence as set forth in any one of Tables R-W herein. Tables R-W herein set forth sequences of the 206-2.B111, 206-3. D8, 206-3.C7, 206-3.C11, 206-3.F6 and 206-12.F6 antibodies. Thus, preferred antigen binding proteins are those comprising (or based on) these antibody sequences.

In some embodiments, a preferred antigen binding protein that binds to, or specifically binds to, HLA-DQ2.5:DQ2.5-glia-α1a comprises (or is based on) the antibody sequences (e.g. three VH CDR sequences and three VL CDR sequences) of the 107-4.7C antibody described herein (see Table G).

In some embodiments, a preferred antigen binding protein that binds to, or specifically binds to, HLA-DQ2.5:DQ2.5-glia-α2 comprises (or is based on) the antibody sequences (e.g. three VH CDR sequences and three VL CDR sequences) of the 206-2.B111 antibody described herein (see Table R).

In some embodiments, a preferred antigen binding protein that binds to, or specifically binds to, HLA-DQ2.5:DQ2.5-glia-α2 comprises (or is based on) the antibody sequences (e.g. three VH CDR sequences and three VL CDR sequences) of the 206-3.C11 antibody described herein (see Table U).

In some embodiments, the antigen binding protein of the invention is not the R2A1-8E, R3A2-9F or R4A1-3A (also referred to as 107) antibody, e.g. as defined by their light chain variable region and heavy chain variable region sequences herein (see Tables A-C). In some embodiments, the antigen binding protein of the invention is not the 206, 217, 218, 220, 221, 223, 226, 228 antibody e.g. as defined by their light chain variable region and heavy chain variable region sequences herein (see Tables J-Q).

In some embodiments, HLA-DQ2.5:DQ2.5-glia-α1a antigen binding proteins of the invention have a T (threonine) residue at position 5 and/or position 6 of the VH CDR3, and/or a VL FR1 (VL framework 1) sequence other than SEQ ID NO:15.

In some embodiments, HLA-DQ2.5:DQ2.5-glia-α2 antigen binding proteins of the invention do not have an S (serine) residue at position 5 and an S residue at position 6 of the VH CDR1.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:8 or a sequence substantially homologous thereto, (b) a VL CDR2 that comprises the amino acid sequence of SEQ ID NO:9 or a sequence substantially homologous thereto, and (c) a VL CDR3 that comprises the amino acid sequence of SEQ ID NO:10 or a sequence substantially homologous thereto; and/or (preferably "and")

wherein said heavy chain variable region comprises:

(d) a variable heavy (VH) CDR1 that comprises the amino acid sequence of SEQ ID NO:5 or a sequence substantially homologous thereto, (e) a VH CDR2 that comprises the amino acid sequence of SEQ ID NO:6 or a sequence substantially homologous thereto, and (f) a VH CDR3 that comprises the amino acid sequence of SEQ ID NO:7 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:8, a VL CDR2 of SEQ ID NO:9, and a VL CDR3 of SEQ ID NO:10, and a VH domain that comprises a VH CDR1 of SEQ ID NO:5, a VH CDR2 of SEQ ID NO:6, and a VH CDR3 of SEQ ID NO:7.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:3 or a sequence substantially homologous thereto and/or a VL domain that comprises the amino acid sequence of SEQ ID NO:4, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:3 and a VL domain that comprises the amino acid sequence of SEQ ID NO:4.

In some embodiments an antibody in IgG format is preferred. A preferred embodiment of the invention provides an antibody that binds to, or specifically binds to, HLA-DQ2.5:DQ2.5-glia-α1a which has a heavy chain that comprises the amino acid sequence of SEQ ID NO:444 or a sequence substantially homologous thereto and/or a light chain that comprises the amino acid sequence of SEQ ID NO:445 or a sequence substantially homologous thereto. In another preferred embodiment the invention provides an antibody that binds to, or specifically binds to, HLA-DQ2.5:DQ2.5-glia-α1a which has a heavy chain that comprises the amino acid sequence of SEQ ID NO:446 or a sequence substantially homologous thereto and/or a light chain that comprises the amino acid sequence of SEQ ID NO:447 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:444 and a light chain that comprises the amino acid sequence of SEQ ID NO:445.

In another preferred embodiment, an antibody comprises a heavy chain that comprises the amino acid sequence of SEQ ID NO:446 and a light chain that comprises the amino acid sequence of SEQ ID NO:447.

The section immediately above relates to the R2A1-8E antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:26 or a sequence substantially homologous thereto, (b) a VL CDR2 that comprises the amino acid sequence of SEQ ID NO:27 or a sequence substantially homologous thereto, and (c) a VL CDR3 that comprises the amino acid sequence of SEQ ID NO:28 or a sequence substantially homologous thereto; and/or (preferably "and")

wherein said heavy chain variable region comprises:

(d) a variable heavy (VH) CDR1 that comprises the amino acid sequence of SEQ ID NO:23 or a sequence substantially homologous thereto, (e) a VH CDR2 that comprises the amino acid sequence of SEQ ID NO:24 or a sequence substantially homologous thereto, and (f) a VH CDR3 that comprises the amino acid sequence of SEQ ID NO:25 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:26, a VL CDR2 of SEQ ID NO:27, and a VL CDR3 of SEQ ID NO:28, and a VH domain that comprises a VH CDR1 of SEQ ID NO:23, a VH CDR2 of SEQ ID NO:24, and a VH CDR3 of SEQ ID NO:25.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:21 or a sequence substantially homologous thereto and/or a VL domain that comprises the amino acid sequence of SEQ ID NO:22, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:21 and a VL domain that comprises the amino acid sequence of SEQ ID NO:22.

In some embodiments an antibody in IgG format is preferred. A preferred embodiment of the invention provides an antibody that binds to, or specifically binds to, HLA-DQ2.5:DQ2.5-glia-α1a which has a heavy chain that comprises the amino acid sequence of SEQ ID NO:448 or a sequence substantially homologous thereto and/or a light chain that comprises the amino acid sequence of SEQ ID NO:449 or a sequence substantially homologous thereto. In another preferred embodiment the invention provides an antibody that binds to, or specifically binds to, HLA-DQ2.5:DQ2.5-glia-α1a which has a heavy chain that comprises the amino acid sequence of SEQ ID NO:450 or a sequence substantially homologous thereto and/or a light chain that comprises the amino acid sequence of SEQ ID NO:451 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:448 and a light chain that comprises the amino acid sequence of SEQ ID NO:449.

In another preferred embodiment, an antibody comprises a heavy chain that comprises the amino acid sequence of SEQ ID NO:450 and a light chain that comprises the amino acid sequence of SEQ ID NO:451.

The section immediately above relates to the R3A2-9F antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:44 or a sequence substantially homologous thereto, (b) a VL CDR2 that comprises the amino acid sequence of SEQ ID NO:45 or a sequence substantially homologous thereto, and (c) a VL CDR3 that comprises the amino acid sequence of SEQ ID NO:46 or a sequence substantially homologous thereto; and/or (preferably "and")

wherein said heavy chain variable region comprises:

(d) a variable heavy (VH) CDR1 that comprises the amino acid sequence of SEQ ID NO:41 or a sequence substantially homologous thereto, (e) a VH CDR2 that comprises the amino acid sequence of SEQ ID NO:42 or a sequence substantially homologous thereto, and (f) a VH CDR3 that comprises the amino acid sequence of SEQ ID NO:43 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:44, a VL CDR2 of SEQ ID NO:45, and a VL CDR3 of SEQ ID NO:46, and a VH domain that comprises a VH CDR1 of SEQ ID NO:41, a VH CDR2 of SEQ ID NO:42, and a VH CDR3 of SEQ ID NO:43.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:9 or a sequence substantially homologous thereto and/or a VL domain that comprises the amino acid sequence of SEQ ID NO:40, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:39 and a VL domain that comprises the amino acid sequence of SEQ ID NO:40.

In some embodiments an antibody in IgG format is preferred. A preferred embodiment of the invention provides an antibody that binds to, or specifically binds to, HLA-DQ2.5:DQ2.5-glia-α1a which has a heavy chain that comprises the amino acid sequence of SEQ ID NO:452 or a sequence substantially homologous thereto and/or a light chain that comprises the amino acid sequence of SEQ ID NO:453 or a sequence substantially homologous thereto. In another preferred embodiment the invention provides an antibody that binds to, or specifically binds to, HLA-DQ2.5:DQ2.5-glia-α1a which has a heavy chain that comprises the amino acid sequence of SEQ ID NO:454 or a sequence substantially homologous thereto and/or a light chain that comprises the amino acid sequence of SEQ ID NO:455 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:452 and a light chain that comprises the amino acid sequence of SEQ ID NO:453.

In another preferred embodiment, an antibody comprises a heavy chain that comprises the amino acid sequence of SEQ ID NO:454 and a light chain that comprises the amino acid sequence of SEQ ID NO:455.

The section immediately above relates to the R4A1-3A (107) antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:62 or a sequence substantially homologous thereto, (b) a VL CDR2 that comprises the amino acid sequence of SEQ ID NO:63 or a sequence substantially homologous thereto, and (c) a VL CDR3 that comprises the amino acid sequence of SEQ ID NO:64 or a sequence substantially homologous thereto; and/or (preferably "and")

wherein said heavy chain variable region comprises:

(d) a variable heavy (VH) CDR1 that comprises the amino acid sequence of SEQ ID NO:59 or a sequence substantially homologous thereto, (e) a VH CDR2 that comprises the amino acid sequence of SEQ ID NO:60 or a sequence substantially homologous thereto, and (f) a VH CDR3 that comprises the amino acid sequence of SEQ ID NO:61 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:62, a VL CDR2 of SEQ ID NO:63, and a VL CDR3 of SEQ ID NO:64, and a VH domain that comprises a VH CDR1 of SEQ ID NO:59, a VH CDR2 of SEQ ID NO:60, and a VH CDR3 of SEQ ID NO:61.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:57 or a sequence substantially homologous thereto and/or a VL domain that comprises the amino acid sequence of SEQ ID NO:58, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:57 and a VL domain that comprises the amino acid sequence of SEQ ID NO:58.

The section immediately above relates to the 107-4.5D antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:80 or a sequence substantially homologous thereto, (b) a VL CDR2 that comprises the amino acid sequence of SEQ ID NO:81 or a sequence substantially homologous thereto, and (c) a VL CDR3 that comprises the amino acid sequence of SEQ ID NO:82 or a sequence substantially homologous thereto; and/or (preferably "and")

wherein said heavy chain variable region comprises:

(d) a variable heavy (VH) CDR1 that comprises the amino acid sequence of SEQ ID NO:77 or a sequence substantially homologous thereto, (e) a VH CDR2 that comprises the amino acid sequence of SEQ ID NO:78 or a sequence substantially homologous thereto, and (f) a VH CDR3 that comprises the amino acid sequence of SEQ ID NO:79 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:80, a VL CDR2 of SEQ ID NO:81, and a VL CDR3 of SEQ ID NO:82, and a VH domain that comprises a VH CDR1 of SEQ ID NO:77, a VH CDR2 of SEQ ID NO:78, and a VH CDR3 of SEQ ID NO:79.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:75 or a sequence substantially homologous thereto and/or a VL domain that comprises the amino acid sequence of SEQ ID NO:76, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:75 and a VL domain that comprises the amino acid sequence of SEQ ID NO:76.

The section immediately above relates to the 107-4.6D antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:98 or a sequence substantially homologous thereto, (b) a VL CDR2 that comprises the amino acid sequence of SEQ ID NO:99 or a sequence substantially homologous thereto, and (c) a VL CDR3 that comprises the amino acid sequence of SEQ ID NO:100 or a sequence substantially homologous thereto; and/or (preferably "and")

wherein said heavy chain variable region comprises:

(d) a variable heavy (VH) CDR1 that comprises the amino acid sequence of SEQ ID NO:95 or a sequence substantially homologous thereto, (e) a VH CDR2 that comprises the amino acid sequence of SEQ ID NO:96 or a sequence substantially homologous thereto, and (f) a VH CDR3 that comprises the amino acid sequence of SEQ ID NO:97 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:98, a VL CDR2 of SEQ ID NO:99, and a VL CDR3 of SEQ ID NO:100, and a VH domain that comprises a VH CDR1 of SEQ ID NO:95, a VH CDR2 of SEQ ID NO:96, and a VH CDR3 of SEQ ID NO:97.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:93 or a sequence substantially homologous thereto and/or a VL domain that comprises the amino acid sequence of SEQ ID NO:94, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a, comprising a VH domain that comprises the amino acid sequence of SEQ ID NO:93 and a VL domain that comprises the amino acid sequence of SEQ ID NO:94.

The section immediately above relates to the 107-4.6C antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:116 or a sequence substantially homologous thereto,

(b) a VL CDR2 that comprises the amino acid sequence of SEQ ID NO:117 or a sequence substantially homologous thereto, and (c) a VL CDR3 that comprises the amino acid sequence of SEQ ID NO:118 or a sequence substantially homologous thereto; and/or (preferably "and")

wherein said heavy chain variable region comprises:

(d) a variable heavy (VH) CDR1 that comprises the amino acid sequence of SEQ ID NO:113 or a sequence substantially homologous thereto, (e) a VH CDR2 that comprises the amino acid sequence of SEQ ID NO:114 or a sequence substantially homologous thereto, and (f) a VH CDR3 that comprises the amino acid sequence of SEQ ID NO:115 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:116, a VL CDR2 of SEQ ID NO:117, and a VL CDR3 of SEQ ID NO:118, and a VH domain that comprises a VH CDR1 of SEQ ID NO:113, a VH CDR2 of SEQ ID NO:114, and a VH CDR3 of SEQ ID NO:115.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:111 or a sequence substantially homologous thereto and/or a VL domain that comprises the amino acid sequence of SEQ ID NO:112, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:111 and a VL domain that comprises the amino acid sequence of SEQ ID NO:112.

The section immediately above relates to the 107-4.7C antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:134 or a sequence substantially homologous thereto, (b) a VL CDR2 that comprises the amino acid sequence of SEQ ID NO:135 or a sequence substantially homologous thereto, and (c) a VL CDR3 that comprises the amino acid sequence of SEQ ID NO:136 or a sequence substantially homologous thereto; and/or (preferably "and")

wherein said heavy chain variable region comprises:

(d) a variable heavy (VH) CDR1 that comprises the amino acid sequence of SEQ ID NO:131 or a sequence substantially homologous thereto,

(e) a VH CDR2 that comprises the amino acid sequence of SEQ ID NO:132 or a sequence substantially homologous thereto, and (f) a VH CDR3 that comprises the amino acid sequence of SEQ ID NO:133 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:134, a VL CDR2 of SEQ ID NO:135, and a VL CDR3 of SEQ ID NO:136, and a VH domain that comprises a VH CDR1 of SEQ ID NO:131, a VH CDR2 of SEQ ID NO:132, and a VH CDR3 of SEQ ID NO:133.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:129 or a sequence substantially homologous thereto and/or a VL domain that comprises the amino acid sequence of SEQ ID NO:130, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:129 and a VL domain that comprises the amino acid sequence of SEQ ID NO:130.

The section immediately above relates to the 107-5.6A antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:152 or a sequence substantially homologous thereto, (b) a VL CDR2 that comprises the amino acid sequence of SEQ ID NO:153 or a sequence substantially homologous thereto, and (c) a VL CDR3 that comprises the amino acid sequence of SEQ ID NO:154 or a sequence substantially homologous thereto; and/or (preferably "and")

wherein said heavy chain variable region comprises:

(d) a variable heavy (VH) CDR1 that comprises the amino acid sequence of SEQ ID NO:149 or a sequence substantially homologous thereto, (e) a VH CDR2 that comprises the amino acid sequence of SEQ ID NO:150 or a sequence substantially homologous thereto, and (f) a VH CDR3 that comprises the amino acid sequence of SEQ ID NO:151 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:152, a VL CDR2 of SEQ ID NO:153, and a VL CDR3 of SEQ ID NO:154, and a VH domain that comprises a VH CDR1 of SEQ ID NO:149, a VH CDR2 of SEQ ID NO:150, and a VH CDR3 of SEQ ID NO:151.

Certain preferred embodiments of the invention provide an antigen binding protein that binds to, specifically binds to, HLA-DQ2.5:DQ2.5-glia-α1a comprising a VH domain that comprises the amino acid sequence of SEQ ID NO:147 or a sequence substantially homologous thereto and/or a VL domain that comprises the amino acid sequence of SEQ ID NO:148, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:147 and a VL domain that comprises the amino acid sequence of SEQ ID NO:148.

The section immediately above relates to the 107-15.6A antibody.

In one aspect of, and in certain embodiments of, the present invention there is provided an antigen binding protein (e.g. an antibody) which binds to, or specifically binds to, HLA-DQ2.5:DQ2.5-glia-α1a, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:503 or a sequence substantially homologous thereto, (b) a VL CDR2 that comprises the amino acid sequence of SEQ ID NO:504 or a sequence substantially homologous thereto, and (c) a VL CDR3 that comprises the amino acid sequence of SEQ ID NO:505 or a sequence substantially homologous thereto; and/or (preferably "and")

wherein said heavy chain variable region comprises:

(d) a variable heavy (VH) CDR1 that comprises the amino acid sequence of SEQ ID NO:500 or a sequence substantially homologous thereto, (e) a VH CDR2 that comprises the amino acid sequence of SEQ ID NO:501 or a sequence substantially homologous thereto, and (f) a VH CDR3 that comprises the amino acid sequence of SEQ ID NO:502 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α1a and that comprises:

a VL domain that comprises a VL CDR1 of SEQ ID NO:503, a VL CDR2 of SEQ ID NO:504, and a VL CDR3 of SEQ ID NO:505, and a VH domain that comprises a VH CDR1 of SEQ ID NO:500, a VH CDR2 of SEQ ID NO:501, and a VH CDR3 of SEQ ID NO:502.

Certain preferred embodiments of the invention provide an antigen binding protein that binds to, or specifically binds to, HLA-DQ2.5:DQ2.5-glia-α1a comprising a VH domain that comprises the amino acid sequence of SEQ ID NO:498 or a sequence substantially homologous thereto and/or a VL domain that comprises the amino acid sequence of SEQ ID NO:499, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α1a comprising a VH domain that comprises the amino acid sequence of SEQ ID NO:498 and a VL domain that comprises the amino acid sequence of SEQ ID NO:499.

In some embodiments an antibody in IgG format is preferred. A preferred embodiment of the invention provides an antibody that binds to, or specifically binds to, HLA-DQ2.5:DQ2.5-glia-α1a which has a heavy chain that comprises the amino acid sequence of SEQ ID NO:514 or a sequence substantially homologous thereto and/or a light chain that comprises the amino acid sequence of SEQ ID NO:515 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:514 and a light chain that comprises the amino acid sequence of SEQ ID NO:515.

The section immediately above relates to the RF117 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:170 or a sequence substantially homologous thereto, (b) a VL CDR2 that comprises the amino acid sequence of SEQ ID NO:171 or a sequence substantially homologous thereto, and (c) a VL CDR3 that comprises the amino acid sequence of SEQ ID NO:172 or a sequence substantially homologous thereto; and/or (preferably "and")

wherein said heavy chain variable region comprises:

(d) a variable heavy (VH) CDR1 that comprises the amino acid sequence of SEQ ID NO:167 or a sequence substantially homologous thereto, (e) a VH CDR2 that comprises the amino acid sequence of SEQ ID NO:168 or a sequence substantially homologous thereto, and (f) a VH CDR3 that comprises the amino acid sequence of SEQ ID NO:169 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:170, a VL CDR2 of SEQ ID NO:172, and a VL CDR3 of SEQ ID NO:173, and a VH domain that comprises a VH CDR1 of SEQ ID NO:167, a VH CDR2 of SEQ ID NO:168, and a VH CDR3 of SEQ ID NO:169.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:165 or a sequence substantially homologous thereto and/or a VL domain that comprises the amino acid sequence of SEQ ID NO:166, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:165 and a VL domain that comprises the amino acid sequence of SEQ ID NO:166.

In some embodiments an antibody in IgG format is preferred. A preferred embodiment of the invention provides an antibody that binds to, or specifically binds to, HLA-DQ2.5:DQ2.5-glia-α2 which has a heavy chain that comprises the amino acid sequence of SEQ ID NO:456 or a sequence substantially homologous thereto and/or a light chain that comprises the amino acid sequence of SEQ ID NO:457 or a sequence substantially homologous thereto. In another preferred embodiment the invention provides an antibody that binds to, or specifically binds to, HLA-DQ2.5:DQ2.5-glia-α2 which has a heavy chain that comprises the amino acid sequence of SEQ ID NO:458 or a sequence substantially homologous thereto and/or a light chain that comprises the amino acid sequence of SEQ ID NO:459 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:456 and a light chain that comprises the amino acid sequence of SEQ ID NO:457.

In another preferred embodiment, an antibody comprises a heavy chain that comprises the amino acid sequence of SEQ ID NO:458 and a light chain that comprises the amino acid sequence of SEQ ID NO:459.

The section immediately above relates to the 206 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:188 or a sequence substantially homologous thereto, (b) a VL CDR2 that comprises the amino acid sequence of SEQ ID NO:189 or a sequence substantially homologous thereto, and (c) a VL CDR3 that comprises the amino acid sequence of SEQ ID NO:190 or a sequence substantially homologous thereto; and/or (preferably "and")

wherein said heavy chain variable region comprises:

(d) a variable heavy (VH) CDR1 that comprises the amino acid sequence of SEQ ID NO:185 or a sequence substantially homologous thereto, (e) a VH CDR2 that comprises the amino acid sequence of SEQ ID NO:186 or a sequence substantially homologous thereto, and (f) a VH CDR3 that comprises the amino acid sequence of SEQ ID NO:187 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:188, a VL CDR2 of SEQ ID NO:189, and a VL CDR3 of SEQ ID NO:190, and a VH domain that comprises a VH CDR1 of SEQ ID NO:185, a VH CDR2 of SEQ ID NO:186, and a VH CDR3 of SEQ ID NO:187.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:183 or a sequence substantially homologous thereto and/or a VL domain that comprises the amino acid sequence of SEQ ID NO:184, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:183 and a VL domain that comprises the amino acid sequence of SEQ ID NO:184.

The section immediately above relates to the 217 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:206 or a sequence substantially homologous thereto, (b) a VL CDR2 that comprises the amino acid sequence of SEQ ID NO:207 or a sequence substantially homologous thereto, and (c) a VL CDR3 that comprises the amino acid sequence of SEQ ID NO:208 or a sequence substantially homologous thereto; and/or (preferably "and")

wherein said heavy chain variable region comprises:

(d) a variable heavy (VH) CDR1 that comprises the amino acid sequence of SEQ ID NO:203 or a sequence substantially homologous thereto, (e) a VH CDR2 that comprises the amino acid sequence of SEQ ID NO:204 or a sequence substantially homologous thereto, and (f) a VH CDR3 that comprises the amino acid sequence of SEQ ID NO:205 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:206, a VL CDR2 of SEQ ID NO:207, and a VL CDR3 of SEQ ID NO:208, and a VH domain that comprises a VH CDR1 of SEQ ID NO:203, a VH CDR2 of SEQ ID NO:204, and a VH CDR3 of SEQ ID NO:205.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:201 or a sequence substantially homologous thereto and/or a VL domain that comprises the amino acid sequence of SEQ ID NO:202, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:201 and a VL domain that comprises the amino acid sequence of SEQ ID NO:202.

The section immediately above relates to the 218 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:224 or a sequence substantially homologous thereto, (b) a VL CDR2 that comprises the amino acid sequence of SEQ ID NO:225 or a sequence substantially homologous thereto, and (c) a VL CDR3 that comprises the amino acid sequence of SEQ ID NO:226 or a sequence substantially homologous thereto; and/or (preferably "and")

wherein said heavy chain variable region comprises:

(d) a variable heavy (VH) CDR1 that comprises the amino acid sequence of SEQ ID NO:221 or a sequence substantially homologous thereto, (e) a VH CDR2 that comprises the amino acid sequence of SEQ ID NO:222 or a sequence substantially homologous thereto, and (f) a VH CDR3 that comprises the amino acid sequence of SEQ ID NO:223 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:224, a VL CDR2 of SEQ ID NO:225, and a VL CDR3 of SEQ ID NO:226, and a VH domain that comprises a VH CDR1 of SEQ ID NO:221, a VH CDR2 of SEQ ID NO:222, and a VH CDR3 of SEQ ID NO:223.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:219 or a sequence substantially homologous thereto and/or a VL domain that comprises the amino acid sequence of SEQ ID NO:220, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:219 and a VL domain that comprises the amino acid sequence of SEQ ID NO:220.

In some embodiments an antibody in IgG format is preferred. A preferred embodiment of the invention provides an antibody that binds to, or specifically binds to, HLA-DQ2.5:DQ2.5-glia-α2 which has a heavy chain that comprises the amino acid sequence of SEQ ID NO:460 or a sequence substantially homologous thereto and/or a light chain that comprises the amino acid sequence of SEQ ID NO:461 or a sequence substantially homologous thereto. In another preferred embodiment the invention provides an antibody that binds to, or specifically binds to, HLA-DQ2.5:DQ2.5-glia-α2 which has a heavy chain that comprises the amino acid sequence of SEQ ID NO:462 or a sequence substantially homologous thereto and/or a light chain that comprises the amino acid sequence of SEQ ID NO:463 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:460 and a light chain that comprises the amino acid sequence of SEQ ID NO:461.

In another preferred embodiment, an antibody comprises a heavy chain that comprises the amino acid sequence of SEQ ID NO:462 and a light chain that comprises the amino acid sequence of SEQ ID NO:463.

The section immediately above relates to the 220 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:242 or a sequence substantially homologous thereto, (b) a VL CDR2 that comprises the amino acid sequence of SEQ ID NO:243 or a sequence substantially homologous thereto, and (c) a VL CDR3 that comprises the amino acid sequence of SEQ ID NO:244 or a sequence substantially homologous thereto; and/or (preferably "and")

wherein said heavy chain variable region comprises:

(d) a variable heavy (VH) CDR1 that comprises the amino acid sequence of SEQ ID NO:239 or a sequence substantially homologous thereto, (e) a VH CDR2 that comprises the amino acid sequence of SEQ ID NO:240 or a sequence substantially homologous thereto, and (f) a VH CDR3 that comprises the amino acid sequence of SEQ ID NO:241 or a sequence substantially homologous thereto.

US 12,606,626 B2

23

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:242, a VL CDR2 of SEQ ID NO:243, and a VL CDR3 of SEQ ID NO:244, and a VH domain that comprises a VH CDR1 of SEQ ID NO:239, a VH CDR2 of SEQ ID NO:240, and a VH CDR3 of SEQ ID NO:241.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:237 or a sequence substantially homologous thereto and/or a VL domain that comprises the amino acid sequence of SEQ ID NO:238, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:237 and a VL domain that comprises the amino acid sequence of SEQ ID NO:238.

The section immediately above relates to the 221 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:260 or a sequence substantially homologous thereto, (b) a VL CDR2 that comprises the amino acid sequence of SEQ ID NO:261 or a sequence substantially homologous thereto, and (c) a VL CDR3 that comprises the amino acid sequence of SEQ ID NO:262 or a sequence substantially homologous thereto; and/or (preferably "and")

wherein said heavy chain variable region comprises:

(d) a variable heavy (VH) CDR1 that comprises the amino acid sequence of SEQ ID NO:257 or a sequence substantially homologous thereto, (e) a VH CDR2 that comprises the amino acid sequence of SEQ ID NO:258 or a sequence substantially homologous thereto, and (f) a VH CDR3 that comprises the amino acid sequence of SEQ ID NO:259 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:260, a VL CDR2 of SEQ ID NO:261, and a VL CDR3 of SEQ ID NO:262, and

a VH domain that comprises a VH CDR1 of SEQ ID NO:257, a VH CDR2 of SEQ ID NO:258, and a VH CDR3 of SEQ ID NO:259.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:255 or a sequence substantially homologous thereto and/or a VL domain that comprises the amino acid sequence of SEQ ID NO:256, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:255 and a VL domain that comprises the amino acid sequence of SEQ ID NO:256.

The section immediately above relates to the 223 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:278 or a sequence substantially homologous thereto, (b) a VL CDR2 that comprises the amino acid sequence of SEQ ID NO:279 or a sequence substantially homologous thereto, and (c) a VL CDR3 that comprises the amino acid sequence of SEQ ID NO:280 or a sequence substantially homologous thereto; and/or (preferably "and")

wherein said heavy chain variable region comprises:

(d) a variable heavy (VH) CDR1 that comprises the amino acid sequence of SEQ ID NO:275 or a sequence substantially homologous thereto, (e) a VH CDR2 that comprises the amino acid sequence of SEQ ID NO:276 or a sequence substantially homologous thereto, and (f) a VH CDR3 that comprises the amino acid sequence of SEQ ID NO:277 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:278, a VL CDR2 of SEQ ID NO:279, and a VL CDR3 of SEQ ID NO:280, and a VH domain that comprises a VH CDR1 of SEQ ID NO:275, a VH CDR2 of SEQ ID NO:276, and a VH CDR3 of SEQ ID NO:277.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:273 or a sequence substantially homologous thereto and/or a VL domain that comprises the amino acid sequence of SEQ ID NO:274, or a sequence substantially homologous thereto. A preferred "sequence substantially homologous thereto" is a sequence having at least 80% sequence identity thereto.

Further preferred embodiments provide an antigen binding protein that specifically binds to, or specifically binds to, HLA-DQ2.5:DQ2.5-glia-α2 comprising a VH domain that comprises the amino acid sequence of SEQ ID NO:273 and a VL domain that comprises the amino acid sequence of SEQ ID NO:274.

The section immediately above relates to the 226 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:296 or a sequence substantially homologous thereto, (b) a VL CDR2 that comprises the amino acid sequence of SEQ ID NO:297 or a sequence substantially homologous thereto, and (c) a VL CDR3 that comprises the amino acid sequence of SEQ ID NO:298 or a sequence substantially homologous thereto; and/or (preferably "and")

wherein said heavy chain variable region comprises:

(d) a variable heavy (VH) CDR1 that comprises the amino acid sequence of SEQ ID NO:293 or a sequence substantially homologous thereto, (e) a VH CDR2 that comprises the amino acid sequence of SEQ ID NO:294 or a sequence substantially homologous thereto, and (f) a VH CDR3 that comprises the amino acid sequence of SEQ ID NO:295 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:296, a VL CDR2 of SEQ ID NO:297, and a VL CDR3 of SEQ ID NO:298, and a VH domain that comprises a VH CDR1 of SEQ ID NO:293, a VH CDR2 of SEQ ID NO:294, and a VH CDR3 of SEQ ID NO:295.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:291 or a sequence substantially homologous thereto and/or a VL domain that comprises the amino acid sequence of SEQ ID NO:292, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:291 and a VL domain that comprises the amino acid sequence of SEQ ID NO:292.

In some embodiments an antibody in IgG format is preferred. A preferred embodiment of the invention provides an antibody that binds to, or specifically binds to, HLA- DQ2.5:DQ2.5-glia-α2 which has a heavy chain that comprises the amino acid sequence of SEQ ID NO:464 or a sequence substantially homologous thereto and/or a light chain that comprises the amino acid sequence of SEQ ID NO:465 or a sequence substantially homologous thereto. In another preferred embodiment the invention provides an antibody that binds to, or specifically binds to, HLA-DQ2.5:DQ2.5-glia-α2, which has a heavy chain that comprises the amino acid sequence of SEQ ID NO:466 or a sequence substantially homologous thereto and/or a light chain that comprises the amino acid sequence of SEQ ID NO:467 or a sequence substantially homologous thereto. A preferred "sequence substantially homologous thereto" is a sequence having at least 80% sequence identity thereto.

In a preferred embodiment, an antibody comprises a heavy chain that comprises the amino acid sequence of SEQ ID NO:464 and a light chain that comprises the amino acid sequence of SEQ ID NO:465.

In another preferred embodiment, an antibody comprises a heavy chain that comprises the amino acid sequence of SEQ ID NO:466 and a light chain that comprises the amino acid sequence of SEQ ID NO:467.

The section immediately above relates to the 228 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:314 or a sequence substantially homologous thereto, (b) a VL CDR2 that comprises the amino acid sequence of SEQ ID NO:315 or a sequence substantially homologous thereto, and (c) a VL CDR3 that comprises the amino acid sequence of SEQ ID NO:316 or a sequence substantially homologous thereto; and/or (preferably "and")

wherein said heavy chain variable region comprises:

(d) a variable heavy (VH) CDR1 that comprises the amino acid sequence of SEQ ID NO:311 or a sequence substantially homologous thereto, (e) a VH CDR2 that comprises the amino acid sequence of SEQ ID NO:312 or a sequence substantially homologous thereto, and (f) a VH CDR3 that comprises the amino acid sequence of SEQ ID NO:313 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:314, a VL CDR2 of SEQ ID NO:315, and a VL CDR3 of SEQ ID NO:316, and a VH domain that comprises a VH CDR1 of SEQ ID NO:311, a VH CDR2 of SEQ ID NO:312, and a VH CDR3 of SEQ ID NO:313.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:309 or a sequence substantially homologous thereto and/or a VL domain that comprises the amino acid sequence of SEQ ID NO:310, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:309 and a VL domain that comprises the amino acid sequence of SEQ ID NO:310.

The section immediately above relates to the 206-2.B111 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:332 or a sequence substantially homologous thereto,
(b) a VL CDR2 that comprises the amino acid sequence of SEQ ID NO:333 or a sequence substantially homologous thereto, and
(c) a VL CDR3 that comprises the amino acid sequence of SEQ ID NO:334 or a sequence substantially homologous thereto; and/or (preferably "and")
wherein said heavy chain variable region comprises:
(d) a variable heavy (VH) CDR1 that comprises the amino acid sequence of SEQ ID NO:329 or a sequence substantially homologous thereto,
(e) a VH CDR2 that comprises the amino acid sequence of SEQ ID NO:330 or a sequence substantially homologous thereto, and
(f) a VH CDR3 that comprises the amino acid sequence of SEQ ID NO:331 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:
a VL domain that comprises a VL CDR1 of SEQ ID NO:332, a VL CDR2 of SEQ ID NO:333, and a VL CDR3 of SEQ ID NO:334, and
a VH domain that comprises a VH CDR1 of SEQ ID NO:329, a VH CDR2 of SEQ ID NO:330, and a VH CDR3 of SEQ ID NO:331.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:327 or a sequence substantially homologous thereto and/or a VL domain that comprises the amino acid sequence of SEQ ID NO:328, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:327 and a VL domain that comprises the amino acid sequence of SEQ ID NO:328.

The section immediately above relates to the 206-3. D8 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:350 or a sequence substantially homologous thereto,
(b) a VL CDR2 that comprises the amino acid sequence of SEQ ID NO:351 or a sequence substantially homologous thereto, and
(c) a VL CDR3 that comprises the amino acid sequence of SEQ ID NO:352 or a sequence substantially homologous thereto; and/or (preferably "and")
wherein said heavy chain variable region comprises:
(d) a variable heavy (VH) CDR1 that comprises the amino acid sequence of SEQ ID NO:347 or a sequence substantially homologous thereto,
(e) a VH CDR2 that comprises the amino acid sequence of SEQ ID NO:348 or a sequence substantially homologous thereto, and
(f) a VH CDR3 that comprises the amino acid sequence of SEQ ID NO:349 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:
a VL domain that comprises a VL CDR1 of SEQ ID NO:350, a VL CDR2 of SEQ ID NO:351, and a VL CDR3 of SEQ ID NO:352, and
a VH domain that comprises a VH CDR1 of SEQ ID NO:347, a VH CDR2 of SEQ ID NO:348, and a VH CDR3 of SEQ ID NO:349.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:345 or a sequence substantially homologous thereto and/or a VL domain that comprises the amino acid sequence of SEQ ID NO:346, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:345 and a VL domain that comprises the amino acid sequence of SEQ ID NO:346.

The section immediately above relates to the 206-3.C7 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:368 or a sequence substantially homologous thereto, (b) a VL CDR2 that comprises the amino acid sequence of SEQ ID NO:369 or a sequence substantially homologous thereto, and (c) a VL CDR3 that comprises the amino acid sequence of SEQ ID NO:370 or a sequence substantially homologous thereto; and/or (preferably "and")

wherein said heavy chain variable region comprises:

(d) a variable heavy (VH) CDR1 that comprises the amino acid sequence of SEQ ID NO:365 or a sequence substantially homologous thereto, (e) a VH CDR2 that comprises the amino acid sequence of SEQ ID NO:366 or a sequence substantially homologous thereto, and (f) a VH CDR3 that comprises the amino acid sequence of SEQ ID NO:367 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:368, a VL CDR2 of SEQ ID NO:369, and a VL CDR3 of SEQ ID NO:370, and a VH domain that comprises a VH CDR1 of SEQ ID NO:365, a VH CDR2 of SEQ ID NO:366, and a VH CDR3 of SEQ ID NO:367.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:363 or a sequence substantially homologous thereto and/or a VL domain that comprises the amino acid sequence of SEQ ID NO:364, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:363 and a VL domain that comprises the amino acid sequence of SEQ ID NO:364.

The section immediately above relates to the 206-3.C11 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:386 or a sequence substantially homologous thereto, (b) a VL CDR2 that comprises the amino acid sequence of SEQ ID NO:387 or a sequence substantially homologous thereto, and (c) a VL CDR3 that comprises the amino acid sequence of SEQ ID NO:388 or a sequence substantially homologous thereto; and/or (preferably "and")

wherein said heavy chain variable region comprises:

(d) a variable heavy (VH) CDR1 that comprises the amino acid sequence of SEQ ID NO:383 or a sequence substantially homologous thereto, (e) a VH CDR2 that comprises the amino acid sequence of SEQ ID NO:384 or a sequence substantially homologous thereto, and (f) a VH CDR3 that comprises the amino acid sequence of SEQ ID NO:385 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:386, a VL CDR2 of SEQ ID NO:387, and a VL CDR3 of SEQ ID NO:388, and a VH domain that comprises a VH CDR1 of SEQ ID NO:383, a VH CDR2 of SEQ ID NO:384, and a VH CDR3 of SEQ ID NO:385.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:381 or a sequence substantially homologous thereto and/or a VL domain that comprises the amino acid sequence of SEQ ID NO:382, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:381 and a VL domain that comprises the amino acid sequence of SEQ ID NO:382.

The section immediately above relates to the 206-3.F6 antibody.

In one aspect of, and in certain embodiments of, the present invention there is provided an antigen binding protein (e.g. an antibody) which binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein said light chain variable region comprises:

(a) a variable light (VL) CDR1 that comprises the amino acid sequence of SEQ ID NO:404 or a sequence substantially homologous thereto, (b) a VL CDR2 that comprises the amino acid sequence of SEQ ID NO:405 or a sequence substantially homologous thereto, and (c) a VL CDR3 that comprises the amino acid sequence of SEQ ID NO:406 or a sequence substantially homologous thereto; and/or (preferably "and")

wherein said heavy chain variable region comprises:

(d) a variable heavy (VH) CDR1 that comprises the amino acid sequence of SEQ ID NO:401 or a sequence substantially homologous thereto, (e) a VH CDR2 that comprises the amino acid sequence of SEQ ID NO:402 or a sequence substantially homologous thereto, and (f) a VH CDR3 that comprises the amino acid sequence of SEQ ID NO:403 or a sequence substantially homologous thereto.

A preferred "sequence substantially homologous thereto" is a sequence containing 1, 2 or 3 amino acid substitutions, additions or deletions relative to the stated CDR sequence.

In a preferred embodiment, the invention provides an antigen binding protein that binds to, or specifically binds to, HLA-DQ2.5:DQ2.5-glia-α2 and that comprises:

a VL domain that comprises a VL CDR1 of SEQ ID NO:404, a VL CDR2 of SEQ ID NO:405, and a VL CDR3 of SEQ ID NO:406, and a VH domain that comprises a VH CDR1 of SEQ ID NO:401, a VH CDR2 of SEQ ID NO:402, and a VH CDR3 of SEQ ID NO:403.

Certain preferred embodiments of the invention provide an antigen binding protein that binds to, or specifically binds to, HLA-DQ2.5:DQ2.5-glia-α2 comprising a VH domain that comprises the amino acid sequence of SEQ ID NO:399 or a sequence substantially homologous thereto and/or a VL domain that comprises the amino acid sequence of SEQ ID NO:400, or a sequence substantially homologous thereto. A preferred "sequence substantially homologous thereto" is a sequence having at least 80% sequence identity thereto.

Further preferred embodiments provide an antigen binding protein that binds to, or specifically binds to, HLA-DQ2.5:DQ2.5-glia-α2 comprising a VH domain that comprises the amino acid sequence of SEQ ID NO:399 and a VL domain that comprises the amino acid sequence of SEQ ID NO:400.

The section immediately above relates to the 206-12.F6 antibody.

In some preferred embodiments of the present invention, the antigen binding protein binds to, or specifically binds to, HLA-DQ2.5:DQ2.5-glia-α1a and comprises a VL CDR1 that has a H at position 1 and/or an S at position 4. In some embodiments, the antigen binding protein binds to, or specifically binds to, HLA-DQ2.5:DQ2.5-glia-α1a and has a VL CDR3 that has a P at position 7.

In some preferred embodiments of the present invention, the antigen binding protein binds to, or specifically binds to, HLA-DQ2.5:DQ2.5-glia-α2 and comprises a VL CDR1 that has a Q at position 1 and/or an S position 4. In some embodiments, the antigen binding protein binds to, or specifically binds to, HLA-DQ2.5:DQ2.5-glia-α2 and has a VL CDR3 that has a P at position 7.

In one aspect, the present invention provides an antigen binding protein which binds to, or specifically binds to, HLA-DQ2.5:DQ2.5 presenting a peptide (e.g. a gliadin peptide (or gliadin derived peptide) or a celiac disease associated peptide or a gluten-derived peptide), said antigen binding protein comprising at least one light chain variable domain and at least one heavy chain variable domain, each domain comprising three complementarity determining regions (CDRs), wherein said antigen binding protein (e.g. antibody) comprises CDRs and/or variable domains as defined elsewhere herein. Other features and properties of other aspects and embodiments of the invention apply, mutatis mutandis, to this aspect of the invention.

In another aspect, the present invention provides an antigen binding protein (e.g. an antibody), said antigen binding protein comprising at least one light chain variable domain and at least one heavy chain variable domain, each domain comprising three complementarity determining regions (CDRs), wherein said antigen binding protein (e.g. antibody) comprises CDRs and/or variable domains as defined elsewhere herein. Other features and properties of other aspects and embodiments of the invention apply, mutatis mutandis, to this aspect of the invention.

In one aspect, and in certain embodiments, the invention provides an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein binding of the antigen binding protein to HLA-DQ2.5:DQ2.5-glia-α1a or HLA-DQ2.5:DQ2.5-glia-α2 is characterized by a recognition motif (or "footprint" or "codon") which comprises the amino acids at positions corresponding to N92, S93, Y94, D28 and S30 of the light chain variable region of SEQ ID NO:40 or SEQ ID NO:166.

The light chain variable region residues mentioned above, N92, S93, Y94, D28 and S30, correspond to IMGT (ImMunoGeneTics) light chain variable region residue numbers (or residue positions) N108, S114, Y115, D28, S36 in relation to antibody 107 and N108, S109, Y114, D28, S36 in relation to antibody 206.

In one aspect, and in certain embodiments, the invention provides an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein binding of the antigen binding protein to HLA-DQ2.5:DQ2.5-glia-α1a or HLA-DQ2.5:DQ2.5-glia-α2 is characterized by a recognition motif (or "footprint" or "codon") which comprises the amino acids at positions corresponding to N92, S93, Y94, D28 and S30 of the light chain variable region of SEQ ID NO:40 or SEQ ID NO:166, and the amino acids at positions corresponding to a Y60, Q64, D66 and R70 of the MHC beta chain of SEQ ID NO:494 (the beta chain of the HLA-DQ2.5), and the amino acids at positions corresponding to H68 S72 and R76 of the MHC alpha chain of SEQ ID NO:493 (the alpha chain of the HLA-DQ2.5).

In one aspect, and in certain embodiments, the invention provides an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein binding of the antigen binding protein to HLA-DQ2.5:DQ2.5-glia-α1a or HLA-DQ2.5:DQ2.5-glia-α2 is characterized by a recognition motif (or "footprint" or "codon") which comprises the amino acids at positions N92, S93, Y94, D28 and S30 of said light chain variable region.

In one aspect, and in certain embodiments, the invention provides an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2, said antigen binding protein comprising at least one heavy chain variable region that comprises three CDRs and at least one light chain variable region that comprises three CDRs, wherein binding of the antigen binding protein to HLA-DQ2.5:DQ2.5-glia-α1a or HLA-DQ2.5:DQ2.5-glia-α2 is characterized by a recognition motif (or "footprint" or "codon") which comprises the amino acids at positions N92, S93, Y94, D28 and S30 of said light chain variable region, and the amino acids at positions Y60, Q64, D66 and R70 of the MHC beta chain of SEQ ID NO:494 (the beta chain of the HLA-DQ2.5), and the amino acids at positions H68 S72 and R76 of the MHC alpha chain of SEQ ID NO:493 (the alpha chain of the HLA-DQ2.5).

In some embodiments, the invention provides an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2 wherein binding of the antigen binding protein to HLA-DQ2.5:DQ2.5-glia-α1a or HLA-DQ2.5:DQ2.5-glia-α2 is characterized by a recognition motif as described above, has three VL CDRs and/or three VH CDRs, or a light chain variable domain and/or a heavy chain variable domain, or a light chain and/or a heavy chain as described elsewhere herein. Thus, other features and properties of other aspects and embodiments of the invention apply, mutatis mutandis, to these aspects of the invention.

A "recognition motif" (or "footprint" or "codon" or "binding motif") may be defined as a group of amino acids that contribute to (or participate in), or a group of amino acids that are predicted to contribute to (or predicted to participate in), the binding (or interaction) between the antigen binding protein and the target antigen (in this case the pMHCs HLA-DQ2.5:DQ2.5-glia-α1a or HLA-DQ2.5:DQ2.5-glia-α2). A person skilled in the art will be familiar with suitable methods and techniques for identifying or predicting recognition motifs and any suitable method may be used. For example, the recognition motif may be as determined or predicted using antibody modeling or antibody docking methods (e.g. antibody modeling or antibody docking software). The RosettaAntibody and/or SnugDock applications (software) may be used for such methods in order to generate models of the docked complexes of an antigen binding protein (e.g. antibody) and its pMHC target, for example as described in Example 4 herein. In some embodiments, antibody modeling (or antibody docking) may be done using the crystal structure of the binary complex of HLA-DQ2.5:DQ2.5-glia-α1a (PDB ID 1S9V [C.-Y. Kim, 2004]) or the crystal structure of HLA-DQ2.5:DQ2.5-glia-α2 (PDB ID 4OZF [Petersen et al., 2014]) as docking partners, e.g. as described in Example 4 herein. In some embodiments, the recognition motif is as determined by crystallographic methods (e.g. the crystal structure of the antigen binding protein: HLA-DQ2.5:DQ2.5-glia-α1a complex or antigen binding protein: HLA-DQ2.5:DQ2.5-glia-α2 complex.

In one aspect, the invention provides an antigen binding protein that binds to HLA-DQ2.5 presenting a gliadin peptide, said antigen binding protein comprising at least one heavy chain variable region that comprises three CDRs and at least one light chain variable region that comprises three CDRs, said light chain variable region comprising a variable light (VL) CDR1 comprising the amino acid sequence of SEQ ID NO:435;
a variable light (VL) CDR2 comprising the amino acid sequence of SEQ ID NO:437; and
a variable light (VL) CDR3 comprising the amino acid sequence of SEQ ID NO:439.

In one aspect, the invention provides an antigen binding protein that binds to, or specifically binds to, HLA-DQ2.5:DQ2.5-glia-α1a or to HLA-DQ2.5:DQ2.5-glia-α2, said antigen binding protein comprising at least one heavy chain variable region that comprises three CDRs and at least one light chain variable region that comprises three CDRs, said light chain variable region comprising a variable light (VL) CDR1 comprising the amino acid sequence of SEQ ID NO:435;
a variable light (VL) CDR2 comprising the amino acid sequence of SEQ ID NO:437; and a variable light (VL) CDR3 comprising the amino acid sequence of SEQ ID NO:439.

In some embodiments, the antigen binding protein that binds to, or specifically binds to, HLA-DQ2.5:DQ2.5-glia-α1a or an antigen binding protein that binds to, or specifically binds to, HLA-DQ2.5:DQ2.5-glia-α2 comprising a light chain variable region as defined in the paragraph immediately above, comprises three VL CDRs and/or three VH CDRs, or a light chain variable domain and/or a heavy chain variable domain, or a light chain and/or a heavy chain as described elsewhere herein. Thus, other features and properties of other aspects and embodiments of the invention apply, mutatis mutandis, to these aspects of the invention.

For example, in preferred embodiments, the antigen binding protein comprises a light chain variable domain that comprises a variable light (VL) CDR1 comprising the amino acid sequence of SEQ ID NO:436;
a variable light (VL) CDR2 comprising the amino acid sequence of SEQ ID NO:438; and
a variable light (VL) CDR3 comprising the amino acid sequence of SEQ ID NO:440 or SEQ ID NO:521.

In preferred embodiments, the antigen binding protein comprises a heavy chain variable domain that comprises a variable heavy (VH) CDR1 comprising the amino acid sequence of SEQ ID NO:441 (preferably SEQ ID NO:442) or SEQ ID NO:522 (preferably SEQ ID NO:523);
a variable heavy (VH) CDR2 comprising the amino acid sequence of SEQ ID NO:42 or a sequence containing 1, 2 or 3 amino acid substitutions, additions or deletions relative to SEQ ID NO:42, or SEQ ID NO:168 or a sequence containing 1, 2 or 3 amino acid substitutions, additions or deletions relative to SEQ ID NO:168; and
a variable heavy (VH) CDR3 comprising the amino acid sequence of SEQ ID NO:443.

Antigen binding proteins are described herein as comprising certain elements or regions (e.g. CDRs) "comprising" or "that comprise" the stated amino acid sequences. In some embodiments, antigen binding proteins of the invention are those comprising elements or regions (e.g. CDRs) "consisting of" or "that consist of" the stated amino acid sequences.

In preferred embodiments of the present invention, an antigen binding protein that binds to, or specifically binds to, HLA-DQ2.5:DQ2.5-glia-α1a comprises a heavy chain variable region that is an IGHV6 (or IGHV6-1) heavy chain variable region. IGHV6-1 stands for immunoglobulin heavy variable 6-1. Thus, in some embodiments, an antigen binding protein that binds to, or specifically binds to, HLA-DQ2.5:DQ2.5-glia-α1a comprises a heavy chain variable region that is characterised by IGHV6 (or IGHV6-1) gene usage. Put another way, in some embodiments an antigen binding protein that binds to, or specifically binds to, HLA-DQ2.5:DQ2.5-glia-α1a comprises a heavy chain variable region that is characterised by an IGHV6 (or IGHV6-1) heavy chain gene segment. Characteristics of IGHV6 (or IGHV6-1) are known to a person skilled in the art (for example from IMGT®, the international ImMunoGeneTics Information System®).

In preferred embodiments of the present invention, an antigen binding protein that binds to, or specifically binds to, HLA-DQ2.5:DQ2.5-glia-α2 comprises a heavy chain variable region that is an IGHV1 (or IGHV1-69) heavy chain variable region. IGHV1-69 stands for immunoglobulin heavy variable 1-69. Thus, in some embodiments, an antigen binding protein that binds to, or specifically binds to, HLA-DQ2.5:DQ2.5-glia-α2 comprises a heavy chain variable region that is characterised by IGHV1 (or IGHV1-69) gene usage. Put another way, in some embodiments an antigen binding protein that binds to, or specifically binds to, HLA-DQ2.5:DQ2.5-glia-α2 comprises a heavy chain variable region that is characterised by an IGHV1 (or IGHV1-69) heavy chain gene segment. Characteristics of IGHV1 (or IGHV1-69) are known to a person skilled in the art (for example from IMGT®, the international ImMunoGeneTics Information System®).

In preferred embodiments of the present invention, an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2 comprises a light chain variable region that is an IGKV1 light chain variable region. IGKV1 stands for immunoglobulin kappa variable 1. Thus, in some embodiments, an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2 comprises a light chain variable region that is characterised by IGKV1 gene usage. Put another way, in some embodiments an antigen binding protein that binds to, or specifically binds to, HLA-DQ2.5:DQ2.5-glia-α1a or an antigen binding protein that binds to, or specifically binds to, HLA-DQ2.5:DQ2.5-glia-α2 comprises a light chain variable region that is characterised by an IGKV1 light chain gene segment. Characteristics of IGKV1 are known to a person skilled in the art (for example from IMGT®, the international ImMunoGeneTics Information System®).

In preferred embodiments of the present invention, the IGKV1 mentioned above in connection with an antigen binding protein that binds to, or specifically binds to, HLA-DQ2.5:DQ2.5-glia-α1a is IGKV1-9.

In preferred embodiments of the present invention, the IGKV1 mentioned above in connection with an antigen binding protein that binds to, or specifically binds to, HLA-DQ2.5:DQ2.5-glia-α2 is IGKV1-12.

Further details and options in connection with IGHV for IGKV gene usage are set forth in the sequence Tables herein and any of these may be used in accordance with the present invention Details and options in connection with IGHD (immunoglobulin heavy diversity), IGHJ (immunoglobulin heavy joining), IGKD (immunoglobulin kappa diversity) and IGKJ (immunoglobulin kappa joining) usage are also set forth in the sequence Tables herein. In some embodiments, antigen binding proteins of the invention may be characterised by the presence (or usage) of any one or more of the IGHV, IGKV, IGHD, IGKD, IGHJ or IGKJ mentioned in the sequence Tables herein (or combinations thereof, e.g. the specific combinations mentioned in the sequence Tables).

The term "substantially homologous" as used herein in connection with an amino acid or nucleic acid sequence includes sequences having at least 65%, 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain up to 5, e.g. only 1, 2, 3, 4 or 5, preferably 1, 2 or 3, more preferably 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

In certain embodiments, if a given starting sequence is relatively short (e.g. five amino acids in length or three amino acids in length), then fewer amino acid substitutions may be present in sequences substantially homologous thereto as compared with the number of amino acid substitutions that might optionally be made in a sequence substantially homologous to a longer starting sequence. For example, in certain preferred embodiments the VL CDR2 sequence of antigen binding proteins of the invention is three amino acids in length. A sequence substantially homologous to a starting VH CDR2 sequence in accordance with the present invention, e.g. a starting VH CDR2 sequence which in some embodiments may be three amino acid residues in length, preferably has 1 or 2 (more preferably 1) altered amino acids in comparison with the starting sequence. Accordingly, in some embodiments the number of altered amino acids in substantially homologous sequences (e.g. in substantially homologous CDR sequences) can be tailored to the length of a given starting CDR sequence. For example, different numbers of altered amino acids can be present depending on the length of a given starting CDR sequence such as to achieve a particular % sequence identity in the CDRs, for example a sequence identity of at least 60%, 70%, 80%, or at least, 90%.

Routine methods in the art such as αlanine scanning mutagenesis and/or analysis of crystal structure of the antigen-antibody complex can be used in order to determine which amino acid residues of the CDRs do not contribute or do not contribute significantly to antigen binding and therefore are good candidates for alteration or substitution in the embodiments of the invention involving substantially homologous sequences.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antigen binding protein (e.g. antibody) should retain the ability to bind to the antigen (pMHC antigen) as described herein. Preferably, any substantially homologous antigen binding protein (e.g. antibody) should retain one or more (or all) of the functional capabilities of the starting antigen binding protein (e.g. antibody).

Preferably, any substantially homologous antigen binding protein (e.g antibody) should retain the ability to bind to, or specifically bind to, the same epitope of the antigen as recognized by the antigen binding protein (e.g. antibody) in question, for example, the same epitope recognized by the CDR domains of the invention or the VH and VL domains of the invention as described herein. Thus, preferably, any substantially homologous antigen binding protein (e.g. antibody) should retain the ability to compete with one or more of the various antigen binding proteins of the invention for binding to the relevant antigen. Binding to the same epitope/antigen can be readily tested by methods well known and described in the art, e.g. using binding assays, e.g. a competition assay. Retention of other functional properties can also readily be tested by methods well known and described in the art or herein.

Thus, a person skilled in the art will appreciate that binding assays can be used to test whether "substantially homologous" antigen binding proteins (e.g. antibodies) have the same binding specificities as the antigen binding proteins of the invention, for example, binding assays such as competition assays or ELISA assays, e.g. as described elsewhere herein. Surface Plasmon Resonance (e.g. Biacore™) assays could also readily be used to establish whether "substantially homologous" antigen binding proteins can bind to the relevant antigen. The skilled person will be aware of other suitable methods and variations.

As outlined below, a competition binding assay can be used to test whether "substantially homologous" antibodies retain the ability to bind to, or specifically bind to, substantially the same epitope of the relevant antigen as recognized by the antigen binding proteins of the invention (e.g. the 107 antibody or the 206 antibody), or have the ability to compete with one or more of the various antigen binding proteins of the invention. The method described below is only one example of a suitable competition assay. The skilled person will be aware of other suitable methods and variations.

An exemplary competition assay involves assessing the binding of various effective concentrations of an antigen binding protein of the invention to the relevant antigen in the presence of varying concentrations of a test antigen binding protein (e.g. a substantially homologous antigen binding protein e.g. antibody). The amount of inhibition of binding induced by the test antigen binding protein can then be assessed. A test antigen binding protein that shows increased competition with an antigen binding protein of the invention at increasing concentrations (i.e. increasing concentrations of the test antigen binding protein result in a corresponding reduction in the amount of antigen binding protein of the invention binding to the relevant antigen) is evidence of binding to substantially the same epitope. Preferably, the test antigen binding protein significantly reduces the amount of antigen binding protein of the invention that binds to the relevant antigen. Preferably, the test antigen binding protein reduces the amount of antigen binding protein of the invention that binds to the relevant antigen by at least about 95%. ELISA and flow cytometry assays may be used for assessing inhibition of binding in such a competition assay but other suitable techniques would be well known to a person skilled in the art.

In some embodiments, "substantially homologous" antigen binding proteins which retain the ability to bind to, or specifically bind to, substantially the same (or the same) epitope of the relevant antigen as recognized by antigen binding proteins of the invention (e.g. the 107 or 206 antibodies) or which have the ability to compete with one or more of the various antigen binding proteins of the invention (e.g. the 107 or 2016 antibodies) are preferred.

The term "competing antigen binding protein", as used herein, refers to antigen binding proteins that bind to about, substantially or essentially the same, or even the same, epitope as a "reference antigen binding protein". Competing antigen binding proteins are thus able to effectively compete with a reference antibody for binding to the relevant antigen. Preferably, the competing antigen binding protein can bind to the same epitope as the reference antigen binding protein. Alternatively viewed, the competing antigen binding protein preferably has the same epitope specificity as the reference antigen binding protein.

"Reference antigen binding proteins" as used herein are antigen binding proteins which can bind to the relevant antigen in accordance with the invention. Preferably, reference antigen binding proteins have a VH and a VL domain as defined herein. For example, a reference antigen binding protein which binds to, or specifically binds to, HLA-DQ2.5:DQ2.5-glia-α1a may comprise a VL domain an a VH domain of the 107 antibody (i.e. comprise a VL domain of SEQ ID NO:40 and a VH domain of SEQ ID NO:39), and a reference antigen binding protein which binds to, or specifically binds to, HLA-DQ2.5:DQ2.5-glia-α2 may comprise a VL domain an a VH domain of the 206 antibody (i.e. comprise a VL domain of SEQ ID NO:166 and a VH domain of SEQ ID NO:165). Thus a preferred reference antigen binding protein may be the 107 antibody or the 206 antibody as defined herein.

The identification of one or more competing antigen binding proteins (e.g. antibodies) is a straightforward technical matter now that reference antibodies such as the 107 antibody and the 206 antibody have been provided. As the identification of competing antigen binding proteins (e.g. antibodies) is determined in comparison to a reference antigen binding protein (e.g. antibody), it will be understood that actually determining the epitope to which either or both antigen binding proteins bind is not in any way required in order to identify a competing antigen binding protein. However, epitope mapping can be performed using standard techniques, if desired.

Substantially homologous sequences of proteins of the invention include, without limitation, conservative amino acid substitutions, or for example alterations that do not affect the VH, VL or CDR domains of the antibodies, e.g. antibodies where tag sequences, toxins or other components are added that do not contribute to the binding of antigen, or alterations to convert one type or format of antibody molecule or fragment to another type or format of antibody molecule or fragment (e.g. conversion from Fab to scFv or whole antibody or vice versa), or the conversion of an antibody molecule to a particular class or subclass of antibody molecule (e.g. the conversion of an antibody molecule to IgG or a subclass thereof, e.g. $IgG_2$).

A "conservative amino acid substitution", as used herein, is one in which the amino acid residue is replaced with another amino acid residue having a similar side chain. Families of amino acid residues having similar side chains have been defined in the art, including basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. glycine, cysteine, α1anine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine).

Homology may be assessed by any convenient method. However, for determining the degree of homology between sequences, computer programs that make multiple alignments of sequences are useful, for instance Clustal W (Thompson, Higgins, Gibson, *Nucleic Acids Res.,* 22:4673-4680, 1994). If desired, the Clustal W algorithm can be used together with BLOSUM 62 scoring matrix (Henikoff and Henikoff, *Proc. Natl. Acad. Sci. USA,* 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.,* 48:443, 1970) as revised by Smith and Waterman (Smith and Waterman, *Adv. Appl. Math.,* 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS*, 4:11-17, 1988), FASTA (Pearson and Lipman, *Proc. Natl. Acad. Sci. USA*, 85:2444-2448, 1988; Pearson, *Methods in Enzymology*, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose. Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

By way of providing a reference point, sequences according to the present invention having 65%, 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

As described above, the present invention provides antigen binding proteins (e.g. antibodies) that bind to, or specifically bind to, HLA-DQ2.5:DQ2.5-glia-α1a and antigen binding proteins (e.g. antibodies) that bind to, or specifically bind to, HLA-DQ2.5:DQ2.5-glia-α2.

HLA-DQ2.5 (encoded by DQA1*05 and DQB1*02) is specific type of MHC Class 2 molecule that has a strong association with celiac disease.

HLA-DQ2.5 comprises a α-chain (typically having an $\alpha_1$ domain and an $\alpha_2$ domain and typically encoded by DQA1*05) and a β-chain (typically having a $\beta_1$ domain and a $\beta_2$ domain and typically encoded by DQB1*02). Amino acid sequences of the α- and β-chains of HLA-DQ2.5 are set forth herein (the α-chain sequence is set forth in SEQ ID NO:493; the β-chain sequence is set forth in SEQ ID NO:494).

HLA-DQ2.5 can present gliadin epitopes, for example epitopes of α-gliadin, for example DQ2.5-glia-α1a and DQ2.5-glia-α2. The amino acid sequence of the deamidated DQ2.5-glia-α1a epitope is set forth in SEQ ID NO:472. The amino acid sequence of the deamidated DQ2.5-glia-α2 epitope is set forth in SEQ ID NO:473. These deamidated forms of the DQ2.5-glia-α1a and DQ2.5-glia-α2 epitopes may be considered to be celiac disease-associated forms of DQ2.5-glia-α1a and DQ2.5-glia-α2 epitopes. These epitopes of α-gliadin are typically present on a proteolysis resistant α-gliadin 33-mer peptide (SEQ ID NO:476). However, for the avoidance of doubt, and as is evident from elsewhere herein, antigen binding proteins (e.g. antibodies) of the invention can bind to HLA-DQ2.5:DQ2.5-glia-α1a or HLA-DQ2.5:DQ2.5-glia-α2 when the DQ2.5-glia-α1a or DQ2.5-glia-α2 epitope is not comprised within (i.e. is not in the context of) the proteolysis resistant α-gliadin 33-mer peptide. Although the α-gliadin 33-mer peptide can associate with (or bind to) HLA-DQ2.5, the binding groove (or binding pocket) of the HLA-DQ2.5 molecule (i.e. the MHC molecule) can only present, or accommodate, a single 9-mer epitope (e.g. the DQ2.5-glia-α1a epitope or the DQ2.5-glia-α2 epitope) at a given time. Which epitope is presented by HLA-DQ2.5 is determined by the "register" (or position) in which the 33-mer is bound to (associated with) the HLA- DQ2.5. HLA-DQ2.5 may also present, or accommodate, epitopes of other gliadins, for example ω-gliadin (e.g. DQ2.5-glia-ω1 (SEQ ID NO:477) or DQ2.5-glia-ω2 (SEQ ID NO:478)).

The non-disease associated form of the DQ2.5-glia-α1a epitope (or "native" form or non-deamidated form is set forth in SEQ ID NO:491). The non-disease associated form of the DQ2.5-glia-α2 epitope (or "native" form or non-deamidated form) is set forth in SEQ ID NO:492.

At its broadest "DQ2.5-glia-α1a" includes the disease associated form of the epitope (deamidated form) of SEQ ID NO:472 and the non-disease associated form of the epitope (non-deamidated form or native form) of SEQ ID NO:491.

At its broadest "DQ2.5-glia-α2" includes the disease associated form of the epitope (deamidated form) of SEQ ID NO:473 and the non-disease associated form of the epitope (non-deamidated form or native form) of SEQ ID NO:492.

The non-disease associated forms of the epitopes may also be present on a proteolysis resistant α-gliadin 33-mer peptide.

In some embodiments, an antigen binding protein which binds to, or binds specifically to, HLA-DQ2.5:DQ2.5-glia-α1a does not bind to (or cross-react with), or does not significantly bind to (or cross-react with), a HLA-DQ2.5:DQ2.5-glia-α1a complex in which the DQ2.5-glia-α1a epitope sequence has a Q residue instead of an E residue at position 6 of the 9-mer. Thus, in some embodiments, an antigen binding protein which binds to, or binds specifically to, HLA-DQ2.5:DQ2.5-glia-α1a does not bind to (or cross-react with), or does not significantly bind to (or cross-react with), a HLA-DQ2.5 complex presenting a DQ2.5-glia-α1a epitope of SEQ ID NO:491. Thus, in some embodiments, an antigen binding protein which binds to, or binds specifically to, HLA-DQ2.5:DQ2.5-glia-α1a does not bind to (or cross-react with), or does not significantly bind to (or cross-react with), a HLA-DQ2.5 complex presenting a native or non-deamidated form of DQ2.5-glia-α1a. Without wishing to be bound by theory, the DQ2.5-glia-α1a epitope of SEQ ID NO:472 (PFPQPELPY) represents a deamidated form of the DQ2.5-glia-α1a epitope and may be considered to be a celiac disease-associated form of the epitope. In some embodiments, an antigen binding protein that binds to, or specifically binds to, HLA-DQ2.5:DQ2.5-glia-α1a is specific for the disease associated form (or version) of the DQ2.5-glia-α1a epitope (SEQ ID NO:472), which may be advantageous (e.g. in celiac disease therapy). Put another way, in some embodiments the DQ2.5-glia-α1a epitope is as set forth in SEQ ID NO:472.

In some embodiments, an antigen binding protein that binds to, or binds specifically to, HLA-DQ2.5:DQ2.5-glia-α2 may bind to HLA-DQ2.5:DQ2.5-glia-α2 in which the DQ2.5-glia-α2 epitope is as set forth in SEQ ID NO:473 (PQPELPYPQ) and/or a DQ2.5-glia-α2 epitope which has a Q residue instead of an E residue at position 4 of the 9-mer. Thus, in some embodiments an antigen binding protein that binds to, or binds specifically to, HLA-DQ2.5:DQ2.5-glia-α2 may bind to HLA-DQ2.5:DQ2.5-glia-α2 in which the DQ2.5-glia-α2 epitope is as set forth SEQ ID NO:473 (PQPELPYPQ) and/or as set forth in SEQ ID NO:492. In other embodiments, an antigen binding protein that binds to, or binds specifically to, HLA-DQ2.5:DQ2.5-glia-α2 may bind to HLA-DQ2.5:DQ2.5-glia-α2 in which the DQ2.5-glia-α2 epitope is as set forth SEQ ID NO:473 (PQPELPYPQ) but not bind (or cross-react), or not significantly bind (or significantly) cross-react, with non-deamidated the DQ2.5-glia-α2 epitope as set forth in SEQ ID NO:492.

HLA-DQ2.5:DQ2.5-glia-α1a means a HLA-DQ2.5 molecule that is presenting (or "loaded" with) a DQ2.5-glia-α1a epitope. Put another way, HLA-DQ2.5:DQ2.5-glia-α1a means a HLA-DQ2.5-peptide complex (pMHC) in which the DQ2.5-glia-α1a epitope is presented in the antigen binding groove (or accommodated in the antigen binding groove).

HLA-DQ2.5:DQ2.5-glia-α2 means a HLA-DQ2.5 molecule that is presenting (or "loaded" with) a DQ2.5-glia-α2 epitope. Put another way, HLA-DQ2.5:DQ2.5-glia-α2 means a HLA-DQ2.5-peptide complex (pMHC) in which the DQ2.5-glia-α2 epitope is presented in the antigen binding groove (or accommodated in the antigen binding groove).

In some embodiments, the invention provides antigen binding proteins (e.g. antibodies) that bind to, or specifically bind to, HLA-DQ2.5:DQ2.5-glia-α1a. As used herein, the term "that specifically binds to HLA-DQ2.5:DQ2.5-glia-α1a" in the context of antigen binding proteins means those antigen binding proteins that are capable of binding to HLA-DQ2.5:DQ2.5-glia-α1a and which do not cross-react (or do not bind) or do not significantly cross-react (or do not significantly bind) HLA-DQ2.5:DQ2.5-glia-α2. In some embodiments, an antigen binding protein which "binds specifically to HLA-DQ2.5:DQ2.5-glia-α1a" in accordance with the present invention also does not cross-react with other HLA-DQ2.5:DQ2.5-glia complexes (antigens) or non-HLA-DQ2.5:DQ2.5-glia complexes (antigens).

In some embodiments, antigen binding proteins (e.g. antibodies) "bind to" HLA-DQ2.5:DQ2.5-glia-α1a but do not "specifically bind to" HLA-DQ2.5:DQ2.5-glia-α1a. The term "bind to" is broader than the term "specifically bind to". In this regard, in some embodiments, antigen binding proteins (e.g. antibodies) that bind to HLA-DQ2.5:DQ2.5-glia-α1a may have a degree of promiscuity (or cross-reactivity) in relation to the HLA-DQ2.5:epitope bound, for example they may in some embodiments cross-react (or bind) with other peptides, for example other peptides presented by HLA-DQ2.5 (e.g. other celiac disease associated peptides, or other gliadin or gliadin-derived peptides, or variants of gliadin derived peptides, or other gluten-derived peptides). Typically and preferably, antigen binding proteins (e.g. antibodies) that bind to HLA-DQ2.5:DQ2.5-glia-α1a do not cross-react (or do not bind) or do not significantly cross-react (or do not significantly bind) with DQ2.5:DQ2.5-glia-α2.

The specific HLA-DQ2.5:DQ2.5-glia-α1a antibodies exemplified herein (e.g. the 107 antibody) are examples of antigen binding proteins that bind to, or specifically bind to, HLA-DQ2.5:DQ2.5-glia-α1a.

In some embodiments, the invention provides antigen binding proteins (e.g. antibodies) that bind to, specifically bind to, HLA-DQ2.5:DQ2.5-glia-α2. As used herein, the term "that specifically binds to HLA-DQ2.5:DQ2.5-glia-α2" in the context of antigen binding proteins means those antigen binding proteins that are capable of binding to HLA-DQ2.5:DQ2.5-glia-α2 and which do not cross-react (or do not bind) or do not significantly cross-react (or do not significantly bind) HLA-DQ2.5:DQ2.5-glia-α1a. In some embodiments, an antigen binding protein which "binds specifically to HLA-DQ2.5:DQ2.5-glia-α2" in accordance with the present invention also does not cross-react with other HLA-DQ2.5:DQ2.5-glia complexes (antigens) or non-HLA-DQ2.5:DQ2.5-glia complexes (antigens).

In some embodiments, antigen binding proteins (e.g. antibodies) "bind to" HLA-DQ2.5:DQ2.5-glia-α2 but do not "specifically bind to" HLA-DQ2.5:DQ2.5-glia-α2. The term "bind to" is broader than the term "specifically bind to". In this regard, in some embodiments, antigen binding proteins (e.g. antibodies) that bind to HLA-DQ2.5:DQ2.5-glia-α2 may have a degree of promiscuity (or cross-reactivity) in relation to the HLA-DQ2.5:epitope bound, for example they may in some embodiments cross-react (or bind) with other peptides, for example other peptides presented by HLA-DQ2.5 (e.g. other celiac disease associated peptides, or other gliadin peptides or gliadin-derived peptides, or variants of gliadin derived peptides, or other gluten-derived peptides). Typically and preferably, antigen binding proteins (e.g. antibodies) that bind to HLA-DQ2.5:DQ2.5-glia-α2 do not cross-react (or do not bind) or do not significantly cross-react (or do not significantly bind) with DQ2.5:DQ2.5-glia-α1a.

The specific HLA-DQ2.5:DQ2.5-glia-α2 antibodies exemplified herein (e.g. the 206 antibody) are examples of antigen binding proteins that bind to, or specifically bind to, HLA-DQ2.5:DQ2.5-glia-α2.

The skilled person is familiar with methods and techniques that can be used for assessing whether or not a given antigen binding protein can bind to, or specifically bind to, HLA-DQ2.5:DQ2.5-glia-α1a, or can bind to, or specifically bind to, HLA-DQ2.5:DQ2.5-glia-α2 and any appropriate method or technique can be used, for example an ELISA assay or a surface plasmon resonance assay. Exemplary and preferred methods are described in the Example section herein.

In some embodiments, the HLA-DQ2.5:DQ2.5-glia-α1a is a recombinant soluble molecule in which a glia-α1a epitope (or peptide), for example in the context of SEQ ID NO:474, is covalently attached to the HLA-DQ2.5 (MHC) molecule. Such recombinant soluble molecules may be made by any appropriate means, for example as described in Example 1 herein (and by Fallang et al., 2008 and Quartsen et al., 2001).

In some embodiments, the HLA-DQ2.5:DQ2.5-glia-α2 is a recombinant soluble molecule in which a glia-α2 epitope (or peptide), for example in the context of SEQ ID NO:475, is covalently attached to the HLA-DQ2.5 (MHC) molecule. Such recombinant soluble molecules may be made by any appropriate means, for example as described in Example 1 herein (and by Fallang et al. 2008 and Quartsen et al. 2001).

In some embodiments, the HLA-DQ2.5:DQ2.5-glia-α1a is on cells (e.g. DQ2.5⁺ dendritic cells) that have been loaded with a soluble DQ-2.5-glia-α1a epitope (or peptide), for example in the context of SEQ ID NO:474, e.g. by contacting the cells with a soluble DQ-2.5-glia-α1a epitope (or peptide), for example in the context of SEQ ID NO:474, e.g. as described in the Example section herein. Thus, in some embodiments, the HLA-DQ2.5:DQ2.5-glia-α1a does not have a DQ-2.5-glia-α1a epitope (or peptide) covalently attached to the HLA-DQ2.5 molecule.

In some embodiments, the HLA-DQ2.5:DQ2.5-glia-α2 is on cells (e.g. DQ2.5⁺ dendritic cells) that have been loaded with a soluble DQ-2.5-glia-α2 epitope (or peptide), for example in the context of SEQ ID NO:475, e.g. by contacting the cells with a soluble DQ-2.5-glia-α2 epitope (or peptide), for example in the context of SEQ ID NO:475, e.g. analogously to as described in the Example section herein in relation to HLA-DQ2.5:DQ2.5-glia-α1a. Thus, in some embodiments, the HLA-DQ2.5:DQ2.5-glia-α2 does not have a DQ-2.5-glia-α2 epitope (or peptide) covalently attached to the HLA-DQ2.5 molecule.

In some embodiments, the antigen binding proteins of the invention bind to their antigen (HLA-DQ2.5:DQ2.5-glia-α1a or HLA-DQ2.5:DQ2.5-glia-α2) with a binding affinity ($K_D$) of 10 µM or less (e.g. 0.1 nM to 10 µM), preferably 5 µM or less, or 4 µM or less, or 3 µM or less, or 2 µM or less, or 1 µM or less.

In some embodiments, the antigen binding proteins of the invention bind to their antigen (HLA-DQ2.5:DQ2.5-glia-α1a or HLA-DQ2.5:DQ2.5-glia-α2) with a binding affinity ($K_D$) of 500 nM or less (e.g. 0.1 nM to 500 nM), or 400 nM or less, or 300 nM or less, or 200 nM or less, more preferably 100 nM or less.

In preferred embodiments, the antigen binding proteins of the invention bind to their antigen (HLA-DQ2.5:DQ2.5-glia-α1a or HLA-DQ2.5:DQ2.5-glia-α2) with a binding affinity ($K_D$) of 100 nM or less (e.g. 0.1 nM to 100 nM), preferably 90 nM or less, 80 nM or less, 70 nM or less, 60 nM or less, 50 nM or less, 40 nM or less, 30 nM or less, 20 nM or less (e.g. 20, 19, 18, 17, 16, 15, 14, 13, 12, 11, 10, 9, 8, 7, 6, 5, 4.5, 4, 3.5, 3, 2.5, 2, 1.5 or 1 nM, or less), or 10 nM or less (e.g. 9, 8, 7, 6, 5, 4.5, 4, 3.5, 3, 2.5, 2, 1.5 or 1 nM, or less).

In some embodiments, the antigen binding proteins of the invention bind to their antigen (HLA-DQ2.5:DQ2.5-glia-α1a or HLA-DQ2.5:DQ2.5-glia-α2) with a binding affinity ($K_D$) of 1 nM or less (e.g. 1 pM to 1 nM, or 10 pM to 1 nM, or 20 pM to 1 nM, or 50 pM to 1 nM, or 100 pM to 1 nM, or 1 pM to 500 pM, or 10 pM to 500 pM, or 20 pM to 500 pM, or 50 pM to 500 pM, or 100 pM to 500 pM, or 1 pM to 100 pM, or 10 pM to 100 pM, or 20 pM to 100 pM, or 50 pM to 100 pM), preferably 900 pM or less, 800 pM or less, 700 pM or less, 600 pM or less, 500 pM or less, 400 pM or less, 300 pM or less, 200 pM or less (e.g. 200, 190, 180, 170, 160, 150, 140, 130, 120, 110, 100, 90, 80, 70, 60, 50, 45, 40, 35, 30, 25, 20, 15 or 10 pM, or less), or 100 pM or less (e.g. 90, 80, 70, 60, 50, 45, 40, 35, 30, 25, 20, 15 or 1 pM, or less).

In certain preferred embodiments, the HLA-DQ2.5:DQ2.5-glia-α1a antigen binding proteins of the invention bind to their antigen (HLA-DQ2.5:DQ2.5-glia-α1a) with a binding affinity ($K_D$) that is less than 74 nM, preferably 70 nM or less, or 60 nM or less, or 50 nM or less, or 40 nM or less, or 30 nM or less, or 20 nM or less, or 10 nM or less, or 5 nM or less, or 2 nM or less, or 1 nM or less).

In certain preferred embodiments, the HLA-DQ2.5:DQ2.5-glia-α2 antigen binding proteins of the invention bind to their antigen (HLA-DQ2.5:DQ2.5-glia-α2) with a binding affinity ($K_D$) that is less than 20 nM, preferably 15 nM or less, or 10 nM or less, or 5 nM or less, or 2 nM or less, or 1 nM or less.

Preferably, the above-mentioned affinities and affinity range values apply when the antigen binding protein is an antibody or antigen binding fragment thereof. Particularly preferably the above-mentioned affinities and affinity range values apply when the antigen binding protein is a scFv (i.e. an antibody in the scFv format or in the Fab format).

Binding affinities ($K_D$) may be determined by any appropriate means, an exemplary and preferred method being to use surface plasmon resonance (SPR), e.g. Biacore™, for example as described in the Example section herein. In preferred embodiments, the binding affinities are as determined using SPR (e.g. Biacore™) single-cycle kinetic analysis (single-cycle kinetic method), for example using a protocol as described in Example 1 herein. In some embodiments, binding affinities (e.g. of Fab fragments) may be determined using SPR (e.g. Biacore™) multi-cycle analysis (multi-cycle kinetic method).

In certain preferred embodiments, the HLA-DQ2.5:DQ2.5-glia-α1a antigen binding proteins of the invention (e.g. antibodies) bind to their antigen (HLA-DQ2.5:DQ2.5- glia-α1a) with a binding affinity that is higher (or improved), preferably significantly higher, than the binding affinity for HLA-DQ2.5:DQ2.5-glia-α1a of the specifically described R2A1-8E, R3A2-9F or R4A1-3A (107) antibodies. The R2A1-8E antibody is characterised by a VL domain of SEQ ID NO:4 and a VH domain of SEQ ID NO:3; the R3A2-9F antibody is characterised by a VL domain of SEQ ID NO:22 and a VH domain of SEQ ID NO:21; the R4A1-3A (107) antibody is characterised by a VL domain of SEQ ID NO:40 and a VH domain of SEQ ID NO:39. A higher (or improved) binding affinity is characterised by a $K_D$ (equilibrium dissociation constant) value (e.g. in nM) that is lower.

Thus, in some embodiments, the HLA-DQ2.5:DQ2.5-glia-α1a antigen binding proteins of the invention (e.g. antibodies) have a higher (or improved), preferably significantly higher, affinity for HLA-DQ2.5:DQ2.5-glia-α1a relative to the R2A1-8E, R3A2-9F and R4A1-3A (107) antibodies.

In a particularly preferred embodiment, the HLA-DQ2.5:DQ2.5-glia-α1a antigen binding proteins of the invention (e.g. antibodies) have a higher (or improved), preferably significantly higher, affinity for HLA-DQ2.5:DQ2.5-glia-α1a relative to the R4A1-3A (107) antibody.

A significantly higher affinity may be any meaningfully improved affinity, for example an affinity that is at least 2-fold, 3-fold, 4-fold, 5-fold, 10-fold, 20-fold higher, 50-fold higher or 100-fold higher than the binding affinity of the specifically described R2A1-8E, R3A2-9F or R4A1-3A (107) antibodies (preferably the R4A1-3A (107) antibody). In some embodiments, a significantly higher affinity may be characterised by an affinity value (e.g. $K_D$ in nM) that is at least 10%, at least 20%, at least 30%, at least 40%, at least 50%, at least 60%, at least 70%, at least 80%, at least 90% or at least 95% lower than the affinity value of the specifically described R2A1-8E, R3A2-9F or R4A1-3A (107) antibodies (preferably the R4A1-3A (107) antibody).

In certain preferred embodiments, the HLA-DQ2.5:DQ2.5-glia-α2 antigen binding proteins of the invention (e.g. antibodies) bind to their antigen (HLA-DQ2.5:DQ2.5-glia-α2) with a binding affinity that is higher, preferably significantly higher, than the binding affinity for HLA-DQ2.5:DQ2.5-glia-α2 of the specifically described 206, 217, 218, 220, 221, 223, 226 or 228 antibodies. The 206 antibody is characterised by a VL domain of SEQ ID NO:166 and a VH domain of SEQ ID NO:165; the 217 antibody is characterised by a VL domain of SEQ ID NO:184 and a VH domain of SEQ ID NO:183; the 218 antibody is characterised by a VL domain of SEQ ID NO:202 and a VH domain of SEQ ID NO:201; the 220 antibody is characterised by a VL domain of SEQ ID NO:220 and a VH domain of SEQ ID NO:219; the 221 antibody is characterised by a VL domain of SEQ ID NO:238 and a VH domain of SEQ ID NO:237; the 223 antibody is characterised by a VL domain of SEQ ID NO:256 and a VH domain of SEQ ID NO:255; the 226 antibody is characterised by a VL domain of SEQ ID NO:274 and a VH domain of SEQ ID NO:273; the 228 antibody is characterised by a VL domain of SEQ ID NO:292 and a VH domain of SEQ ID NO:291. A higher (or improved) binding affinity is characterised by a $K_D$ (equilibrium dissociation constant) value (e.g. in nM) that is lower.

Thus, in some embodiments, the HLA-DQ2.5:DQ2.5-glia-α2 antigen binding proteins of the invention (e.g. antibodies) have a higher (or improved), preferably significantly higher, affinity for HLA-DQ2.5:DQ2.5-glia-α2 relative to the 206, 217, 218, 220, 221, 223, 226 or 228 antibodies.

In a particularly preferred embodiment, the HLA-DQ2.5:DQ2.5-glia-α2 antigen binding proteins of the invention (e.g. antibodies) have a higher (or improved), preferably significantly higher, affinity for HLA-DQ2.5:DQ2.5-glia-α2 relative to the 206 antibody.

A significantly higher affinity may be any meaningfully improved affinity, for example an affinity that is at least 2-fold, 3-fold, 4-fold, 5-fold, 10-fold, 20-fold, 50-fold or 100-fold higher than the binding affinity of the specifically described 206, 217, 218, 220, 221, 223, 226 or 228 antibodies (preferably the 206 antibody). In some embodiments, a significantly higher affinity may be characterised by an affinity value (e.g. $K_D$ in nM) that is at least 10%, at least 20%, at least 30%, at least 40%, at least 50%, at least 60%, at least 70%, at least 80%, at least 90% or at least 95% lower than the affinity value of the specifically described 206, 217, 218, 220, 221, 223, 226 or 228 antibodies (preferably the 206 antibody).

Although a binding affinity value (e.g. $K_D$ in nM) may be determined for an antigen binding protein (e.g. antibody) that may have a higher affinity for the relevant antigen than the specifically described R2A1-8E, R3A2-9F, R4A1-3A (107), 206, 217, 218, 220, 221, 223, 226 or 228 antibodies, it is not necessary to determine such a binding affinity value (e.g. $K_D$ in nM) in order to determine whether or not there is a higher binding affinity. It can be sufficient to simply compare the R2A1-8E, R3A2-9F, R4A1-3A (107), 206, 217, 218, 220, 221, 223, 226 or 228 antibodies with a putative affinity improved (or affinity matured) antibody by any appropriate means (e.g. SPR or ELISA) and to assess whether or not a relative increase (or improvement) in binding affinity is observed (e.g. by inspecting SPR traces/graphs obtained); determining actual affinity ($K_D$) values is not necessary (although it may be done).

In some embodiments, HLA-DQ2.5:DQ2.5-glia-α1a antigen binding proteins of the invention (e.g. antibodies) have a $K_{off}$ (or "off-rate" or dissociation constant) (s$^{-1}$) for HLA-DQ2.5:DQ2.5-glia-α1a that is ≤0.05, or ≤0.02, or ≤0.01, or ≤1×10$^{-3}$, or ≤1×10$^{-4}$, or ≤1×10$^{-5}$, or ≤1×10$^{-6}$, or ≤1×10$^{-7}$ (s$^{-1}$). In some embodiments, antigen binding proteins of the invention have a $K_{off}$ (or "off-rate") (s$^{-1}$) for HLA-DQ2.5:DQ2.5-glia-α1a that is between about 0.05 and 1×10$^{-7}$).

In some embodiments, HLA-DQ2.5:DQ2.5-glia-α1a antigen binding proteins of the invention (e.g. antibodies) have a $K_{off}$ (or "off-rate" or dissociation constant) (s$^{-1}$) for HLA-DQ2.5:DQ2.5-glia-α1a that is lower (preferably significantly lower, e.g. statistically significantly lower such as with a probability value of ≤0.05) than the $K_{off}$ (or "off-rate") (s$^{-1}$) for HLA-DQ2.5:DQ2.5-glia-α1a of the antibody 107 of the invention (e.g. when antibodies are in the Fab format). In some embodiments, antigen binding proteins (e.g. antibodies) of the present invention have a $K_{off}$ (or "off-rate") (s$^{-1}$) for HLA-DQ2.5:DQ2.5-glia-α1a that is at least 50%, at least 75%, at least 80%, at least 85%, at least 90% or at least 95% lower than the $K_{off}$ (or "off-rate") (s$^{-1}$) for HLA-DQ2.5:DQ2.5-glia-α1a of the 107 antibody of the invention (e.g. when antibodies are in the Fab format).

In some embodiments, HLA-DQ2.5:DQ2.5-glia-α2 antigen binding proteins of the invention (e.g. antibodies) have a Kou (or "off-rate" or dissociation constant) (s$^{-1}$) for HLA-DQ2.5:DQ2.5-glia-α2 that is ≤0.5, ≤0.4 ≤0.3, ≤0.2, ≤0.1, ≤0.05, or ≤0.02, or ≤0.01, or ≤1×10$^{-3}$, or ≤1×10$^{-4}$, or ≤1×10$^{-5}$, or ≤1×10$^{-6}$, or ≤1×10$^{-7}$ (s$^{-1}$). In some embodiments, antigen binding proteins of the invention have a $K_{off}$ (or "off-rate") (s$^{-1}$) for HLA-DQ2.5:DQ2.5-glia-α2 that is between about 0.5 and 1×10$^{-7}$).

In some embodiments, HLA-DQ2.5:DQ2.5-glia-α2 antigen binding proteins of the invention (e.g. antibodies) have a $K_{off}$ (or "off-rate" or dissociation constant) (s$^{-1}$) for HLA-DQ2.5:DQ2.5-glia-α2 that is lower (preferably significantly lower, e.g. statistically significantly lower such as with a probability value of 50.05) than the $K_{off}$ (or "off-rate") (s$^{-1}$) for HLA-DQ2.5:DQ2.5-glia-α2 of the antibody 206 of the invention (e.g. when antibodies are in the Fab format). In some embodiments, antibodies of the present invention have a $K_{off}$ (or "off-rate") (s$^{-1}$) for HLA-DQ2.5:DQ2.5-glia-α2 that is at least 50%, at least 75%, at least 80%, at least 85%, at least 90% or at least 95% lower than the $K_{off}$ (or "off-rate") (s$^{-1}$) for HLA-DQ2.5:DQ2.5-glia-α2 of the 206 antibody of the invention (e.g. when antibodies are in the Fab format).

The $K_{off}$ (or "off-rate") may be determined by any suitable method and the skilled person is familiar with these. For example, $K_{off}$ (or "off-rate") can be determined in a Surface Plasmon Resonance assay (e.g. Biacore™ assay), e.g. as described in the Example section herein. In preferred embodiments, the above discussion of "off-rates" applies when the antigen binding protein is in the Fab format.

As described above, certain preferred antibodies of the invention have a lower (or slower) "off-rate" ($K_{off}$ or dissociation constant) than antibodies 107 or 206). Differing off-rates can lead to differences in pharmacokinetics. Without wishing to be bound by theory, antibodies with lower off-rates may be particularly beneficial as they may sit more tightly on the target antigen and thus may be more effective, e.g. at inhibiting T-cell activation.

Typically, antigen binding proteins (e.g. antibodies) of the invention do not bind (or do not significantly bind) to the soluble form of the respective gluten-derived peptide. Thus, typically, HLA-DQ2.5:DQ2.5-glia-α1a antigen binding proteins do not significantly bind (or do not bind) to a soluble DQ2.5-glia-α1a epitope. Typically, HLA-DQ2.5:DQ2.5-glia-α2 antigen binding proteins do not significantly bind (or do not bind) to a soluble DQ2.5-glia-α2 epitope. Thus, typically, antigen binding proteins (e.g. antibodies) of the invention do not bind (or do not significantly bind) to the respective gluten-derived peptide unless the peptide is presented by a HLA-DQ2.5 complex. Determination of whether or not a given antigen binding protein can significantly bind to the soluble form of DQ2.5-glia-α1a or DQ2.5-glia-α2 can be done by any appropriate means, e.g. a competition assay such as a competition ELISA assay, e.g. as described in the Example section herein.

Thus, HLA-DQ2.5:DQ2.5-glia-α1a antigen binding proteins of the invention typically bind to, or specifically bind to, the DQ2.5-glia-α1a epitope (or peptide), solely (or strictly) in the context of the MHC, i.e. HLA-DQ2.5. This may be assessed by any appropriate means, for example by a competition ELISA, for example as set forth in the Example section herein.

HLA-DQ2.5:DQ2.5-glia-α2 antigen binding proteins of the invention typically bind to, or specifically bind to, the DQ2.5-glia-α2 epitope (or peptide), solely (or strictly) in the context of the MHC, i.e. HLA-DQ2.5. This may be assessed by any appropriate means, for example by a competition ELISA, for example a competition ELISA modified from the Example section herein.

In accordance with the present invention, HLA-DQ2.5:DQ2.5-glia-α1a antigen binding proteins do not specifically bind to the HLA-DQ2.5 molecule itself (i.e. the MHC molecule itself), e.g. in the absence of a presented DQ2.5-glia-α1a epitope. In accordance with the present invention, HLA-DQ2.5:DQ2.5-glia-α2 antigen binding proteins do not specifically bind to the HLA-DQ2.5 molecule itself (i.e. the MHC molecule itself), e.g. in the absence of a presented DQ2.5-glia-α2 epitope. Put another way, antigen binding proteins of the present invention do not bind to an "unloaded" HLA-DQ2.5 molecule.

As discussed above, in some embodiments, an antigen binding protein which "binds specifically to HLA-DQ2.5: DQ2.5-glia-α1a" in accordance with the present invention does not bind (or cross-react), or does not significantly bind or (significantly cross-react) to other HLA-DQ2.5:DQ2.5-glia complexes (antigens). Thus, in some embodiments, antigen binding proteins which bind specifically to HLA-DQ2.5:DQ2.5-glia-α1a do not bind (or cross-react), or do not significantly bind (or significantly cross-react) to HLA-DQ2.5:DQ2.5-glia-γ1, HLA-DQ2.5:DQ2.5-glia-γ2, HLA-DQ2.5:DQ2.5-glia-γ3, HLA-DQ2.5:DQ2.5-glia-γ4c, HLA-DQ2.5:DQ2.5-glia-ω1, HLA-DQ2.5:DQ2.5-glia-ω2 or HLA-DQ2.5:DQ2.5-glia-α2. In some embodiments, antigen binding proteins which bind specifically to HLA-DQ2.5:DQ2.5-glia-α1a do not bind (or cross-react), or do not significantly bind (or significantly cross-react) to HLA-DQ2.5:CLIP2. In some embodiments, antigen binding proteins which bind specifically to HLA-DQ2.5:DQ2.5-glia-α1a do not bind (or cross-react), or do not significantly bind (or significantly cross-react) to HLA-DQ2.5:DQ2.5-hor3. Whether or not a given antigen binding protein cross-reacts with these other HLA-DQ2.5:DQ2.5-glia complexes (antigens) or HLA-DQ2.5-CLIP2 or HLA-DQ2.5:DQ2.5-hor-3 can be assessed by any appropriate means, for example using an ELISA assay as described in the Example section herein.

In some embodiments, an antigen binding protein which "binds to HLA-DQ2.5:DQ2.5-glia-α1a" in accordance with the present invention also does not bind (or does not significantly bind) to one or more (or all) of HLA-DQ2.5:DQ2.5-glia-γ1, HLA-DQ2.5:DQ2.5-glia-γ2, HLA-DQ2.5:DQ2.5-glia-γ3, HLA-DQ2.5:DQ2.5-glia-γ4c, HLA-DQ2.5:DQ2.5-glia-ω1, HLA-DQ2.5:DQ2.5-glia-ω2, HLA-DQ2.5:DQ2.5-glia-α2, HLA-DQ2.5:CLIP2 or HLA-DQ2.5:DQ2.5-hor-3.

As discussed above, in some embodiments, an antigen binding protein which "binds specifically to HLA-DQ2.5:DQ2.5-glia-α2" in accordance with the present invention does not bind (or cross-react), or does not significantly bind or (significantly cross-react) to other HLA-DQ2.5:DQ2.5-glia complexes (antigens). In some embodiments, antigen binding proteins which bind specifically to HLA-DQ2.5:DQ2.5-glia-α2 do not bind (or cross-react), or do not significantly bind (or significantly cross-react) to HLA-DQ2.5:DQ2.5-glia-γ1, HLA-DQ2.5:DQ2.5-glia-γ2, HLA-DQ2.5:DQ2.5-glia-γ3, HLA-DQ2.5:DQ2.5-glia-γ4c, HLA-DQ2.5:DQ2.5-glia-ω1, HLA-DQ2.5:DQ2.5-glia-ω2 or HLA-DQ2.5:DQ2.5-glia-α1a. In some embodiments, antigen binding proteins which bind specifically to HLA-DQ2.5:DQ2.5-glia-α2 do not bind (or cross-react), or do not significantly bind (or significantly cross-react) to HLA-DQ2.5:CLIP2 or HLA-DQ2.5:DQ2.5-hor-3. Whether or not a given antigen binding protein cross-reacts with these other HLA-DQ2.5:DQ2.5-glia complexes (antigens) or HLA-DQ2.5-CLIP2 or HLA-DQ2.5:DQ2.5-hor-3 can be assessed by any appropriate means, for example using an ELISA assay as described in the Example section herein.

In some embodiments, an antigen binding protein which "binds to HLA-DQ2.5:DQ2.5-glia-α2" in accordance with the present invention also does not bind (or does not significantly bind) to one or more (or all) of HLA-DQ2.5:DQ2.5-glia-γ1, HLA-DQ2.5:DQ2.5-glia-γ2, HLA-DQ2.5:DQ2.5-glia-γ3, HLA-DQ2.5:DQ2.5-glia-γ4c, HLA-DQ2.5:

48

DQ2.5-glia-ω1, HLA-DQ2.5:DQ2.5-glia-ω2, HLA-DQ2.5:DQ2.5-glia-α1a, HLA-DQ2.5:CLIP2 or HLA-DQ2.5:DQ2.5-hor-3.

In some embodiments, an antigen binding protein which binds to, or binds specifically to, HLA-DQ2.5:DQ2.5-glia-α1a or which binds to, or binds specifically to, HLA-DQ2.5:DQ2.5-glia-α2 binds to the respective HLA-DQ2.5:DQ2.5-glia peptide complex when said complex is present on (or in) cells (or is expressed on or in cells, or has been transduced into cells), e.g. murine A20 B cells. In some embodiments, the cells have been transduced with HLA-DQ2.5 covalently linked to a DQ2.5-glia-α1a epitope (or peptide) or a DQ2.5-glia-α2 epitope (or peptide), e.g. as described in the Example section herein. Binding to HLA-DQ2.5:DQ2.5-glia-α1a or HLA-DQ2.5:DQ2.5-glia-α2 on or in cells (e.g. murine A20 B cells) can be assessed by any appropriate means, e.g. by flow cytometry, for example as described in the Example section herein.

In some embodiments, antigen binding proteins that bind to, or bind specifically to, HLA-DQ2.5:DQ2.5-glia-α1a are capable of binding to HLA-DQ2.5$^+$ cells that are loaded with soluble DQ2.5-glia-α1a peptide. In some such embodiments the cells are HLA-DQ2.5$^+$ dendritic cells (DCs), for example HLA-DQ2.5$^+$ dendritic cells derived from a donor (e.g. a human donor). In some embodiments, the cells are HLA-DQ2.5$^+$ monocyte-derived dendritic cells derived (or obtained) via in vitro differentiation of PBMCs (peripheral blood mononuclear cells) from a HLA-DQ2.5$^+$ donor. Methods of in vitro differentiation of PBMCs to DCs are known in the art and an exemplary and preferred method is set out in the Example section herein. HLA-DQ2.5$^+$ dendritic cells may be loaded with a soluble DQ2.5-glia-α1a peptide by any appropriate means, for example by supplementation of the culture media with a HLADQ2.5-glia-α1a peptide (e.g. SEQ ID NO:474), for example with 40 μM peptide, during the DC maturation process. An exemplary and preferred method is set out in the Example section. Assessment of whether a given antigen binding protein is capable of binding to HLA-DQ2.5$^+$ cells (e.g. HLA-DQ2.5$^+$ dendritic cells) that are loaded with soluble DQ2.5-glia-α1a peptide may be done by any appropriate method, but flow cytometry is typically preferred, e.g. as described in the Example section.

In some embodiments, antigen binding proteins that bind to, or bind specifically to, HLA-DQ2.5:DQ2.5-glia-α2 are capable of binding to HLA-DQ2.5$^+$ cells that are loaded with soluble DQ2.5-glia-α2 peptide. In some such embodiments the cells are HLA-DQ2.5$^+$ dendritic cells (DCs), for example as described above. HLA-DQ2.5$^+$ dendritic cells may be loaded with a soluble DQ2.5-glia-α2 peptide by any appropriate means, for example by supplementation of the culture media with a HLADQ2.5-glia-α2 peptide (e.g. SEQ ID NO:475), for example with 40 μM peptide, during the DC maturation process. An exemplary and preferred method is set out in the Example section. Assessment of whether a given antigen binding protein is capable of binding to HLA-DQ2.5$^+$ cells (e.g. HLA-DQ2.5$^+$ dendritic cells) that are loaded with soluble DQ2.5-glia-α2 peptide may be done by any appropriate method, but flow cytometry is typically preferred, e.g. as described in the Example section.

In some embodiments, antigen binding proteins that bind to, or bind specifically to, HLA-DQ2.5:DQ2.5-glia-α1a are capable of binding to HLA-DQ2.5:DQ2.5-glia-α1a on cells (e.g. single-cell suspensions) isolated from intestinal (e.g. duodenal) biopsies from HLA-DQ2.5$^+$ individuals (human subjects, e.g. with a Marsh score of 3A, 3B or 3C) that have fed on gluten-containing food and thereby have generated a DQ2.5-glia-α1a epitope (native or deamidated). Such individuals may be confirmed or non-confirmed celiacs, treated or non-treated (or inadequately treated in the sense that they have trace presentation of the pMHC). In some embodiments, the individual is an untreated celiac disease subject (a subject not on a gluten-free diet). In some such embodiments, the cells are B cells (CD19$^+$ CD38$^-$) or plasma cells, PCs (CD27$^+$ CD38$^+$). Isolation of cells from intestinal (e.g. duodenal) biopsies may be done by any suitable method. An exemplary method is described in the example section herein. Assessment of whether a given antibody is capable of binding to HLA-DQ2.5:DQ2.5-glia-α1a on such cells from intestinal biopsies may be done by any appropriate method, but flow cytometry is typically preferred, e.g. as described in the Example section.

Small intestinal plasma cells can be separated into three major subsets based on CD45 expression; CD19$^+$CD45$^+$, CD19$^-$CD45$^+$ and CD19$^-$CD45$^-$. In some embodiments, antigen binding proteins that bind to, or bind specifically to, HLA-DQ2.5:DQ2.5-glia-α1a are capable of binding to plasma cells in each of these cell populations.

In some embodiments, antigen binding proteins that bind to, or bind specifically to, HLA-DQ2.5:DQ2.5-glia-α2 are capable of binding to HLA-DQ2.5:DQ2.5-glia-α2 on cells (e.g. single-cell suspensions) isolated from intestinal (e.g. duodenal) biopsies from HLA-DQ2.5$^+$ individuals (human subjects, e.g. with a Marsh score of 3A, 3B or 3C) that have fed on gluten-containing food and thereby have generated an DQ2.5-glia-α2 epitope (native or deamidated). Such individuals may be confirmed or non-confirmed celiacs, treated or non-treated (or inadequately treated in the sense that they have trace presentation of the pMHC). In some embodiments, the individual is an untreated celiac disease subject (a subject not on a gluten-free diet). In some such embodiments, the cells are B cells (CD19$^+$ CD38$^-$) or plasma cells, PCs (CD27$^+$ CD38$^+$). Assessment of whether a given antibody is capable of binding to HLA-DQ2.5:DQ2.5-glia-α2 on such cells from intestinal biopsies may be done by any appropriate method, but flow cytometry is typically preferred, e.g. as described in the Example section.

Small intestinal plasma cells can be separated into three major subsets based on CD45 expression; CD19$^+$CD45$^+$, CD19$^-$CD45$^+$ and CD19$^-$CD45$^-$. In some embodiments, antigen binding proteins that bind to, or bind specifically to, HLA-DQ2.5:DQ2.5-glia-α2 are capable of binding to plasma cells in each of these cell populations.

The "Marsh" scoring system is a classification system used in the art to rate (or score) damage to the small intestine. Scores of 0 to 4 may be given, with higher scores representing increased damage.

In some embodiments, antigen binding proteins (e.g. antibodies) that bind to HLA-DQ2.5:DQ2.5-glia-α1a or that bind to HLA-DQ2.5:DQ2.5-glia-α2 are capable of inhibiting T-cell activation (e.g. T-cell activation by antigen presenting cells having HLA-DQ2.5:DQ2.5-glia-α1a or HLA-DQ2.5:DQ2.5-glia-α2, as the case may be). In some embodiments, antigen binding proteins (e.g. antibodies) that bind to HLA-DQ2.5:DQ2.5-glia-α1a or that bind to HLA-DQ2.5:DQ2.5-glia-α2 are capable of inhibiting T-cell activation in vitro. This may be assessed by any suitable methods and the skilled person will be familiar with such methods.

In some embodiments, antigen binding proteins (e.g. antibodies) that bind to HLA-DQ2.5:DQ2.5-glia-α1a or that bind to HLA-DQ2.5:DQ2.5-glia-α2 are capable of inhibiting T-cell activation by at least 10%, preferably at least 20%, at least 30%, at least 40%, at least 50%, at least 60%, at least 70%, at least 80%, at least 90% or even 100%. In preferred embodiments, 0% inhibition (or conversely 100% activation) is the degree of inhibition in the absence of an antigen binding protein (e.g. antibody). Thus, relative inhibitory capacity (or activity) of an antigen binding protein (e.g. antibody) may be determined by normalizing to the T-cell activation in the absence of antigen binding protein (e.g. antibody), which may be set as 100% activation.

In some embodiments, inhibition of T-cell activation by an antigen binding protein (e.g. antibody) that binds to HLA-DQ2.5:DQ2.5-glia-α1a is as assessed in vitro by:

Contacting (e.g. overnight) DQ2.5$^+$ antigen presenting cells (APCs), e.g. Raji B-cells, with a DQ2.5-glia-α1a peptide (e.g. loading with soluble DQ2.5-glia-α1a peptide) and typically washing away the unloaded (free) peptide;

Contacting said (peptide-loaded) cells with the antigen binding protein (e.g. antibody) that binds to HLA-DQ2.5:DQ2.5-glia-α1a (e.g. 1 μM final concentration of antigen binding protein);

Contacting (e.g. overnight at e.g. 37° C.) a T-cell clone (e.g. SKW3 cells) expressing a T-cell receptor (TCR) that is specific for DQ2.5:DQ2.5-glia-α1a (suitable Examples of TCRs are provided in Example 9 herein) with the peptide loaded cells that have been contacted with the antigen binding protein (e.g. antibody);

Determining or measuring T-cell activation, e.g. based on an increase or upregulation of CD69, e.g. as assessed by flow cytometry.

A particularly preferred method for assessing (or determining or measuring) T-cell activation (and the inhibition of T-cell activation by an antigen binding protein (e.g. antibody) that binds to HLA-DQ2.5:DQ2.5-glia-α1a) is provided in Example 9 herein.

In some embodiments, inhibition of T-cell activation by an antigen binding protein (e.g. antibody) that binds to HLA-DQ2.5:DQ2.5-glia-α2 is as assessed in vitro by:

Contacting (e.g. overnight) DQ2.5$^+$ antigen presenting cells (APCs), e.g. Raji B-cells, with a DQ2.5-glia-α2 peptide (e.g. loading with soluble DQ2.5-glia-α2 peptide) and typically washing away the unloaded (free) peptide;

Contacting said (peptide-loaded) cells with the antigen binding protein (e.g. antibody) that binds to HLA-DQ2.5:DQ2.5-glia-α2 (e.g. 1 μM final concentration of antigen binding protein);

Contacting (e.g. overnight at e.g. 37° C.) a T-cell clone expressing a T-cell receptor (TCR) that is specific for DQ2.5:DQ2.5-glia-α2 (suitable Examples are provided in Example 9 herein) with the peptide loaded cells that have been contacted with the antigen binding protein (e.g. antibody);

Determining or measuring T-cell activation, e.g. based on an increase or upregulation of CD69, e.g. as assessed by flow cytometry.

A particularly preferred method for assessing (or determining or measuring) T-cell activation (and the inhibition of T-cell activation by an antigen binding protein (e.g. antibody) that binds to HLA-DQ2.5:DQ2.5-glia-α2) is provided in Example 9 herein.

In some embodiments, antigen binding proteins that bind to, or bind specifically to, HLA-DQ2.5:DQ2.5-glia-α1a are capable of inhibiting and/or killing cells (e.g. antigen presenting cells such as B cells or plasma cells, for example as defined elsewhere herein) that express or present HLA-DQ2.5:DQ2.5-glia-α1a. Thus, in some embodiments, antigen binding proteins that bind to, or bind specifically to, HLA-DQ2.5:DQ2.5-glia-α1a have inhibitory or cytotoxic activity.

In some embodiments, antigen binding proteins that bind to, or bind specifically to, HLA-DQ2.5:DQ2.5-glia-α2 are capable of inhibiting and/or killing cells (e.g. antigen presenting cells such as B cells or plasma cells, for example as defined elsewhere herein) that express or present HLA-DQ2.5:DQ2.5-glia-α2. Thus, in some embodiments, antigen binding proteins that bind to, or bind specifically to, HLA-DQ2.5:DQ2.5-glia-α2 have inhibitory or cytotoxic activity.

Described herein are antigen binding proteins of the invention that bind specifically to HLA-DQ2.5:DQ2.5-glia-α1a or bind specifically to HLA-DQ2.5:DQ2.5-glia-α2. However, in an alternative aspect, also disclosed and provided herein are antigen binding proteins that do not have the same epitope specificity. Thus, although antigen binding proteins that bind specifically to HLA-DQ2.5:DQ2.5-glia-α1a or that bind specifically to HLA-DQ2.5:DQ2.5-glia-α2 are in certain circumstances preferred, in an alternative aspect, the invention provides certain antigen binding proteins that show a degree of promiscuity (or cross-reactivity) in relation to the HLA-DQ2.5:DQ2.5-glia epitopes bound. As described above, in some embodiments, antigen binding proteins that bind to HLA-DQ2.5:DQ2.5-glia-α1a may additionally bind to other peptides, for example other peptides presented by HLA-DQ2.5 (e.g. other celiac disease associated peptides, or other gliadin peptides or gliadin-derived peptides, or variants of gliadin derived peptides, or other gluten-derived peptides). As described above, in some embodiments, antigen binding proteins that bind to HLA-DQ2.5:DQ2.5-glia-α2 may additionally bind to other peptides, for example other peptides presented by HLA-DQ2.5 (e.g. other celiac disease associated peptides, or other gliadin peptides or gliadin-derived peptides, or variants of gliadin derived peptides, or other gluten-derived peptides). For example, certain antibodies may bind to HLA-DQ2.5:DQ2.5-glia-α1a or HLA-DQ2.5:DQ2.5-glia-α2 and additionally bind to one or more of HLA-DQ2.5:DQ2.5-glia-γ1, HLA-DQ2.5:DQ2.5-glia-γ2, HLA-DQ2.5:DQ2.5-glia-γ3, HLA-DQ2.5:DQ2.5-glia-γ4c, HLA-DQ2.5:DQ2.5-glia-ω1 or HLA-DQ2.5:DQ2.5-glia-ω2. Certain antibodies may bind to HLA-DQ2.5:DQ2.5-glia-α1a or HLA-DQ2.5:DQ2.5-glia-α2 and additionally bind to HLA-DQ2.5:CLIP2 or HLA-DQ2.5:DQ2.5-hor-3. Certain antibodies may bind to HLA-DQ2.5:DQ2.5-glia-α1a and to HLA-DQ2.5:DQ2.5-glia-α2. However, typically and preferably, antigen binding proteins (e.g. antibodies) that bind to HLA-DQ2.5:DQ2.5-glia-α1a do not bind to (or do not significantly bind to) HLA-DQ2.5:DQ2.5-glia-α2. Typically and preferably, antigen binding proteins (e.g. antibodies) that bind to HLA-DQ2.5:DQ2.5-glia-α2 do not bind to (or do not significantly bind to) HLA-DQ2.5:DQ2.5-glia-α1a.

Thus, in one alternative aspect, the present invention provides an antigen binding protein which binds to HLA-DQ2.5:DQ2.5 presenting a peptide (e.g. a celiac disease associated peptide, such as a gliadin peptide or a gliadin derived peptide or a gluten-derived peptide), said antigen binding protein comprising at least one light chain variable domain and at least one heavy chain variable domain, each domain comprising three complementarity determining regions (CDRs), wherein (a) said antigen binding protein binds to HLA-DQ2.5:DQ2.5-glia-α1a and comprises a variable heavy (VH) CDR1 comprising the amino acid sequence of SEQ ID NO:5, or a sequence containing 1, 2 or 3 amino acid substitutions, additions or deletions relative to SEQ ID NO:5;

a variable heavy (VH) CDR2 comprising the amino acid sequence of SEQ ID NO:6, or a sequence containing 1, 2 or 3 amino acid substitutions, additions or deletions relative to SEQ ID NO:6;

a variable heavy (VH) CDR3 comprising the amino acid sequence of SEQ ID NO:417;

a variable light (VL) CDR1 comprising the amino acid sequence of SEQ ID NO:8 or a sequence containing 1, 2 or 3 amino acid substitutions, additions or deletions relative to SEQ ID NO:8;

a variable light (VL) CDR2 comprising the amino acid sequence of SEQ ID NO:9 or a sequence containing 1 amino acid substitution, addition or deletion relative to SEQ ID NO:9; and a variable light (VL) CDR3 comprising the amino acid sequence of SEQ ID NO:415; or wherein (b) said antigen binding protein binds to HLA-DQ2.5:DQ2.5-glia-α2 and comprises a variable heavy (VH) CDR1 comprising the amino acid sequence of SEQ ID NO:425;

a variable heavy (VH) CDR2 comprising the amino acid sequence of SEQ ID NO:427;

a variable heavy (VH) CDR3 comprising the amino acid sequence of SEQ ID NO:429;

a variable light (VL) CDR1 comprising the amino acid sequence of SEQ ID NO:419;

a variable light (VL) CDR2 comprising the amino acid sequence of SEQ ID NO:421; and a variable light (VL) CDR3 comprising the amino acid sequence of SEQ ID NO:423.

All of the discussion elsewhere herein in relation to, for example, sequences and aspects and preferred embodiments, may be applied, mutatis mutandis, to aspects of the invention in which antibodies which bind to HLA-DQ2.5:DQ2.5-glia-α1a or to HLA-DQ2.5:DQ2.5-glia-α2 may exhibit binding to other epitopes (i.e. exhibit epitope cross-reactivity).

In another alternative aspect, also disclosed and provided herein are antigen binding proteins that bind to HLA-DQ2.5:DQ2.5-glia-α1a or to HLA-DQ2.5:DQ2.5-glia-α2 and do not significantly bind to (or do not significantly cross-react with) HLA-DQ2.5 complexes without a gliadin peptide presented. All of the discussion elsewhere herein in relation to, for example, sequences and aspects and preferred embodiments, may be applied, mutatis mutandis, to this aspect of the invention.

In another alternative aspect, also disclosed and provided herein are antigen binding proteins that bind to HLA-DQ2.5:DQ2.5-glia-α1a or to HLA-DQ2.5:DQ2.5-glia-α2 and do not significantly bind to (or do not significantly cross-react with) gliadin peptides unless they are presented by HLA-DQ2.5 complexes. All of the discussion elsewhere herein in relation to, for example, sequences and aspects and preferred embodiments, may be applied, mutatis mutandis, to this aspect of the invention.

An antigen binding protein according to any aspect of the present invention and disclosure may be defined as a binding protein comprising an antigen-binding domain obtained or derived from an antibody, or based on an antigen binding domain of an antibody. Thus, for example, light and heavy chain variable regions as described herein are those obtained or derived from an antibody, or based on an antigen binding domain of an antibody. For the avoidance of doubt, in accordance with the present invention the antigen binding domain is not from a T-cell receptor (TCR). Thus, for the avoidance of doubt, antigen binding proteins in accordance with the present invention do not include TCRs.

Preferably, the protein having an antigen binding domain is an antibody or an antigen binding fragment thereof.

The terms "antibody" and "immunoglobulin", as used herein, refer broadly to any immunological binding agent that comprises an antigen binding domain (e.g. a human antigen binding domain), including polyclonal and mono- clonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\varepsilon$, $\gamma$ and $\mu$, respectively. The subunit structures and three-dimen- sional configurations of different classes of immunoglobu- lins are well known.

Generally, where whole antibodies rather than antigen binding regions are used in the invention, IgG (e.g. $\text{IgG}_1$ or $\text{IgG}_{2b}$ such as human $\text{IgG}_1$ or mouse $\text{IgG}_{2b}$) and/or IgM are preferred because they are the most common antibodies in the physiological situation and because they are most easily made in a laboratory setting.

The "light chains" of mammalian antibodies are assigned to one of two clearly distinct types: kappa ($\kappa$) and lambda ($\lambda$), based on the amino acid sequences of their constant domains and some amino acids in the framework regions of their variable domains. In some embodiments, kappa ($\kappa$) light chains are preferred.

As will be understood by those in the art, the immuno- logical binding reagents encompassed by the term "anti- body" includes or extends to all antibodies and antigen binding fragments thereof, including whole antibodies, dimeric, trimeric and multimeric antibodies; bispecific anti- bodies; chimeric antibodies; recombinant and engineered antibodies, and fragments thereof.

The term "antibody" is thus used to refer to any antibody- like molecule that has an antigen binding region, and this term includes antibody fragments that comprise an antigen binding domain such as Fab', Fab, F(ab')$_2$, single domain antibodies (DABs), TandAbs dimer, Fv, scFv (single chain Fv), dsFv, ds-scFv, Fd, linear antibodies, minibodies, dia- bodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTar- geting"); small antibody mimetics.

The techniques for preparing and using various antibody- based constructs and fragments are well known in the art. Diabodies, in particular, are further described in EP 404 097 and WO 93/11161; whereas linear antibodies are further described in the art.

Antibodies of the present invention are typically and preferably human antibodies (e.g. fully human antibodies).

However, antibodies may also be of other types e.g. murine antibodies or humanized antibodies. "Humanized" versions of antibodies are based on substantially non-human variable region domains, e.g. mouse variable region domains, and typically certain amino acids have been changed to better correspond with the amino acids typically present in human antibodies. Methods for generating humanized antibodies are well known in the art. For example, humanized antibodies can be accomplished by inserting the appropriate CDRs (e.g. murine CDRs) into a human antibody "scaffold".

In preferred embodiments the antibodies of the invention are human antibodies, more preferably fully human anti- bodies. In this regard, human antibodies generally have at least two potential advantages for use in human therapy. First, the human immune system should not recognize the antibody as foreign. Second, the half-life in the human circulation will be similar to naturally occurring human antibodies, allowing smaller and less frequent doses to be given.

However, although human antibodies are generally rec- ognized to display these advantages, it is known that the development of human antibodies that have high enough affinities and appropriate functional properties to make them candidates for successful human therapy is by no means straightforward.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human reper- toire or derived from or corresponding to sequences found in humans or a human repertoire, e.g., in the human germline or somatic cells.

The "human" antibodies and binding proteins of the invention further include amino acid residues not encoded by human sequences, e.g., mutations introduced by random or site directed mutations in vitro, for example mutations introduced by in vitro cloning or PCR, for example in an affinity maturation method. Particular examples of such mutations are mutations that involve conservative substitu- tions or other mutations in a small number of residues of the antibody or binding protein, e.g., in up to 5, 4, 3, 2 or 1 of the residues of the antibody or binding protein, preferably e.g., in up to 5, 4, 3, 2 or 1 of the residues making up one or more of the CDRs of the antibody or binding protein. Certain examples of such "human" antibodies include anti- bodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of $V_H$, $V_L$, CDR or FR regions that are themselves found in combination in human antibody molecules. Thus, the human antibodies and binding proteins of the invention can include or correspond to combinations of such regions that do not necessarily exist naturally in humans (e.g. are not naturally occurring antibodies).

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

Antibodies of the present invention may also be CDR grafted antibodies. Such antibodies are antibodies comprising the CDR sequences (e.g. 3 VH CDRs and/or 3 VL CDRs) of an antibody of the invention grafted into a framework region that is different from the framework region with which the CDRs are associated in the VL and/or VH domains described herein.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs. Preferred heavy chain variable region framework sequences are set forth in the sequence tables herein. Thus, the invention provides antigen binding proteins (e.g. antibodies) which comprise a heavy chain variable region comprising three CDRs that are separated by (or flanked by) framework FR regions.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs. Preferred light chain variable region framework sequences are set forth in the sequence tables herein. Thus, the invention provides antigen binding proteins (e.g. antibodies) which comprise a light chain variable region comprising three CDRs that are separated by (or flanked by) framework FR regions.

The term "light chain variable region" ($V_L$ domain) as used herein refers to the variable region of a light chain of an antibody molecule.

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

In certain embodiments, the antibody or antibody fragment of the present invention comprises all or a portion of a heavy chain constant region, such as an IgG1, IgG2, IgG3, IgG4, IgA1, IgA2, IgE, IgM or IgD constant region. Preferably, the heavy chain constant region is an IgG heavy chain constant region, e.g. an IgG$_1$ or an IgG$_{2b}$ heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies. In some embodiments, IgG$_1$ antibodies are preferred (e.g. human IgG$_1$ antibodies). In some embodiments, IgG$_{2b}$ antibodies are preferred (e.g. mouse IgG$_{2b}$ antibodies).

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not always necessary for antigen binding. Thus, constructs smaller than the above classical antibody fragment are known to be effective.

For example, camelid antibodies have an extensive antigen binding repertoire but are devoid of light chains. Also, results with single domain antibodies comprising VH domains alone or VL domains alone show that these domains can bind to antigen with acceptably high affinities. Thus, three CDRs can effectively bind antigen.

The term "fragment" as used herein refers to fragments of biological relevance, e.g. fragments that contribute to antigen binding, e.g. form part of the antigen binding site, and/or contribute to the functional properties of the antibodies of the invention. Certain preferred fragments comprise a heavy chain variable region ($V_H$ domain) and a light chain variable region ($V_L$ domain) of the antibodies of the invention.

Thus, although antibodies of the invention comprise six CDR regions (three from a light chain and three from a heavy chain), antibodies can have fewer than six CDR regions (e.g. 3 CDR regions). Antibodies can have CDRs from only the heavy chain or light chain.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds HLA-DQ2.5:DQ2.5-gliadin peptides in accordance with the invention can be readily identified by a person skilled in the art.

For example, a heavy chain variable region of the invention can be combined with a single light chain variable region or a repertoire of light chain variable regions and the resulting antibodies tested for binding to HLA-DQ2.5:DQ2.5-glia-α1a or HLA-DQ2.5:DQ2.5-glia-α2.

If desired, similar methods could be used to identify alternative heavy chain variable regions for use in combination with preferred light chain variable regions of the invention.

A yet further aspect of the invention provides an antibody, preferably an isolated antibody, more preferably a human (or fully human) antibody, which binds to or specifically recognizes HLA-DQ2.5:DQ2.5-glia-α1a or HLA-DQ2.5:DQ2.5-glia-α2 and which has the ability to compete with (i.e. bind to the same or substantially the same epitope as) one or more of the specific antibodies of the invention described herein, or the ability to compete with an antibody comprising the same CDRs as one or more of the specific antibodies described herein for binding to HLA-DQ2.5:DQ2.5-glia-α1a or HLA-DQ2.5:DQ2.5-glia-α2. Other features and properties of other aspects of the invention apply, mutatis mutandis, to this aspect of the invention.

Binding to the same epitope/antigen can be readily tested by methods well known and described in the art, e.g. using binding assays such as a competitive inhibition assay. Thus, a person skilled in the art will appreciate that binding assays can be used to identify other antibodies and antibody fragments with the same binding specificities as the antibodies and antibody fragments of the invention. Suitable binding assays are discussed elsewhere herein.

Preferably, the above described abilities and properties are observed at a measurable or significant level and more preferably at a statistically significant level, when compared to appropriate control levels. More preferably, one or more of the above described abilities and properties are observed at a level which is measurably better, or more preferably significantly better, when compared to the abilities observed for reference antigen binding proteins (e.g. one or more of the R2A1-8E, R3A2-9F, R4A1-3A (also referred to as 107), 206, 217, 218, 220, 221, 223, 226 or 228 antibodies).

In any statistical analysis referred to herein, preferably the statistically significant difference over a relevant control or other comparative entity or measurement has a probability value of <0.1, preferably <0.05. Appropriate methods of determining statistical significance are well known and documented in the art and any of these may be used.

In other preferred embodiments, second generation antigen binding proteins (e.g. antibodies) are provided that have enhanced or superior properties in comparison to an original HLA-DQ2.5:DQ2.5-glia-α1a or HLA-DQ2.5:DQ2.5-glia-α2 antigen binding protein (e.g. antibody) of the invention.

Comparisons to identify effective second generation antigen binding proteins (e.g. antibodies) are readily conducted and quantified, e.g. using one or more of the various assays described in detail herein or in the art. Second generation antibodies that have an enhanced biological property or activity of at least about 2-fold, 5-fold, 10-fold, 20-fold, and preferably, at least about 50-fold, in comparison to the specific HLA-DQ2.5:DQ2.5-glia-α1a or HLA-DQ2.5:DQ2.5-glia-α2 antigen binding proteins (e.g. antibodies) of the present invention, are encompassed by the present invention.

Other constructs, conjugates and molecules (e.g. soluble binding molecules) containing an antigen binding domain (or antigen binding region), e.g. an antibody-derived antigen bind region or domain are encompassed by the present invention. In such constructs, conjugates (e.g. targeting conjugates) and molecules, the VL CDRs and VH CDRs may be on the same chain (same polypeptide) or be on separate chains (separate polypeptides). In such constructs, conjugates and molecules, the VL domain and VH domain may be on the same chain (same polypeptide) or may be on separate chains (separate polypeptides). When the VL CDRs and VH CDRs (or VL domain and VH domain) are on separate chains (separate polypeptides), the separate chains may be linked by any convenient means and the skilled person is familiar with different possibilities for such linking (e.g. covalent linkages e.g. via the introduction of cysteine residues into a constant region to enable disulphide bonding, i.e. linkage via a disulphide bond).

In some embodiments the invention provides CARs (chimeric antigen receptors) or CAR (chimeric antigen receptor) T cells. Thus, in one embodiment the invention provides CARs or CAR T cells comprising (or based on) an antibody of the invention. A protein comprising an antigen binding domain of the present invention may be coupled to (e.g. fused with) transmembrane domain or a intracellular domain of a CAR.

A CAR is a chimeric antigen receptor. As is known to the skilled person, a CAR commonly comprises a single-chain Fv domain (scFv) derived from an antibody fused to a signalling tail which, upon antigen binding, transduces a signal across a cell membrane to activate the effector functions of an immune effector cell, e.g. a T-cell or an NK cell. CARs may be used to redirect immune effector cells to a target of interest in immunotherapy. CARs, and their therapeutic uses, are described in Maude et al. (Blood, Volume 125(26), 4017-4023, 2015). CAR immunotherapy has proven successful in a number of trials, but is limited by the breadth of available targets.

CARs are discussed in WO 2017/118745 (which is incorporated herein by reference), including suitable transmembrane domains and intracellular signalling domains which may be included in CARs. The transmembrane domain may be based on or derived from the transmembrane domain of any transmembrane protein. Typically it may be, or may be derived from, a transmembrane domain from CD8a, CD28, CD4, CD3ζ, CD45, CD9, CD16, CD22, CD33, CD64, CD80, CD86, CD134, CD137, or CD154, preferably from a human said protein. In one embodiment, the transmembrane domain may be, or may be derived from, a transmembrane domain from CD8a, CD28, CD4, or CD3ζ, preferably from human CD28, CD4, or CD3ζ. In another embodiment the transmembrane domain may be synthetic in which case it would comprise predominantly hydrophobic residues such as leucine and valine. The transmembrane domain may be the transmembrane domain of the human TCR α-chain constant region or a human TCR β-chain constant region.

The term "intracellular signalling domain" refers herein to the part of the CAR signalling tail that participates in transducing the message of effective CAR binding to a target antigen-MHC complex into the interior of an immune effector cell expressing the CAR, to elicit effector cell function, e.g. activation, cytokine production, proliferation and/or cytotoxic activity, including the release of cytotoxic factors to the CAR-bound target cell, or other cellular responses elicited with antigen binding to the extracellular CAR domain. The term "effector function" refers to a specialised function of the cell. Effector function of a T-cell, for example, may be cytolytic activity or helper activity including the secretion of a cytokine. Thus, the term "intracellular signalling domain" refers to a protein domain which transduces the effector function signal and directs the cell to perform a specialised function. While an entire natural intracellular signalling domain can be employed, in many cases it is not necessary to use an entire domain as found in nature. To the extent that a truncated portion of an intracellular signalling domain is used, such a truncated portion may be used in place of the entire domain as long as it transduces the effector function signal. The term intracellular signalling domain is meant to include any truncated portion of an intracellular signalling domain sufficient to transduce effector function signal. The intracellular signalling domain is also known as the, "signal transduction domain," and is typically derived from portions of the human CD3ζ or FcRy chains.

Additionally, to allow or to augment full activation of the immune effector cell the CAR may be provided with a secondary, or co-stimulatory domain. Thus, the intracellular signalling domain may initiate antigen-dependent primary activation (i.e. may be a primary cytoplasmic signalling sequence) and the co-stimulatory domain may act in an antigen-independent manner to provide a secondary or co-stimulatory signal (secondary cytoplasmic signalling sequence(s)). Primary cytoplasmic signalling sequences may regulate primary activation, including in an inhibitory way. Primary cytoplasmic signalling sequences that act in a co-stimulatory manner may contain signalling motifs which are known as immunoreceptor tyrosine-based activation motifs or ITAMs.

The term "co-stimulatory signalling domain" or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of an immune effector cell (e.g. a T-cell) upon binding to antigen. Examples of such co-stimulatory molecules include CD27, CD28, 4-IBB (CD137), OX40 (CD134), CD30, CD40, PD-1, ICOS (CD278), LFA-1, CD2, CD7, LIGHT, NKD2C, B7-H2 and a ligand that specifically binds CD83, more particularly the intracellular domains of such molecules. Preferably the molecules are human. Accordingly, while exemplary or preferred co-stimulatory domains are derived from 4-1 BB, CD28 or OX40 (CD134), other co-stimulatory domains are contemplated for use with the CARs described herein. The co-stimulatory domains may be used singly or in combination (i.e. one or more co-stimulatory domains may be included). The inclusion of one or more co-stimulatory signalling domains may enhance the efficacy and expansion of immune effector cells expressing the CARs.

In some embodiments, an antigen binding protein of the present invention comprises two variable domains, i.e. a variable domain comprising three VH CDRs and a variable domain comprising three VL CDRs, each fused to a constant region (typically to the N-terminus of the constant region), wherein the two constant regions are linked (e.g. via a covalent linkage, such a disulphide bond), and optionally a targeting moiety is attached to one (or both) of the constant regions (e.g. at the C-terminus of the constant domain).

In some embodiments, an antigen binding protein of the present invention comprises two variable domains, i.e. a variable domain comprising three VH CDRs and a variable domain comprising three VL CDRs (typically fused together), one constant region that is fused to (typically the C-terminus of) one of the variable domains (e.g. a heavy chain or a light chain constant region), one transmembrane domain and one intracellular signalling domain (typically the transmembrane domain being fused to (e.g. the C-terminus of) the constant domain and the intracellular signalling domain being fused to (e.g. the C-terminus of) the transmembrane domain).

In some embodiments, an antigen binding protein of the present invention comprises two variable domains, i.e. a variable domain comprising three VH CDRs and a variable domain comprising three VL CDRs, each fused to a constant region (typically to the N-terminus of the constant region), wherein the two constant regions are linked (e.g. via a covalent linkage, such as a disulphide bond), and one of the constant regions has fused thereto (typically at the C-terminus of said constant region) a transmembrane domain and the transmembrane domain has fused thereto (typically at the C-terminus of said transmembrane domain) an intracellular signalling domain.

In some embodiments, an antigen binding protein of the present invention comprises two variable domains, i.e. a variable domain comprising three VH CDRs and a variable domain comprising three VL CDRs, each fused to a constant region (typically to the N-terminus of the constant region), wherein the two constant regions are linked (e.g. via a covalent linkage, such a disulphide bond), and one (or both) of the constant regions is linked (or connected) to a lipid (e.g. a membrane anchoring lipid) which can target micelles (e.g. micelles comprising or containing a drug). Typically, the lipid is connected to (or linked to or attached to) the C-terminus of the constant region.

In some embodiments, an antigen binding protein of the present invention comprises two Fv domains, which may be fused together (e.g. at their respective C-terminuses) and each Fv domain may have a linkage (e.g. a covalent linkage, such as a disulphide bond) linking the two chains of the Fv domain.

In one aspect, the present invention provides a bispecific antigen binding protein (e.g. an antibody or antigen binding fragment thereof), wherein said bispecific antigen binding protein comprises at least one heavy chain variable region and at least one light chain variable region of an antibody that binds to, or specifically binds to, HLA-DQ2.5:DQ2.5-glia-α1a as defined elsewhere herein and at least one heavy chain variable region and at least one light chain variable region of an antibody that binds to, or specifically binds to, HLA-DQ2.5:DQ2.5-glia-α2 as defined elsewhere herein.

In some embodiments, the antigen binding protein of the invention is a BiTe molecule (Bispecific T-cell engager). The BiTe format (BiTe molecule) is known to a person skilled in the art. In brief, two scFv molecules, targeting (or binding) different antigens, are operatively coupled (attached) through a linker (typically a genetically encoded synthetic linker) which brings (or places) both scFvs (or scFv units) into a single open reading frame (ORF). In certain embodiments, one scFv (or scFv unit) of a BiTe binds (or targets) HLA-DQ2.5:DQ2.5-glia-α1a or HLA-DQ2.5:DQ2.5-glia-α2 in accordance with the present invention and the other scFv (or scFv unit) targets CD3.

In some embodiments, the present invention provides a bispecific antigen binding protein (e.g. an antibody or antigen binding fragment thereof), wherein said bispecific antigen binding protein comprises at least one heavy chain variable region and at least one light chain variable region of an antibody that binds to, or specifically binds to, HLA-DQ2.5:DQ2.5-glia-α1a as defined elsewhere herein or at least one heavy chain variable region and at least one light chain variable region of an antibody that binds to, or specifically binds to, HLA-DQ2.5:DQ2.5-glia-α2 as defined elsewhere herein, and at least one heavy chain variable region and at least one light chain variable region of an antibody that binds to CD3.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g. antibodies, refers to such molecules when isolated from, purified from, or substantially free of their natural environment, e.g. isolated from or purified from the human or animal body (if indeed they occur naturally), or refers to such molecules when produced by a technical process, i.e. includes recombinant and synthetically produced molecules.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized.

Nucleic acid molecules comprising nucleotide sequences that encode the antigen binding proteins (e.g. antibodies) of the present invention as defined herein or parts or fragments thereof, or nucleic acid molecules substantially homologous thereto, form yet further aspects of the invention. Preferred nucleic acid molecules are those encoding a VH region of an antibody of the present invention. Other preferred nucleic acid molecules are those encoding a VL region of an antibody of the present invention. Other preferred nucleic acid molecules are those encoding a VH region of an antibody of the present invention and a VL region of an antibody of the present invention.

In some embodiments, preferred nucleic acid molecules are those encoding a VL region of SEQ ID NO:4 (such as SEQ ID NO:2) and/or a VH region of SEQ ID NO:3 (such as SEQ ID NO:1).

In some embodiments, preferred nucleic acid molecules are those encoding a VL region of SEQ ID NO:22 (such as SEQ ID NO:20) and/or a VH region of SEQ ID NO:21 (such as SEQ ID NO:19).

In some embodiments, preferred nucleic acid molecules are those encoding a VL region of SEQ ID NO:40 (such as SEQ ID NO:38) and/or a VH region of SEQ ID NO:39 (such as SEQ ID NO:37).

In some embodiments, preferred nucleic acid molecules are those encoding a VL region of SEQ ID NO:58 (such as SEQ ID NO:56) and/or a VH region of SEQ ID NO:57 (such as SEQ ID NO:55).

In some embodiments, preferred nucleic acid molecules are those encoding a VL region of SEQ ID NO:76 (such as SEQ ID NO:74) and/or a VH region of SEQ ID NO:75 (such as SEQ ID NO:73).

In some embodiments, preferred nucleic acid molecules are those encoding a VL region of SEQ ID NO:94 (such as SEQ ID NO:92) and/or a VH region of SEQ ID NO:93 (such as SEQ ID NO:91).

In some embodiments, preferred nucleic acid molecules are those encoding a VL region of SEQ ID NO:112 (such as SEQ ID NO:110) and/or a VH region of SEQ ID NO:111 (such as SEQ ID NO:109).

In some embodiments, preferred nucleic acid molecules are those encoding a VL region of SEQ ID NO:130 (such as SEQ ID NO:128) and/or a VH region of SEQ ID NO:129 (such as SEQ ID NO:127).

In some embodiments, preferred nucleic acid molecules are those encoding a VL region of SEQ ID NO:148 (such as SEQ ID NO:146) and/or a VH region of SEQ ID NO:147 (such as SEQ ID NO:145).

In some embodiments, preferred nucleic acid molecules are those encoding a VL region of SEQ ID NO:166 (such as SEQ ID NO:164) and/or a VH region of SEQ ID NO:165 (such as SEQ ID NO:163).

In some embodiments, preferred nucleic acid molecules are those encoding a VL region of SEQ ID NO:184 (such as SEQ ID NO:182) and/or a VH region of SEQ ID NO:183 (such as SEQ ID NO:181).

In some embodiments, preferred nucleic acid molecules are those encoding a VL region of SEQ ID NO:202 (such as SEQ ID NO:200) and/or a VH region of SEQ ID NO:201 (such as SEQ ID NO:199).

In some embodiments, preferred nucleic acid molecules are those encoding a VL region of SEQ ID NO:220 (such as SEQ ID NO:218) and/or a VH region of SEQ ID NO:219 (such as SEQ ID NO:217).

In some embodiments, preferred nucleic acid molecules are those encoding a VL region of SEQ ID NO:238 (such as SEQ ID NO:236) and/or a VH region of SEQ ID NO:237 (such as SEQ ID NO:235).

In some embodiments, preferred nucleic acid molecules are those encoding a VL region of SEQ ID NO:256 (such as SEQ ID NO:254) and/or a VH region of SEQ ID NO:255 (such as SEQ ID NO:253).

In some embodiments, preferred nucleic acid molecules are those encoding a VL region of SEQ ID NO:274 (such as SEQ ID NO:272) and/or a VH region of SEQ ID NO:273 (such as SEQ ID NO:271).

In some embodiments, preferred nucleic acid molecules are those encoding a VL region of SEQ ID NO:292 (such as SEQ ID NO:290) and/or a VH region of SEQ ID NO:291 (such as SEQ ID NO:289).

In some embodiments, preferred nucleic acid molecules are those encoding a VL region of SEQ ID NO:310 (such as SEQ ID NO:308) and/or a VH region of SEQ ID NO:309 (such as SEQ ID NO:307).

In some embodiments, preferred nucleic acid molecules are those encoding a VL region of SEQ ID NO:328 (such as SEQ ID NO:326) and/or a VH region of SEQ ID NO:327 (such as SEQ ID NO:325).

In some embodiments, preferred nucleic acid molecules are those encoding a VL region of SEQ ID NO:346 (such as SEQ ID NO:344) and/or a VH region of SEQ ID NO:345 (such as SEQ ID NO:343).

In some embodiments, preferred nucleic acid molecules are those encoding a VL region of SEQ ID NO:364 (such as SEQ ID NO:362) and/or a VH region of SEQ ID NO:363 (such as SEQ ID NO:361).

In some embodiments, preferred nucleic acid molecules are those encoding a VL region of SEQ ID NO:382 (such as SEQ ID NO:380) and/or a VH region of SEQ ID NO:381 (such as SEQ ID NO:379).

In some embodiments, preferred nucleic acid molecules are those encoding a VL region of SEQ ID NO:400 (such as SEQ ID NO:398) and/or a VH region of SEQ ID NO:399 (such as SEQ ID NO:397).

In some embodiments, preferred nucleic acid molecules are those encoding a VL region of SEQ ID NO:499 (such as SEQ ID NO:497) and/or a VH region of SEQ ID NO:498 (such as SEQ ID NO:496).

In some embodiments, nucleic acid molecules are those encoding the IgG heavy and/or light chain sequences defined herein, or sequences substantially homologous thereto.

In some embodiments nucleic acid molecules are those having a nucleic acid sequence that is substantially homologous to the specific nucleic acid sequences defined herein, for example having at least 80% sequence identity to specific nucleic acid sequences defined herein.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g. by cloning or synthesis.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g. Fab fragments, scFv fragments, etc. Typically, or as part of this further manipulation procedure, the nucleic acid fragments encoding the antibody molecules of the invention are generally incorporated into one or more appropriate expression vectors in order to facilitate production of the antibodies of the invention.

Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and Maniatis,

*Molecular Cloning: A Laboratory Manual,* 2nd Ed., Cold Spring Harbor Press, Cold Spring Harbor, NY, 1989) and other laboratory textbooks.

Suitable host cells include a wide variety of eukaryotic host cells and prokaryotic cells. For example, the proteins of the invention may be expressed in yeast cells or mammalian cells. In addition, the proteins of the invention may be expressed in prokaryotic cells, such as *Escherichia coli.*

Given the teachings provided herein, promoters, terminators, and methods for introducing expression vectors of an appropriate type into plant, avian, and insect cells may also be readily accomplished.

Alternatively, the proteins of the invention may also be expressed in non-human transgenic animals such as, rats, rabbits, sheep and pigs.

The proteins of the invention may also be prepared by chemical synthesis using techniques well known in the chemistry of proteins such as solid phase synthesis.

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate.

A yet further aspect provides an expression construct or expression vector comprising one or more of the nucleic acid fragments or segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell (e.g. a mammalian host cell) or virus expressing an antibody of the invention forms a yet further aspect.

A yet further aspect of the invention provides a method of producing (or manufacturing) a protein (e.g. antibody) of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production (or manufacture) may also comprise a step of purification of the antibody or protein product and/or formulating the antibody or product into a composition including at least one additional component, such as a pharmaceutically acceptable carrier or excipient.

In embodiments when the protein (e.g. antibody) of the invention is made up of more than one polypeptide chain (e.g. certain fragments such as Fab fragments or whole antibodies), then all the polypeptides are preferably expressed in the host cell, either from the same or a different expression vector, so that the complete proteins, e.g. antibody proteins of the invention, can assemble in the host cell and be isolated or purified therefrom.

In another aspect, the invention provides a method of binding HLA-DQ2.5:DQ2.5-glia-α1a or HLA-DQ2.5:DQ2.5-glia-α2, comprising contacting a composition comprising HLA-DQ2.5:DQ2.5-glia-α1a or HLA-DQ2.5:DQ2.5-glia-α2 with an antigen binding protein of the invention, or an immunoconjugate thereof.

In yet another aspect, the invention provides a method of detecting HLA-DQ2.5:DQ2.5-glia-α1a or HLA-DQ2.5:DQ2.5-glia-α2, comprising contacting a composition suspected of containing HLA-DQ2.5:DQ2.5-glia-α1a or HLA-DQ2.5:DQ2.5-glia-α2 with an antigen binding protein of the invention, or an immunoconjugate thereof, under conditions effective to allow the formation of HLA-DQ2.5:DQ2.5-glia-α1a or HLA-DQ2.5:DQ2.5-glia-α2/antibody complexes and detecting the complexes so formed.

In another aspect, and in some embodiments, the invention provides a method of detecting HLA-DQ2.5:DQ2.5 presenting a celiac disease associated peptide, or another gliadin peptide or gliadin-derived peptide, or variant of a gliadin derived peptide, or another gluten-derived peptide, comprising contacting a composition suspected of containing such a pMHC with an antigen binding protein of the invention, or an immunoconjugate thereof, under conditions effective to allow the formation of pMHC/antibody complexes and detecting the complexes so formed.

The antibodies of the invention may also be used to produce further antigen binding proteins, e.g. antibodies, that bind to HLA-DQ2.5:DQ2.5-glia-α1a or HLA-DQ2.5:DQ2.5-glia-α2. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to HLA-DQ2.5:DQ2.5-glia-α1a or HLA-DQ2.5:DQ2.5-glia-α2 in accordance with the invention. Such methods can be used to form multiple new antibodies that can all be tested for their ability to bind HLA-DQ2.5:DQ2.5-glia-α1a or HLA-DQ2.5:DQ2.5-glia-α2. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, or homology/docking modelling of the binding protein-antigen complex to identify the key residues involved in the antigen binding. Alanine scanning mutagenesis is also a routine method which can be used to identify the key residues involved in the antigen binding. Subsequently, those residues can be mutated to enhance the interaction. Alternatively, one or more amino acid residues can simply be targeted for directed mutagenesis and the effect on binding to HLA-DQ2.5:DQ2.5-glia-α1a or HLA-DQ2.5:DQ2.5-glia-α2 assessed.

Random mutagenesis can be carried out in any appropriate way, e.g., by error-prone PCR, chain shuffling or mutator *E. coli* strains.

Thus, one or more of the $V_H$ domains of the invention can be combined with a single $V_L$ domain or a repertoire of $V_L$ domains from any appropriate source and the resulting new antigen binding proteins (e.g. antibodies) tested to identify antibodies which bind to HLA-DQ2.5:DQ2.5-glia-α1a or HLA-DQ2.5:DQ2.5-glia-α2. Conversely, one or more of the $V_L$ domains of the invention can be combined with a single $V_H$ domain or repertoire of $V_H$ domains from any appropriate source and the resulting new antigen binding proteins (e.g. antibodies) tested to identify antibodies that bind to HLA-DQ2.5:DQ2.5-glia-α1a or HLA-DQ2.5:DQ2.5-glia-α2.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antigen binding proteins (e.g. antibodies) tested to identify antibodies that bind to HLA-DQ2.5:DQ2.5-glia-α1a or HLA-DQ2.5:DQ2.5-glia-α2.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

The new antibodies produced by these methods will preferably have improved functional properties, e.g. a higher or enhanced affinity (or at least an equivalent affinity) for HLA-DQ2.5:DQ2.5-glia-α1a or HLA-DQ2.5:DQ2.5-glia-α2 as the parent antibodies, and can be treated and used in the same way as the antibodies of the invention as described elsewhere herein (e.g., for therapy, diagnosis, in compositions etc.). Alternatively, or additionally, the new antibodies will have one or more other improved functional properties as described elsewhere herein.

New antibodies produced, obtained or obtainable by these methods form a yet further aspect of the invention.

Testing the ability of one or more antigen binding proteins (e.g. antibodies) to bind to HLA-DQ2.5:DQ2.5-glia-α1a or HLA-DQ2.5:DQ2.5-glia-α2 can be carried out by any appropriate method, which are well known and described in the art. Suitable methods are also described in the Examples section.

The invention also provides a range of conjugated antigen binding proteins (e.g. antibodies) and fragments thereof in which the antigen binding protein is operatively attached to at least one other therapeutic or diagnostic agent. The term "immunoconjugate" is broadly used to define the operative association of the antigen binding protein (e.g. antibody) with another effective agent (e.g. therapeutic agent) and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

The therapeutic agent may be a drug molecule, e.g. a toxin to kill a target cell. A suitable toxin is a toxin which, alone, is unable to enter, kill or otherwise disrupt a human cell but, when taken up by a human cell via the immunoconjugate, is able to exert its toxic effects. Such a toxin will thus only be taken up by, and exert its target effects on, a cell bound by the immunoconjugate, into which the immunoconjugate is taken up. The toxin may be any known appropriate cytotoxic species, i.e. it may be any suitable cytotoxin. By "cytotoxin" as used herein is meant any toxin which inhibits the growth and/or viability of a cell. Growth includes the division of a target cell (i.e. a cell into which it enters). The toxin may thus be any toxin which reduces or has a negative impact on the viability or survival of a cell and in particular includes any toxin which induces death of a target cell, e.g. the toxin may induce apoptosis or necrosis of a target cell.

Such a toxin may be a peptide toxin lacking a targeting domain. For instance, it may be a peptide toxin which natively lacks a targeting domain, or it may be a peptide toxin modified relative to its native form to remove its targeting domain. Examples of such toxins include saporin and gelonin, which are ribosome-inactivating proteins (RIPs) of the same family as e.g. ricin, but which are unable to cross the plasma membrane of a cell. Similarly, the enzymatic domains (i.e. catalytic domains) of a cytotoxin of a pathogen may be used, such as the enzymatic domain of a bacterial cytotoxin, e.g. the enzymatic domain of diphtheria toxin, *Pseudomonas* exotoxin A or a Clostridial cytotoxin, e.g. TcsL of *Clostridium sordellii*.

The immunoconjugate may be encoded as a fusion protein, with the toxin linked for example to a single chain antigen binding protein construct, or to one of the chains of antigen binding protein with 2 or more chains, at the N or C terminus. Alternatively, the toxin may be conjugated to the antigen binding protein using any suitable method known in the art. For instance, the antigen binding protein may be biotinylated and conjugated to streptavidin-conjugated toxin (or vice versa). Other suitable methods are known to those skilled in the art.

The therapeutic agent may be any other useful therapeutic agent, for instance any other agent capable of killing or abrogating a cell, e.g. a radioisotope.

A diagnostic agent is an agent useful for diagnostic purposes. Such an agent may in particular be a tracer or a label, i.e. an agent which can be detected in order to follow its passage through a human body. A tracer or label may in particular be detected by a scan, e.g. a PET scan or a CT scan. Many tracers and labels are known in the art, including radiolabels. Any suitable tracer or label may be used according to the present disclosure, including the common radioisotopes $^{11}$C, $^{13}$N, $^{15}$O, $^{18}$F, $^{99}$Tc and $^{123}$I and $^{125}$I. A diagnostic agent may be conjugated to an antigen binding protein using any suitable labelling group, such as are known in the art. For instance, the antigen binding protein may be radiolabelled using radiolabelled biotin.

The antigen binding protein may be conjugated to a carrier comprising or containing a therapeutic or diagnostic agent. Pharmaceutical carriers are known in the art. Examples of suitable carriers include in particular micelles and liposomes. As is known to the skilled person, a micelle is an aggregate of surfactants (e.g. fatty acids) in an aqueous liquid, in which the hydrophilic head groups of the surfactants form the surface of the aggregate and the hydrophobic tail groups the core. A liposome is a spherical vesicle formed from a lipid bilayer surrounding an aqueous core. The therapeutic or diagnostic agent may be located within the core of a micelle or liposome.

Liposomes and micelles may be synthesised using any method known in the art. Suitable methods for liposome synthesis and drug loading are described in e.g. Akbarzadeh et al., Nanoscale Res Lett 8(1): 102, 2013. Liposomes and micelles may be conjugated to antigen binding proteins using methods known in the art, e.g. the methods taught in Reulen et al., Bioconjug Chem 18(2): 590-596, 2007; or Kung & Redemann, Biochim Biophys Acta 862(2): 435-439, 1986.

An immunoconjugate comprising a therapeutic agent, or a carrier comprising a therapeutic agent, may be used in therapy. An immunoconjugate comprising a diagnostic agent, or a carrier comprising a diagnostic agent, may be used in in vivo diagnostic methods.

In some embodiments, antigen binding proteins (e.g. antibodies) of the invention are used (e.g. used therapeutically) in their "naked" unconjugated form.

Compositions comprising at least a first antigen binding protein (e.g. antibody) of the invention or an immunoconjugate thereof constitute a further aspect of the present invention. Formulations (compositions) comprising one or more antigen binding protein (e.g. antibody) of the invention in admixture with a suitable diluent, carrier or excipient constitute a preferred embodiment of the present invention. Such formulations may be for pharmaceutical use and thus compositions of the invention are preferably pharmaceutically acceptable. Suitable diluents, excipients and carriers are known to the skilled man.

The compositions according to the invention may be presented, for example, in a form suitable for oral, nasal, parenteral, intravenal, topical or rectal administration. In a preferred embodiment, compositions according to the invention are presented in a form suitable for intravenal administration. In some embodiments, compositions according to the invention are presented in a form suitable for intraperitoneal (i.p.) administration. In some embodiments, compositions according to the invention are presented in a form suitable for injection.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Injection solutions may, for example, be produced in the conventional manner, such as by the addition of preservation agents, such as p-hydroxybenzoates, or stabilizers, such as EDTA. The solutions may then be filled into injection vials or ampoules.

Nasal sprays may be formulated similarly in aqueous solution and packed into spray containers, either with an aerosol propellant or provided with means for manual compression.

The pharmaceutical compositions (formulations) of the present invention are preferably administered parenterally. Intravenous administration is preferred. In some embodiments, administration is intraperitoneal (i.p.) administration. Parenteral administration may be performed by subcutaneous, intramuscular or intravenous injection by means of a syringe. Alternatively, parenteral administration can be performed by means of an infusion pump. A further option is a composition which may be a powder or a liquid for the administration of the antigen binding protein (e.g. antibody) in the form of a nasal or pulmonal spray. As a still further option, the antigen binding proteins of the invention can also be administered transdermally, e.g. from a patch, optionally an iontophoretic patch, or transmucosally, e.g. bucally.

Suitable dosage units can be determined by a person skilled in the art.

The pharmaceutical compositions may additionally comprise further active ingredients (e.g. as described elsewhere herein) in the context of co-administration regimens or combined regimens.

A further aspect of the present invention provides the antigen binding proteins (e.g. antibodies) defined herein for use in therapy.

By "therapy" as used herein is meant the treatment of any medical condition. Such treatment may be prophylactic (i.e.

preventative), curative (or treatment intended to be curative), or palliative (i.e. treatment designed merely to limit, relieve or improve the symptoms of a condition).

Preferably, antigen binding proteins (e.g. antibodies) defined herein are for use in the treatment of celiac disease. Thus, in one aspect, the present invention provides the antibodies defined herein for use in the treatment of celiac disease.

In another aspect, the present invention provides immunoconjugates of the invention for use in therapy, in particular for use in the treatment of celiac disease.

In another aspect, the present invention provides antigen binding proteins, or immunoconjugates thereof, for use in inhibiting and/or killing cells (e.g. antigen presenting cells such as B cells or plasma cells, for example as defined elsewhere herein) that express or present HLA-DQ2.5:DQ2.5-glia-$\alpha$1a and/or HLA-DQ2.5:DQ2.5-glia-$\alpha$2.

The in vivo methods and uses as described herein are generally carried out in a human.

Thus, the term "animal" or "patient" as used herein typically means human.

Alternatively viewed, the present invention provides a method of treating celiac disease which method comprises administering to a patient in need thereof a therapeutically effective amount of an antigen binding protein (e.g. antibody) of the invention as defined herein. Embodiments of the therapeutic uses of the invention described herein apply, mutatis mutandis, to this aspect of the invention.

In another aspect, the present invention provides a method of inhibiting and/or killing cells (e.g. antigen presenting cells such as B cells or plasma cells, for example as defined elsewhere herein) that express or present HLA-DQ2.5:DQ2.5-glia-$\alpha$1a and/or HLA-DQ2.5:DQ2.5-glia-$\alpha$2, which method comprises administering to a patient (e.g. a celiac disease patient) in need thereof a therapeutically effective amount of an antigen binding protein (e.g. antibody) of the invention as defined herein.

By "therapeutically effective amount" is meant an amount sufficient to show benefit to the condition of the subject. Whether an amount is sufficient to show benefit to the condition of the subject may be determined by the subject him/herself or a physician.

Further alternatively viewed, the present invention provides the use of an antigen binding protein (e.g. antibody) of the invention as defined herein in the manufacture of a medicament for use in therapy. Preferred therapy is the treatment of celiac disease. Embodiments of the therapeutic uses of the invention described herein apply, mutatis mutandis, to this aspect of the invention.

Further alternatively viewed, the present invention provides the use of an antigen binding protein (e.g. antibody) of the invention as defined herein for the treatment of celiac disease. Embodiments of the therapeutic uses of the invention described herein apply, mutatis mutandis, to this aspect of the invention.

The antigen binding proteins (e.g. antibodies) and compositions and methods and uses of the present invention may be used in combination with other therapeutics and diagnostics. In terms of biological agents, preferably diagnostic or therapeutic agents, for use "in combination" with an antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where an antigen binding protein (e.g. antibody) of the invention is a naked antigen binding protein and is used in combination with an agent or therapeutic agent that is not operatively attached thereto. In other "combined" embodiments of the invention, an antigen binding protein (e.g. antibody) of the invention is an immunoconjugate wherein the antigen binding protein is itself operatively associated or combined with the agent or therapeutic agent. The operative attachment includes all forms of direct and indirect attachment as described herein and known in the art.

The "combined" uses, particularly in terms of an antigen binding protein (e.g. antibody) of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the antigen binding protein (e.g. antibodies) of the present invention.

In certain embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antigen binding protein (e.g. antibody) of the invention is operatively attached to a component capable of converting the prodrug to the active drug, not that the antigen binding protein (e.g. antibody) is attached to the prodrug itself. However, there is no requirement that the prodrug embodiments of the invention need to be used as prodrug combinations. Accordingly, prodrugs may be used in any manner that they are used in the art.

Thus, where combined compositions, pharmaceuticals, cocktails, kits, methods, and first and second medical uses are described, preferably in terms of diagnostic agents, and more preferably therapeutic agents, the combinations include antigen binding protein (e.g. antibody) that are "naked" (e.g. "naked" antibodies) and immunoconjugates, and wherein practice of the in vivo embodiments of the invention involves the prior, simultaneous or subsequent administration of the naked antigen binding protein or immunoconjugate and the biological, diagnostic or therapeutic agent; so long as, in some conjugated or unconjugated form, the overall provision of some form of the antigen binding protein (e.g. antibody) and some form of the biological, diagnostic or therapeutic agent is achieved.

The invention therefore provides compositions, pharmaceutical compositions, therapeutic kits and medicinal cocktails comprising, optionally in at least a first composition or container, a biologically effective amount of at least a first antigen binding protein (e.g. antibody) of the invention, or an antigen-binding fragment or immunoconjugate of such protein; and a biologically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antigen binding protein (e.g. antibody) and/or for attaching other agents to the antigen binding protein. Certain preferred second biological agents, components or systems are prodrugs or components for making and using prodrugs, including components for making the prodrug itself and components for adapting the antigen binding proteins (e.g. antibodies) of the invention to function in such prodrug or ADEPT embodiments.

Where therapeutic or diagnostic agents are included as the at least a second biological agent, component or system, such therapeutics and/or diagnostics will typically be those for use in connection with the treatment or diagnosis of disease, preferably celiac disease.

Thus, in certain embodiments "at least a second therapeutic agent" will be included in the therapeutic kit or cocktail. The term is chosen in reference to the antigen binding protein (e.g. antibody) of the invention being the first therapeutic agent.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antigen binding protein (e.g. antibody) and the one or more other biological agents included.

Speaking generally, the at least a second therapeutic agent may be administered to the animal or patient substantially simultaneously with an antigen binding protein (e.g. antibody) of the invention; such as from a single pharmaceutical composition or from two pharmaceutical compositions administered closely together.

Alternatively, the at least a second therapeutic agent may be administered to the animal or patient at a time sequential to the administration of the antigen binding protein (e.g. antibody) of the invention. "At a time sequential", as used herein, means "staggered", such that the at least a second therapeutic agent is administered to the animal or patient at a time distinct to the administration of the antigen binding protein (e.g. antibody) of the invention. Generally, the two agents are administered at times effectively spaced apart to allow the two agents to exert their respective therapeutic effects, i.e., they are administered at "biologically effective time intervals". The at least a second therapeutic agent may be administered to the animal or patient at a biologically effective time prior to the antigen binding protein (e.g. antibody) of the invention, or at a biologically effective time subsequent to that therapeutic.

Yet further aspects are methods of diagnosis or imaging of a subject comprising the administration of an appropriate amount of an antibody or other protein of the invention as defined herein to the subject and detecting the presence and/or amount and/or the location of the antibody or other protein of the invention in the subject.

A preferred disease to be imaged or diagnosed in accordance with the present invention is celiac disease.

In one embodiment, the invention provides a method of diagnosing celiac disease in a mammal comprising the step of:

(a) contacting a test sample taken from said mammal with one or more of the antigen binding proteins (e.g. antibodies) of the invention.

In a further embodiment, the invention provides a method of diagnosing celiac disease in a mammal comprising the steps of:

(a) contacting a test sample taken from said mammal with one or more of the antigen binding proteins (e.g. antibodies) of the invention;

(b) measuring the presence and/or amount and/or location of antigen binding protein (e.g. antibody)-antigen complex in the test sample; and, optionally (c) comparing the presence and/or amount of antigen binding protein (e.g. antibody)-antigen complex in the test sample to a control.

In the above methods, said contacting step is carried out under conditions that permit the formation of an antigen binding protein (e.g. antibody)-antigen complex. Appropriate conditions can readily be determined by a person skilled in the art.

In the above methods any appropriate test sample may be used, for example a blood sample, biopsy cells, tissues or organs suspected of being affected by celiac disease (e.g. small intestine) or histological sections.

In certain of the above methods, the presence of any amount of antigen binding protein (e.g. antibody)-antigen complex in the test sample would be indicative of the presence of celiac disease. Preferably, for a positive diagnosis to be made, the amount of antigen binding protein (e.g. antibody)-antigen complex in the test sample is greater than, preferably significantly greater than, the amount found in an appropriate control sample. More preferably, the significantly greater levels are statistically significant, preferably with a probability value of <0.05. Appropriate methods of determining statistical significance are well known and documented in the art and any of these may be used.

Appropriate control samples could be readily chosen by a person skilled in the art, for example, in the case of diagnosis of celiac disease, an appropriate control would be a sample from a subject that did not have celiac disease. Appropriate control "values" could also be readily determined without running a control "sample" in every test, e.g. by reference to the range for normal subjects known in the art.

For use in the diagnostic or imaging applications, the antigen binding proteins (e.g. antibodies) of the invention may be labeled with a detectable marker such as a radioopaque or radioisotope, such as $^3$H, $^{14}$C $^{32}$P, $^{35}$S, $^{123}$I, $^{125}$I, $^{131}$I; a radioactive emitter (e.g. $\alpha$, $\beta$ or $\gamma$ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g. labelled avidin/streptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antigen binding proteins (e.g. antibodies) of the invention attached to a label that produces a detectable signal, directly or indirectly. Appropriate labels are described elsewhere herein.

In one embodiment the method of diagnosing celiac disease is an in vitro method.

In one embodiment the method of diagnosing celiac disease is an in vivo method.

Alternatively viewed, the present invention provides a method for screening for celiac disease in a subject.

In some embodiments, antigen binding proteins (e.g. antibodies) of the present invention can be used as companion diagnostics.

In one embodiment (e.g. of methods of diagnosing), the subject (e.g. a human) is a subject at risk of developing celiac disease or at risk of the occurrence of celiac disease, e.g. a healthy subject or a subject not displaying any symptoms of celiac disease or any other appropriate "at risk" subject. In another embodiment the subject is a subject having, or suspected of having (or developing), or potentially having (or developing) celiac disease.

In some aspects, a method of the invention may further comprise an initial step of selecting a subject (e.g. a human subject) at risk of developing celiac disease, or at risk of the occurrence of celiac disease, or suspected of having (or developing) celiac disease, or potentially having (or developing) celiac disease. Subjects may be selected on the basis that, for example, the subject (or sample, e.g. tissue biopsy, from the subject) is positive for one or more celiac disease markers or risk factors.

In some aspects, diagnostic methods of the invention are provided which further comprise a step of treating celiac disease by therapy, e.g. using an antigen binding protein (e.g. antibody) of the present invention. For example, if the result of a method of the invention is indicative of celiac disease in the subject (e.g. a positive diagnosis of celiac disease is made), then an additional step of treating the celiac disease by therapy or surgery can be performed.

The invention further includes kits comprising one or more of the antigen binding proteins (e.g. antibodies), immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably, said kits are for use in the methods and uses as described herein, e.g. the therapeutic, diagnostic or imaging methods as described herein, or are for use in the in vitro assays or methods as described herein. The antigen binding protein (e.g. antibody) in such kits may be a conjugate as described elsewhere herein, e.g. may be conjugated to a detectable moiety or may be an immunoconjugate. Preferably said kits comprise instructions for use of the kit components. Preferably said kits are for diagnosing or treating celiac disease, and optionally comprise instructions for use of the kit components to diagnose or treat this disease.

The antigen binding proteins (e.g. antibodies) of the invention as defined herein may also be used as molecular tools for in vitro or in vivo applications and assays. As the antigen binding proteins (e.g. antibodies) have an antigen binding site, these can function as members of specific binding pairs and these molecules can be used in any assay where the particular binding pair member is required.

Thus, yet further aspects of the invention provide a reagent that comprises an antigen binding protein (e.g. antibody) of the invention as defined herein and the use of such antigen binding proteins as molecular tools, for example in in vitro or in vivo assays.

Tables of Nucleotide and Amino Acid Sequences Disclosed Herein and their Sequence Identifiers (Seq Id Nos)

All nucleotide sequences are recited herein 5' to 3' in line with convention in this technical field.

Tables A, B, C, D, E, F, G, H, I and AA contain sequences of antibodies that bind to, or specifically bind to, HLA-DQ2.5:DQ2.5-glia-α1a. Tables A-I herein set forth sequences of the R2A1-8E, R3A2-9F, R4A1-3A (also referred to as 107), 107-4.5D, 107-4.6D, 107-4.6C, 107-4.7C, 107-5.6A and 107-15.6A antibodies. Table AA herein sets forth sequences of the RF117 antibody.

Tables J, K, L, M, N, O, P, Q, R, S, T, U, V and W contain sequences of antibodies that bind to, or specifically bind to, HLA-DQ2.5:DQ2.5-glia-α2. Tables J-W herein set forth sequences of the 206, 217, 218, 220, 221, 223, 226, 228, 206-2.B11, 206-3. D8, 206-3.C7, 206-3.C11, 206-3.F6 and 206-12.F6 antibodies.

TABLE A

| SEQ ID NO: | Description | Sequence |
|---|---|---|
| | | R2A1-8E |
| 1 | VH domain (nt) | IGHV6-1*01/IGHJ6*02/IGHD6-19*01 CAGGTACAGCTGCAGCAGTCAGGTCCAGGACTGG TGAAGCCCTCGCAGACCCTCTCACTCACCTGTGCC ATCTCCGGGGACAGTGTCTCTAGCAACAGTGCTG CTTGGAACTGGATCAGGCAGTCCCCATCGAGAGG CCTTGAGTGGCTGGGAAGGACATACTACAGGTCC AAGTGGTATAATGATTATGCAGTATCTGTGAAAAGT CGAATAACCATCAACCCAGACACATCCAAGAACCA GTTCTCCCTGCAGCTGAACTCTGTGACTCCCGAGG ACACGGCTGTGTATTACTGTGCAAGAGATAGCAGC AGTGGCTGGCATCCTTACGGTATGGACGTCTGGG GCCAAGGGACCACGGTCACCGTCTCCTCA |
| 2 | VL domain (nt) | IGKV1-9*01/IGKJ4*01 GACATCCAGGTGACCCAGTCTC CATCCTTCCTGTCTGCATCTGTAGGAGACAGAGTC ACCATCACTTGCCGGGCCAGTCACGACATTAGCA GTTATTTAGCCTGGTATCAACACAAACCAGGGAAA GCCCCCAAACTCCTGATCCATGCTGCATCCATTTT GCAAAGTGGGGTCCCATCAAGGTTCAGCGGAAGT GGATCTGGGACAGAATTCACTCTCACAATCAGCAG CCTGCAGCCTGAAGATTTTGCAACGTACTACTGTC AACAGCTTAATAGTTACCCTCTGCTCACTTTCGGC GGAGGGACCAAAGTGGATATCAAA |
| 3 | VH domain (aa) | QVQLQQSGPGLVKPSQTLSLTCAISGDSVSSNSAA WNWIRQSPSRGLEWLGRTYYRSKWYNDYAVSVK SRITINPDTSKNQFSLQLNSVTPEDTAVYYCARDSS SGWHPYGMDVWGQGTTVTVSS |
| 4 | VL domain (aa) | DIQVTQSPSFLSASVGDRVTITCRASHDISSYLAWY QHKPGKAPKLLIHAASILQSGVPSRFSGSGSGTEFT LTISSLQPEDFATYYCQQLNSYPLLTFGGGTKVDIK |
| 5 | Heavy CDR1 | GDSVSSNSAA |
| 6 | Heavy CDR2 | TYYRSKWYN |
| 7 | Heavy CDR3 | ARDSSSGWHPYGMDV |
| 8 | Light CDR1 | HDISSY |
| 9 | Light CDR2 | AAS |
| 10 | Light CDR3 | QQLNSYPLLT |
| 11 | Heavy FR1 | QVQLQQSGPGLVKPSQTLSLTCAIS |
| 12 | Heavy FR2 | WNWIRQSPSRGLEWLGR |
| 13 | Heavy FR3 | DYAVSVKSRITINPDTSKNQFSLQLNSVTPEDTAVYYC |
| 14 | Heavy FR4 | WGQGTTVTVSS |
| 15 | Light FR1 | DIQVTQSPSFLSASVGDRVTITCRAS |
| 16 | Light FR2 | LAWYQHKPGKAPKLLIH |
| 17 | Light FR3 | ILQSGVPSRFSGSGSGTEFTLTISSLQPEDFATYYC |
| 18 | Light FR4 | FGGGTKVDIK |

TABLE A-continued

| SEQ ID NO: | Description | Sequence |
|---|---|---|
| 444 | Heavy chain (aa) (variable + constant domain). mIgG$_{2b}$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSAKTTPPSVYPLAPGCGDTTGSSVTLGCLVKGYFPESV TVTWNSGSLSSSVHTFPALLQSGLYTMSSSVTVPSSTWPSQ TVTCSVAHPASSTTVDKKLEPSGPISTINPCPPCKECHKCPAP NLEGGPSVFIFPPNIKDVLMISLTPKVTCVVVDVSEDDPDVQ ISWFVNNVEVHTAQTQTHREDYASTIRVVSTLPIQHQDWM SGKEFKCKVNNKDLPSPIERTISKIKGLVRAPQVYILPPPAEQL SRKDVSLTCLVVGFNPGDISVEWTSNGHTEENYKDTAPVLD SDGSYFIYSKLNMKTSKWEKTDSFSCNVRHEGLKNYYLKKTI SRSPGK |
| 445 | Light chain (aa) (variable + constant domain). mIgG$_{2b}$ | DIQVTQSPSFLSASVGDRVTITCRASHDISSYLAWYQHKPGK APKLLIHAASILQSGVPSRFSGSGSGTEFTLTISSLQPEDFATY YCQQLNSYPLLTFGGGTKVDIKRADAAPTVSIFPPSSEQLTSG GASVVCFLNNFYPKDINVKWKIDGSERQNGVLNSWTDQDS KDSTYSMSSTLTLTKDEYERHNSYTCEATHKTSTSPIVKSFNR NEC |
| 446 | Heavy chain (aa) (variable + constant domain). hIgG$_1$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGPS VFLFPPKPKDTLMISRTPEVTCVVVDVSHEDPEVKFNWYVD GVEVHNAKTKPREEQYGSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGS FFLYSKLTVDKSRWQQGNVFSCSVMHEALHNHYTQKSLSLS PGK |
| 447 | Light chain (aa) (variable + constant domain). hIgG$_1$ | DIQVTQSPSFLSASVGDRVTITCRASHDISSYLAWYQHKPGK APKLLIHAASILQSGVPSRFSGSGSGTEFTLTISSLQPEDFATY YCQQLNSYPLLTFGGGTKVDIKRTVAAPSVFIFPPSDEQLKS GTASVVCLLNNFYPREAKVQWKVDNALQSGNSQESVTEQ DSKDSTYSLSSTLTLSKADYEKHKVYACEVTHQGLSSPVTKSF NRGEC |

TABLE B

| SEQ ID NO: | Description | Sequence |
|---|---|---|
| | | R3A2-9F |
| 19 | VH domain (nt) | IGHV6-1*01/IGHJ6*02/IGHD6-19*01 CAGGTACAGCTGCAGCAGTCAGGTCCAGGACTGG TGAAGCCCTCGCAGACCCTCTCACTCACCTGTGCC ATCTCCGGGGACAGTGTCTCTAGCAACAGTGCTG CTTGGAACTGGATCAGGCAGTCCCCATCGAGAGG CCTTGAGTGGCTGGGAAGGACATACTACAGGTCC AAGTGGTATAATGATTATGCAGTATCTGTGAAAAGT CGAATAACCATCAACCCAGACACATCCAAGAACCA GTTCTCCCTGCAGCTGAACTCTGTGACTCCCGAGG ACACGGCTGTGTATTACTGTGCAAGAGATAGCAGC AGTGGCTGGCATCCTTACGGTATGGACGTCTGGG GCCAAGGGACCACGGTCACCGTCTCCTCA |
| 20 | VL domain (nt) | IGKV1-9*01/IGKJ5*01 GACATCCAGGTGACCCAGTCTCCATCCTTCCTGTC TGCATCTGTAGGAGACAGAGTCACCATCACTTGCC GGGCCAGTCACGACATTAGCAGTTATTTAGCCTGG TATCAACACAAACCAGGGAAAGCCCCCAAACTCCT GATCCATGCTGCATCCATTTTGCAAAGTGGGGTCC CATCAAGGTTCAGCGGAAGTGGATCTGGGACAGA ATTCACTCTCACAATCAGCAGCCTGCAGCCTGAAG ATTTTGCAACGTACTACTGTCAAGATCTCAATAGTT ATCCTCTCTTCGGCCAAGGGACACGACTGGAGATT AAA |

TABLE B-continued

| SEQ ID NO: | Description | Sequence |
|---|---|---|
| 21 | VH domain (aa) | QVQLQQSGPGLVKPSQTLSLTCAISGDSVSSNSAA WNWIRQSPSRGLEWLGRTYYRSKWYNDYAVSVK SRITINPDTSKNQFSLQLNSVTPEDTAVYYCARDSS SGWHPYGMDVWGQGTTVTVSS |
| 22 | VL domain (aa) | DIQVTQSPSFLSASVGDRVTITCRASHDISSYLAWYQ HKPGKAPKLLIHAASILQSGVPSRFSGSGSGTEFTLTI SSLQPEDFATYYCQDLNSYPLFGQGTRLEIK |
| 23 | Heavy CDR1 | GDSVSSNSAA |
| 24 | Heavy CDR2 | TYYRSKWYN |
| 25 | Heavy CDR3 | ARDSSSGWHPYGMDV |
| 26 | Light CDR1 | HDISSY |
| 27 | Light CDR2 | AAS |
| 28 | Light CDR3 | QDLNSYPL |
| 29 | Heavy FR1 | QVQLQQSGPGLVKPSQTLSLTCAIS |
| 30 | Heavy FR2 | WNWIRQSPSRGLEWLGR |
| 31 | Heavy FR3 | DYAVSVKSRITINPDTSKNQFSLQLNSVTPEDTAVYYC |
| 32 | Heavy FR4 | WGQGTTVTVSS |
| 33 | Light FR1 | DIQVTQSPSFLSASVGDRVTITCRAS |
| 34 | Light FR2 | LAWYQHKPGKAPKLLIH |
| 35 | Light FR3 | ILQSGVPSRFSGSGSGTEFTLTISSLQPEDFATYYC |
| 36 | Light FR4 | FGQGTRLEIK |
| 448 | Heavy chain (aa) (variable + constant domain). mIgG$_{2b}$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSAKTTPPSVYPLAPGCGDTTGSSVTLGCLVKGYFPESV TVTWNSGSLSSSVHTFPALLQSGLYTMSSSVTVPSSTWPSQ TVTCSVAHPASSTTVDKKLEPSGPISTINPCPPCKECHKCPAP NLEGGPSVFIFPPNIKDVLMISLTPKVTCVVVDVSEDDPDVQ ISWFVNNVEVHTAQTQTHREDYASTIRVVSTLPIQHQDWM SGKEFKCKVNNKDLPSPIERTISKIKGLVRAPQVYILPPPAEQL SRKDVSLTCLVVGFNPGDISVEWTSNGHTEENYKDTAPVLD SDGSYFIYSKLNMKTSKWEKTDSFSCNVRHEGLKNYYLKKTI SRSPGK |
| 449 | Light chain (aa) (variable + constant domain). mIgG$_{2b}$ | DIQVTQSPSFLSASVGDRVTITCRASHDISSYLAWYQHKPGK APKLLIHAASILQSGVPSRFSGSGSGTEFTLTISSLQPEDFATY YCQDLNSYPLFGQGTRLEIKRADAAPTVSIFPPSSEQLTSGG ASVVCFLNNFYPKDINVKWKIDGSERQNGVLNSWTDQDSK DSTYSMSSTLTLTKDEYERHNSYTCEATHKTSTSPIVKSFNRN EC |
| 450 | Heavy chain (aa) (variable + constant domain). hIgG$_1$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGPS VFLFPPKPKDTLMISRTPEVTCVVVDVSHEDPEVKFNWYVD GVEVHNAKTKPREEQYGSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGS FFLYSKLTVDKSRWQQGNVFSCSVMHEALHNHYTQKSLSLS PGK |
| 451 | Light chain (aa) (variable + constant domain). hIgG$_1$ | DIQVTQSPSFLSASVGDRVTITCRASHDISSYLAWYQHKPGK APKLLIHAASILQSGVPSRFSGSGSGTEFTLTISSLQPEDFATY YCQDLNSYPLFGQGTRLEIKRTVAAPSVFIFPPSDEQLKSGTA SVVCLLNNFYPREAKVQWKVDNALQSGNSQESVTEQDSKD STYSLSSTLTLSKADYEKHKVYACEVTHQGLSSPVTKSFNRGE C |

TABLE C

| SEQ ID NO: | Description | Sequence |
|---|---|---|
| | | R4A1-3A (107) |
| 37 | VH domain (nt) | IGHV6-1*01/IGHJ6*02/IGHD6-19*01 CAGGTACAGCTGCAGCAGTCAGGTCCAGGACTGG TGAAGCCCTCGCAGACCCTCTCACTCACCTGTGCC ATCTCCGGGGACAGTGTCTCTAGCAACAGTGCTG CTTGGAACTGGATCAGGCAGTCCCCATCGAGAGG CCTTGAGTGGCTGGGAAGGACATACTACAGGTCC AAGTGGTATAATGATTATGCAGTATCTGTGAAAAGT CGAATAACCATCAACCCAGACACATCCAAGAACCA GTTCTCCCTGCAGCTGAACTCTGTGACTCCCGAGG ACACGGCTGTGTATTACTGTGCAAGAGATAGCAGC AGTGGCTGGCATCCTTACGGTATGGACGTCTGGG GCCAAGGGACCACGGTCACCGTCTCCTCA |
| 38 | VL domain (nt) | IGKV1-9*01/IGKJ5*01 GACATCCAGGTGACCCAGTCTCCATCCTTCCTGTC TGCATCTGTAGGAGACAGAGTCACCATCACTTGCC GGGCCAGTCACGACATTAGCAGTTATTTAGCCTGG TATCAACACAAACCATGGAAAGCCCCCAAACTCCT GATCCATGCTGCATCCATTTTGCAAAGTGGGGTCC CATCAAGGTTCAGCGGAAGTGGATCTGGGACAGA ATTCACTCTCACAATCAGCAGCCTGCAGCCTGAAG ATTTTGCAACGTACTACTGTCAAGATCTCAATAGTT ATCCTCTCTTCGGCCAAGGGACACGACTGGAGATT AAA |
| 39 | VH domain (aa) | QVQLQQSGPGLVKPSQTLSLTCAISGDSVSSNSAA WNWIRQSPSRGLEWLGRTYYRSKWYNDYAVSVK SRITINPDTSKNQFSLQLNSVTPEDTAVYYCARDSS SGWHPYGMDVWGQGTTVTVSS |
| 40 | VL domain (aa) | DIQVTQSPSFLSASVGDRVTITCRASHDISSYLAWYQ HKPWKAPKLLIHAASILQSGVPSRFSGSGSGTEFTLTI SSLQPEDFATYYCQDLNSYPLFGQGTRLEIK |
| 41 | Heavy CDR1 | GDSVSSNSAA |
| 42 | Heavy CDR2 | TYYRSKWYN |
| 43 | Heavy CDR3 | ARDSSSGWHPYGMDV |
| 44 | Light CDR1 | HDISSY |
| 45 | Light CDR2 | AAS |
| 46 | Light CDR3 | QDLNSYPL |
| 47 | Heavy FR1 | QVQLQQSGPGLVKPSQTLSLTCAIS |
| 48 | Heavy FR2 | WNWIRQSPSRGLEWLGR |
| 49 | Heavy FR3 | DYAVSVKSRITINPDTSKNQFSLQLNSVTPEDTAVYYC |
| 50 | Heavy FR4 | WGQGTTVTVSS |
| 51 | Light FR1 | DIQVTQSPSFLSASVGDRVTITCRAS |
| 52 | Light FR2 | LAWYQHKPWKAPKLLIH |
| 53 | Light FR3 | ILQSGVPSRFSGSGSGTEFTLTISSLQPEDFATYYC |
| 54 | Light FR4 | FGQGTRLEIK |
| 452 | Heavy chain (aa) (variable + constant domain). mIgG$_{2b}$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSAKTTPPSVYPLAPGCGDTTGSSVTLGCLVKGYFPESV TVTWNSGSLSSSVHTFPALLQSGLYTMSSSVTVPSSTWPSQ TVTCSVAHPASSTTVDKKLEPSGPISTINPCPPCKECHKCPAP NLEGGPSVFIFPPNIKDVLMISLTPKVTCVVVDVSEDDPDVQ ISWFVNNVEVHTAQTQTHREDYASTIRVVSTLPIQHQDWM SGKEFKCKVNNKDLPSPIERTISKIKGLVRAPQVYILPPPAEQL SRKDVSLTCLVVGFNPGDISVEWTSNGHTEENYKDTAPVLD SDGSYFIYSKLNMKTSKWEKTDSFSCNVRHEGLKNYYLKKTI SRSPGK |

TABLE C-continued

| SEQ ID NO: | Description | Sequence |
|---|---|---|
| 453 | Light chain (aa) (variable + constant domain). mIgG$_{2b}$ | DIQVTQSPSFLSASVGDRVTITCRASHDISSYLAWYQHKPW KAPKLLIHAASILQSGVPSRFSGSGSGTEFTLTISSLQPEDFAT YYCQDLNSYPLFGQGTRLEIKRADAAPTVSIFPPSSEQLTSGG ASVVCFLNNFYPKDINVKWKIDGSERQNGVLNSWTDQDSK DSTYSMSSTLTLTKDEYERHNSYTCEATHKTSTSPIVKSFNRN EC |
| 454 | Heavy chain (aa) (variable + constant domain). hIgG$_1$ | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSSSGWHPYGMDVWGQGTT VTVSSASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGPS VFLFPPKPKDTLMISRTPEVTCVVVDVSHEDPEVKFNWYVD GVEVHNAKTKPREEQYGSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGS FFLYSKLTVDKSRWQQGNVFSCSVMHEALHNHYTQKSLSLS PGK |
| 455 | Light chain (aa) (variable + constant domain). hIgG$_1$ | DIQVTQSPSFLSASVGDRVTITCRASHDISSYLAWYQHKPW KAPKLLIHAASILQSGVPSRFSGSGSGTEFTLTISSLQPEDFAT YYCQDLNSYPLFGQGTRLEIKRTVAAPSVFIFPPSDEQLKSGT ASVVCLLNNFYPREAKVQWKVDNALQSGNSQESVTEQDSK DSTYSLSSTLTLSKADYEKHKVYACEVTHQGLSSPVTKSFNRG EC |

TABLE D

| SEQ ID NO: | Description | Sequence |
|---|---|---|
| | | 107-4.5D |
| 55 | VH domain (nt) | IGHV6-1*01 IGHJ6*02 IGHD6-19*01 CAGGTACAGCTGCAGCAGTCAGGTCCAGGACTGGTGAA GCCCTCGCAGACCCTCTCACTCACCTGTGCCATCTCCGGG GACAGTGTCTCTAGCAACAGTGCTGCTTGGAACTGGATC AGGCAGTCCCCATCGAGAGGCCTTGAGTGGCTGGGAAG GACATACTACAGGTCCAAGTGGTATAATGATTATGCAGT ATCTGTGAAAAGTCGAATAACCATCAACCCAGACACATCC AAGAACCAGTTCTCCCTGCAGCTGAACTCTGTGACTCCCG AGGACACGGCTGTGTATTACTGTGCAAGAGATTCTACTA CTGGGTGGAATGCTTACGGTATGGACGTCTGGGGCCAAG GGACCACGGTCACCGTCTCCTCA |
| 56 | VL domain (nt) | IGKV1-9*01 IGKJ5*01 GACATCCAGGTGACCCAGTCTCCATCCTTCCTGTCTGCAT CTGTAGGAGACAGAGTCACCATCACTTGCCGGGCCAGTC ACGACATTAGCAGTTATTTAGCCTGGTATCAACACAAACC GTGGAAAGCCCCCAAACTCCTGATCCATGCTGCATCCATT TTGCAAAGTGGGGTCCCATCAAGGTTCAGCGGAAGTGGA TCTGGGACAGAATTCACTCTCACAATCAGCAGCCTGCAGC CTGAAGATTTTGCAACGTACTACTGTCAAGATCTCAATAG TTATCCTCTCTTCGGCCAAGGGACACGACTGGAGATTAAA |
| 57 | VH domain (aa) | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSTTGWNAYGMDVWGQGTT VTVSS |
| 58 | VL domain (aa) | DIQVTQSPSFLSASVGDRVTITCRASHDISSYLAWYQHKPW KAPKLLIHAASILQSGVPSRFSGSGSGTEFTLTISSLQPED-FAT YYCQDLNSYPLFGQGTRLEIK |
| 59 | Heavy CDR1 | GDSVSSNSAA |
| 60 | Heavy CDR2 | TYYRSKWYN |
| 61 | Heavy CDR3 | ARDSTTGWNAYGMDV |

TABLE D-continued

| SEQ ID NO: | Description | Sequence |
|---|---|---|
| 62 | Light CDR1 | HDISSY |
| 63 | Light CDR2 | AAS |
| 64 | Light CDR3 | QDLNSYPL |
| 65 | Heavy FR1 | QVQLQQSGPGLVKPSQTLSLTCAIS |
| 66 | Heavy FR2 | WNWIRQSPSRGLEWLGR |
| 67 | Heavy FR3 | DYAVSVKSRITINPDTSKNQFSLQLNSVTPEDTAVYYC |
| 68 | Heavy FR4 | WGQGTTVTVSS |
| 69 | Light FR1 | DIQVTQSPSFLSASVGDRVTITCRAS |
| 70 | Light FR2 | LAWYQHKPWKAPKLLIH |
| 71 | Light FR3 | ILQSGVPSRFSGSGSGTEFTLTISSLQPEDFATYYC |
| 72 | Light FR4 | FGQGTRLEIK |

TABLE E

| SEQ ID NO: | Description | Sequence |
|---|---|---|
| | | 107-4.6D |
| 73 | VH domain (nt) | IGHV6-1*01<br>IGHJ6*02<br>IGHD6-19*01<br>CAGGTACAGCTGCAGCAGTCAGGTCCAGGACTGGTGAA<br>GCCCTCGCAGACCCTCTCACTCACCTGTGCCATCTCCGGG<br>GACAGTGTCTCTAGCAACAGTGCTGCTTGGAACTGGATC<br>AGGCAGTCCCCATCGAGAGGCCTTGAGTGGCTGGGAAG<br>GACATACTACAGGTCCAAGTGGTATAATGATTATGCAGT<br>ATCTGTGAAAGTCGAATAACCATCAACCCAGACACATCC<br>AAGAACCAGTTCTCCCTGCAGCTGAACTCTGTGACTCCCG<br>AGGACACGGCTGTGTATTACTGTGCAAGAGATTCTACGA<br>GTGGGTGGCATCCTTACGGTATGGACGTCTGGGGCCAAG<br>GGACCACGGTCACCGTCTCCTCA |
| 74 | VL domain (nt) | IGKV1-9*01<br>IGKJ5*01<br>GACATCCAGGTGACCCAGTCTCCATCCTTCCTGTCTGCAT<br>CTGTAGGAGACAGAGTCACCATCACTTGCCGGGCCAGTC<br>ACGACATTAGCAGTTATTTAGCCTGGTATCAACACAAACC<br>GTGGAAAGCCCCCAAACTCCTGATCCATGCTGCATCCATT<br>TTGCAAAGTGGGGTCCCATCAAGGTTCAGCGGAAGTGGA<br>TCTGGGACAGAATTCACTCTCACAATCAGCAGCCTGCAGC<br>CTGAAGATTTTGCAACGTACTACTGTCAAGATCTCAATAG<br>TTATCCTCTCTTCGGCCAAGGGACACGACTGGAGATTAAA |
| 75 | VH domain (aa) | QVQLQQSGPGLVKPSQTLSLTCAISGDSVSSNSAAWNWIR<br>QSPSRGLEWLGRTYYRSKWYNDYAVSVKSRITINPDTSKNQ<br>FSLQLNSVTPEDTAVYYCARDSTSGWHPYGMDVWGQGTT<br>VTVSS |
| 76 | VL domain (aa) | DIQVTQSPSFLSASVGDRVTITCRASHDISSYLAWYQHKPW<br>KAPKLLIHAASILQSGVPSRFSGSGSGTEFTLTISSLQPEDFAT<br>YYCQDLNSYPLFGQGTRLEIK |
| 77 | Heavy CDR1 | GDSVSSNSAA |
| 78 | Heavy CDR2 | TYYRSKWYN |
| 79 | Heavy CDR3 | ARDSTSGWHPYGMDV |
| 80 | Light CDR1 | HDISSY |
| 81 | Light CDR2 | AAS |
| 82 | Light CDR3 | QDLNSYPL |

TABLE E-continued

| SEQ ID NO: | Description | Sequence |
|---|---|---|
| 83 | Heavy FR1 | QVQLQQSGPGLVKPSQTLSLTCAIS |
| 84 | Heavy FR2 | WNWIRQSPSRGLEWLGR |
| 85 | Heavy FR3 | DYAVSVKSRITINPDTSKNQFSLQLNSVTPEDTAVYYC |
| 86 | Heavy FR4 | WGQGTTVTVSS |
| 87 | Light FR1 | DIQVTQSPSFLSASVGDRVTITCRAS |
| 88 | Light FR2 | LAWYQHKPWKAPKLLIH |
| 89 | Light FR3 | ILQSGVPSRFSGSGSGTEFTLTISSLQPEDFATYYC |
| 90 | Light FR4 | FGQGTRLEIK |

TABLE F

| SEQ ID NO: | Description | Sequence |
|---|---|---|
| | | 107-4.6C |
| 91 | VH domain (nt) | IGHV6-1*01 IGHJ6*02 IGHD6-19*01 CAGGTACAGCTGCAGCAGTCAGGTCCAGGACTGGTGAA GCCCTCGCAGACCCTCTCACTCACCTGTGCCATCTCCGGG GACAGTGTCTCTAGCAACAGTGCTGCTTGGAACTGGATC AGGCAGTCCCCATCGAGAGGCCTTGAGTGGCTGGGAAG GACATACTACAGGTCCAAGTGGTATAATGATTATGCAGT ATCTGTGAAAAGTCGAATAACCATCAACCCAGACACATCC AAGAACCAGTTCTCCCTGCAGCTGAACTCTGTGACTCCCG AGGACACGGCTGTGTATTACTGTGCAAGAGATTCGACTA CGGGGTGGGGTGCGTACGGTATGGACGTCTGGGGCCAA GGGACCACGGTCACCGTCTCCTCA |
| 92 | VL domain (nt) | IGKV1-9*01 IGKJ5*01 GACATCCAGGTGACCCAGTCTCCATCCTTCCTGTCTGCAT CTGTAGGAGACAGAGTCACCATCACTTGCCGGGCCAGTC ACGACATTAGCAGTTATTTAGCCTGGTATCAACACAAACC GTGGAAAGCCCCCAAACTCCTGATCCATGCTGCATCCATT TTGCAAAGTGGGGTCCCATCAAGGTTCAGCGGAAGTGGA TCTGGGACAGAATTCACTCTCACAATCAGCAGCCTGCAGC CTGAAGATTTTGCAACGTACTACTGTCAAGATCTCAATAG TTATCCTCTCTTCGGCCAAGGGACACGACTGGAGATTAAA |
| 93 | VH domain (aa) | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDSTTGWGAYGMDVWGQGTT VTVSS |
| 94 | VL domain (aa) | DIQVTQSPSFLSASVGDRVTITCRASHDISSYLAWYQHKPW KAPKLLIHAASILQSGVPSRFSGSGSGTEFTLTISSLQPEDFAT YYCQDLNSYPLFGQGTRLEIK |
| 95 | Heavy CDR1 | GDSVSSNSAA |
| 96 | Heavy CDR2 | TYYRSKWYN |
| 97 | Heavy CDR3 | ARDSTTGWGAYGMDV |
| 98 | Light CDR1 | HDISSY |
| 99 | Light CDR2 | AAS |
| 100 | Light CDR3 | QDLNSYPL |
| 101 | Heavy FR1 | QVQLQQSGPGLVKPSQTLSLTCAIS |
| 102 | Heavy FR2 | WNWIRQSPSRGLEWLGR |

TABLE F-continued

| SEQ ID NO: | Description | Sequence |
|---|---|---|
| 103 | Heavy FR3 | DYAVSVKSRITINPDTSKNQFSLQLNSVTPEDTAVYYC |
| 104 | Heavy FR4 | WGQGTTVTVSS |
| 105 | Light FR1 | DIQVTQSPSFLSASVGDRVTITCRAS |
| 106 | Light FR2 | LAWYQHKPWKAPKLLIH |
| 107 | Light FR3 | ILQSGVPSRFSGSGSGTEFTLTISSLQPEDFATYYC |
| 108 | Light FR4 | FGQGTRLEIK |

TABLE G

| SEQ ID NO: | Description | Sequence |
|---|---|---|
| | | 107-4.7C |
| 109 | VH domain (nt) | IGHV6-1*01 IGHJ6*02 IGHD6-19*01 CAGGTACAGCTGCAGCAGTCAGGTCCAGGACTGGTGAA GCCCTCGCAGACCCTCTCACTCACCTGTGCCATCTCCGGG GACAGTGTCTCTAGCAACAGTGCTGCTTGGAACTGGATC AGGCAGTCCCCATCGAGAGGCCTTGAGTGGCTGGGAAG GACATACTACAGGTCCAAGTGGTATAATGATTATGCAGT ATCTGTGAAAAGTCGAATAACCATCAACCCAGACACATCC AAGAACCAGTTCTCCCTGCAGCTGAACTCTGTGACTCCCG AGGACACGGCTGTGTATTACTGTGCAAGAGATAGGACTA CTGGGTGGCATCCGTACGGTATGGACGTCTGGGGCCAAG GGACCACGGTCACCGTCTCCTCA |
| 110 | VL domain (nt) | IGKV1-9*01 IGKJ5*01 GACATCCAGGTGACCCAGTCTCCATCCTTCCTGTCTGCAT CTGTAGGAGACAGAGTCACCATCACTTGCCGGGCCAGTC ACGACATTAGCAGTTATTTAGCCTGGTATCAACACAAACC GTGGAAAGCCCCCAAACTCCTGATCCATGCTGCATCCATT TTGCAAAGTGGGGTCCCATCAAGGTTCAGCGGAAGTGGA TCTGGGACAGAATTCACTCTCACAATCAGCAGCCTGCAGC CTGAAGATTTTGCAACGTACTACTGTCAAGATCTCAATAG TTATCCTCTCTTCGGCCAAGGGACACGACTGGAGATTAAA |
| 111 | VH domain (aa) | QVQLQQSGPGLVKPSQTLSLTCAISGDSVSSNSAAWNWIR QSPSRGLEWLGRTYYRSKWYNDYAVSVKSRITINPDTSKNQ FSLQLNSVTPEDTAVYYCARDRTTGWHPYGMDVWGQGTT VTVSS |
| 112 | VL domain (aa) | DIQVTQSPSFLSASVGDRVTITCRASHDISSYLAWYQHKPW KAPKLLIHAASILQSGVPSRFSGSGSGTEFTLTISSLQPEDFAT YYCQDLNSYPLFGQGTRLEIK |
| 113 | Heavy CDR1 | GDSVSSNSAA |
| 114 | Heavy CDR2 | TYYRSKWYN |
| 115 | Heavy CDR3 | ARDRTTGWHPYGMDV |
| 116 | Light CDR1 | HDISSY |
| 117 | Light CDR2 | AAS |
| 118 | Light CDR3 | QDLNSYPL |
| 119 | Heavy FR1 | QVQLQQSGPGLVKPSQTLSLTCAIS |
| 120 | Heavy FR2 | WNWIRQSPSRGLEWLGR |
| 121 | Heavy FR3 | DYAVSVKSRITINPDTSKNQFSLQLNSVTPEDTAVYYC |
| 122 | Heavy FR4 | WGQGTTVTVSS |
| 123 | Light FR1 | DIQVTQSPSFLSASVGDRVTITCRAS |

TABLE G-continued

| SEQ ID NO: | Description | Sequence |
|---|---|---|
| 124 | Light FR2 | LAWYQHKPWKAPKLLIH |
| 125 | Light FR3 | ILQSGVPSRFSGSGSGTEFTLTISSLQPEDFATYYC |
| 126 | Light FR4 | FGQGTRLEIK |

TABLE H

| SEQ ID NO: | Description | Sequence |
|---|---|---|
| | | 107-5.6A |
| 127 | VH domain (nt) | IGHV6-1*01<br>IGHJ6*02<br>IGHD6-19*01<br>CAGGTACAGCTGCAGCAGTCAGGTCCAGGACTGGTGAA<br>GCCCTCGCAGACCCTCTCACTCACCTGTGCCATCTCCGGG<br>GACAGTGTCTCTAGCAGCAGTGCTGCTTGGAACTGGATC<br>AGGCAGTCCCCATCGAGAGGCCTTGAGTGGCTGGGAAG<br>GACATACTACAGGTCCAAGTGGTATAATGATTATGCAGT<br>ATCTGTGAAAAGTCGAATAACCATCAACCCAGACACATCC<br>AAGAACCAGTTCTCCCTGCAGCTGAACTCTGTGACTCCCG<br>AGGACACGGCTGTGTATTACTGTGCAAGAGATAGCAGCA<br>GTGGCTGGCATCCTTACGGTATGGACGTCTGGGGCCAAG<br>GGACCACGGTCACCGTCTCCTCA |
| 128 | VL domain (nt) | IGKV1-9*01<br>IGKJ5*01<br>GACGTCCAGGTGACCCAGTCTCCATCCTTCCTGTCTGCAT<br>CTGTAGGAGACAGAGTCACCATCACTTGCCGGGCCAGTC<br>ACGACATTAGCAGTTATTTAGCCTGGTATCAACACAAACC<br>GTGGAAAGCCCCCAAACTCCTGATCCATGCTGCATCCGTT<br>TTGCAAAGTGGGGTCCCATCAAGGTTCAGCGGAAGTGGA<br>TCTGGGACAGAATTCACTCTCACAATCAGCAGCCTGCAGC<br>CTGAAGATTTTGCAACGTACTACTGTCAAAATCTCAATAG<br>TTATCCTCTCTTCGGCCAAGGGACACGACTGGAGATTAAA |
| 129 | VH domain (aa) | QVQLQQSGPGLVKPSQTLSLTCAISGDSVSSSSAAWNWIR<br>QSPSRGLEWLGRTYYRSKWYNDYAVSVKSRITINPDTSKNQ<br>FSLQLNSVTPEDTAVYYCARDSSSGWHPYGMDVWGQGTT<br>VTVSS |
| 130 | VL domain (aa) | DVQVTQSPSFLSASVGDRVTITCRASHDISSYLAWYQHKPW<br>KAPKLLIHAASVLQSGVPSRFSGSGSGTEFTLTISSLQPEDFAT<br>YYCQNLNSYPLFGQGTRLEIK |
| 131 | Heavy CDR1 | GDSVSSSSAA |
| 132 | Heavy CDR2 | TYYRSKWYN |
| 133 | Heavy CDR3 | ARDSSSGWHPYGMDV |
| 134 | Light CDR1 | HDISSY |
| 135 | Light CDR2 | AAS |
| 136 | Light CDR3 | QNLNSYPL |
| 137 | Heavy FR1 | QVQLQQSGPGLVKPSQTLSLTCAIS |
| 138 | Heavy FR2 | WNWIRQSPSRGLEWLGR |
| 139 | Heavy FR3 | DYAVSVKSRITINPDTSKNQFSLQLNSVTPEDTAVYYC |
| 140 | Heavy FR4 | WGQGTTVTVSS |
| 141 | Light FR1 | DVQVTQSPSFLSASVGDRVTITCRAS |

TABLE H-continued

| SEQ ID NO: | Description | Sequence |
|---|---|---|
| 142 | Light FR2 | LAWYQHKPWKAPKLLIH |
| 143 | Light FR3 | VLQSGVPSRFSGSGSGTEFTLTISSLQPEDFATYYC |
| 144 | Light FR4 | FGQGTRLEIK |

TABLE I

| SEQ ID NO: | Description | Sequence |
|---|---|---|
| | | 107-15.6A |
| 145 | VH domain (nt) | IGHV6-1*01<br>IGHJ6*02<br>IGHD6-19*01<br>CAGGTACAGCTGCAGCAGTCAGGTCCAGA<br>ACTGGTGAAGCCCTCGCAGACCCTCTCAC<br>TCACCTGTGCCATCTCCGGGGACAGTGTC<br>TCTAGCAACAGTGCTGCTTGGAACTGGAT<br>CAGGCAGTCCCCATCGAGAGGCCTTGAGT<br>GGCTGGGAAGGACATACTACAGGTCCAAG<br>TGGTATAATGATTATGCAGTATCTGTGAA<br>AAGTCGAATAACCATCAACCCAGACACAT<br>CCAAGAACCAGTTCTCCCTGCAGCTGAAC<br>TCTGTGACTCCCGAGGACACGGCTGTGTA<br>TTACTGTGCAAGAGATAGCAGCAGTGGCT<br>GGCATCCTTACGGTATGGACGTCTGGGGC<br>CAAGGGACCACGGTCACCGTCTCCTCA |
| 146 | VL domain (nt) | IGKV1-9*01<br>IGKJ5*01<br>GACATCCGGGTGACCCAGTCTCCATCCTT<br>CCTGTCTGCATCTGTAGGAGACAGAGTCA<br>CCATCACTTGCCGGACCAGTCACGACATT<br>AGCAGTTATTTAGCCTGGTATCAACACAA<br>ACCGTGGAAAGCCCCCAAACTCCTGATCC<br>ATGCTGCATCCATTTTGCAAAGTGGGGTC<br>CCATCAAGGTTCAGCGGAAGTGGATCTGG<br>GACAGAATTCACTCTCACAATCAGCAGCC<br>TGCAGCCTGAAGATTTTGCAACGTACTAC<br>TGTCAAGATCTCAATAGTTATCCTCTCTT<br>CGGCCAAGGGACACGACTGGAGATTAAA |
| 147 | VH domain (aa) | QVQLQQSGPELVKPSQTLSLTCAISGDSV<br>SSNSAAWNWIRQSPSRGLEWLGRTYYRSK<br>WYNDYAVSVKSRITINPDTSKNQFSLQLN<br>SVTPEDTAVYYCARDSSSGWHPYGMDVWG<br>QGTTVTVSS |

TABLE I-continued

| SEQ ID NO: | Description | Sequence |
|---|---|---|
| 148 | VL domain (aa) | DIRVTQSPSFLSASVGDRVTITCRTSHDI<br>SSYLAWYQHKPWKAPKLLIHAASILQSGV<br>PSRFSGSGSGTEFTLTISSLQPEDFATYY<br>CQDLNSYPLFGQGTRLEIK |
| 149 | Heavy CDR1 | GDSVSSNSAA |
| 150 | Heavy CDR2 | TYYRSKWYN |
| 151 | Heavy CDR3 | ARDSSSGWHPYGMDV |
| 152 | Light CDR1 | HDISSY |
| 153 | Light CDR2 | AAS |
| 154 | Light CDR3 | QDLNSYPL |
| 155 | Heavy FR1 | QVQLQQSGPELVKPSQTLSLTCAIS |
| 156 | Heavy FR2 | WNWIRQSPSRGLEWLGR |
| 157 | Heavy FR3 | DYAVSVKSRITINPDTSKNQFSLQLNSVT<br>PEDTAVYYC |
| 158 | Heavy FR4 | WGQGTTVTVSS |
| 159 | Light FR1 | DIRVTQSPSFLSASVGDRVTITCRTS |
| 160 | Light FR2 | LAWYQHKPWKAPKLLIH |
| 161 | Light FR3 | ILQSGVPSRFSGSGSGTEFTLTISSLQPE<br>DFATYYC |
| 162 | Light FR4 | FGQGTRLEIK |

TABLE J

| SEQ ID NO: | Description | Sequence |
|---|---|---|
| | | 206 |
| 163 | VH domain (nt) | IGHV1-69*12<br>IGHJ6*02<br>IGHD2-8*01<br>CAGGTCCAGCTTGTGCAGTCTGGGGCTGAGGTGAAGAA<br>GCCTGGGTCCTCGGTGAAGGTCTCCTGCAAGGCTTCTG<br>GAGGCACCTTCAGCAGCTATGCTATCAGCTGGGTGCGA<br>CAGGCCCCTGGACAAGGGCTTGAGTGGATGGGAGGGAT<br>CATCCCTATCTTTGGTACAGCAAACTACGCACAGAAGT<br>TCCAGGGCAGAGTCACGATTACCGCGGACGAATCCACG<br>AGCACAGCCTACATGGAGCTGAGCAGCCTGAGATCGA<br>GGACACGGCCGTGTATTACTGTGCGAGAGACGTACAGA<br>GGATGGGGATGGACGTCTGGGGCCAAGGGACCACGGTC<br>ACCGTCTCCTCA |

TABLE J-continued

| SEQ ID NO: | Description | Sequence |
|---|---|---|
| 164 | VL domain (nt) | IGKV1-12*01 or IGKV1-12*02 or IGKV1D-12*02 IGKJ4*01 GACATCCAGATGACCCAGTCTCCTTCTTCCGTCTCTACA TCTGTAGGAGACAGAGTCACCATCACTTGTCGGGCGAGT CAGGATATTAGTAACTGGTTAGCCTGGTATCAGCAGAAA CCAGGAAAAGCCCCTAAGCTCCTGATCTATGATTCATCC ACTTTGCAAAGTGGGGTCCCATCAAGGTTCAGCGGCAGT GGATCTGGGACAGATTTCACTCTCACCATCAGCACCCTG CAGCCTGAGGATTTTGCAACTTATTACTGTCAACAGTTT AATAGTTATCCCCTCACTTTCGGCGGAGGGACCAAAGTG GATATCAAA |
| 165 | VH domain (aa) | QVQLVQSGAEVKKPGSSVKVSCKASGGTFSSYAISWVRQ APGQGLEWMGGIIPIFGTANYAQKFQGRVTITADESTST AYMELSSLRSEDTAVYYCARDVQRMGMDVWGQGTTVTVS S |
| 166 | VL domain (aa) | DIQMTQSPSSVSTSVGDRVTITCRASQDISNWLAWYQQK PGKAPKLLIYDSSTLQSGVPSRFSGSGSGTDFTLTISTL QPEDFATYYCQQFNSYPLTFGGGTKVDIK |
| 167 | Heavy CDR1 | GGTFSSYA |
| 168 | Heavy CDR2 | IIPIFGTA |
| 169 | Heavy CDR3 | ARDVQRMGMDV |
| 170 | Light CDR1 | QDISNW |
| 171 | Light CDR2 | DSS |
| 172 | Light CDR3 | QQFNSYPLT |
| 173 | Heavy FR1 | QVQLVQSGAEVKKPGSSVKVSCKAS |
| 174 | Heavy FR2 | ISWVRQAPGQGLEWMGG |
| 175 | Heavy FR3 | NYAQKFQGRVTITADESTSTAYMELSSLRSEDTAVYYC |
| 176 | Heavy FR4 | WGQGTTVTVSS |
| 177 | Light FR1 | DIQMTQSPSSVSTSVGDRVTITCRAS |
| 178 | Light FR2 | LAWYQQKPGKAPKLLIY |
| 179 | Light FR3 | TLQSGVPSRFSGSGSGTDFTLTISTLQPEDFATYY |
| 180 | Light FR4 | FGGGTKVDIK |
| 456 | Heavy chain (aa) (variable + constant domain). mIgG$_{2b}$ | QVQLVQSGAEVKKPGSSVKVSCKASGGTFSSYAISWVRQA PGQGLEWMGGIIPIFGTANYAQKFQGRVTITADESTSTAY MELSSLRSEDTAVYYCARDVQRMGMDVWGQGTTVTVSSAK TTPPSVYPLAPGCGDTTGSSVTLGCLVKGYFPESVTVTWN SGSLSSSVHTFPALLQSGLYTMSSSVTVPSSTWPSQTVTC SVAHPASSTTVDKKLEPSGPISTINPCPPCKECHKCPAPN LEGGPSVFIFPPNIKDVLMISLTPKVTCVVVDVSEDDPDV QISWFVNNVEVHTAQTQTHREDYASTIRVVSTLPIQHQDW MSGKEFKCKVNNKDLPSPIERTISKIKGLVRAPQVYILPP PAEQLSRKDVSLTCLVVGFNPGDISVEWTSNGHTEENYKD TAPVLDSDGSYFIYSKLNMKTSKWEKTDSFSCNVRHEGLK NYYLKKTISRSPGK |
| 457 | Light chain (aa) (variable + constant domain). mIgG$_{2b}$ | DIQMTQSPSSVSTSVGDRVTITCRASQDISNWLAWYQQKP GKAPKLLIYDSSTLQSGVPSRFSGSGSGTDFTLTISTLQP EDFATYYCQQFNSYPLTFGGGTKVDIKRADAAPTVSIFPP SSEQLTSGGASVVCFLNNFYPKDINVKWKIDGSERQNGVL NSWTDQDSKDSTYSMSSTLTLTKDEYERHNSYTCEATHKT STSPIVKSFNRNEC |
| 458 | Heavy chain (aa) (variable + constant domain). hIgG$_1$ | QVQLVQSGAEVKKPGSSVKVSCKASGGTFSSYAISWVRQ APGQGLEWMGGIIPIFGTANYAQKFQGRVTITADESTST AYMELSSLRSEDTAVYYCARDVQRMGMDVWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE |

TABLE J-continued

| SEQ ID NO: | Description | Sequence |
|---|---|---|
| | | LLGGPSVFLFPPKPKDTLMISRTPEVTCVVVDVSHEDPE VKFNWYVDGVEVHNAKTKPREEQYGSTYRVVSVLTVLHQ DWLNGKEYKCKVSNKALPAPIEKTISKAKGQPREPQVYT LPPSRDELTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| 459 | Light chain (aa) (variable + constant domain). hIgG₁ | DIQMTQSPSSVSTSVGDRVTITCRASQDISNWLAWYQQ KPGKAPKLLIYDSSTLQSGVPSRFSGSGSGTDFTLTIS TLQPEDFATYYCQQFNSYPLTFGGGTKVDIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |

TABLE K

| SEQ ID NO: | Description | Sequence |
|---|---|---|
| | | 217 |
| 181 | VH domain (nt) | IGHV1-69*12 IGHJ4*02 IGHD2-8*01 CAGGTCCAGCTGGTGCAGTCTGGGGCTGAGGTG AAGAAGCCTGGGTCCTCGGTGAAGGTCTCCTGC AAGGCTTCTGGAGGCACCTTCAGCAGCTATGCT ATCAGCTGGGTGCGACAGGCCCCTGGACAAGGG CTTGAGTGGATGGGAGGGATCATCCCTATCTTT GGTACAGCAAACTACGCACAGAAGTTCCAGGGC AGAGTCACGATTACCGCGGACGAATCCACGAGC ACAGCCTACATGGAGCTGAGCAGCCTGAGATCT GAGGACACGGCCGTGTATTACTGTGCGAGAGGG GCTATTGGCGTATTCTCGGGCTACTTTGACTAC TGGGGCCAGGGAACCCTGGTCACCGTCTCCTCA |
| 182 | VL domain (nt) | IGKV44*01 IGKJ4*0 GATATTGTGCTGACGCAGACTCCAGACTCCCTG GCTGTGTCTCCGGGCGAGAGGGCCACCATCAAC TGCAAGTCCAGCCAGAGTGTTTTATACAGCTCC AACAATAAGAACTACTTAGCTTGGTACCAGCAG AAACCAGGACAGCCTCCTAAGCTGCTCATTTAC TGGGCATCTACCCGGGAATCCGGGGTCCCTGAC CGATTCAGTGGCAGCGGGTCTGGGACAGATtTC ACTCTCACCATCAGCAGCCTGCAGGCTGAAGAT GTGGCAGTGTATTACTGTCAGCAATATTATGAT ACCCCTCTCACTTTCGGCGGAGGGACCAAGGTG GAGATCAAA |
| 183 | VH domain (aa) | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARG AIGVFSGYFDYWGQGTLVTVSS |
| 184 | VL domain (aa) | DIVLTQTPDSLAVSPGERATINCKSSQSVLYSS NNKNYLAWYQQKPGQPPKLLIYWASTRESGVPD RFSGSGSGTDFTLTISSLQAEDVAVYYCQQYYD TPLTFGGGTKVEIK |
| 185 | Heavy CDR1 | GGTFSSYA |
| 186 | Heavy CDR2 | IIPIFGTA |
| 187 | Heavy CDR3 | ARGAIGVFSGYFDY |
| 188 | Light CDR1 | QSVLYSSNNKN |
| 189 | Light CDR2 | WAS |
| 190 | Light CDR3 | QQYYDTPLT |

TABLE K-continued

| SEQ ID NO: | Description | Sequence |
|---|---|---|
| 191 | Heavy FR1 | QVQLVQSGAEVKKPGSSVKVSCKAS |
| 192 | Heavy FR2 | ISWVRQAPGQGLEWMGG |
| 193 | Heavy FR3 | NYAQKFQGRVTITADESTSTAYMELSSLRSEDT AVYYC |
| 194 | Heavy FR4 | WGQGTLVTVSS |
| 195 | Light FR1 | DIVLTQTPDSLAVSPGERATINCKSS |
| 196 | Light FR2 | LAWYQQKPGQPPKLLIY |
| 197 | Light FR3 | TRESGVPDRFSGSGSGTDFTLTISSLQAEDVAV YYC |
| 198 | Light FR4 | FGGGTKVEIK |

TABLE L

| SEQ ID NO: | Description | Sequence |
|---|---|---|
| | | 218 |
| 199 | VH domain (nt) | IGHV1-69*01 or IGHV1-69D*01 IGHJ4*02 IGHD3-22*01 CAGGTGCAGCTGGTGCAGTCTGGGGCTGAG GTGAAGAAGCCTGGGTCCTCGGTGAAGGTC TCCTGCAAGGCTTCTGGAGGCACCTTCAGC AGCTATGCTATCAGCTGGGTGCGACAGGCC CCTGGACAAGGGCTTGAGTGGATGGGAGGG ATCATCCCTATCTTTGGTACAGCAAACTAC GCACAGAAGTTCCAGGGCAGAGTCACGATT ACCGCGGACGAATCCACGAGCACAGCCTAC ATGGAGCTGAGCAGCCTGAGATCTGAGGAC ACGGCCGTGTATTACTGTGCGAGAGGGTAT TACTATGATAGCAGTGCCCTGGACTACTGG GGCCAGGGAACCCTGGTCACCGTCTCCTCA |
| 200 | VL domain (nt) | IGKV2-40*02 IGKJ4*01 or IGKJ4*02 CAGTCTGCTCTGATTCAGCCTGCCTCCGTG TCTGGGTCTCCTGGACAGTCGATCACCATC TCCTGCACTGGAACCAGCAGTGACGTTGGT GGTTATGGCTATGTCCTGGTACCAACAC CACCCAGGCAAAGCCCCCAAACTCATCATT TATGATGTCTCCAATCGGCCCTCAGGGGTT TCTGATCGCTTCTCTGGCTCCAAGTCTGCC |

TABLE L-continued

| SEQ ID NO: | Description | Sequence |
|---|---|---|
| | | AACACGGCCTCcCTGACCATCTCTGGGCTC CAGACTGAGGACGAGGCTGATTATTACTGC AGCTCATATACAAGCAGCGGCACTGTGCTC TTCGGCGGAGGGACCAAGCTCACCGTCCTA |
| 201 | VH domain (aa) | QVQLVQSGAEVKKPGSSVKVSCKASGGTFS SYAISWVRQAPGQGLEWMGGIIPIFGTANY AQKFQGRVTITADESTSTAYMELSSLRSED TAVYYCARGYYYDSSALDYWGQGTLVTVSS |
| 202 | VL domain (aa) | QSALIQPASVSGSPGQSITISCTGTSSDVG GYGYVSWYQHHPGKAPKLIIYDVSNRPSGV SDRFSGSKSANTASLTISGLQTEDEADYYC SSYTSSGTVLFGGGTKLTVL |
| 203 | Heavy CDR1 | GGTFSSYA |
| 204 | Heavy CDR2 | IIPIFGTA |
| 205 | Heavy CDR3 | ARGYYYDSSALDY |
| 206 | Light CDR1 | GTSSDVGGYG |
| 207 | Light CDR2 | DVS |
| 208 | Light CDR3 | SSYTSSGTVL |
| 209 | Heavy FR1 | QVQLVQSGAEVKKPGSSVKVSCKAS |
| 210 | Heavy FR2 | ISWVRQAPGQGLEWMGG |
| 211 | Heavy FR3 | NYAQKFQGRVTITADESTSTAYMELS SLRSEDTAVYYC |
| 212 | Heavy FR4 | WGQGTLVTVSS |
| 213 | Light FR1 | QSALIQPASVSGSPGQSITISCT |
| 214 | Light FR2 | VSWYQHHPGKAPKLIIY |
| 215 | Light FR3 | NRPSGVSDRFSGSKSANT ASLTISGLQTEDEADYYC |
| 216 | Light FR4 | FGGGTKLTVL |

TABLE M

| SEQ ID NO: | Description | Sequence |
|---|---|---|
| | | 220 |
| 217 | VH domain (nt) | IGHV1-69*01 or IGHV1-69D*01 IGHJ4*02 IGHD2-15*01 CAGGTGCAGctgGTGGAATCTGGGGCT GAGGTGAAGAAGCCTGGGTCCTCGGTG AAGGTCTCCTGCAAGGCTTCTGGAGGC ACCTTCAGCAGCTATGCTATCAGCTGG gtGCGACAGGCCCCTGGACAAGGGCTT GAGTGGATGGGAGGGATCATCCCTATC TTTGGTACAGCAAACTACGGCACAGAAG TTCCAGGGCAGAGCCACGATTACCGCG GACGAATCCACGAGCACAGCCTACATG GAGCTGAGCAGCCTGAGATCTGAGGAC ACGGCCGTGTATTACTGTGCGAGAGGC CGAAATACCTATTGTAGTGGTGGTAGC TGCTACTCCCCGCACTTTGACTACTGG GGCCAGGGAACCCTGGTCACCGTCTCC TCA |

TABLE M-continued

| SEQ ID NO: | Description | Sequence |
|---|---|---|
| 218 | VL domain (nt) | IGKV1-33*01 or IGKV1D-33*01 IGKJ4*01 GACATCCAGGTGACCCAGTCTCCATC CTCCCTGTCTGCATCTGTAGGAGACA GAGTCACCATCACTTGCCAGGCGAGT CAGGACATTAGCAACTATTTAAATTG GTATCAGCAGAAACCAGGGAAAGCCC CTAAGCTCCTGATCTACGATGCATCC AATTTGGAAACAGGGGTCCCATCAAG GTTCAGTGGAAGTGGATCTGGGACAG ATTTTACTTTCACCATCAGCAGCCTG CAGCCTGAAGATATTGCAACATATTA CTGTCAACAGTATGATAATCTCCCAA CTTTCGGCGGAGGGACCAAGGTGGAG ATCAAA |
| 219 | VH domain (aa) | QVQLVESGAEVKKPGSSVKVSCKASG GTFSSYAISWVRQAPGQGLEWMGGII PIFGTANYAQKFQGRATITADESTST AYMELSSLRSEDTAVYYCARGRNTYC SGGSCYSPHFDYWGQGTLVTVSS |
| 220 | VL domain (aa) | DIQVTQSPSSLSASVGDRVTITCQASQ DISNYLNWYQQKPGKAPKLLIYDASNL ETGVPSRFSGSGSGTDFTFTISSLQPE DIATYYCQQYDNLPTFGGGTKVEIK |
| 221 | Heavy CDR1 | GGTFSSYA |
| 222 | Heavy CDR2 | IIPIFGTA |
| 223 | Heavy CDR3 | ARGRNTYCSGGSCYSPHFDY |
| 224 | Light CDR1 | QDISNY |
| 225 | Light CDR2 | DAS |
| 226 | Light CDR3 | QQYDNLPT |
| 227 | Heavy FR1 | QVQLVESGAEVKKPGSSVKVSCKAS |
| 228 | Heavy FR2 | ISWVRQAPGQGLEWMGG |
| 229 | Heavy FR3 | NYAQKFQGRATITADESTSTAYMELSS LRSEDTAVYYC |
| 230 | Heavy FR4 | WGQGTLVTVSS |
| 231 | Light FR1 | DIQVTQSPSSLSASVGDRVTITCQAS |
| 232 | Light FR2 | LNWYQQKPGKAPKLLIY |
| 233 | Light FR3 | NLETGVPSRFSGSGSGTDFTFTISSL QPEDIATYYC |
| 234 | Light FR4 | FGGGTKVEIK |
| 460 | Heavy chain (aa) (variable + constant domain). mIgG$_{2b}$ | QVQLVESGAEVKKPGSSVKVSCKASGG TFSSYAISWVRQAPGQGLEWMGGIIPI FGTANYAQKFQGRATITADESTSTAYM ELSSLRSEDTAVYYCARGRNTYCSGGS CYSPHFDYWGQGTLVTVSSAKTTPPSV YPLAPGCGDTTGSSVTLGCLVKGYFPE SVTVTWNSGSLSSSVHTFPALLQSGLY TMSSSVTVPSSTWPSQTVTCSVAHPAS STTVDKKLEPSGPISTINPCPPCKECH KCPAPNLEGGPSVFIFPPNIKDVLMIS LTPKVTCVVVDVSEDDPDVQISWFVNN VEVHTAQTQTHREDYASTIRVVSTLPI QHQDWMSGKEFKCKVNNKDLPSPIERT ISKIKGLVRAPQVYILPPPAEQLSRKD VSLTCLVVGFNPGDISVEWTSNGHTEE NYKDTAPVLDSDGSYFIYSKLNMKTSK WEKTDSFSCNVRHEGLKNYYLKKTISR SPGK |

TABLE M-continued

| SEQ ID NO: | Description | Sequence |
|---|---|---|
| 461 | Light chain (aa) (variable + constant domain). mIgG$_{2b}$ | DIQVTQSPSSLSASVGDRVTITCQAS QDISNYLNWYQQKPGKAPKLLIYDAS NLETGVPSRFSGSGSGTDFTFTISSL QPEDIATYYCQQYDNLPTFGGGTKVE IKRADAAPTVSIFPPSSEQLTSGGAS VVCFLNNFYPKDINVKWKIDGSERQN GVLNSWTDQDSKDSTYSMSSTLTLTK DEYERHNSYTCEATHKTSTSPIVKSF NRNEC |
| 462 | Heavy chain (aa) (variable + constant domain). hIgG$_1$ | QVQLVESGAEVKKPGSSVKVSCKASG GTFSSYAISWVRQAPGQGLEWMGGII PIFGTANYAQKFQGRATITADESTST AYMELSSLRSEDTAVYYCARGRNTYC SGGSCYSPHFDYWGQGTLVTVSSAST KGPSVFPLAPSSKSTSGGTAALGCLV KDYFPEPVTVSWNSGALTSGVHTFPA VLQSSGLYSLSSVVTVPSSSLGTQTY ICNVNHKPSNTKVDKKVEPKSCDKTH TCPPCPAPELLGGPSVFLFPPKPKDT |

TABLE M-continued

| SEQ ID NO: | Description | Sequence |
|---|---|---|
| | | LMISRTPEVTCVVVDVSHEDPEVKFN WYVDGVEVHNAKTKPREEQYGSTYRV VSVLTVLHQDWLNGKEYKCKVSNKAL PAPIEKTISKAKGQPREPQVYTLPPS RDELTKNQVSLTCLVKGFYPSDIAVE WESNGQPENNYKTTPPVLDSDGSFFL YSKLTVDKSRWQQGNVFSCSVMHEAL HNHYTQKSLSLSPGK |
| 463 | Light chain (aa) (variable + constant domain). hIgG$_1$ | DIQVTQSPSSLSASVGDRVTITCQAS QDISNYLNWYQQKPGKAPKLLIYDAS NLETGVPSRFSGSGSGTDFTFTISSL QPEDIATYYCQQYDNLPTFGGGTKVE IKRTVAAPSVFIFPPSDEQLKSGTAS VVCLLNNFYPREAKVQWKVDNALQSG NSQESVTEQDSKDSTYSLSSTLTLSK ADYEKHKVYACEVTHQGLSSPVTKSF NRGEC |

TABLE N

| SEQ ID NO: | Description | Sequence |
|---|---|---|
| | | 221 |
| 235 | VH domain (nt) | IGHV1-69*01 or IGHV1-69D*01 IGHJ4*02 IGHD6-19*01 CAGgtGCAGCTGGTGGAATCTGGGGCTGAGGTGAAGAAGCCTG GGTCCTCGGTGAAGGTCTCCTGCAAGGCTTCTGGAGGCACCTT CAGCAGCTATGCTATCAGCTGGGTGCGACAGGCCCCTGGACAA GGGCTTGAGTGGATGGGAGGGATCATCCCTATCTTTGGTACAG CAAACTACGCACAGAAGTTCCAGGGCAGAGTCACGATTACCGC GGACGAATCCACGAGCACAGCCTACATGGAGCTGAGCAGCCTG AGATCTGAGGACACGGCCGTGTATTACTGTGCGAGAGGAGTG CCGTCCGGGTATAGCAGTGGCTGGTTTTACTACTTTGACTACT GGGGCCAGGGAACCCTGGTCACCGTCTCCTCA |
| 236 | VL domain (nt) | IGKV3-15*01 IGKJ1*01 GAAATTGTGATGACACAGTCTCCATCCTCCCTGTCTGCATCTGT AGGAGACAGAGCCACCCTCTCCTGCAGGGCCAGTCAGAGTGTT AACACCAACTTAGCCTGGTACCAGCAGAAACCTGGCCAGGCTC CCAGGCTCCTCATCTATGGTGCATCTACCAGGGCCACTGGTAGC CCAGCCAGGTTCAGTGGCAGTGGGTCTGGGACAGAGTTCACTC TCACCATCAGCAGCCTGCAGCCTGGTGATTTTGCAACTTATTAC TGCCAACAGTATGATAATTATCCCCTGACGTTCGGCCAAGGGA CCAAGGTGGAAATCAAA |
| 237 | VH domain (aa) | QVQLVESGAEVKKPGSSVKVSCKASGGTFSSYAISWVRQAPGQ GLEWMGGIIPIFGTANYAQKFQGRVTITADESTSTAYMELSSL RSEDTAVYYCARGVPSGYSSGWFYYFDYWGQGTLVTVSS |
| 238 | VL domain (aa) | EIVMTQSPSSLSASVGDRATLSCRASQSVNTNLAWYQQKPGQAP RLLIYGASTRATGSPARFSGSGSGTEFTLTISSLQPGDFATYYC QQYDNYPLTFGQGTKVEIK |
| 239 | Heavy CDR1 | GGTFSSYA |
| 240 | Heavy CDR2 | IIPIFGTA |
| 241 | Heavy CDR3 | ARGVPSGYSSGWFYYFDY |
| 242 | Light CDR1 | QSVNTN |
| 243 | Light CDR2 | GAS |
| 244 | Light CDR3 | QQYDNYPLT |
| 245 | Heavy FR1 | QVQLVESGAEVKKPGSSVKVSCKAS |

TABLE N-continued

| SEQ ID NO: | Description | Sequence |
|---|---|---|
| 246 | Heavy FR2 | ISWVRQAPGQGLEWMGG |
| 247 | Heavy FR3 | NYAQKFQGRVTITADESTSTAYMELSSLRSEDTAVYYC |
| 248 | Heavy FR4 | WGQGTLVTVSS |
| 249 | Light FR1 | EIVMTQSPSSLSASVGDRATLSCRAS |
| 250 | Light FR2 | LAWYQQKPGQAPRLLIY |
| 251 | Light FR3 | TRATGSPARFSGSGSGTEFTLTISSLQPGDFATYYC |
| 252 | Light FR4 | FGQGTKVEIK |

TABLE O

| SEQ ID NO: | Description | Sequence |
|---|---|---|
| | | 223 |
| 253 | VH domain (nt) | IGHV1-69*1<br>IGHJ6*02<br>IGHD2-15*01<br>CAGGTCCAGCTGgtACAGTCTGGGGCTGAGGTGAAGAAG<br>CCTGGGTCCTCGGTGAAGGTCTCCTGCAAGGCTTCTGGA<br>GGCACCTTCAGCAGCTATGCTATCAGCTGGGTGCGACAG<br>GCCCCTGGACAAGGGCTTGAGTGGATGGGAGGGATCAT<br>CCCTATCTTTGGTACAGTAAACTACGCACAGAAGTTCCAG<br>GGCAGAGTCACGATTACCGCGGACGAATCCACGAGCACA<br>GCCTACATGGAGCTGAGCAGCCTGAGATCTGAGGACACG<br>GCCGTGTATTACTGTGCGAGAGTCGCGGTTATTCCCCCG<br>GACTACTACTACGGTATGGACGTCTGGGGCCAAGGGACC<br>ACGGTCACCGTCTCCTCA |
| 254 | VL domain (nt) | IGKV3-15*01<br>IGKJ3*01<br>GAAACGACACTCACGCAGTCTCCAGCCACCCTGTCTGTGT<br>CTCCAGGGGAAAGAGCCACCCTCTCCTGCAGGGCCAGTC<br>AGAGTGTTAGCAGCAACTTAGCCTGGTACCAGCAGAGAC<br>CTGGCCAGGCTCCCAGGCTCCTCATCTATGGTGCATCCAC<br>CAGGGCCGCTGGTATCCCAGTCAGGTTCAGTGGCAGTGG<br>GTCTGGGACAGAGTTCACTCTCACCATCAGCAGCCTGCA<br>GTCTGAAGATTTTGCAGTTTATTACTGTCAGCACTATGAT<br>AACTGGCCTCCGCGATTCACTTTCGGCCCTGGGACCAAA<br>GTGGATATTAAA |
| 255 | VH domain (aa) | QVQLVQSGAEVKKPGSSVKVSCKASGGTFSSYAISWVRQAP<br>GQGLEWMGGIIPIFGTVNYAQKFQGRVTITADESTSTAYME<br>LSSLRSEDTAVYYCARVAVIPPDYYYGMDVWGQGTTVTVSS |
| 256 | VL domain (aa) | ETTLTQSPATLSVSPGERATLSCRASQSVSSNLAWYQQRPG<br>QAPRLLIYGASTRAAGIPVRFSGSGSGTEFTLTISSLQSED<br>FAVYYCQHYDNWPPRFTFGPGTKVDIK |
| 257 | Heavy CDR1 | GGTFSSYA |
| 258 | Heavy CDR2 | IIPIFGTV |
| 259 | Heavy CDR3 | ARVAVIPPDYYYGMDV |
| 260 | Light CDR1 | QSVSSN |
| 261 | Light CDR2 | GAS |
| 262 | Light CDR3 | QHYDNWPPRFT |
| 263 | Heavy FR1 | QVQLVQSGAEVKKPGSSVKVSCKAS |
| 264 | Heavy FR2 | ISWVRQAPGQGLEWMGG |
| 265 | Heavy FR3 | NYAQKFQGRVTITADESTSTAYMELSSLRSEDTAVYYC |
| 266 | Heavy FR4 | WGQGTTVTVSS |

TABLE O-continued

| SEQ ID NO: | Description | Sequence |
|---|---|---|
| 267 | Light FR1 | ETTLTQSPATLSVSPGERATLSCRAS |
| 268 | Light FR2 | LAWYQQRPGQAPRLLIY |
| 269 | Light FR3 | TRAAGIPVRFSGSGSGTEFTLTISSLQSEDFAVYYC |
| 270 | Light FR4 | FGPGTKVDIK |

TABLE P

| SEQ ID NO: | Description | Sequence |
|---|---|---|
| | | 226 |
| 271 | VH domain (nt) | IGHV1-69*12<br>IGHJ1*01<br>IGHD3-10*01<br>CAGGTCCAGctgGTGCAGTCTGGGGCTGAGGTGAAGAAG<br>CCTGGGTCCTCGGTGAAGGTCTCATGCAAGGCTTCTGGA<br>GGCACCTTCAGCAGCTATGCTATCAGCTGGGTGCGACAG<br>GCCCCTGGACAAGGGCTTGAGTGGATGGGAGGGATCATC<br>CCTATCTTTGGTACAGCAAACTACGCACAGAAGTTCCAG<br>GGCAGAGTCACGATTACCGCGGACGAATCCACGAGCACA<br>GCCTACATGGAGCTGAGCAGCCTGAGATCTGAGGACACG<br>GCCGTGTATTACTGTGCGAGGGGAGCCGGCCCGTTATGG<br>TTCAGGGAGTTAGTGTACTTCCAGCACTGGGGCCAGGGA<br>ACCCTGGTCACCGTCTCCTCA |
| 272 | VL domain (nt) | IGKV3-15*01<br>IGKJ3*0<br>GAAATTGTGATGACGCAGTCTCCAGCCACTCTGTCTGTGT<br>CTCCAGGGGAGAGGGCCACCCTCTCCTGCAGGGTCAGTC<br>AGAATATAATAAAAAACTTAGCCTGGTACCAACAGAAAC<br>CTGGCCAGGCTCCCAGGCTCCTCATTTATGATGCCTCCA<br>CCAGGGCCACTGGTATCCCAGCCAGGTTCACTGGCAGTG<br>GGTCTGGGACAGAGTTCACTCTCACCATCGACGACCTGC<br>AGTCTGAAGATTCTGCAGTTTATTTCTGTCAGCAGTACA<br>ATTGGTGGCCTCGTTTCGGCCCTGGGACCAAAGTGGATA<br>TCAAA |
| 273 | VH domain (aa) | QVQLVQSGAEVKKPGSSVKVSCKASGGTFSSYAISWVRQA<br>PGQGLEWMGGIIPIFGTANYAQKFQGRVTITADESTSTAY<br>MELSSLRSEDTAVYYCARGAGPLWFRELVYFQHWGQGTLV<br>TVSS |
| 274 | VL domain (aa) | EIVMTQSPATLSVSPGERATLSCRVSQNIIKNLAWYQQKP<br>GQAPRLLIYDASTRATGIPARFTGSGSGTEFTLTIDDLQS<br>SEDAVYFCQQYNWWPRFGPGTKVDIK |
| 275 | Heavy CDR1 | GGTFSSYA |
| 276 | Heavy CDR2 | IIPIFGTA |
| 277 | Heavy CDR3 | ARGAGPLWFRELVYFQH |
| 278 | Light CDR1 | QNIIKN |
| 279 | Light CDR2 | DAS |
| 280 | Light CDR3 | QQYNWWPR |
| 281 | Heavy FR1 | QVQLVQSGAEVKKPGSSVKVSCKAS |
| 282 | Heavy FR2 | ISWVRQAPGQGLEWMGG |
| 283 | Heavy FR3 | NYAQKFQGRVTITADESTSTAYMELSSLRSEDTAVYYC |
| 284 | Heavy FR4 | WGQGTLVTVSS |
| 285 | Light FR1 | EIVMTQSPATLSVSPGERATLSCRVS |
| 286 | Light FR2 | LAWYQQKPGQAPRLLIY |

TABLE P-continued

| SEQ ID NO: | Description | Sequence |
|---|---|---|
| 287 | Light FR3 | TRATGIPARFTGSGSGTEFTLTIDDLQSEDSAVYFC |
| 288 | Light FR4 | FGPGTKVDIK |

TABLE Q

| SEQ ID NO: | Description | Sequence |
|---|---|---|
| | | 228 |
| 289 | VH domain (nt) | IGHV1-69*01 or IGHV1-69D*01<br>IGHJ6*02<br>IGHD3-3*01<br>CAGGTGCAGCTGGTGCAATCTGGGGCTGAGGTGAAGAA<br>GCCTGGGTCCTCGGTGAAGGTCTCCTGCAAGGCTTCTGG<br>AGGCACCTTCAGCAGCTATGCTATCAGCTGGGTGCGACA<br>GGCCCCTGGACAAGGGCTTGAGTGGATGGGAGGGGATCA<br>TCCCTATCTTTGGTACAGCAAACTACGCACAGAAGTTCCA<br>GGGCAGAGTCACGATTACCGCGGACGAATCCACGAGCAC<br>AGCCTACATGGAGCTGAGCAGCCTGAGATCTGAGGACAC<br>GGCCGTGTATTACTGTGCGAGAGGCCAGGTTTTGATCTG<br>GACGTACTACTACGGTATGACGTCTGGGGCCAAGGGAC<br>CACGGTCACCGTCTCCTCA |
| 290 | VL domain (nt) | IGKV1-33*01 or IGKV1D-33*01<br>IGKJ4*01<br>GACATCCGGTTGACCCAGTCTCCATCCTCCCTGTCTGCAT<br>CTGTAGGAGATAGAGTCACCATCACTTGCCAGGCGAGTC<br>AGGACATTAGCAACTATTTAAATTGGTATCAGCAGAAACC<br>AGGGAAAGCCCCTAAGCTCCTGATCTACGATGCATCCAA<br>TTTAGAAACAGGGGTCCCATCAAGGTTCAGTGGAAGTGG<br>ATCTGGGACAGATTTTACTTTCATCATCAGCAGCCTGCAG<br>CCTGAAGATATTGCAACATATTACTGTCAACAGTATGATA<br>ATCTCCCGCTCACTTTCGGTGGAGGGACCAAGCTGGAGA<br>TCAAA |
| 291 | VH domain (aa) | QVQLVQSGAEVKKPGSSVKVSCKASGGTFSSYAISWVRQAP<br>GQGLEWMGGIIPIFGTANYAQKFQGRVTITADESTSTAYME<br>LSSLRSEDTAVYYCARGQVLIWTYYYGMDVWGQGTTVTVS<br>S |
| 292 | VL domain (aa) | DIRLTQSPSSLSASVGDRVTITCQASQDISNYLNWYQQKPG<br>KAPKLLIYDASNLETGVPSRFSGSGSGTDFTFIISSLQPEDIAT<br>YYCQQYDNLPLTFGGGTKLEIK |
| 293 | Heavy CDR1 | GGTFSSYA |
| 294 | Heavy CDR2 | IIPIFGTA |
| 295 | Heavy CDR3 | ARGQVLIWTYYYGMDV |
| 296 | Light CDR1 | QDISNY |
| 297 | Light CDR2 | DAS |
| 298 | Light CDR3 | QQYDNLPLT |
| 299 | Heavy FR1 | QVQLVQSGAEVKKPGSSVKVSCKAS |
| 300 | Heavy FR2 | ISWVRQAPGQGLEWMGG |
| 301 | Heavy FR3 | NYAQKFQGRVTITADESTSTAYMELSSLRSEDTAVYYC |
| 302 | Heavy FR4 | WGQGTTVTVSS |
| 303 | Light FR1 | DIRLTQSPSSLSASVGDRVTITCQAS |
| 304 | Light FR2 | LNWYQQKPGKAPKLLIY |
| 305 | Light FR3 | NLETGVPSRFSGSGSGTDFTFIISSLQPEDIATYYC |
| 306 | Light FR4 | FGGGTKLEIK |

TABLE Q-continued

| SEQ ID NO: | Description | Sequence |
|---|---|---|
| 464 | Heavy chain (aa) (variable + constant domain). mIgG$_{2b}$ | QVQLVQSGAEVKKPGSSVKVSCKASGGTFSSYAISWVRQAP GQGLEWMGGIIPIFGTANYAQKFQGRVTITADESTSTAYME LSSLRSEDTAVYYCARGQVLIWTYYYGMDVWGQGTTVTVS SAKTTPPSVYPLAPGCGDTTGSSVTLGCLVKGYFPESVTVTW NSGSLSSSVHTFPALLQSGLYTMSSSVTVPSSTWPSQTVTCS VAHPASSTTVDKKLEPSGPISTINPCPPCKECHKCPAPNLEG GPSVFIFPPNIKDVLMISLTPKVTCVVVDVSEDDPDVQISWF VNNVEVHTAQTQTHREDYASTIRVVSTLPIQHQDWMSGKE FKCKVNNKDLPSPIERTISKIKGLVRAPQVYILPPPAEQLSRKD VSLTCLVVGFNPGDISVEWTSNGHTEENYKDTAPVLDSDGS YFIYSKLNMKTSKWEKTDSFSCNVRHEGLKNYYLKKTISRSP GK |
| 465 | Light chain (aa) (variable + constant domain). mIgG$_{2b}$ | DIRLTQSPSSLSASVGDRVTITCQASQDISNYLNWYQQKPG KAPKLLIYDASNLETGVPSRFSGSGSGTDFTFIISSLQPEDIAT YYCQQYDNLPLTEGGGTKLEIKRADAAPTVSIFPPSSEQLTSG GASVVCFLNNFYPKDINVKWKIDGSERQNGVLNSWTDQDS KDSTYSMSSTLTLTKDEYERHNSYTCEATHKTSTSPIVKSFNR NEC |
| 466 | Heavy chain (aa) (variable + constant domain). hIgG$_1$ | QVQLVQSGAEVKKPGSSVKVSCKASGGTFSSYAISWVRQAP GQGLEWMGGIIPIFGTANYAQKFQGRVTITADESTSTAYME LSSLRSEDTAVYYCARGQVLIWTYYYGMDVWGQGTTVTVS SASTKGPSVFPLAPSSKSTSGGTAALGCLVKDYFPEPVTVSW NSGALTSGVHTFPAVLQSSGLYSLSSVVTVPSSSLGTQTYICN VNHKPSNTKVDKKVEPKSCDKTHTCPPCPAPELLGGPSVFLF PPKPKDTLMISRTPEVTCVVVDVSHEDPEVKFNWYVDGVE VHNAKTKPREEQYGSTYRVVSVLTVLHQDWLNGKEYKCKV SNKALPAPIEKTISKAKGQPREPQVYTLPPSRDELTKNQVSLT CLVKGFYPSDIAVEWESNGQPENNYKTTPPVLDSDGSFFLYS KLTVDKSRWQQGNVFSCSVMHEALHNHYTQKSLSLSPGK |
| 467 | Light chain (aa) (variable + constant domain). hIgG$_1$ | DIRLTQSPSSLSASVGDRVTITCQASQDISNYLNWYQQKPG KAPKLLIYDASNLETGVPSRFSGSGSGTDFTFIISSLQPEDIAT YYCQQYDNLPLTFGGGTKLEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSFNR GEC |

TABLE R

| SEQ ID NO: | Description | Sequence |
|---|---|---|
| | | 206-2.B11 |
| 307 | VH domain (nt) | IGHV1-69*12 IGHJ6*02 IGHD2-8*01 CAGGTCCAGCTTGTGCAGTCTGGGGCTGAGGTGAAGAA GCCTGGGTCCTCGGTGAAGGTCTCCTGCAAGGCTTCTGG AGGCACCTCTACGGGTTTTATTGGTGCTATCAGCTGGGTG CGACAGGCCCCTGGACAAGGGCTTGAGTGGATGGGAGG GATCATCCCTATCTTTGGTACAGCAAACTACGCACAGAAG TTCCAGGGCAGAGTCACGATTACCGCGGACGAATCCACG AGCACAGCCTACATGGAGCTGAGCAGCCTGAGATCTGAG GACACGGCCGTGTATTACTGTGCGAGAGACGTACAGAG GATGGGGATGGACGTCTGGGGCCAAGGGACCACGGTCA CCGTCTCCTCA |
| 308 | VL domain (nt) | IGKV1-12*01 OR IGKV1-12*02 OR IGKV1D-12*02 IGKJ4*01 GACATCCAGATGACCCAGTCTCCTTCTTCCGTCTCTACAT CTGTAGGAGACAGAGTCACCATCACTTGTCGGGCGAGTCA GGATATTAGTAACTGGTTAGCCTGGTATCAGCAGAAACCA GGAAAAGCCCCTAAGCTCCTGATCTATGATTCATCCACT TTGCAAAGTGGGGTCCCATCAAGGTTCAGCGGCAGTGGA TCTGGGACAGATTTCACTCTCACCATCAGCACCCTGCAGC CTGAGGATTTTGCAACTTATTACTGTCAACAGTTTAATAG TTATCCCCTCACTTTCGGCGGAGGGACCAAAGTGGATATC AAA |

TABLE R-continued

| SEQ ID NO: | Description | Sequence |
|---|---|---|
| 309 | VH domain (aa) | QVQLVQSGAEVKKPGSSVKVSCKASGGTSTGFIGAISWV RQAPGQGLEWMGGIIPIFGTANYAQKFQGRVTITADEST STAYMELSSLRSEDTAVYYCARDVQRMGMDVWGQGTTVT VSS |
| 310 | VL domain (aa) | DIQMTQSPSSVSTSVGDRVTITCRASQDISNWLAWYQQKP GKAPKLLIYDSSTLQSGVPSRFSGSGSGTDFTLTISTLQP EDFATYYCQQFNSYPLTFGGGTKVDIK |
| 311 | Heavy CDR1 | GGTSTGFIGA |
| 312 | Heavy CDR2 | IIPIFGTA |
| 313 | Heavy CDR3 | ARDVQRMGMDV |
| 314 | Light CDR1 | QDISNW |
| 315 | Light CDR2 | DSS |
| 316 | Light CDR3 | QQFNSYPLT |
| 317 | Heavy FR1 | QVQLVQSGAEVKKPGSSVKVSCKAS |
| 318 | Heavy FR2 | ISWVRQAPGQGLEWMGG |
| 319 | Heavy FR3 | NYAQKFQGRVTITADESTSTAYMELSSLRSEDTAVYYC |
| 320 | Heavy FR4 | WGQGTTVTVSS |
| 321 | Light FR1 | DIQMTQSPSSVSTSVGDRVTITCRAS |
| 322 | Light FR2 | LAWYQQKPGKAPKLLIY |
| 323 | Light FR3 | TLQSGVPSRFSGSGSGTDFTLTISTLQPEDFATYYC |
| 324 | Light FR4 | FGGGTKVDIK |

TABLE S

| SEQ ID NO: | Description | Sequence |
|---|---|---|
| | | 206-3.D8 |
| 325 | VH domain (nt) | IGHV1-69*12 IGHJ6*02 IGHD2-8*01 CAGGTCCAGCTTGTGCAGTCTGGGGCTGAGGTGAAGAA GCCTGGGTCCTCGGTGAAGGTCTCCTGCAAGGCTTCTGG AGGCACCTTTCAGTCTTATTATGGGGCTATCAGCTGGTG CGACAGGCCCCTGGACAAGGGCTTGAGTGGATGGGAGG GATCATCCCTATCTTTGGTACAGCAAACTACGCACAGAAG TTCCAGGGCAGAGTCACGATTACCGCGGACGAATCCACG AGCACAGCCTACATGGAGCTGAGCAGCCTGAGATCTGAG GACACGGCCGTGTATTACTGTGCGAGAGACGTACAGAG GATGGGGATGGACGTCTGGGGCCAAGGGACCACGGTCA CCGTCTCCTCA |
| 326 | VL domain (nt) | IGKV1-12*01 OR IGKV1-12*02 OR IGKV1D-12*02 IGKJ4*01 GACATCCAGATGACCCAGTCTCCTTCTTCCGTCTCTACATC TGTAGGAGACAGAGTCACCATCACTTGTCGGGCGAGTCA GGATATTAGTAACTGGTTAGCCTGGTATCAGCAGAAACC AGGAAAAGCCCCTAAGCTCCTGATCTATGATTCATCCACT TTGCAAAGTGGGGTCCCATCAAGGTTCAGCGGCAGTGGA TCTGGGACAGATTTCACTCTCACCATCAGCACCCTGCAGC CTGAGGATTTTGCAACTTATTACTGTCAACAGTTTAATAG TTATCCCCTCACTTTCGGCGGAGGGACCAAAGTGGATATC AAA |
| 327 | VH domain (aa) | QVQLVQSGAEVKKPGSSVKVSCKASGGTFQSYYGAISWVR QAPGQGLEWMGGIIPIFGTANYAQKFQGRVTITADESTSTA YMELSSLRSEDTAVYYCARDVQRMGMDVWGQGTTVTVSS |

TABLE S-continued

| SEQ ID NO: | Description | Sequence |
|---|---|---|
| 328 | VL domain (aa) | DIQMTQSPSSVSTSVGDRVTITCRASQDISNWLAWYQQKP GKAPKLLIYDSSTLQSGVPSRFSGSGSGTDFTLTISTLQPEDFA TYYCQQFNSYPLTFGGGTKVDIK |
| 329 | Heavy CDR1 | GGTFQSYYGA |
| 330 | Heavy CDR2 | IIPIFGTA |
| 331 | Heavy CDR3 | ARDVQRMGMDV |
| 332 | Light CDR1 | QDISNW |
| 333 | Light CDR2 | DSS |
| 334 | Light CDR3 | QQFNSYPLT |
| 335 | Heavy FR1 | QVQLVQSGAEVKKPGSSVKVSCKAS |
| 336 | Heavy FR2 | ISWVRQAPGQGLEWMGG |
| 337 | Heavy FR3 | NYAQKFQGRVTITADESTSTAYMELSSLRSEDTAVYYC |
| 338 | Heavy FR4 | WGQGTTVTVSS |
| 339 | Light FR1 | DIQMTQSPSSVSTSVGDRVTITCRAS |
| 340 | Light FR2 | LAWYQQKPGKAPKLLIY |
| 341 | Light FR3 | TLQSGVPSRFSGSGSGTDFTLTISTLQPEDFATYYC |
| 342 | Light FR4 | FGGGTKVDIK |

TABLE T

| SEQ ID NO: | Description | Sequence |
|---|---|---|
| | | 206-3.C7 |
| 343 | VH domain (nt) | IGHV1-69*12 IGHJ6*02 IGHD2-8*01 CAGGTCCAGCTTGTGCAGTCTGGGGCTGAGGTGAAGAA GCCTGGGTCCTCGGTGAAGGTCTCCTGCAAGGCTTCTGG AGGCACCAATTTGATGGGGTATTATGGTGCTATCAGCTG GGTGCGACAGGCCCCTGGACAAGGGCTTGAGTGGATGG GAGGGATCATCCCTATCTTTGGTACAGCAAACTACGCACA GAAGTTCCAGGGCAGAGTCACGATTACCGCGGACGAATC CACGAGCACAGCCTACATGGAGCTGAGCAGCCTGAGATC TGAGGACACGGCCGTGTATTACTGTGCGAGAGACGTACA GAGGATGGGGATGGACGTCTGGGGCCAAGGGACCACG GTCACCGTCTCCTCA |
| 344 | VL domain (nt) | IGKV1-12*01 OR IGKV1-12*02 OR IGKV1D-12*02 IGKJ4*01 GACATCCAGATGACCCAGTCTCCTTCTTCCGTCTCTACATC TGTAGGAGACAGAGTCACCATCACTTGTCGGGCGAGTCA GGATATTAGTAACTGGTTAGCCTGGTATCAGCAGAAACC AGGAAAAGCCCCTAAGCTCCTGATCTATGATTCATCCACT TTGCAAAGTGGGGTCCCATCAAGGTTCAGCGGCAGTGGA TCTGGGACAGATTTCACTCTCACCATCAGCACCCTGCAGC CTGAGGATTTTGCAACTTATTACTGTCAACAGTTTAATAG TTATCCCCTCACTTTCGGCGGAGGGACCAAAGTGGATATC AAA |
| 345 | VH domain (aa) | QVQLVQSGAEVKKPGSSVKVSCKASGGTNLMGYYGAISWV RQAPGQGLEWMGGIIPIFGTANYAQKFQGRVTITADESTST AYMELSSLRSEDTAVYYCARDVQRMGMDVWGQGTTVTV SS |
| 346 | VL domain (aa) | DIQMTQSPSSVSTSVGDRVTITCRASQDISNWLAWYQQKP GKAPKLLIYDSSTLQSGVPSRFSGSGSGTDFTLTISTLQPEDFA TYYCQQFNSYPLTFGGGTKVDIK |

TABLE T-continued

| SEQ ID NO: | Description | Sequence |
|---|---|---|
| 347 | Heavy CDR1 | GGTNLMGYYGA |
| 348 | Heavy CDR2 | IIPIFGTA |
| 349 | Heavy CDR3 | ARDVQRMGMDV |
| 350 | Light CDR1 | QDISNW |
| 351 | Light CDR2 | DSS |
| 352 | Light CDR3 | QQFNSYPLT |
| 353 | Heavy FR1 | QVQLVQSGAEVKKPGSSVKVSCKAS |
| 354 | Heavy FR2 | ISWVRQAPGQGLEWMGG |
| 355 | Heavy FR3 | NYAQKFQGRVTITADESTSTAYMELSSLRSEDTAVYYC |
| 356 | Heavy FR4 | WGQGTTVTVSS |
| 357 | Light FR1 | DIQMTQSPSSVSTSVGDRVTITCRAS |
| 358 | Light FR2 | LAWYQQKPGKAPKLLIY |
| 359 | Light FR3 | TLQSGVPSRFSGSGSGTDFTLTISTLQPEDFATYYC |
| 360 | Light FR4 | FGGGTKVDIK |

TABLE U

| SEQ ID NO: | Description | Sequence |
|---|---|---|
| | | 206-3.C11 |
| 361 | VH domain (nt) | IGHV1-69*12<br>IGHJ6*02<br>IGHD2-8*01<br>CAGGTCCAGCTTGTGCAGTCTGGGGCTGAGGTGAAGAA<br>GCCTGGGTCCTCGGTGAAGGTCTCCTGCAAGGCTTCTGG<br>AGGCACCGTTAGGTCTAGGGTTCATGCTATCAGCTGGGT<br>GCGACAGGCCCCTGGACAAGGGCTTGAGTGGATGGGAG<br>GGATCATCCCTATCTTTGGTACAGCAAACTACGCACAGAA<br>GTTCCAGGGCAGAGTCACGATTACCGCGGACGAATCCAC<br>GAGCACAGCCTACATGGAGCTGAGCAGCCTGAGATCTGA<br>GGACACGGCCGTGTATTACTGTGCGAGAGACGTACAGA<br>GGATGGGGATGGACGTCTGGGGCCAAGGGACCACGGTC<br>ACCGTCTCCTCA |
| 362 | VL domain (nt) | IGKV1-12*01 OR IGKV1-12*02 OR IGKV1D-12*02<br>IGKJ4*01<br>GACATCCAGATGACCCAGTCTCCTTCTTCCGTCTCTACATC<br>TGTAGGAGACAGAGTCACCATCACTTGTCGGGCGAGTCA<br>GGATATTAGTAACTGGTTAGCCTGGTATCAGCAGAAACC<br>AGGAAAAGCCCCTAAGCTCCTGATCTATGATTCATCCACT<br>TTGCAAAGTGGGGTCCCATCAAGGTTCAGCGGCAGTGGA<br>TCTGGGACAGATTTCACTCTCACCATCAGCACCCTGCAGC<br>CTGAGGATTTTGCAACTTATTACTGTCAACAGTTTAATAG<br>TTATCCCCTCACTTTCGGCGGAGGGACCAAAGTGGATATC<br>AAA |
| 363 | VH domain (aa) | QVQLVQSGAEVKKPGSSVKVSCKASGGTVRSRVHAISWVR<br>QAPGQGLEWMGGIIPIFGTANYAQKFQGRVTITADESTSTA<br>YMELSSLRSEDTAVYYCARDVQRMGMDVWGQGTTVTVSS |
| 364 | VL domain (aa) | DIQMTQSPSSVSTSVGDRVTITCRASQDISNWLAWYQQKP<br>GKAPKLLIYDSSTLQSGVPSRFSGSGSGTDFTLTISTLQPEDFA<br>TYYCQQFNSYPLTFGGGTKVDIK |
| 365 | Heavy CDR1 | GGTVRSRVHA |
| 366 | Heavy CDR2 | IIPIFGTA |
| 367 | Heavy CDR3 | ARDVQRMGMDV |

TABLE U-continued

| SEQ ID NO: | Description | Sequence |
|---|---|---|
| 368 | Light CDR1 | QDISNW |
| 369 | Light CDR2 | DSS |
| 370 | Light CDR3 | QQFNSYPLT |
| 371 | Heavy FR1 | QVQLVQSGAEVKKPGSSVKVSCKAS |
| 372 | Heavy FR2 | ISWVRQAPGQGLEWMGG |
| 373 | Heavy FR3 | NYAQKFQGRVTITADESTSTAYMELSSLRSEDTAVYYC |
| 374 | Heavy FR4 | WGQGTTVTVSS |
| 375 | Light FR1 | DIQMTQSPSSVSTSVGDRVTITCRAS |
| 376 | Light FR2 | LAWYQQKPGKAPKLLIY |
| 377 | Light FR3 | TLQSGVPSRFSGSGSGTDFTLTISTLQPEDFATYYC |
| 378 | Light FR4 | FGGGTKVDIK |

TABLE V

| SEQ ID NO: | Description | Sequence |
|---|---|---|
| | | 206-3.F6 |
| 379 | VH domain (nt) | IGHV1-69*12<br>IGHJ6*02<br>IGHD2-8*01<br>CAGGTCCAGCTTGTGCAGTCTGGGGCTGAGGTGAAGAA<br>GCCTGGGTCCTCGGTGAAGGTCTCCTGCAAGGCTTCTGG<br>AGGCACCGGGTCGGAGTTTATGGGTGCTATCAGCTGGGT<br>GCGACAGGCCCCTGGACAAGGGCTTGAGTGGATGGGAG<br>GGATCATCCCTATCTTTGGTACAGCAAACTACGCACAGAA<br>GTTCCAGGGCAGAGTCACGATTACCGCGGACGAATCCAC<br>GAGCACAGCCTACATGGAGCTGAGCAGCCTGAGATCTGA<br>GGACACGGCCGTGTATTACTGTGCGAGAGACGTACAGA<br>GGATGGGGATGGACGTCTGGGGCCAAGGGACCACGGTC<br>ACCGTCTCCTCA |
| 380 | VL domain (nt) | IGKV1-12*01 OR IGKV1-12*02 OR IGKV1D-12*02<br>IGKJ4*01<br>GACATCCAGATGACCCAGTCTCCTTCTTCCGTCTCTACATC<br>TGTAGGAGACAGAGTCACCATCACTTGTCGGGCGAGTCA<br>GGATATTAGTAACTGGTTAGCCTGGTATCAGCAGAAACC<br>AGGAAAAGCCCCTAAGCTCCTGATCTATGATTCATCCACT<br>TTGCAAAGTGGGGTCCCATCAAGGTTCAGCGGCAGTGGA<br>TCTGGGACAGATTTCACTCTCACCATCAGCACCCTGCAGC<br>CTGAGGATTTTGCAACTTATTACTGTCAACAGTTTAATAG<br>TTATCCCCTCACTTTCGGCGGAGGGACCAAAGTGGATATC<br>AAA |
| 381 | VH domain (aa) | QVQLVQSGAEVKKPGSSVKVSCKASGGTGSEFMGAISWVR<br>QAPGQGLEWMGGIIPIFGTANYAQKFQGRVTITADESTSTA<br>YMELSSLRSEDTAVYYCARDVQRMGMDVWGQGTTVTVSS |
| 382 | VL domain (aa) | DIQMTQSPSSVSTSVGDRVTITCRASQDISNWLAWYQQKP<br>GKAPKLLIYDSSTLQSGVPSRFSGSGSGTDFTLTISTLQPEDFA<br>TYYCQQFNSYPLTFGGGTKVDIK |
| 383 | Heavy CDR1 | GGTGSEFMGA |
| 384 | Heavy CDR2 | IIPIFGTA |
| 385 | Heavy CDR3 | ARDVQRMGMDV |
| 386 | Light CDR1 | QDISNW |
| 387 | Light CDR2 | DSS |

TABLE V-continued

| SEQ ID NO: | Description | Sequence |
|---|---|---|
| 388 | Light CDR3 | QQFNSYPLT |
| 389 | Heavy FR1 | QVQLVQSGAEVKKPGSSVKVSCKAS |
| 390 | Heavy FR2 | ISWVRQAPGQGLEWMGG |
| 391 | Heavy FR3 | NYAQKFQGRVTITADESTSTAYMELSSLRSEDTAVYYC |
| 392 | Heavy FR4 | WGQGTTVTVSS |
| 393 | Light FR1 | DIQMTQSPSSVSTSVGDRVTITCRAS |
| 394 | Light FR2 | LAWYQQKPGKAPKLLIY |
| 395 | Light FR3 | TLQSGVPSRFSGSGSGTDFTLTISTLQPEDFATYYC |
| 396 | Light FR4 | FGGGTKVDIK |

TABLE W

| SEQ ID NO: | Description | Sequence |
|---|---|---|
| | | 206-12.F6 |
| 397 | VH domain (nt) | IGHV1-69*12<br>IGHJ6*02<br>IGHD2-8*01<br>CAGGTCCAGCTTGTGCAGTCTGGGGCTGAGGTGAAGAA<br>GCCTGGGTCCTCGGTGAAGGTCTCCTGCAAGGCTTCTGG<br>AGGCACCTATAATCCGGGTGTGTCTGCTATCAGCTGGGT<br>GCGACAGGCCCCTGGACAAGGGCTTGAGTGGATGGGAG<br>GGATCATCCCTATCTTTGGTACAGCAAACTACGCACAGAA<br>GTTCCAGGGCAGAGTCACGATTACCGCGGACGAATCCAC<br>GAGCACAGCCTACATGGAGCTGAGCAGCCTGAGATCTGA<br>GGACACGGCCGTGTATTACTGTGCGAGAGACGTACAGA<br>GGATGGGGATGGACGTCTGGGGCCAAGGGACCACGGTC<br>ACCGTCTCCTCA |
| 398 | VL domain (nt) | IGKV1-12*01 OR IGKV1-12*02 OR IGKV1D-12*02<br>IGKJ4*01<br>GACATCCAGATGACCCAGTCTCCTTCTTCCGTCTCTACATC<br>TGTAGGAGACAGAGTCACCATCACTTGTCGGGCGAGTCA<br>GGATATTAGTAACTGGTTAGCCTGGTATCAGCAGAAACC<br>AGGAAAAGCCCCTAAGCTCCTGATCTATGATTCATCCACT<br>TTGCAAAGTGGGGTCCCATCAAGGTTCAGCGGCAGTGGA<br>TCTGGGACAGATTTCACTCTCACCATCAGCACCCTGCAGC<br>CTGAGGATTTTGCAACTTATTACTGTCAACAGTTTAATAG<br>TTATCCCCTCACTTTCGGCGGAGGGACCAAAGTGGATATC<br>AAA |
| 399 | VH domain (aa) | QVQLVQSGAEVKKPGSSVKVSCKASGGTYNPGVSAISWVR<br>QAPGQGLEWMGGIIPIFGTANYAQKFQGRVTITADESTSTA<br>YMELSSLRSEDTAVYYCARDVQRMGMDVWGQGTTVTVSS |
| 400 | VL domain (aa) | DIQMTQSPSSVSTSVGDRVTITCRASQDISNWLAWYQQKP<br>GKAPKLLIYDSSTLQSGVPSRFSGSGSGTDFTLTISTLQPEDFA<br>TYYCQQFNSYPLTFGGGTKVDIK |
| 401 | Heavy CDR1 | GGTYNPGVSA |
| 402 | Heavy CDR2 | IIPIFGTA |
| 403 | Heavy CDR3 | ARDVQRMGMDV |
| 404 | Light CDR1 | QDISNW |
| 405 | Light CDR2 | DSS |
| 406 | Light CDR3 | QQFNSYPLT |
| 407 | Heavy FR1 | QVQLVQSGAEVKKPGSSVKVSCKAS |
| 408 | Heavy FR2 | ISWVRQAPGQGLEWMGG |

TABLE W-continued

| SEQ ID NO: | Description | Sequence |
|---|---|---|
| 409 | Heavy FR3 | NYAQKFQGRVTITADESTSTAYMELSSLRSEDTAVYYC |
| 410 | Heavy FR4 | WGQGTTVTVSS |
| 411 | Light FR1 | DIQMTQSPSSVSTSVGDRVTITCRAS |
| 412 | Light FR2 | LAWYQQKPGKAPKLLIY |
| 413 | Light FR3 | TLQSGVPSRFSGSGSGTDFTLTISTLQPEDFATYYC |
| 414 | Light FR4 | FGGGTKVDIK |

Table X presents certain consensus amino acid sequences.

TABLE X

| SEQ ID NO: | Description | Sequence |
|---|---|---|
| 415 | VL CDR3 consensus sequence relating to all the specifically described HLA-DQ2.5-gliadin-α1a antigen binding proteins described herein (in Tables A-I and AA) | $QX_2LNSYPLX_9X_{10}$ wherein $X_2$ can be any amino acid; $X_9$ can be any amino acid or no amino acid; and $X_{10}$ can be any amino acid or no amino acid. |
| 416 | VL CDR3 consensus sequence relating to certain of the specifically described HLA-DQ2.5-gliadin-α1a antigen binding proteins described herein (in Tables A-G and I) | $QX_2LNSYPLX_9X_{10}$ wherein $X_2$ is Q or D; $X_9$ is no amino acid or L; and $X_{10}$ is no amino acid or T. |
| 417 | VH CDR3 consensus sequence relating to all the specifically described HLA-DQ2.5-gliadin-α1a antigen binding proteins described herein (Tables A-I and AA) | $ARDX_4X_5X_6GWX_9X_{10}YGMDV$ wherein $X_4$ can be any amino acid; $X_5$ can be any amino acid; $X_6$ can be any amino acid; $X_9$ can be any amino acid; and $X_{10}$ can be any amino acid; |
| 418 | VH CDR3 consensus sequence relating to all the specifically described HLA-DQ2.5-gliadin-α1a antigen binding proteins described herein (Tables A-I and AA) | $ARDX_4X_5X_6GWX_9X_{10}YGMDV$ wherein $X_4$ is S or R; $X_5$ is S or T; $X_6$ is S or T; $X_9$ is H or N or G; $X_{10}$ is P or A; |
| 419 | VL CDR1 consensus sequence relating to all the specifically described HLA-DQ2.5-gliadin-α2 antigen binding proteins described herein (Tables J-W) | $X_1X_2X_3X_4X_5X_6X_7X_8X_9X_{10}X_{11}X_{12}$ wherein $X_1$ is Q or G; $X_2$ is D or S or T or N; $X_3$ is I or V or S; $X_4$ is S or L or N or I; $X_5$ is N or S or Y or D or T or K; $X_6$ is W or N or S or V or Y; $X_7$ is no amino acid or any amino acid; $X_8$ is no amino acid or any amino acid; $X_9$ is no amino acid or any amino acid; $X_{10}$ is no amino acid or any amino acid; $X_{11}$ is no amino acid or any amino acid; $X_{12}$ is no amino acid or any amino acid. |
| 420 | VL CDR1 consensus sequence relating to all the specifically described HLA-DQ2.5-gliadin-α2 antigen binding proteins described herein (Tables J-W) | $X_1X_2X_3X_4X_5X_6X_7X_8X_9X_{10}X_{11}X_{12}$ wherein $X_1$ is Q or G $X_2$ is D or S or T or N $X_3$ is I or V or S $X_4$ is S or L or N or I $X_5$ is N or S or Y or D or T or K |

TABLE X-continued

| SEQ ID NO: | Description | Sequence |
|---|---|---|
| | | $X_6$ is W or N or S or V or Y |
| | | $X_7$ is no amino acid or S or G; |
| | | $X_8$ is no amino acid or N or G; |
| | | $X_9$ is no amino acid or N or Y; |
| | | $X_{10}$ is no amino acid or K or G. |
| | | $X_{11}$ is no amino acid or N or Y; |
| | | $X_{12}$ is no amino acid or Y. |
| 421 | VL CDR2 consensus sequence relating to all the specifically described HLA-DQ2.5-gliadin-α2 antigen binding proteins described herein (Tables J-W) | $X_1X_2S$ wherein $X_1$ can be any amino acid; $X_2$ can be any amino acid. |
| 422 | VL CDR2 consensus sequence relating to all the specifically described HLA-DQ2.5-gliadin-α2 antigen binding proteins described herein (Tables J-W) | $X_1X_2S$ wherein $X_1$ is D or G or W; $X_2$ is S or A or V. |
| 423 | VL CDR3 consensus sequence relating to all the specifically described HLA-DQ2.5-gliadin-α2 antigen binding proteins described herein (Tables J-W) | $X_1X_2X_3X_4X_5X_6X_7X_8X_9X_{10}X_{11}$ wherein $X_1$ is Q or S $X_2$ is Q or S or H $X_3$ is F or Y $X_4$ is N or Y or D or T $X_5$ is S or N or D or W $X_6$ is Y or W or T or S or L $X_7$ is P or G $X_8$ is L or T or P or R $X_9$ is no amino acid or any amino acid $X_{10}$ is no amino acid or any amino acid $X_{11}$ is no amino acid or any amino acid |
| 424 | VL CDR3 consensus sequence relating to all the specifically described HLA-DQ2.5-gliadin-α2 antigen binding proteins described herein (Tables J-W) | $X_1X_2X_3X_4X_5X_6X_7X_8X_9X_{10}X_{11}$ wherein $X_1$ is Q or S $X_2$ is Q or S or H $X_3$ is F or Y $X_4$ is N or Y or D or T $X_5$ is S or N or D or W $X_6$ is Y or W or T or S or L $X_7$ is P or G $X_8$ is L or T or P or R $X_9$ is no amino acid or T or V or R $X_{10}$ is no amino acid or L or F $X_{11}$ is no amino acid or T |
| 425 | VH CDR1 consensus sequence relating to all the specifically described HLA-DQ2.5-gliadin-α2 antigen binding proteins described herein (Tables J-W) | $GGTX_4X_5X_6X_7X_8X_9X_{10}X_{11}$ wherein $X_4$ is F or S or N or V or G or Y $X_5$ is S or T or Q or L or R or N $X_6$ is S or G or M or E or P $X_7$ is Y or F or G or R $X_8$ is A or G or I or Y or V or M $X_9$ is no amino acid or any amino acid $X_{10}$ is no amino acid or any amino acid $X_{11}$ is no amino acid or any amino acid |
| 426 | VH CDR1 consensus sequence relating to all the specifically described HLA-DQ2.5-gliadin-α2 antigen binding proteins described herein (Tables J-W) | $GGTX_4X_5X_6X_7X_8X_9X_{10}X_{11}$ wherein $X_4$ is F or S or N or V or G or Y $X_5$ is S or T or Q or L or R or N $X_6$ is S or G or M or E or P $X_7$ is Y or F or G or R $X_8$ is A or G or I or Y or V or M $X_9$ is no amino acid or G or Y or H or S $X_{10}$ is no amino acid or A or G $X_{11}$ is no amino acid or A |
| 427 | VH CDR2 consensus sequence relating to all the specifically described | $IIPIFGTX_8$ wherein $X_8$ can be any amino acid |

TABLE X-continued

| SEQ ID NO: | Description | Sequence |
|---|---|---|
| | HLA-DQ2.5-gliadin-$\alpha$2 antigen binding proteins described herein (Tables J-W) | |
| 428 | VH CDR2 consensus sequence relating to all the specifically described HLA-DQ2.5-gliadin-$\alpha$2 antigen binding proteins described herein (Tables J-W) | IIPIFGTX$_8$<br>wherein<br>X$_8$ is A or V |
| 429 | VH CDR3 consensus sequence relating to all the specifically described HLA-DQ2.5-gliadin-$\alpha$2 antigen binding proteins described herein (Tables J-W) | ARX$_3$X$_4$X$_5$X$_6$X$_7$X$_8$X$_9$X$_{10}$X$_{11}$X$_{12}$X$_{13}$X$_{14}$X$_{15}$X$_{16}$X$_{17}$X$_{18}$X$_{19}$X$_{20}$<br>wherein<br>X$_3$ is D or V or G<br>X$_4$ is V or A or Y or R or Q<br>X$_5$ is Q or I or Y or N or P or V or G<br>X$_6$ is R or G or Y or T or S or I or P or L<br>X$_7$ is M or G or V or D or Y or P or L or I<br>X$_8$ is G or F or S or C or Y or P or W<br>X$_9$ is M or F or S or D or T<br>X$_{10}$ is D or G or A or S or Y or R<br>X$_{11}$ is V or Y or L or G or E<br>X$_{12}$ is no amino acid or any amino acid<br>X$_{13}$ is no amino acid or any amino acid<br>X$_{14}$ is no amino acid or any amino acid<br>X$_{15}$ is no amino acid or any amino acid<br>X$_{16}$ is no amino acid or any amino acid<br>X$_{17}$ is no amino acid or any amino acid<br>X$_{18}$ is no amino acid or any amino acid<br>X$_{19}$ is no amino acid or any amino acid<br>X$_{20}$ is no amino acid or any amino acid |
| 430 | VH CDR3 consensus sequence relating to all the specifically described HLA-DQ2.5-gliadin-$\alpha$2 antigen binding proteins described herein (Tables J-W) | ARX$_3$X$_4$X$_5$X$_6$X$_7$X$_8$X$_9$X$_{10}$X$_{11}$X$_{12}$X$_{13}$X$_{14}$X$_{15}$X$_{16}$X$_{17}$X$_{18}$X$_{19}$X$_{20}$<br>wherein<br>X$_3$ is D or V or G<br>X$_4$ is V or A or Y or R or Q<br>X$_5$ is Q or I or Y or N or P or V or G<br>X$_6$ is R or G or Y or T or S or I or P or L<br>X$_7$ is M or G or V or D or Y or P or L or I<br>X$_8$ is G or F or S or C or Y or P or W<br>X$_9$ is M or F or S or D or T<br>X$_{10}$ is D or G or A or S or Y or R<br>X$_{11}$ is V or Y or L or G or E<br>X$_{12}$ is no amino acid or F or D or S or W or Y or L<br>X$_{13}$ is no amino acid or D or Y or C or F or G or V<br>X$_{14}$ is no amino acid or Y or M<br>X$_{15}$ is no amino acid or S or Y or D or F<br>X$_{16}$ is no amino acid or P or F or V or Q<br>X$_{17}$ is no amino acid or H or D<br>X$_{18}$ is no amino acid or F or Y<br>X$_{19}$ is no amino acid or D<br>X$_{20}$ is no amino acid or Y |
| 431 | VH CDR3 consensus sequence relating to the HLA-DQ2.5-gliadin-$\alpha$1a antibody 107 described herein and the specifically described affinity matured variants thereof described herein (Tables C-I and AA) | ARDX$_4$X$_5$X$_6$GWX$_9$X$_{10}$YGMDV<br>wherein<br>X$_4$ can be any amino acid;<br>X$_5$ can be any amino acid;<br>X$_6$ can be any amino acid;<br>X$_9$ can be any amino acid;<br>X$_{10}$ can be any amino acid. |
| 432 | VH CDR3 consensus sequence relating to the HLA-DQ2.5-gliadin-$\alpha$1a antibody 107 described herein and the specifically described affinity matured variants thereof described herein (Tables C-I and AA) | ARDX$_4$X$_5$X$_6$GWX$_9$X$_{10}$YGMDV<br>wherein<br>X$_4$ is S or R;<br>X$_5$ is S or T;<br>X$_6$ is S or T;<br>X$_9$ is H or N or G;<br>X$_{10}$ is P or A; |
| 433 | VH CDR1 consensus sequence relating to the | GGTX$_4$X$_5$X$_6$X$_7$X$_8$X$_9$X$_{10}$X$_{11}$<br>wherein |

TABLE X-continued

| SEQ ID NO: | Description | Sequence |
|---|---|---|
| | HLA-DQ2.5-gliadin-α2 antibody 206 described herein and the specifically described affinity matured variants thereof described herein (Tables J and R-W) | $X_4$ can be any amino acid; $X_5$ can be any amino acid; $X_6$ can be any amino acid; $X_7$ can be any amino acid; $X_8$ can be any amino acid $X_9$ can be no amino acid or any amino acid; $X_{10}$ can be no amino acid or any amino acid; $X_{11}$ can be no amino acid or any amino acid. |
| 434 | VH CDR1 consensus sequence relating to the HLA-DQ2.5-gliadin-α2 antibody 206 described herein and the specifically described affinity matured variants thereof described herein (Tables J and R-W) | $GGTX_4X_5X_6X_7X_8X_9X_{10}X_{11}$ wherein $X_4$ is F or S or N or V or G or Y; $X_5$ is S or T or Q or L or R or N; $X_6$ is S or G or M or E or P; $X_7$ is Y or F or R or G; $X_8$ is A or I or Y or V or M; $X_9$ is no amino acid or G or Y or H or S; $X_{10}$ is no amino acid or A or G; $X_{11}$ is no amino acid or A. |
| 435 | VL CDR1 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA) | $X_1DISX_5X_6$ wherein $X_1$ can be any amino acid; $X_5$ can be any amino acid; $X_6$ can be any amino acid. |
| 436 | VL CDR1 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA) | $X_1DISX_5X_6$ wherein $X_1$ is H or Q; $X_5$ id S or N; $X_6$ is Y or W. |
| 437 | VL CDR2 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA) | $X_1X_2s$ wherein $X_1$ can be any amino acid; $X_2$ can be any amino acid. |
| 438 | VL CDR2 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA) | $X_1X_2s$ wherein $X_1$ is A or D; $X_2$ is A or S. |
| 439 | VL CDR3 consensus sequence relating to the HLA-DQ2.5-gliadin-α1a antibody 107 described herein, the HLA-DQ2.5- | $QX_2X_3NSYPLX_9$ wherein $X_2$ can be any amino acid; $X_3$ can be any amino acid; $X_9$ can be no amino acid or any amino acid. |

TABLE X-continued

| SEQ ID NO: | Description | Sequence |
|---|---|---|
| | gliadin-$\alpha$2 antibody 206 described herein and the specifically described affinity matured variants thereof described herein (Tables C-J and R to W and AA) | |
| 440 | VL CDR3 consensus sequence relating to the HLA-DQ2.5-gliadin-$\alpha$1a antibody 107 described herein, the HLA-DQ2.5-gliadin-$\alpha$2 antibody 206 described herein and certain of the specifically described affinity matured variants thereof described herein (Tables C-G, I, J and R to W) | $QX_2X_3NSYPLX_9$ wherein $X_2$ is D or Q; $X_3$ is L or F; and $X_9$ is no amino acid or T. |
| 441 | VH CDR1 consensus sequence relating to the HLA-DQ2.5-gliadin-$\alpha$1a antibody 107 described herein, the HLA-DQ2.5-gliadin-$\alpha$2 antibody 206 described herein and certain of the specifically described affinity matured variants thereof described herein (Tables C-G, I, J and R to W). | $GX_2X_3X_4X_5X_6X_7X_8X_9X_{10}X_{11}$ wherein $X_2$ is G or D $X_3$ is S or T $X_4$ is V or F or S or N of G or Y $X_5$ is S or T or Q or L or R or N $X_6$ is S or G or M or E or P $X_7$ is N or Y or F or G or R $X_8$ is S or A or I or Y or V or m $X_9$ is no amino acid or any amino acid $X_{10}$ is no amino acid or any amino acid $X_{11}$ is no amino acid or any amino acid |
| 442 | VH CDR1 consensus sequence relating to the HLA-DQ2.5-gliadin-$\alpha$1a antibody 107 described herein, the HLA-DQ2.5-gliadin-$\alpha$2 antibody 206 described herein and certain of the specifically described affinity matured variants thereof described herein (Tables C-G, I, J and R to W). | $GX_2X_3X_4X_5X_6X_7X_8X_9X_{10}X_{11}$ wherein $X_2$ is G or D $X_3$ is S or T $X_4$ is V or F or S or N of G or Y $X_5$ is S or T or Q or L or R or N $X_6$ is S or G or M or E or P $X_7$ is N or Y or F or G or R $X_8$ is S or A or I or Y or V or M $X_9$ is no amino acid or A or G or Y or H or S $X_{10}$ is no amino acid or A or G $X_{11}$ is no amino acid or A |
| 443 | VH CDR3 consensus sequence relating to the HLA-DQ2.5-gliadin-$\alpha$1a antibody 107 described herein, the HLA-DQ2.5-gliadin-$\alpha$2 antibody 206 described herein and the specifically described affinity matured variants thereof described herein (Tables C-J and R to W and AA). | $ARDX_nGMDV$ X can be any amino acid and n is 4, 5, 6, 7 or 8. |
| 495 | VH CDR1 consensus sequence relating to the HLA-DQ2.5-gliadin-$\alpha$2 specifically described affinity matured antibodies described herein (Tables R-W). | $GGTX_4X_5X_6X_7X_8X_9X_{10}X_{11}$ wherein $X_4$ is F or S or N or V or G or Y; $X_5$ is S or T or Q or L or R or N; $X_6$ is S or G or M or E or P; $X_7$ is Y or F or R or G; $X_8$ is I or Y or V or M; $X_9$ is be no amino acid or G or Y or H or S; $X_{10}$ is be no amino acid or A or G; $X_{11}$ is be no amino acid or A. |
| 518 | VH CDR1 consensus sequence relating to the HLA-DQ2.5-gliadin-$\alpha$1a antibodies described herein (Tables A-I and AA). | $GDSVSSX_7SAA$ wherein $X_7$ can be any amino acid |

TABLE X-continued

| SEQ ID NO: | Description | Sequence |
|---|---|---|
| 519 | VH CDR1 consensus sequence relating to the HLA-DQ2.5-gliadin-α1a antibodies described herein (Tables A-I and AA). | GDSVSSX$_7$SAA wherein X$_7$ is N or S |
| 520 | VL CDR3 consensus sequence relating to all the specifically described HLA-DQ2.5-gliadin-α1a antigen binding proteins described herein (Tables A-I and AA) | QX$_2$LNSYPLX$_9$X$_{10}$ wherein X$_2$ is Q or D or N; X$_9$ is no amino acid or L; and X$_{10}$ is no amino acid or T. |
| 521 | VL CDR3 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA) | QX$_2$X$_3$NSYPLX$_9$ wherein X$_2$ is D or Q or N; X$_3$ is L or F; and X$_9$ is no amino acid or T. |
| 522 | VH CDR1 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA). | GX$_2$X$_3$X$_4$X$_5$X$_6$X$_7$X$_8$X$_9$X$_{10}$X$_{11}$ wherein X$_2$ is G or D X$_3$ is S or T X$_4$ is V or F or S or N of G or Y X$_5$ is S or T or Q or L or R or N X$_6$ is S or G or M or E or P X$_7$ is N or Y or F or G or R or S X$_8$ is S or A or I or Y or V or M X$_9$ is no amino acid or any amino acid X$_{10}$ is no amino acid or any amino acid X$_{11}$ is no amino acid or any amino acid |
| 523 | VH CDR1 consensus sequence relating to the HLA-DQ2.5-gliadin-α1a antibody 107 described herein, the HLA-DQ2.5-gliadin-α2 antibody 206 described herein and the specifically described affinity matured variants thereof described herein (Tables C-J and R to W and AA). | GX$_2$X$_3$X$_4$X$_5$X$_6$X$_7$X$_8$X$_9$X$_{10}$X$_{11}$ wherein X$_2$ is G or D X$_3$ is S or T X$_4$ is V or F or S or N of G or Y X$_5$ is S or T or Q or L or R or N X$_6$ is S or G or M or E or P X$_7$ is N or Y or F or G or R or S X$_8$ is S or A or I or Y or V or M X$_9$ is no amino acid or A or G or Y or H or S X$_{10}$ is no amino acid or A or G X$_{11}$ is no amino acid or A |

TABLE AA

| SEQ ID NO: | Description | Sequence |
|---|---|---|
| | RF117 (combination mutant derived from 4.7C and 5.6A) | |
| 496 | VH domain (nt) | IGHV6-1*01 IGHJ6*02 IGHD6-19*01 CAGGTACAGCTGCAGCAGTCAGGTCCAGGAC TGGTGAAGCCCTCGCAGACCCTCTCACTCAC CTGTGCCATCTCCGGGGACAGTGTCTCTAGC AGCAGTGCTGCTTGGAACTGGATCAGGCAGT CCCCATCGAGAGGCCTTGAGTGGCTGGGAAG GACATACTACAGGTCCAAGTGGTATAATGATT ATGCAGTATCTGTGAAAAGTCGAATAACCATC AACCCAGACACATCCAAGAACCAGTTCTCCCT GCAGCTGAACTCTGTGACTCCCGAGGACACG |

TABLE AA-continued

| SEQ ID NO: | Description | Sequence |
|---|---|---|
| | | GCTGTGTATTACTGTGCAAGAGATAGGACTAC<br>TGGGTGGCATCCGTATGGTATGGACGTCTGG<br>GGCCAAGGGACCACGGTCACCGTCTCCTCA |
| 497 | VL domain (nt) | IGKV1-9*01<br>IGKJ5*01<br>GACGTCCAGGTGACCCAGTCTCCATCCTTCCT<br>GTCTGCATCTGTAGGAGACAGAGTCACCATCA<br>CTTGCCGGGCCAGTCACGACATTAGCAGTTAT<br>TTAGCCTGGTATCAACACAAACCGTGGAAAGC<br>CCCCAAACTCCTGATCCATGCTGCATCCGTTT<br>TGCAAAGTGGGGTCCCATCAAGGTTCAGCGG<br>AAGTGGATCTGGGACAGAATTCACTCTCACAA<br>TCAGCAGCCTGCAGCCTGAAGATTTTGCAAC<br>GTACTACTGTCAAAATCTCAATAGTTATCCTCT<br>CTTCGGCCAAGGGACACGACTGGAGATTAAA |
| 498 | VH domain (aa) | QVQLQQSGPGLVKPSQTLSLTCAISGDSVSSSS<br>AAWNWIRQSPSRGLEWLGRTYYRSKWYNDYA<br>VSVKSRITINPDTSKNQFSLQLNSVTPEDTAVYY<br>CARDRTTGWHPYGMDVWGQGTTVTVSS |
| 499 | VL domain (aa) | DVQVTQSPSFLSASVGDRVTITCRASHDISSYLA<br>WYQHKPWKAPKLLIHAASVLQSGVPSRFSGSG<br>SGTEFTLTISSLQPEDFATYYCQNLNSYPLFGQ<br>GTRLEIK |
| 500 | Heavy CDR1 | GDSVSSSSAA |
| 501 | Heavy CDR2 | TYYRSKWYN |
| 502 | Heavy CDR3 | ARDRTTGWHPYGMDV |
| 503 | Light CDR1 | HDISSY |
| 504 | Light CDR2 | AAS |
| 505 | Light CDR3 | QNLNSYPL |
| 506 | Heavy FR1 | Q V Q L Q Q S G P G L V K P S Q T L S L T C A I S |
| 507 | Heavy FR2 | W N W I R Q S P S R G L E W L G R |
| 508 | Heavy FR3 | D Y A V S V K S R I T I N P D T S K N Q F S L Q L N<br>S V T P E D T A V Y Y C |
| 509 | Heavy FR4 | W G Q G T T V T V S S |
| 510 | Light FR1 | D V Q V T Q S P S F L S A S V G D R V T I T C R A S |
| 511 | Light FR2 | L A W Y Q H K P W K A P K L L I H |
| 512 | Light FR3 | V L Q S G V P S R F S G S G S G T E F T L T I S S L<br>Q P E D F A T Y Y C |
| 513 | Light FR4 | F G Q G T R L E I K |
| 514 | Heavy chain (aa) (variable + constant domain). hIgG₁ | QVQLQQSGPGLVKPSQTLSLTCAISGDSVSSSSAAWNWIR<br>QSPSRGLEWLGRTYYRSKWYNDYAVSVKSRITINPDTSKNQ<br>FSLQLNSVTPEDTAVYYCARDRTTGWHPYGMDVWGQGTT<br>VTVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGPS<br>VFLFPPKPKDTLMISRTPEVTCVVVDVSHEDPEVKFNWYVD<br>GVEVHNAKTKPREEQYGSTYRVVSVLTVLHQDWLNGKEYK<br>CKVSNKALPAPIEKTISKAKGQPREPQVYTLPPSRDELTKNQ<br>VSLTCLVKGFYPSDIAVEWESNGQPENNYKTTPPVLDSDGS<br>FFLYSKLTVDKSRWQQGNVFSCSVMHEALHNHYTQKSLSLS<br>PGK |
| 515 | Light chain (aa) (variable + constant domain). hIgG₁ | DVQVTQSPSFLSASVGDRVTITCRASHDISSYLAWYQHKPW<br>KAPKLLIHAASVLQSGVPSRFSGSGSGTEFTLTISSLQPEDFAT<br>YYCQNLNSYPLFGQGTRLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNRG<br>EC |

EXEMPLARY CONSTANT DOMAIN SEQUENCES
Mouse IgG_{2b} constant domain -heavy chain mouse
gamma 2b (SEQ ID NO: 468)

AKTTPPSVYPLAPGCGDTTGSSVTLGCLVKGYFPESVTVTWNSGSLSSSV

HTFPALLQSGLYTMSSSVTVPSSTWPSQTVTCSVAHPASSTTVDKKLEPS

GPISTINPCPPCKECHKCPAPNLEGGPSVFIFPPNIKDVLMISLTPKVTC

VVVDVSEDDPDVQISWFVNNVEVHTAQTQTHREDYASTIRVVSTLPIQHQ

DWMSGKEFKCKVNNKDLPSPIERTISKIKGLVRAPQVYILPPPAEQLSRK

DVSLTCLVVGFNPGDISVEWTSNGHTEENYKDTAPVLDSDGSYFIYSKLN

MKTSKWEKTDSFSCNVRHEGLKNYYLKKTISRSPGK

Mouse constant domain -IgG kappa (SEQ ID NO: 469)

ADAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKS

FNRNEC

Human IgG_1 constant domain -heavy chain human
gamma 1

(SEQ ID NO: 470)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYGSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human constant domain -IgG kappa (SEQ ID NO: 471)

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

OTHER SEQUENCES
DQ2.5-glia-α1a (SEQ ID NO: 472)

PFPQPELPY

DQ2.5-glia-α2

(SEQ ID NO: 473)

PQPELPYPQ

DQ2.5-glia-α1a plus flanking residues (SEQ ID NO: 474)

QLQPFPQPELPY

DQ2.5-glia-α2 plus flanking residues (SEQ ID NO: 475)

PQPELPYPQPE

α-gliadin 33-mer peptide (SEQ ID NO: 476)

LQLQPFPQPELPYPQPELPYPQPELPYPQPQPF

DQ2.5-glia-ω1

(SEQ ID NO: 477)

PFPQPEQPF

DQ2.5-glia-ω2

(SEQ ID NO: 478)

PQPEQPFPW

-continued

DQ2.5-glia-ω1 plus flanking sequence (SEQ ID NO: 479)

QQPFPQPEQPFP

DQ2.5-glia-ω2 plus flanking sequence (SEQ ID NO: 480)

FPQPEQPFPWQP

DQ2.5-glia-γ1

(SEQ ID NO: 481)

PQQSFPEQE

DQ2.5-glia-γ1 plus flanking sequence (SEQ ID NO: 482)

PEQPQQSFPEQERP

DQ2.5-glia-γ2

(SEQ ID NO: 483)

IQPEQPAQL

DQ2.5-glia-γ2 plus flanking sequence (SEQ ID NO: 484)

QGIIQPEQPAQL

DQ2.5-glia-γ3

(SEQ ID NO: 485)

EQPEQPYPQ

DQ2.5-glia-γ3 plus flanking sequence (SEQ ID NO: 486)

TEQPEQPYPQP

DQ2.5-glia-γ4c (SEQ ID NO: 487)

EQPEQPFPQ

DQ2.5-glia-γ4c plus flanking sequence (SEQ ID NO: 488)

TEQPEQPFPQP

CLIP2

(SEQ ID NO: 489)

PLLMQALPM

CLIP2 plus flanking sequence (SEQ ID NO: 490)

MATPLLMQALPMMGAL

DQ2.5-glia-α1a (native form or non-deamidated
form - SEQ ID NO: 491)
PFPQPQLPY

DQ2.5-glia-α2 (native form or non-deamidated
form - SEQ ID NO: 492)
PQPQLPYPQ

Mature α-chain of HLA-DQ2.5 MHC molecule (IMGT -
HLA allele name: DQA1*05:01:01:01)

(SEQ ID NO: 493)

IVADHVASYGVNLYQSYGPSGQYTHEFDGDEQFYVDLGRKETVWCLPVLR

QFRFDPQFALTNIAVLKHNLNSLIKRSNSTAATNEVPEVTVFSKSPVTLG

QPNILICLVDNIFPPVVNITWLSNGHSVTEGVSETSFLSKSDHSFFKISY

LTLLPSAEESYDCKVEHWGLDKPLLKHWEPEIPAPMSELTETVVCALGLS

VGLVGIVVGTVFIIRGLRSVGASRHQGPL

Mature β-chain of HLA-DQ2.5 MHC molecule (IMGT -
HLA allele name: DQB1*02:01:01)

(SEQ ID NO: 494)

RDSPEDFVYQFKGMCYFTNGTERVRLVSRSIYNREEIVRFDSDVGEFRAV

TLLGLPAAEYWNSQKDILERKRAAVDRVCRHNYQLELRTTLQRRVEPTVT

ISPSRTEALNHHNLLVCSVTDFYPAQIKVRWFRNDQEETAGVVSTPLIRN

GDWTFQILVMLEMTPQRGDVYTCHVEHPSLQSPITVEWRAQSESAQSKML

SGIGGFVLGLIFLGLGLIIHHRSQKGLLH

Figure 1A:
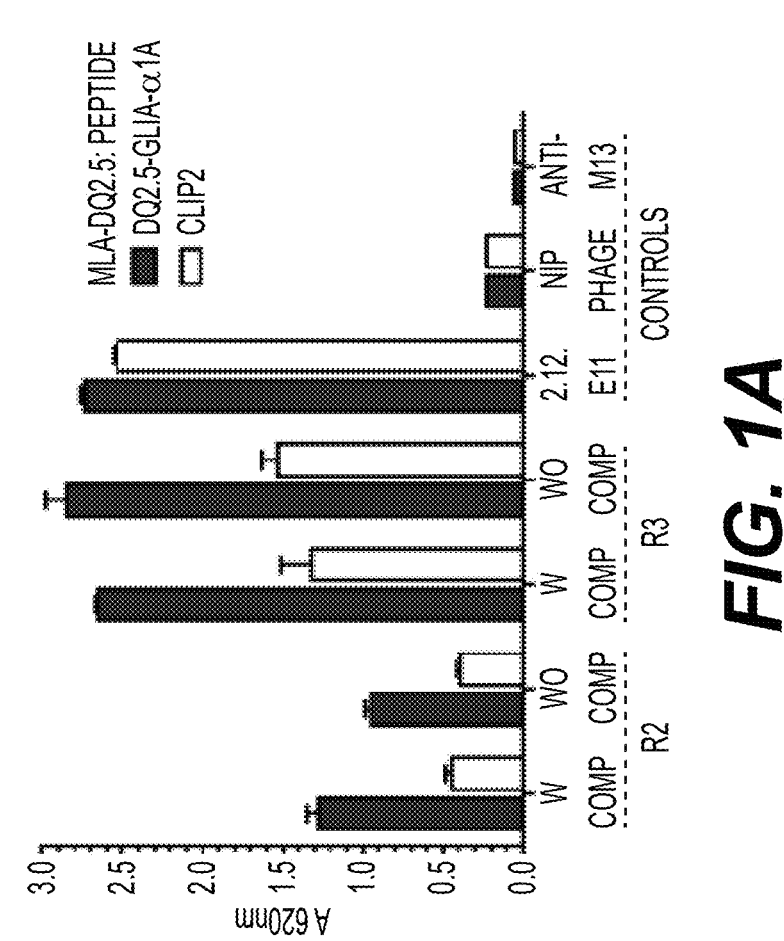
Figure 1C:
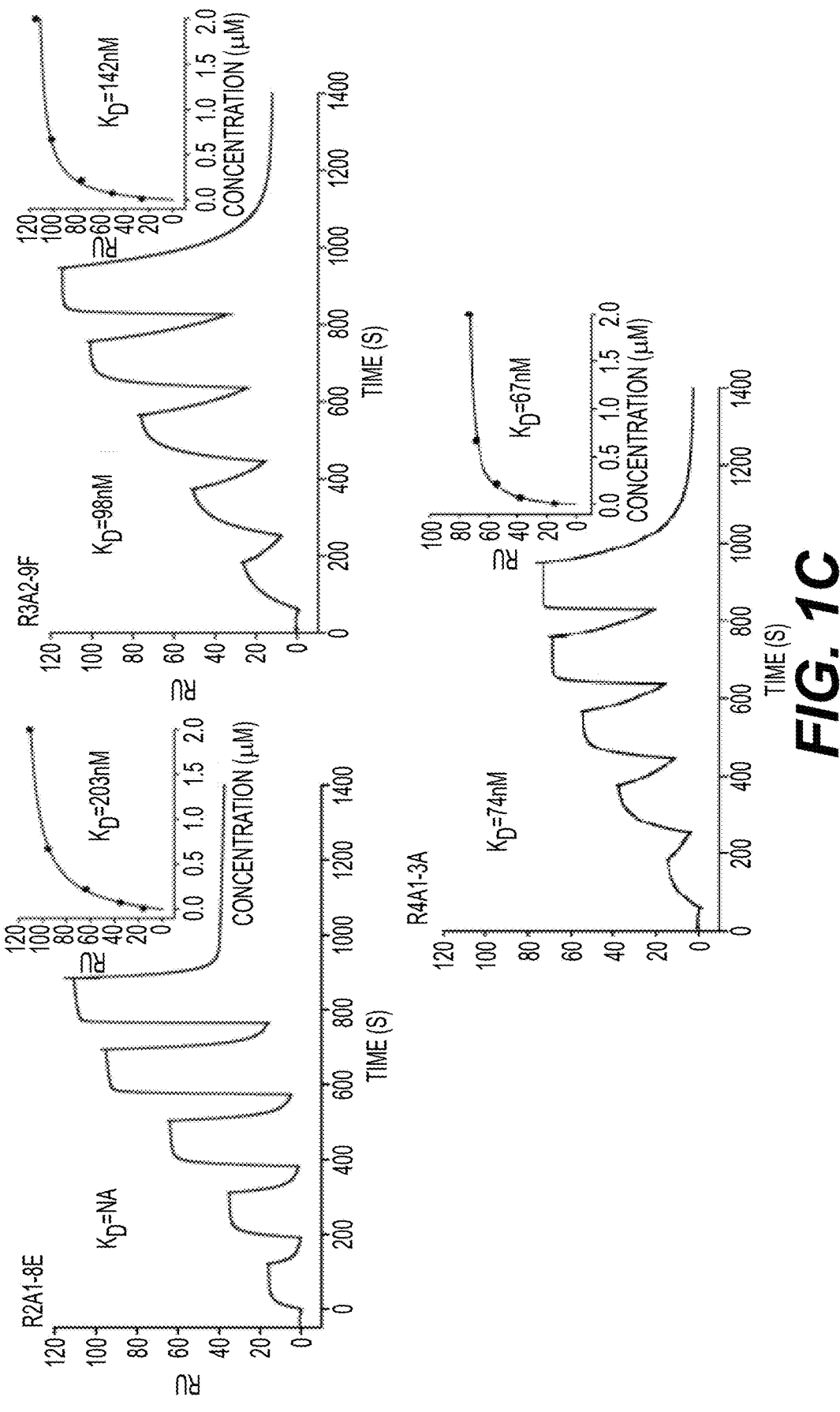

The invention will now be further described in the following non-limiting Examples with reference to the following drawings:

FIGS. 1A-1C. Screening of HLA-DQ2.5:DQ2.5-glia-α1a-specific binders and affinity measurements. (FIG. 1A) Representative ELISA (n=2) of normalized, rescued phage outputs from R2 and R3 analyzed for binding to HLA-DQ2.5 with either DQ2.5-glia-α1a or CLIP2 peptides. Phage displaying an irrelevant specificity (scFv anti-NIP) was included as control. mAb 2.12.E11 specific for the DQ2.5 β-chain was used to assess capture-level of pMHC. Error bars illustrate mean±SD of duplicates. (FIG. 1B) ScFvs selected in R2, R3, and R4 were batch-cloned into a vector for soluble expression and random clones expressed and analyzed for target reactivity by ELISA. Clones preferentially binding HLA-DQ2.5:DQ2.5-glia-α1a compared to HLA-DQ2.5:CLIP2 were chosen and sequenced. IGHV and IGKV gene segment usage was identified from the IMGT database. The pie charts show the gene segments used by the 11 unique clones. (FIG. 1C) The unique clones were expressed and purified and binding affinity to HLA-DQ2.5:DQ2.5-glia-α1a was determined by single cycle kinetics using a 3-fold concentration series ranging from 2 μM-0.025 μM scFv. Representative sensograms of clones R2A1-8E, R3A2-9F, and R4A1-3A which bound specifically and are shown as indicated (n=2-3). $K_D$s were derived by fitting the data to a 1:1 Langmuir model. Steady state affinity evaluations are shown as inset figures. NA=not available.

Figure 2A:
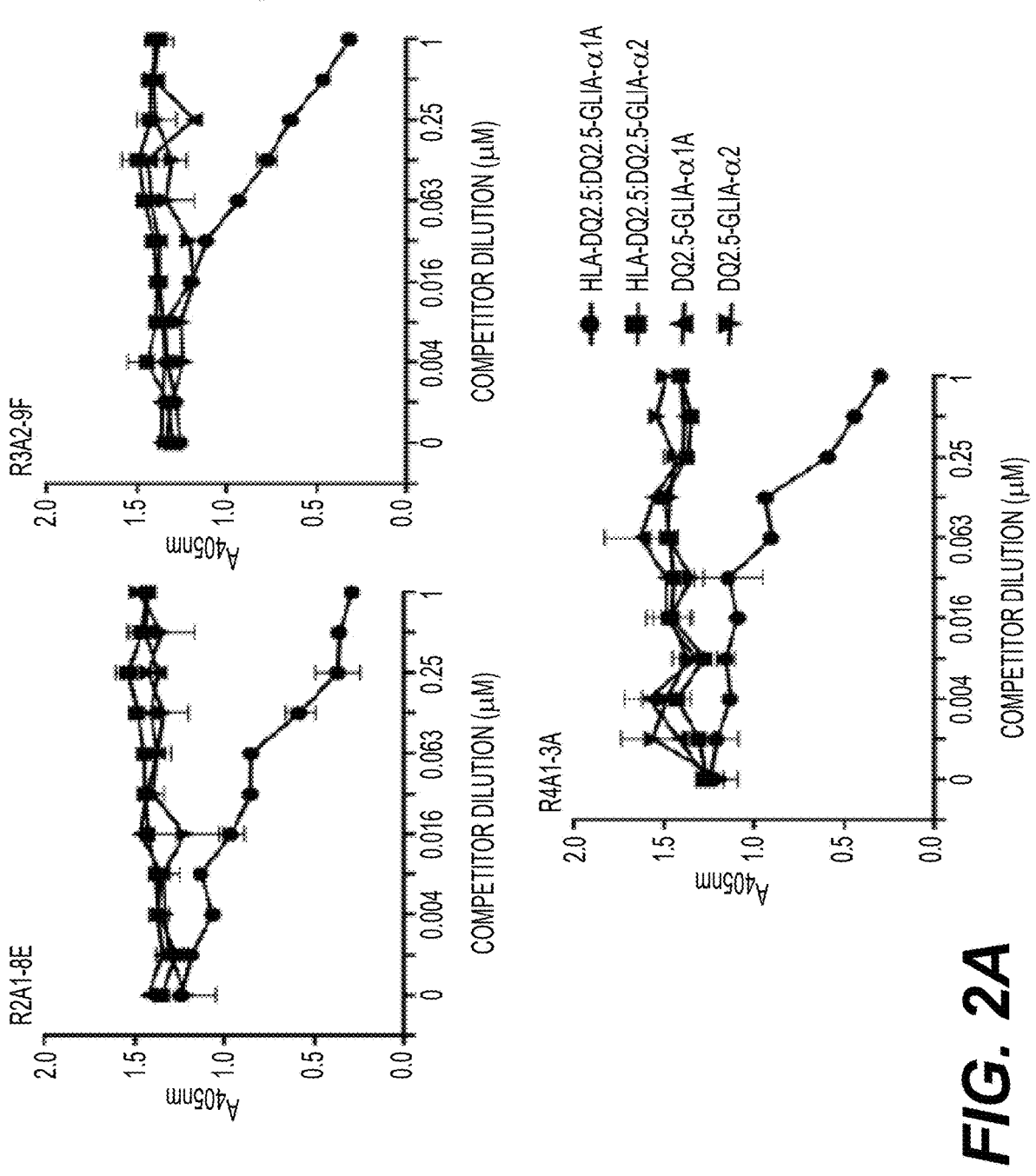
Figures 2B, 2C:
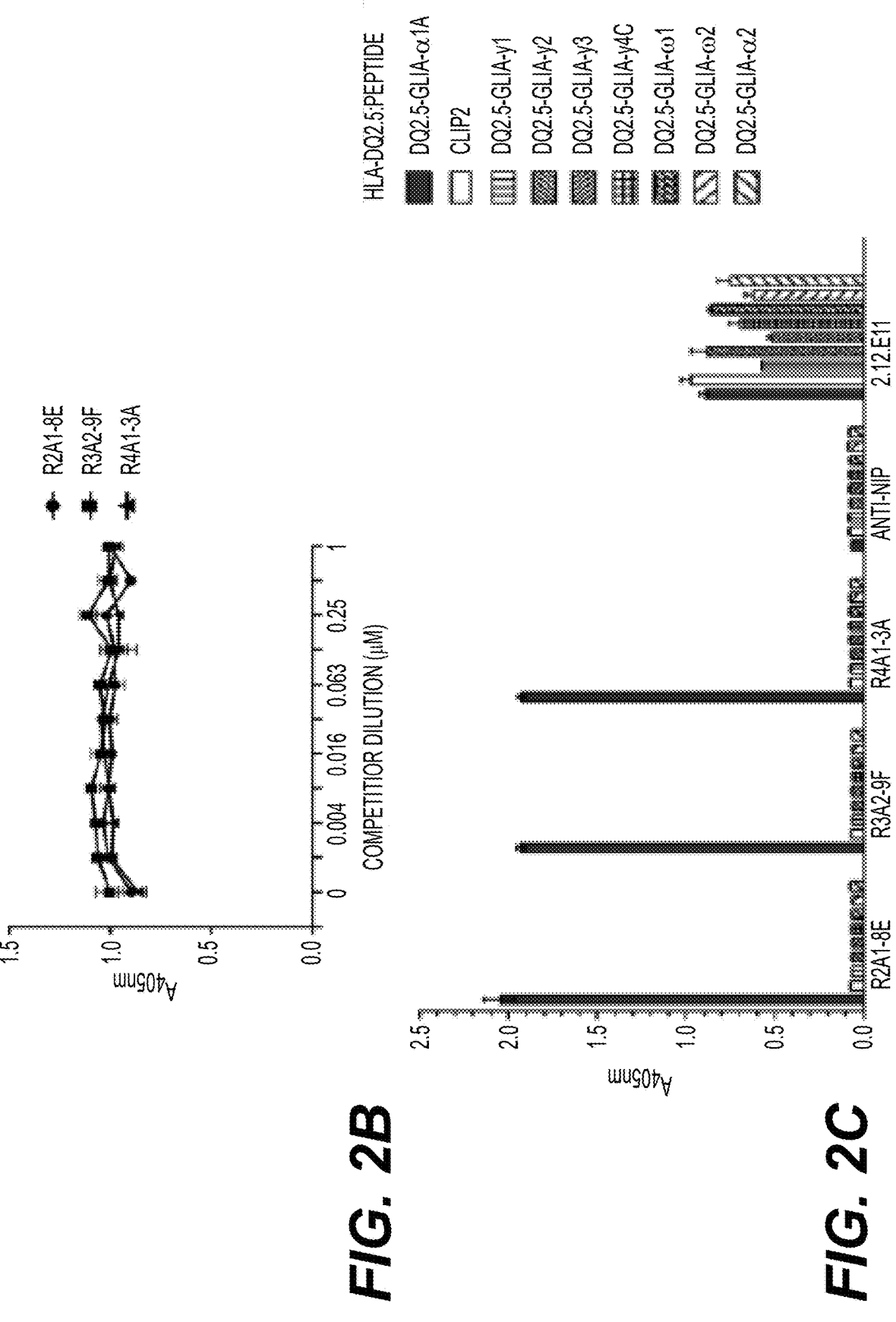

FIGS. 2A-2C. The HLA-DQ2.5:DQ2.5-glia-α1a-specific mAbs are highly specific. The three hIgG1 mAbs and isotype control mAb were reformatted to hIgG1, expressed by transient transfection in human 293E cells and purified from supernatants before assessment of specificity. (FIGS. 2A and 2B) Competition ELISAs where the mAbs were pre-incubated with titrated amounts of (FIG. 2A) soluble pMHCs, HLA-DQ2.5:DQ2.5-glia-α1a and HLA-DQ2.5:DQ2.5-glia-α2, or the corresponding free peptides, or (FIG. 2B) 33mer α-gliadin before assessment of ability to compete with binding to plate-bound HLA-DQ2.5:DQ2.5-glia-α1a (n=3). (FIG. 2C) Eight different HLA-DQ2.5:gluten peptide complexes and HLA-DQ2.5:CLIP2 were used in ELISA for specificity analysis (n=2). mAb 2.12.E11 was included to control pMHC capture levels. In each set of 9 bars, moving from left to right, bar 1 is HLA-DQ2.5-glia-α1a, bar 2 is CLIP2, bar 3 is HLA-DQ2.5-glia-γ1, bar 4 is HLA-DQ2.5-glia-γ2, bar 5 is HLA-DQ2.5-glia-γ3, bar 6 is HLA-DQ2.5-glia-γ4c, bar 7 is HLA-DQ2.5-glia-ω1, bar 8 is HLA-DQ2.5-glia-ω2, bar 9 is HLA-DQ2.5-glia-α2.

FIGS. 3A-3G. Mapping the fine-specificity and the structural basis for specificity. (FIG. 3A) Flow cytometric analysis of A20 B cells expressing HLA-DQ2.5 with covalently coupled DQ2.5-glia-α1a or CLIP2 peptides stained with the hIgG1 mAbs or hIgG1 isotype control mAb. Bound mAbs were detected using a biotinylated secondary anti-human IgG1 followed by streptavidin-RPE (n=2). (FIG. 3B) The hIgG1 mAbs were used to stain a panel of either HLA-DQ2.5:peptide or HLA-DQ2.2:peptide expressing A20 B cells and binding was analyzed by flow cytometry. Data are shown as the ratio median fluorescent intensity (MFI) of the hIgG1 mAbs compared to hIgG1 isotype control mAb (n=2). For each set of 3 bars, moving from left to right, bar 1 represents the mAb R2A1-8E, bar 2 represents the MAb R3A2-9F and bar 3 represents the MAb R4A1-3A. (FIG. 3C) Peptide alignment of DQ2.5-glia-α1a (PFPQPELPY) (SEQ ID NO: 472) (forest green) and DQ2.5-glia-ω1 (PFPQPEQPF) (SEQ ID NO: 477) (cyan). Residues differing are underlined in the peptide sequences. Based on the crystal structure of HLA-DQ2.5:DQ2.5-glia-α1a (PDB ID 1S9V) [Kim, C. Y., et al., 2004]. (FIG. 3D) Overlay of the top three docking models of the Fvs onto HLA-DQ2.5:DQ2.5-glia-α1a [Kim, C. Y., et al., 2004]. Peptide residues that were mutated in the fine-specificity analysis and the HLA-DQ2.5/HLA-DQ2.2 polymorphisms are illustrated (αY22 and αS72). (FIG. 3E) In all three models $V_H$ CDR3 is placed close to p7. (F) CDR1 and CDR3 of $V_L$ both contain residues in close proximity to p9 in two of the Fv models. (FIG. 3G) In two of the Fv models $V_L$ CDR1 (D28 and S36) is placed in close proximity to αS72, with potential H-bond formation. (FIGS. 3D-3G) Coloring in molecular structures as follows: $V_H$ and $V_L$, black; MHCα, grey; MHCβ, light orange; DQ2.5-glia-α1a, forest green; CDR1 and CDR2 of $V_H$, deep purple; CDR3 of $V_H$, red; CDR1 and CDR2 of $V_L$, deep teal; CDR3 of $V_L$, blue; αS72 and αY22, hot pink; p7 and p9, pale green; H-bonds, yellow dashes. (FIGS. 3E-3G) Residues within 5 A of p7, p9 and αS72, respectively, are shown.

Figures 4A, 4B:
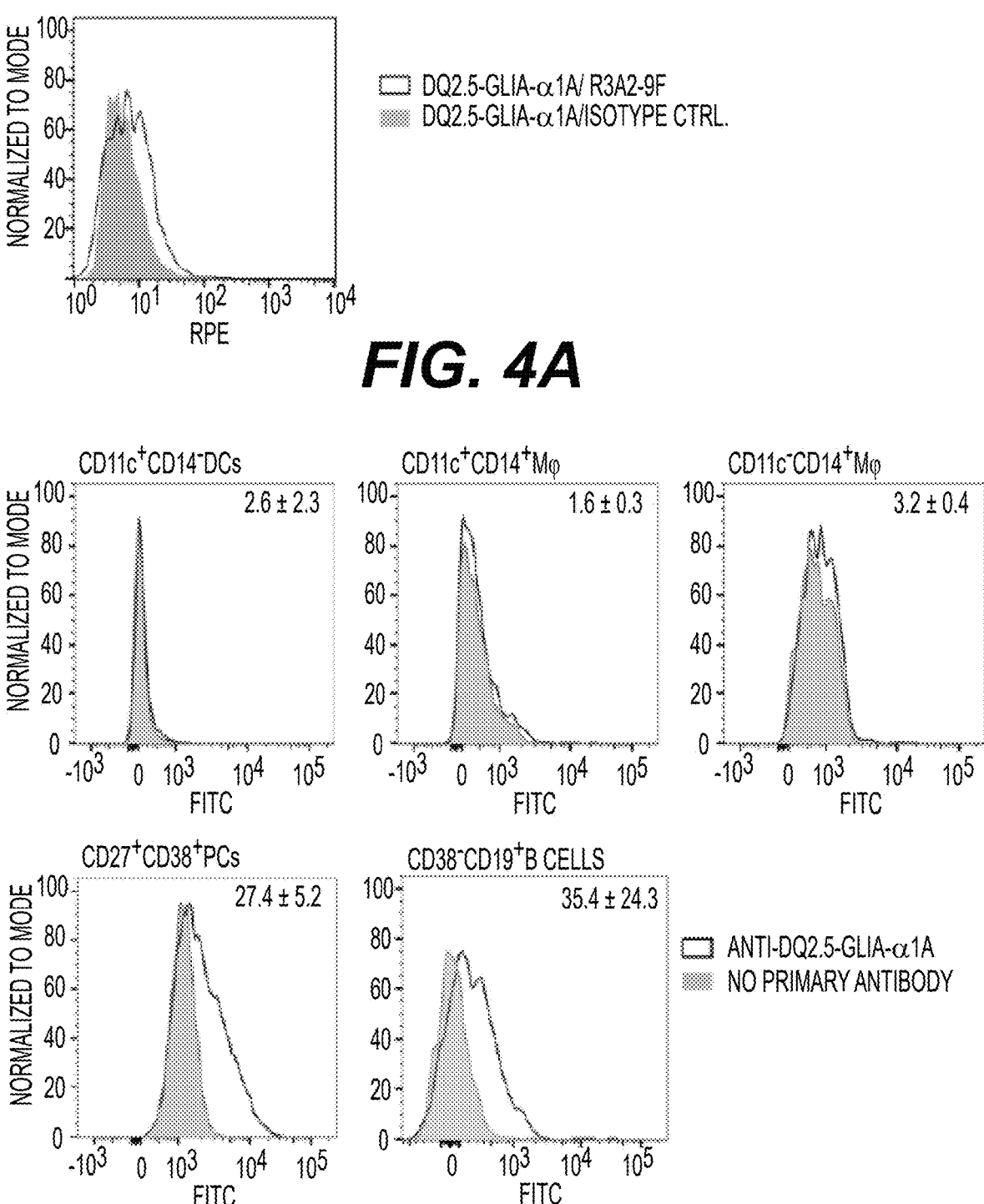

FIGS. 4A-4B. Specific detection of gluten peptide presentation in context of HLA-DQ2.5. (FIG. 4A) Monocytes isolated from human PMBCs were in vitro differentiated to monocyte-derived DCs, loaded with peptide and stained with hIgG1 mAb R3A2-9F or isotype control mAb before flow cytometric analysis (n=1). (FIG. 4B) Single-cell suspensions of intestinal biopsies obtained from patients undergoing gastroduodenoscopy were stained with a panel of antibodies to phenotypically characterize DQ2.5-glia-α1a presenting cells along with R3A2-9F mIgG2b. Bound R3A2-9F was detected using a FITC-conjugated secondary anti-mouse IgG2b Ab. Samples from three HLA-DQ2.5$^+$ untreated CD (UCD) patients with Marsh 3B/C were run in parallel. The mean percent of mIgG2b mAb R3A2-9F positive cells compared to no primary antibody is shown ±SD. Mφ, macrophages.

Figures 5A, 5B:
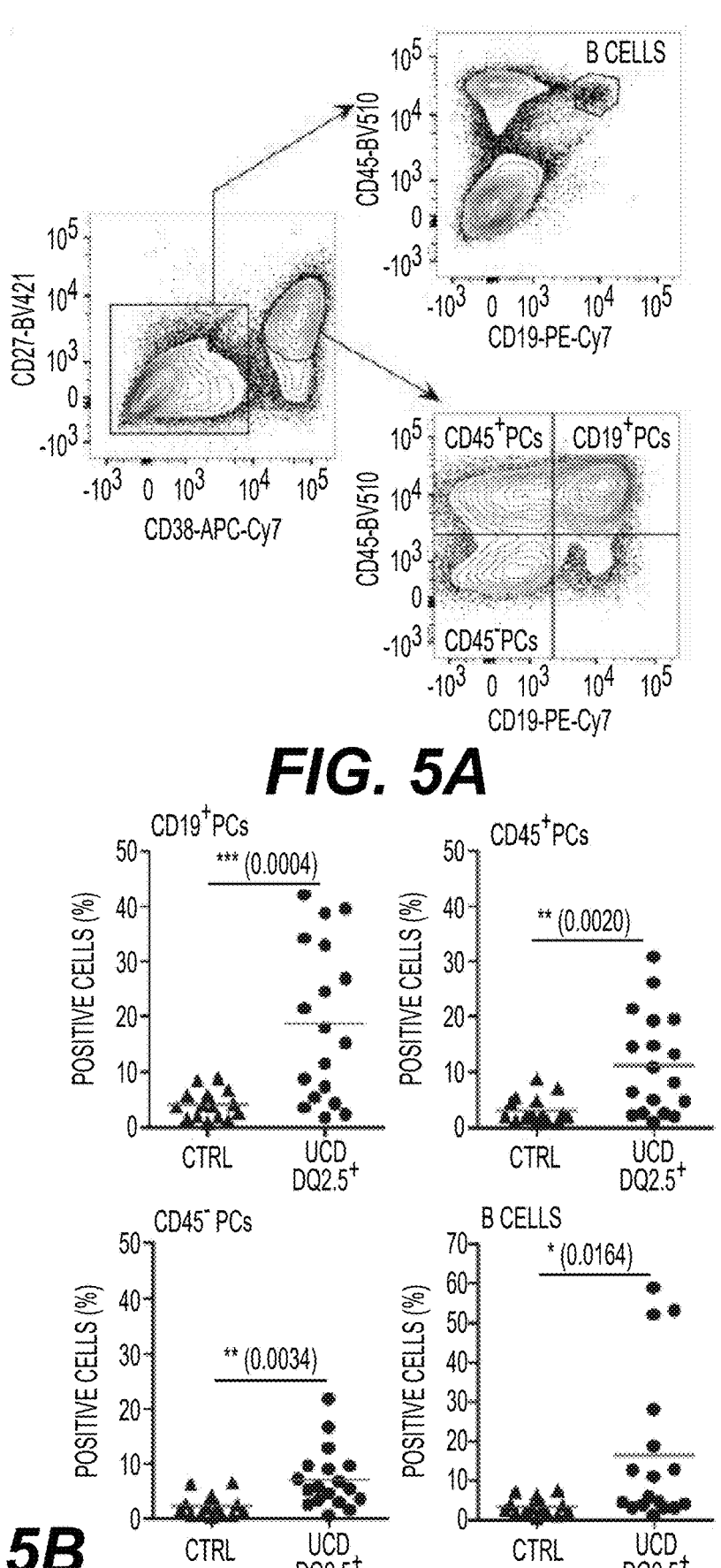

FIGS. 5A-5D. PCs and B cells of gut biopsies present the DQ2.5-glia-α1a peptide. Detection of DQ2.5-glia-α1a presentation among PCs and B cells in single-cells suspension prepared from intestinal biopsies from either untreated CD (UCD) or treated CD (TCD) patients or healthy controls. mIgG2b mAb R3A2-9F or R4A1-3A were used for detection and percent positive cells was determined relative to use of secondary antibody alone. (FIG. 5A) Representative flow cytometric gating strategy to identify PCs and B cells from single-cell suspensions. (FIG. 5B) Percentage of specific HLA-DQ2.5:DQ2.5-glia-α1a detection among CD19$^+$ PCs, CD45$^+$ PCs, CD45 PCs, and B cells in HLA-DQ2.5$^+$ UCD CD patients (n=18) compared to controls (grouped healthy and non-HLA-DQ2.5$^+$ CD patients, n=15). Two-tailed P-values are shown (unpaired t-test). (FIG. 5C) Stratification of the control patients among the CD19$^+$ PCs from (FIG. 5A). Ctrl HLA-DQ2.5$^+$ (n=5), Ctrl HLA-DQ2.5 (n=5), UCD HLA-DQ2.5$^+$ (n=18), TCD HLA-DQ2.5$^+$ (n=3), UCD HLA-DQ8$^+$ (n=1), and UCD HLA-DQ2.2$^+$ (n=1). (FIG. 5D) The HLA-DQ2.5$^+$ UCD patients (n=18) were stratified according to Marsh score as indicated. (FIGS. 5B-5D) Non-CD ctrl patients did not have mucosal alterations. Each data point represents an individual subject. Red (i.e. horizontal) bars indicate mean percentage.

Figures 6A, 6B, 6C:
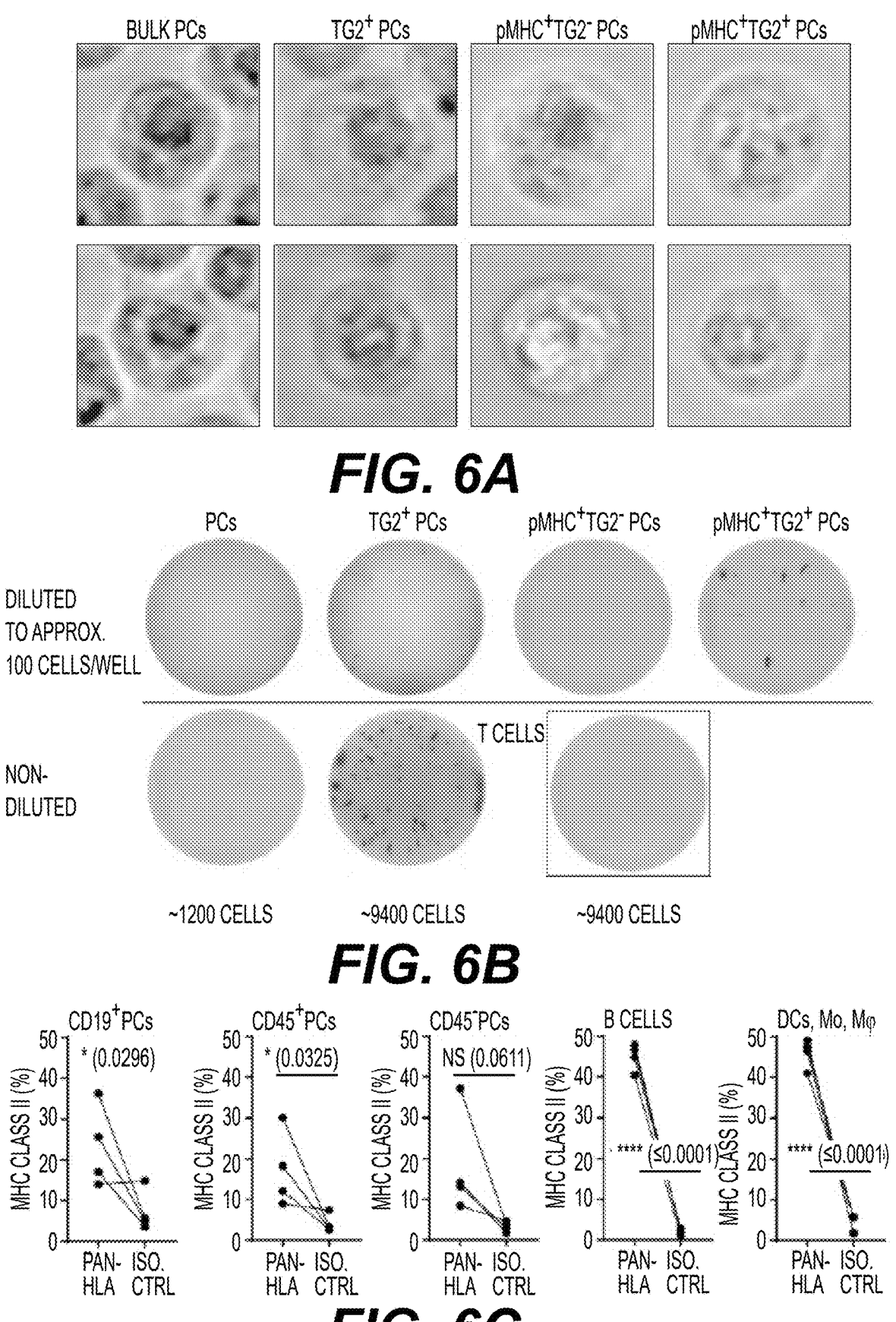
Figure 7A:
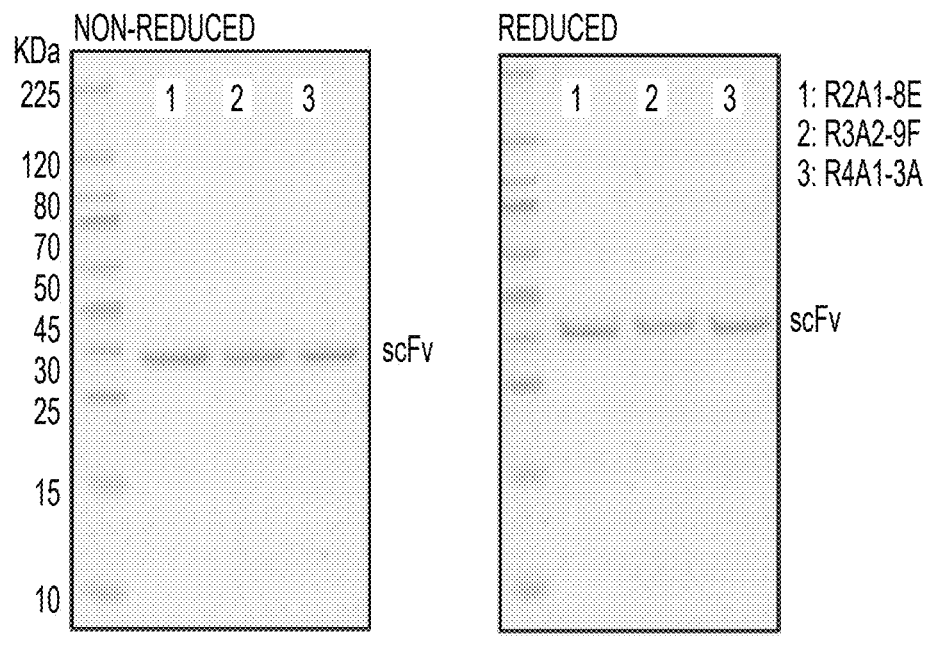
Figure 7B:
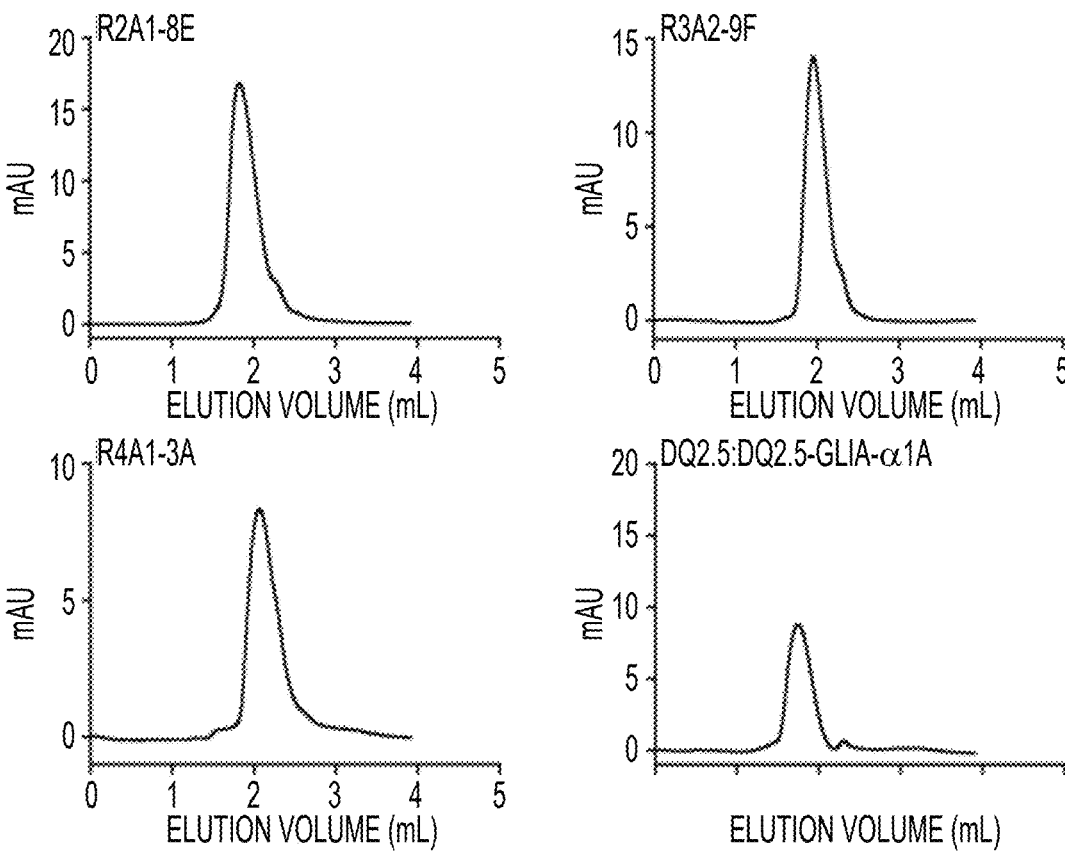
Figures 7C, 7D:
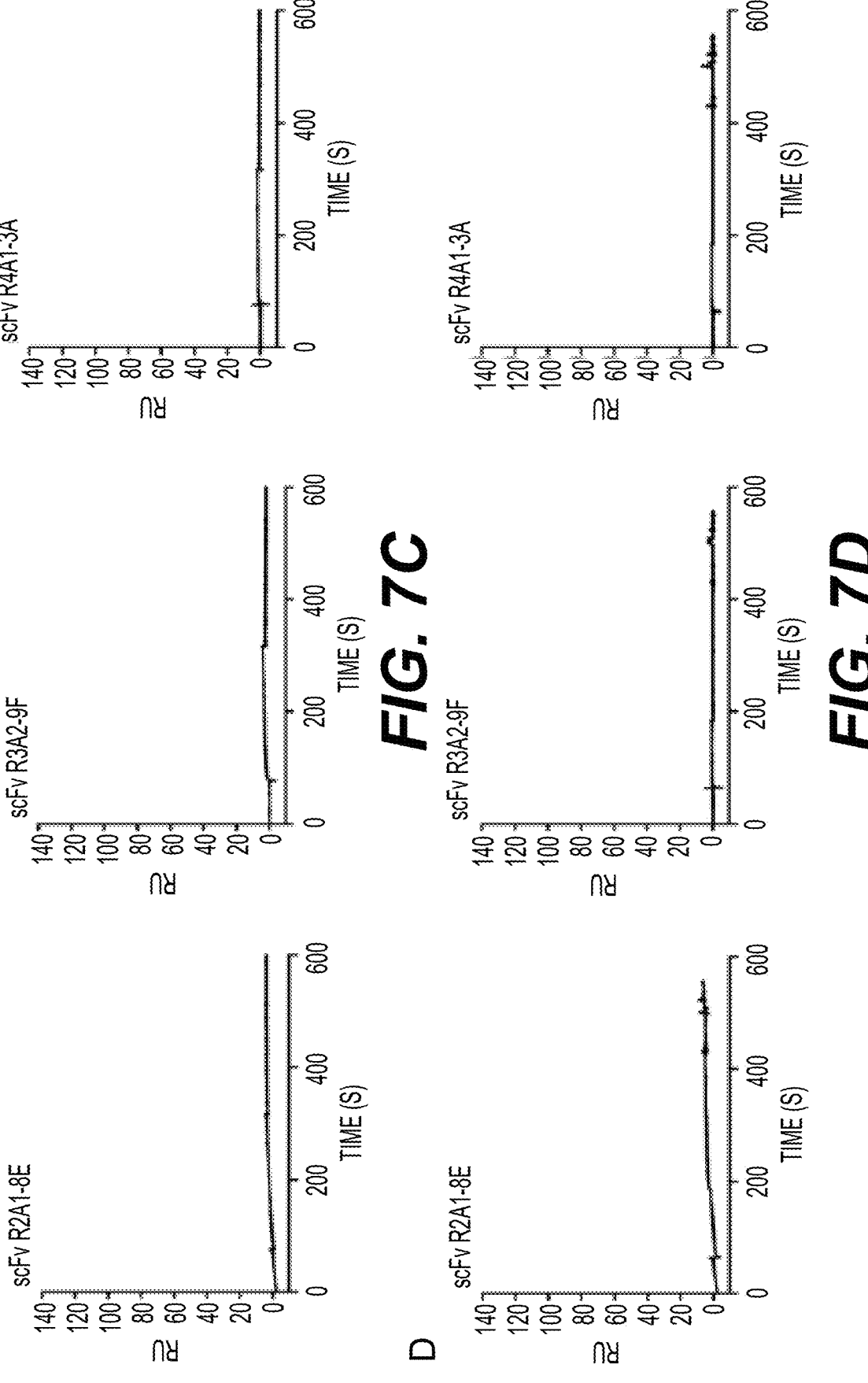
Figure 7E:
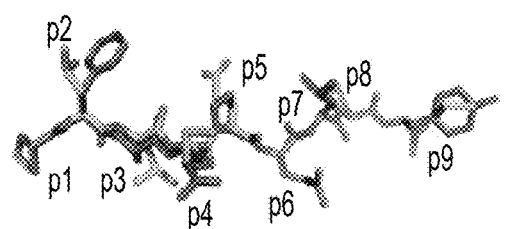
Figure 7F:
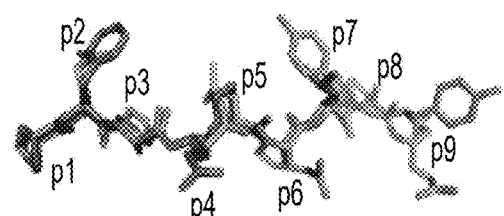

FIGS. 6A-6C. DQ2.5-glia-α1a presenting PCs express TG2-specific IgA and MHC class II. (FIGS. 6A and 6B) PC subsets were sorted by flow cytometry from single-cells suspensions from HLA-DQ2.5$^+$ UCD patients (n=3) all with positive serum anti-TG2 IgA titers and with marsh score 3B/C. (FIG. 6A) Representative micrographs of sorted PCs subsets as indicated. Two individual cells within each group are shown (FIG. 6B) Representative TG2-specific ELISPOT using the sorted PC subsets as indicated. TG2-specific IgA autoantibodies were captured onto TG2-coated plates and detected using AP-conjugated anti-IgA Ab. T cells were used as negative control. (FIG. 6C) Percentage MHC class II expression among APC present in single-cell suspensions from HLA-DQ2.5$^+$ UCD patients (n=4). Each data point represents an individual subject; Mo, monocytes; Mφ, macrophages; two-tailed p-values from unpaired t-test; *, P≤0.05; , P≤0.01; *, P≤0.001; ****, P≤0.0001; ns, not significant.

FIGS. 7A-7F. Validation of purified scFv clones and SPR binding analysis to control pMHCs. The 11 unique scFv clones were expressed and purified from *E. coli* periplasmic fractions. (FIG. 7A) SDS-PAGE gel analysis of the scFv clones which specifically bound DQ2.5:DQ2.5-glia-α1a. Gels were run after purification by IMAC and size exclusion chromatography under non-reducing and reducing conditions. scFv size of approx. 30 KDa is indicated. (FIG. 7B) Analytical gel filtration profiles of the candidate scFv clones and HLA-DQ2.5:DQ2.5-glia-α1a as indicated after a freeze/thaw cycle as the samples were subjected to prior to SPR analysis. (FIGS. 7C and 7D) Representative SPR sensograms of the candidate scFv clones for binding to (FIG. 7C) HLA-DQ2.5:CLIP2 (n=2) and (FIG. 7D) HLA-DQ2.5: DQ2.5-glia-α2 (n=2). (FIGS. 7E and 7F) Overlays of the DQ2.5-glia-α1a peptide with (FIG. 7E) CLIP2 and (FIG. 7F) DQ2.5-glia-α2. Peptide sequences are indicated and the residues differing are underlined. Based on the crystal structures of HLA-DQ2.5:DQ2.5-glia-α1a (PDB: 1S9V) and HLA-DQ2.5:DQ2.5-glia-α2 (PDB: 4OZH) [Kim, C. Y., et al., 2004; Petersen, J., et al., 2014].

Figure 8A:
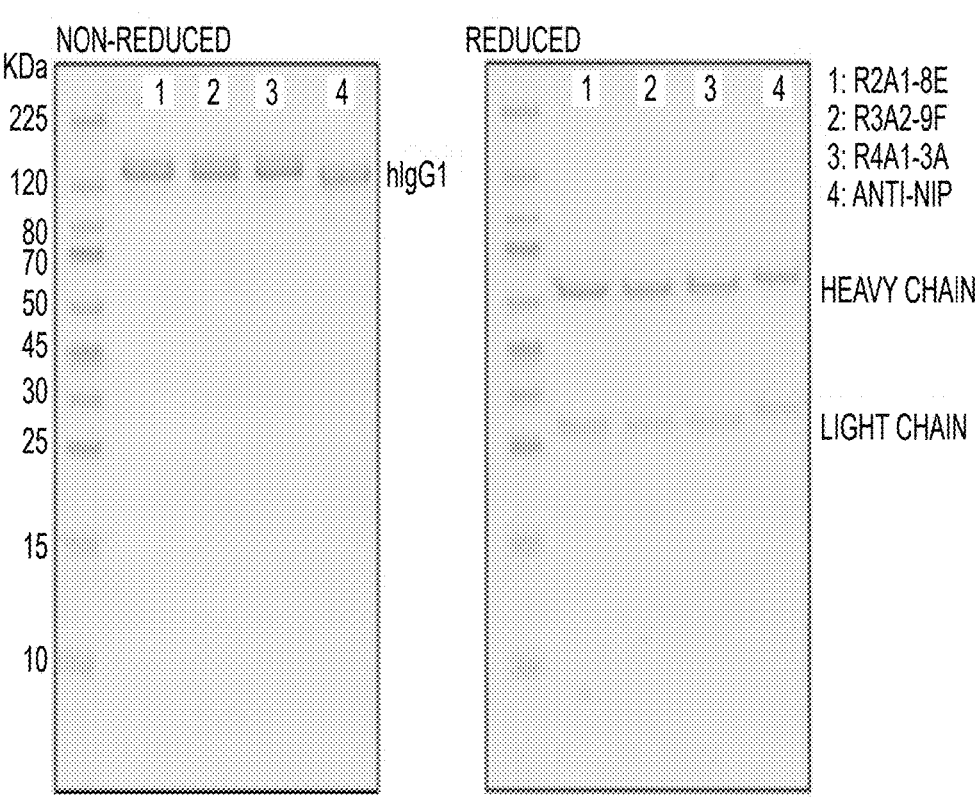
Figure 8B:
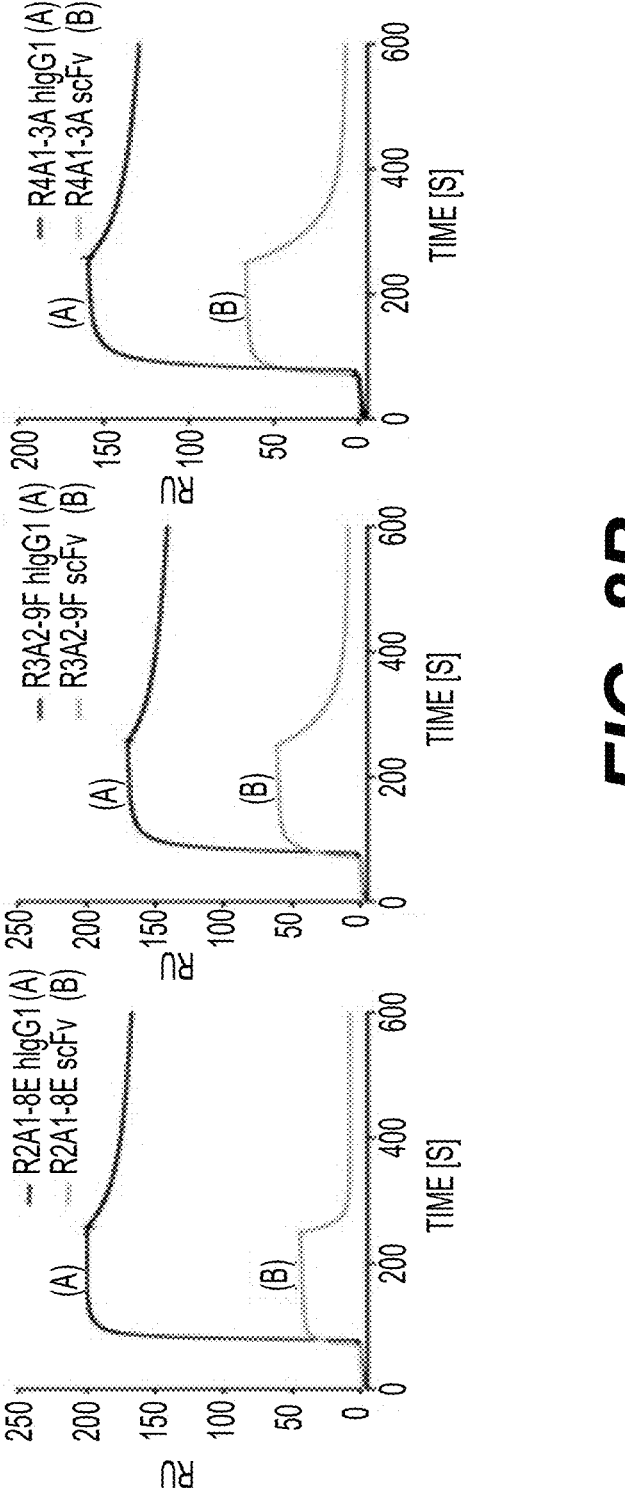

FIGS. 8A-8B. Reformatting of candidate clones to hIgG1 and SPR binding analysis. The three specific clones were reformatted to hIgG1, expressed by transient transfection of human 293E cells and purified from supernatants along with isotype control hIgG1 mAb (anti-NIP). (FIG. 8A) SDS-PAGE gel of purified hIgG1 mAbs run under non-reducing and reducing conditions. Appropriate bands at approx. 150 KDa for full-length hIgG1 and bands at 50 KDa and 23 KDa (reduced heavy and light chains, respectively) are indicated. (FIG. 8B) SPR sensograms of hIgG1 mAbs along with the corresponding scFv fragments were run over HLA-DQ2.5: DQ2.5-glia-α1a to validate gain in functional affinity after reformatting to full-length mAbs.

FIGS. 9A-9E. Fine-specificity assessment. (FIG. 9A) Flow cytometric analysis of A20 B cells transduced to express HLA-DQ2.5 with covalently coupled DQ2.5-glia-α1a or CLIP2 peptides stained with biotinylated mAb 2.12.E11 or isotype control mAb, followed by RPE-conjugated streptavidin (n=2). (FIG. 9B) Flow cytometric assessment of the pMHC expression level of the panel of A20 B cells transduced with either HLA-DQ2.5 or HLA-DQ2.2 with covalently coupled peptide. Q indicated native (glutamine) DQ2.5-glia-α1a epitope. Unless specified, all epitopes are in the deamidated forms. All cells were stained with biotinylated mAb 2.12.E11 followed by streptavidin-RPE (n=2). (FIGS. 9C and 9D) Representative SPR sensograms showing binding to (C) HLA-DQ2.5:DQ2.5-glia-ω1 (n=2) and (D) HLA-DQ2.2:DQ2.5-glia-α1a (n=1) after capture of pHLA on sensor chips and injection of scFv clones as indicated. (FIG. 9E) SPR binding analysis of the DQ2 conformational-specific mAb SPV-L3 to evaluate the conformational integrity of HLA-DQ2.5:DQ2.5-glia-α1a, HLA-DQ2.5:DQ2.5-glia-ω1, HLA-DQ2.5:DQ2.5-glia-ω2, and HLA-DQ2.2:DQ2.5-glia-α1a as indicated after binding experiments.

Figure 3A:
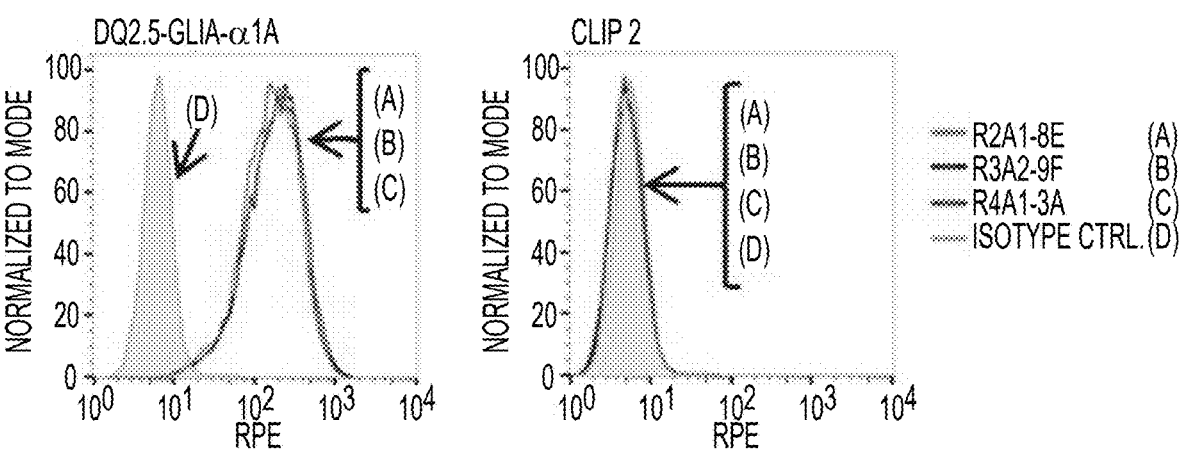
Figure 3B:
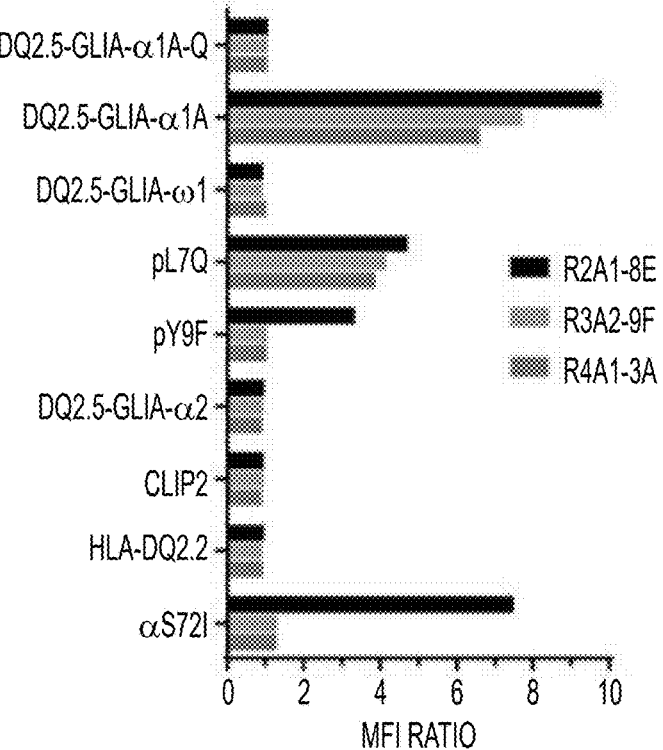
Figures 10A, 10B, 10C:
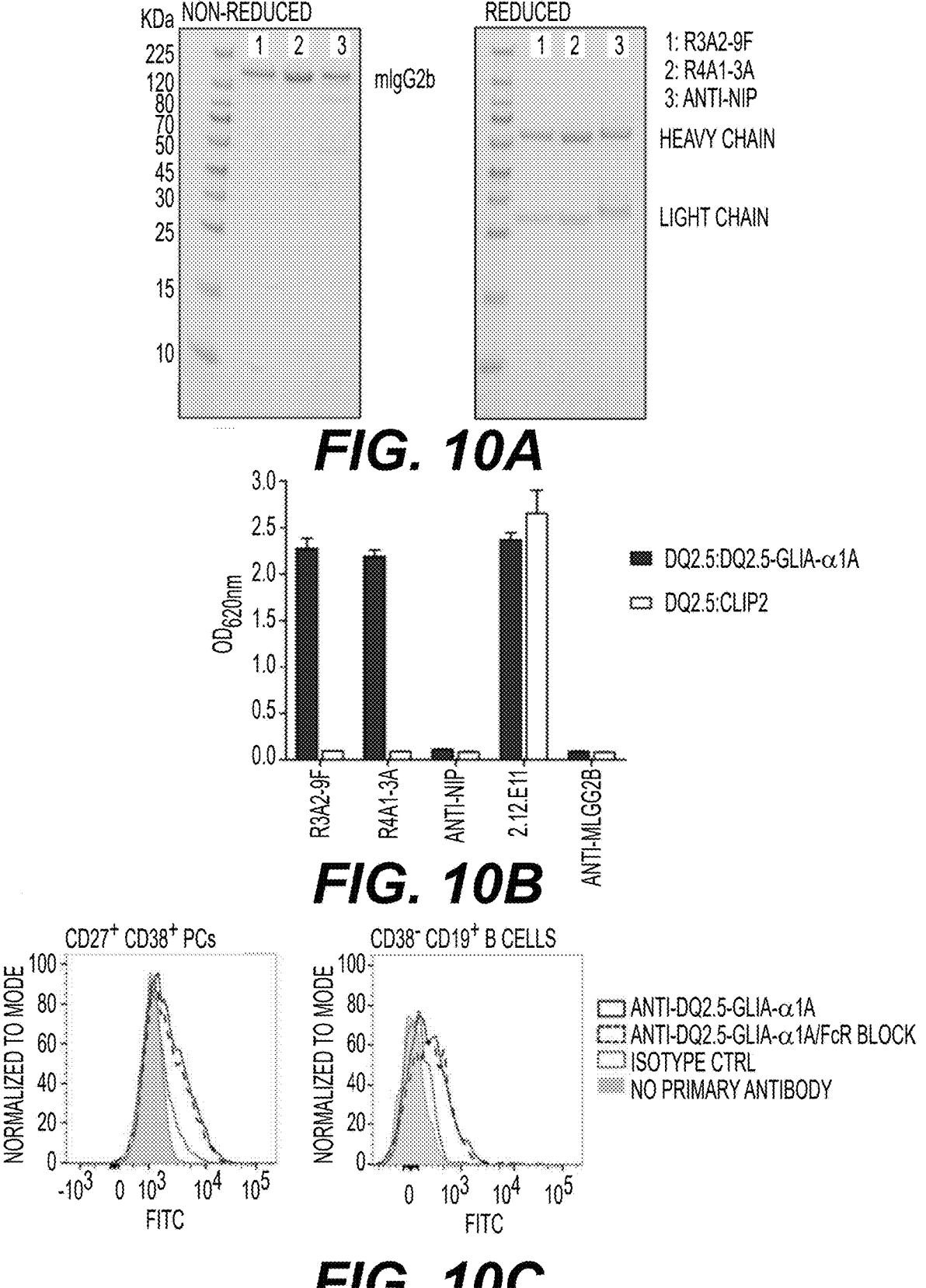

FIGS. 10A-10C. Construction of mIgG2b mAbs and flow cytometric analysis of single-cell suspensions from CD patient biopsies. (FIG. 10A) SDS-PAGE gels of the mAbs R3A2-9F and R4A1-3A and isotype control mAb after reformatting to mIgG2b and purification from supernatants of transfected HEK293E cells. Full-length mIgG2b of approx. 150 KDa run under non-reducing conditions and separated heavy and light chains at approx. 50 KDa and 23 KDa run under reducing conditions are indicated. (FIG. 10B) Representative ELISA showing retained specificity of mIgG2b mAbs R3A2-9F and R4A1-3A after reformatting (n=2). mAb 2.12.E11 was included to control pMHC capture levels. (FIG. 10C) The figure is based on FIG. 3B showing detection of HLA-DQ2.5:DQ2.5-glia-α1a using mAb R3A2-9F with or without use of FcR block. Single-cell suspensions of intestinal biopsies from 3 patients all being HLA-DQ2.5$^+$ with Marsh 3B/C were run in parallel.

FIGS. 11A-11B. Flow cytometric gating strategy and analysis of PCs and B cells presenting DQ2.5-glia-α1a peptide. Single-cell suspensions were prepared from intestinal biopsies, cells were stained with indicated antibodies and immediately analyzed by flow cytometry. (FIG. 11A) Representative gating strategy for detection of gluten peptide presentation is shown. FSC-A, FSC-H and SSC-W were used to gate out doublet cells. (FIG. 11B) Stratification of the control patients among the CD45$^+$ PCs, CD45 PCs and B cells from FIG. 4B. Ctrl HLA-DQ2.5$^+$ (n=5), Ctrl HLA-DQ2.5 (n=5), UCD HLA-DQ2.5$^+$ (n=18), TCD HLA-DQ2.5$^+$ (n=3), UCD HLA-DQ8$^+$ (n=1), and UCD HLA-DQ2.2$^+$ (n=1). mIgG2b mAb R3A2-9F or R4A1-3A were used for detection and percent positive cells was determined relative to use of secondary antibody alone. Each data point represents an individual subject; non-CD ctrl patients did not have mucosal alterations; red (i.e. horizontal) bars indicate mean percentage.

FIG. 12. Gating strategy for detection of MHC class II on APC subsets. Single-cell suspensions prepared from intestinal biopsies were stained with indicated antibodies and immediately analyzed by flow cytometry. Representative gating strategy for detection of MHC class II on PCs, B cells and bulk DCs, monocytes and macrophages are shown. HLA staining (red) is overlaid isotype control staining (black). FSC-A and FSC-H were used to gate out doublet cells.

Figure 13:
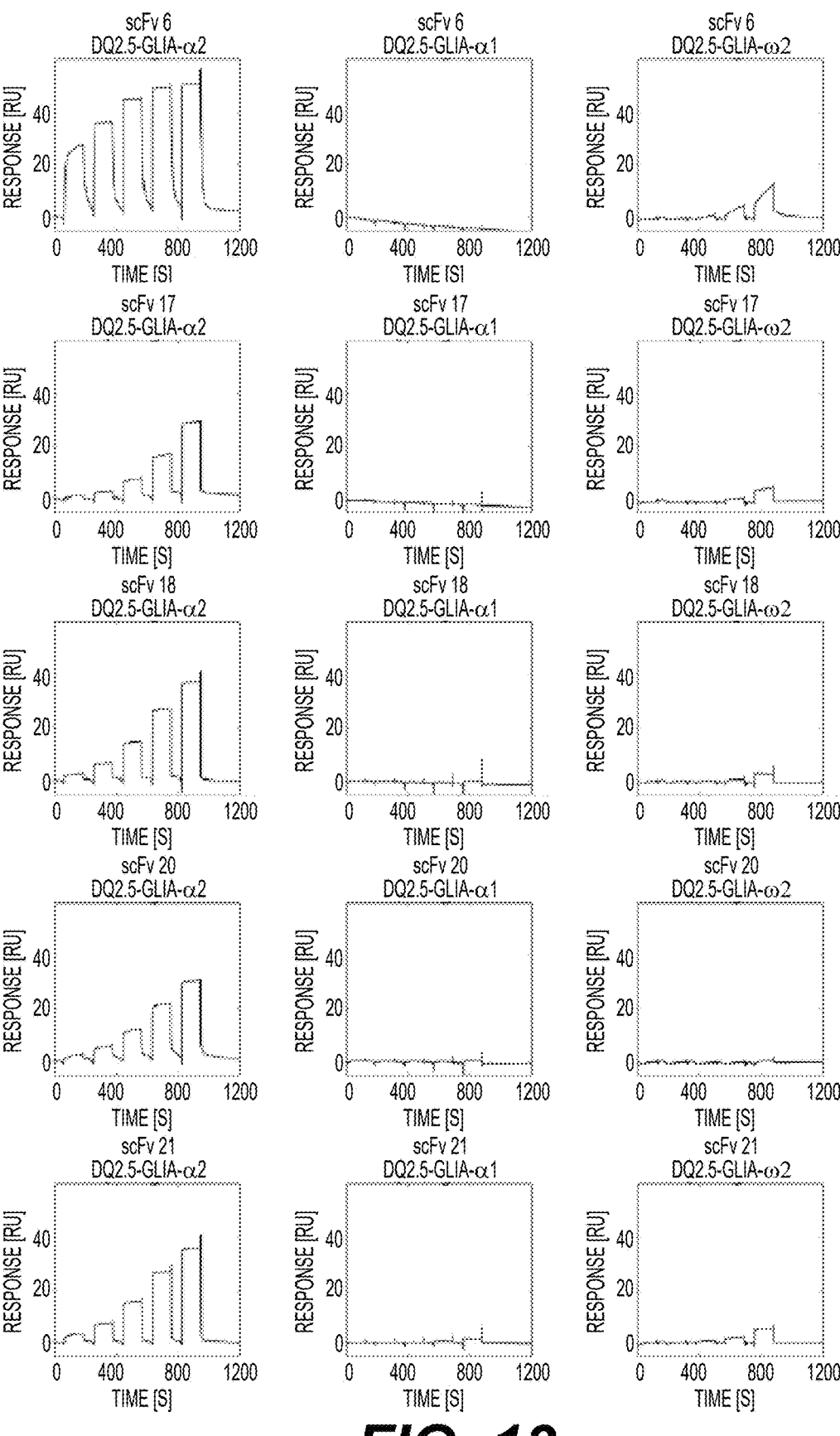
Figure 13:
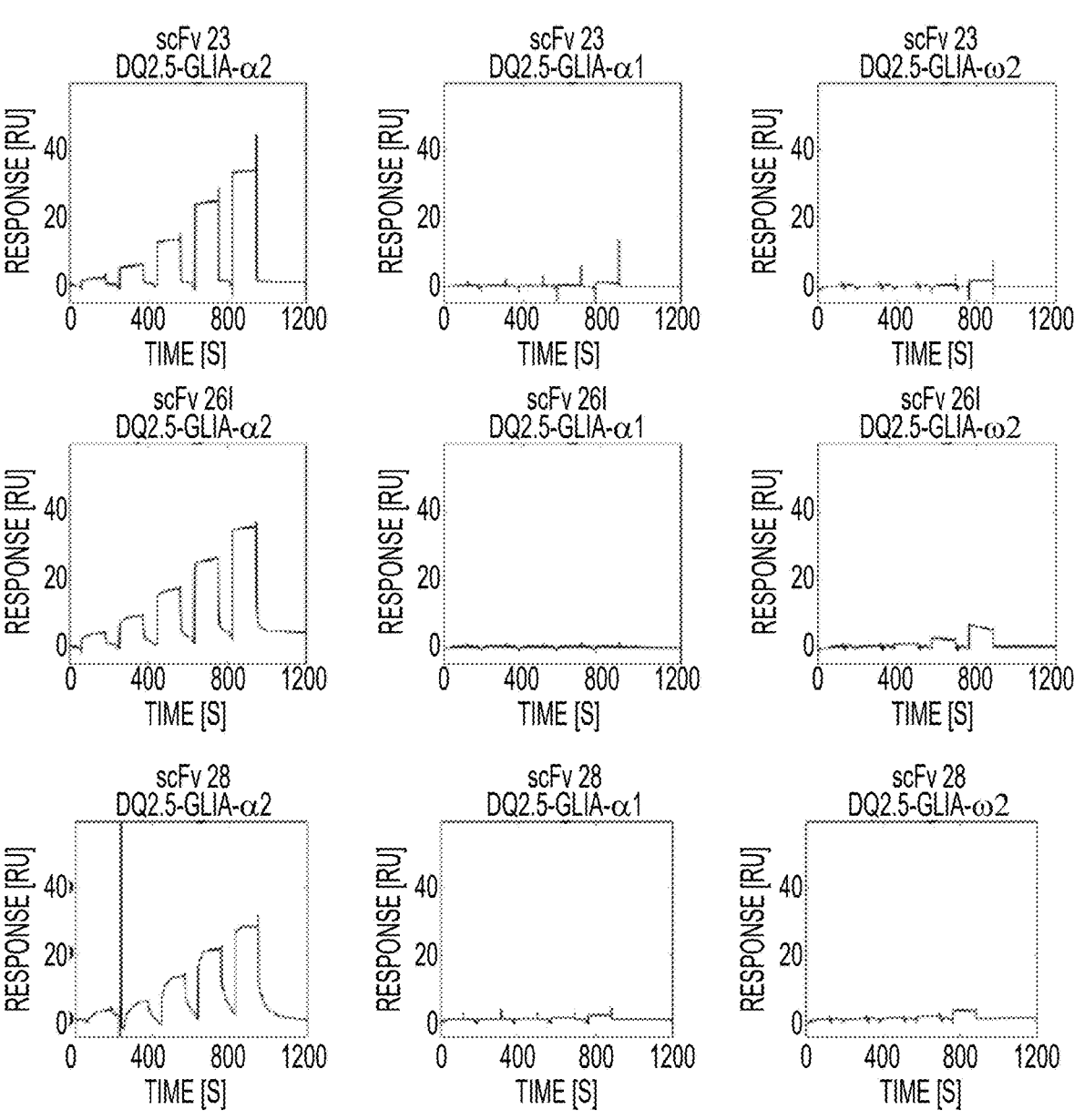

FIG. 13. SPR experiments with candidate scFvs: scFvs were analyzed in SPR using a single cycle kinetics method. They were tested for binding to HLA-DQ2.5:DQ2.5-glia-α2. They were tested for cross-reactivity with HLA-DQ2.5: DQ2.5-glia-α1a and HLA-DQ2.5:DQ2.5-ω2. The scFv concentrations varied for different candidates but were the same for all three antigens.

Figure 14A:
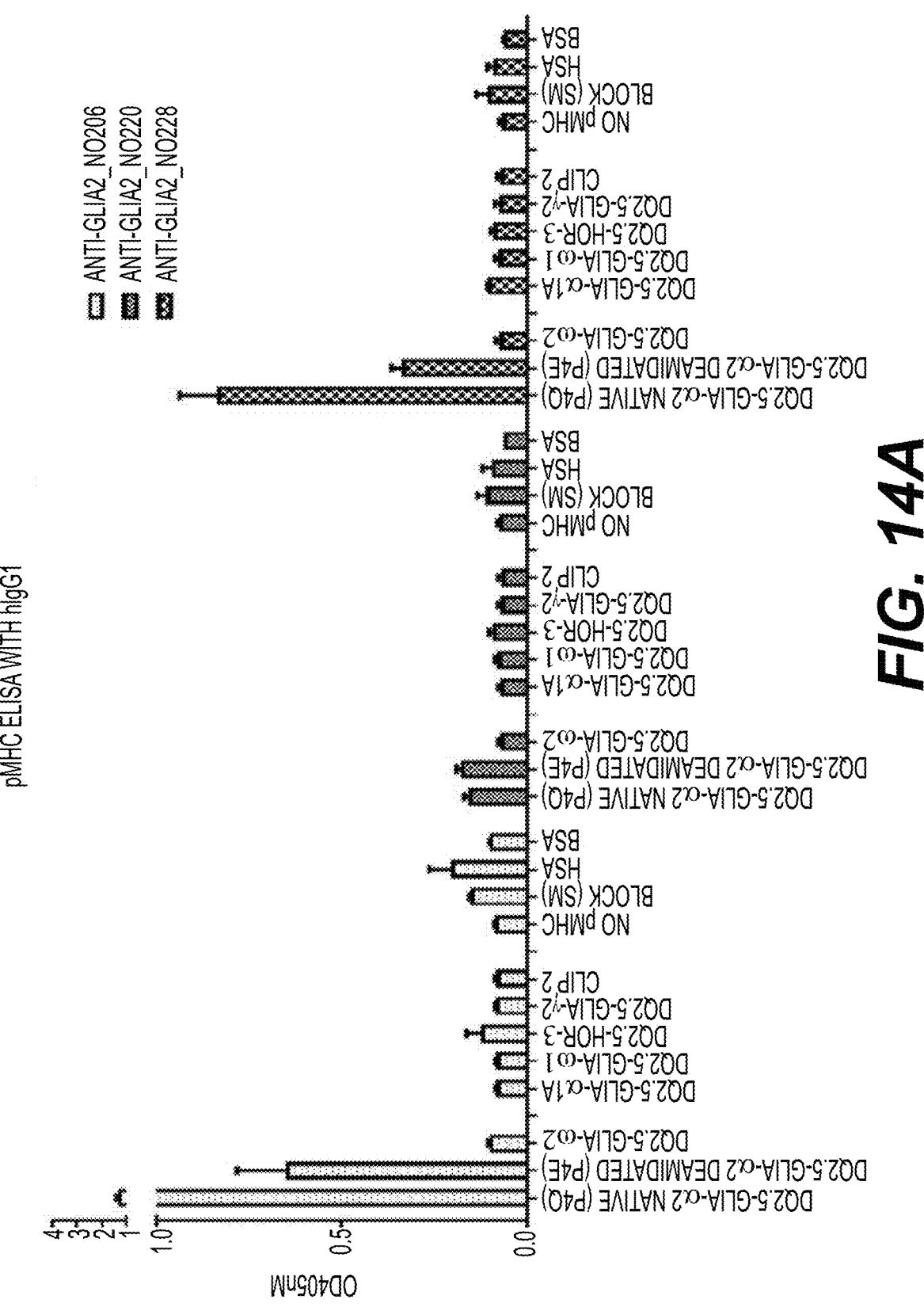
Figures 14B, 14C:
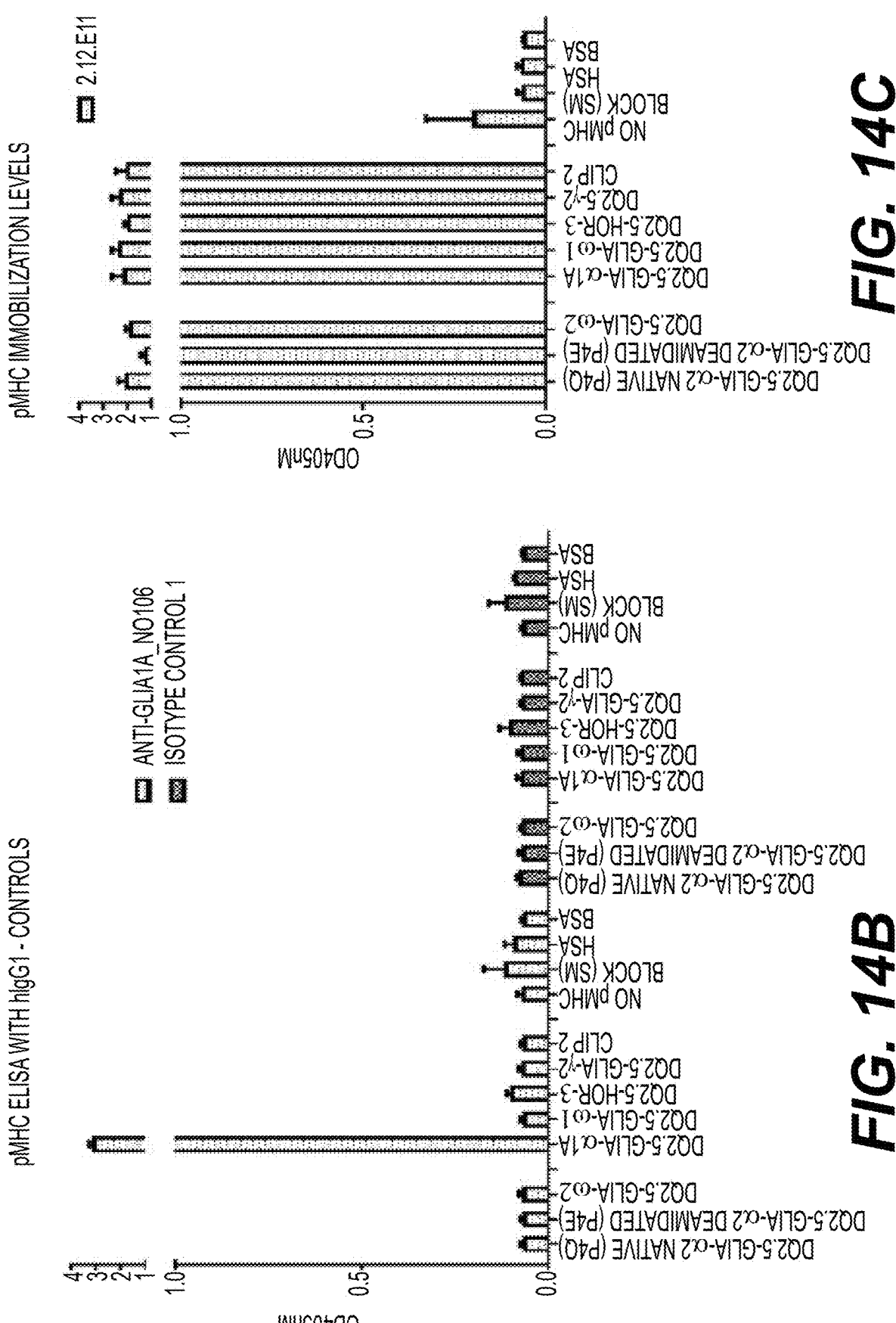

FIGS. 14A-14C. Different HLA-DQ2.5:gluten peptide complexes and HLA-DQ2.5:CLIP2 were used in ELISA for specificity analysis of HLA-DQ2.5:DQ2.5-glia-α2 antibodies. The peptides are annotated according to Sollid, L. M., et al., (*Immunogenetics*, 2012, 64(6): 455-460) (FIG. 14A). An antibody specific for HLA-DQ2.5:DQ2.5-glia-α1a and an antibody with irrelevant specificity were used as positive and negative controls (FIG. 14B). mAb 2.12.E11 specific for the DQ2 β-chain was included to control pMHC capture levels (FIG. 14C). Error bars illustrate mean±SD of duplicates. The biotinylated pMHCs captured were: HLA-DQ2.5: DQ2.5-glia-α2 (native (P4Q)), HLA-DQ2.5:DQ2.5-glia-α2 (deamidated P4E), HLA-DQ2.5:DQ2.5-glia-ω2, HLA-DQ2.5:DQ2.5-α1a, HLA-DQ2.5:DQ2.5-hor3, HLA-DQ2.5:DQ2.5-glia-γ2, and HLA-DQ2.5:CLIP2. HSA=human serum albumin; BSA=bovine serum albumin.

Figure 15:
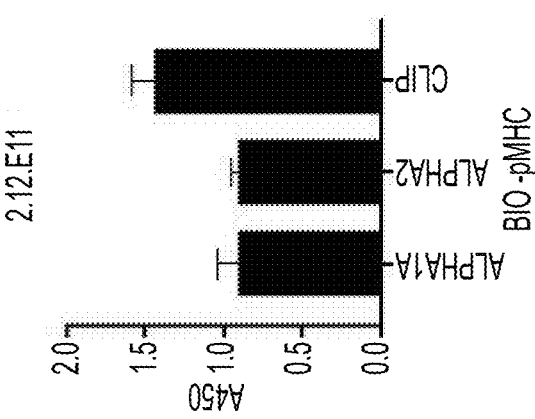
Figure 15:
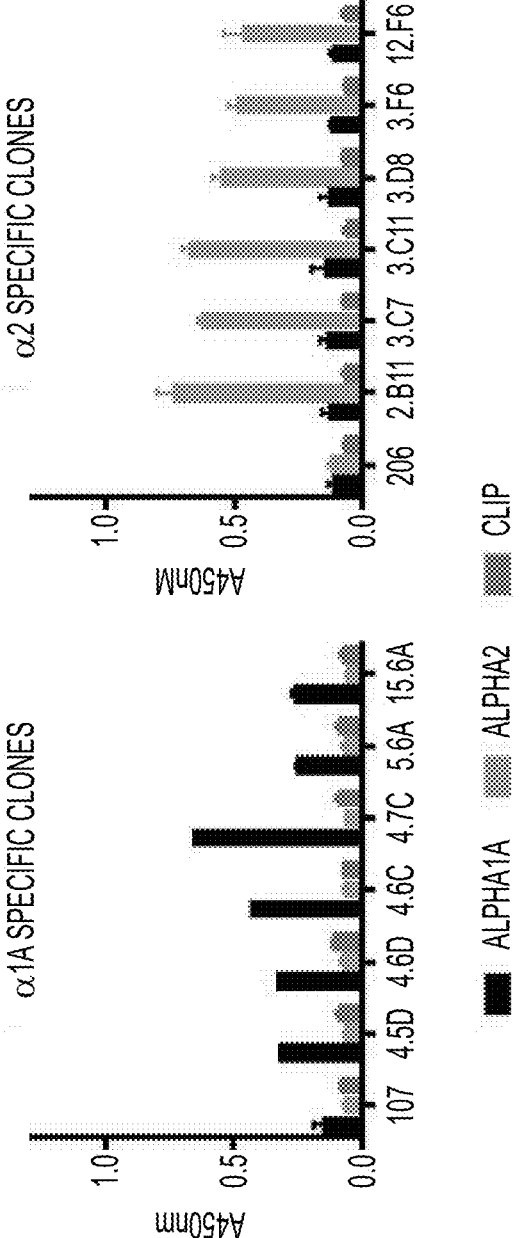

FIG. 15. ELISA against different pMHC complexes with affinity matured clones (scFv): Binding of the affinity matured antibodies to HLA-DQ2.5:CLIP, HLA-DQ2.5:DQ2.5-glia-α1a, and HLA-DQ2.5:DQ2.5-glia-α2. 2.12.E11 was used to control for functionality of pMHC molecules and similar levels of pMHC immobilization. In each set of 3 bars, moving from left to right, bar 1 represents HLA-DQ2.5:DQ2.5-glia-α1a, bar 2 represents HLA-DQ2.5:DQ2.5-glia-α2, bar 3 represents HLA-DQ2.5:CLIP.

Figure 16:
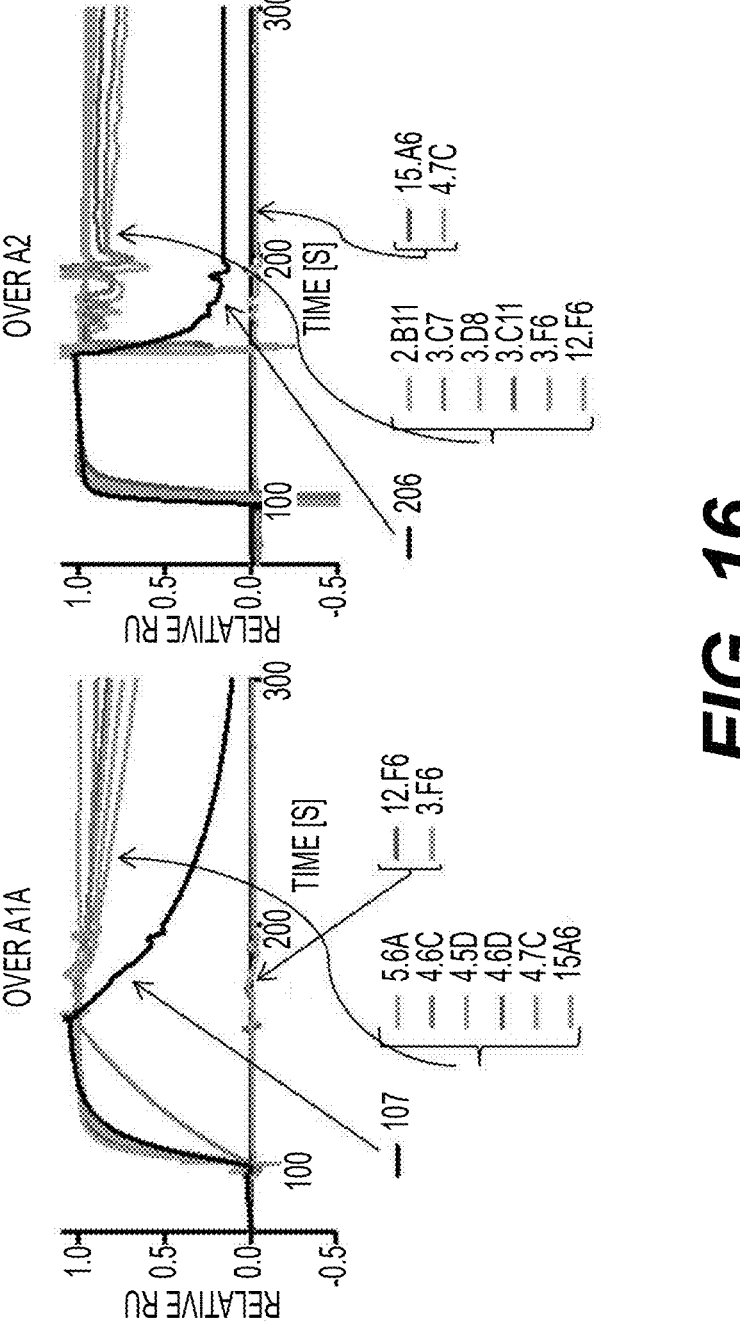

FIG. 16. SPR experiments with affinity matured clones (scFv): Binding kinetics of the affinity matured variants towards the two gliadin complexes (HLA-DQ2.5:DQ2.5-glia-α1a (over α1a) and HLA-DQ2.5:DQ2.5-glia-α2 (over a2)) was analysed in SPR. All curves are normalized to the mother clones. The affinity matured scFv bound their targets and showed different off-rates. All of them showed improved off-rates compared to the mother clone. None of them was cross-reactive to the other α-gliadin complex (only depicted for 12.F6, 3.F6, 15. A6, and 4.7C).

Figures 17A, 17B, 17C, 17D:
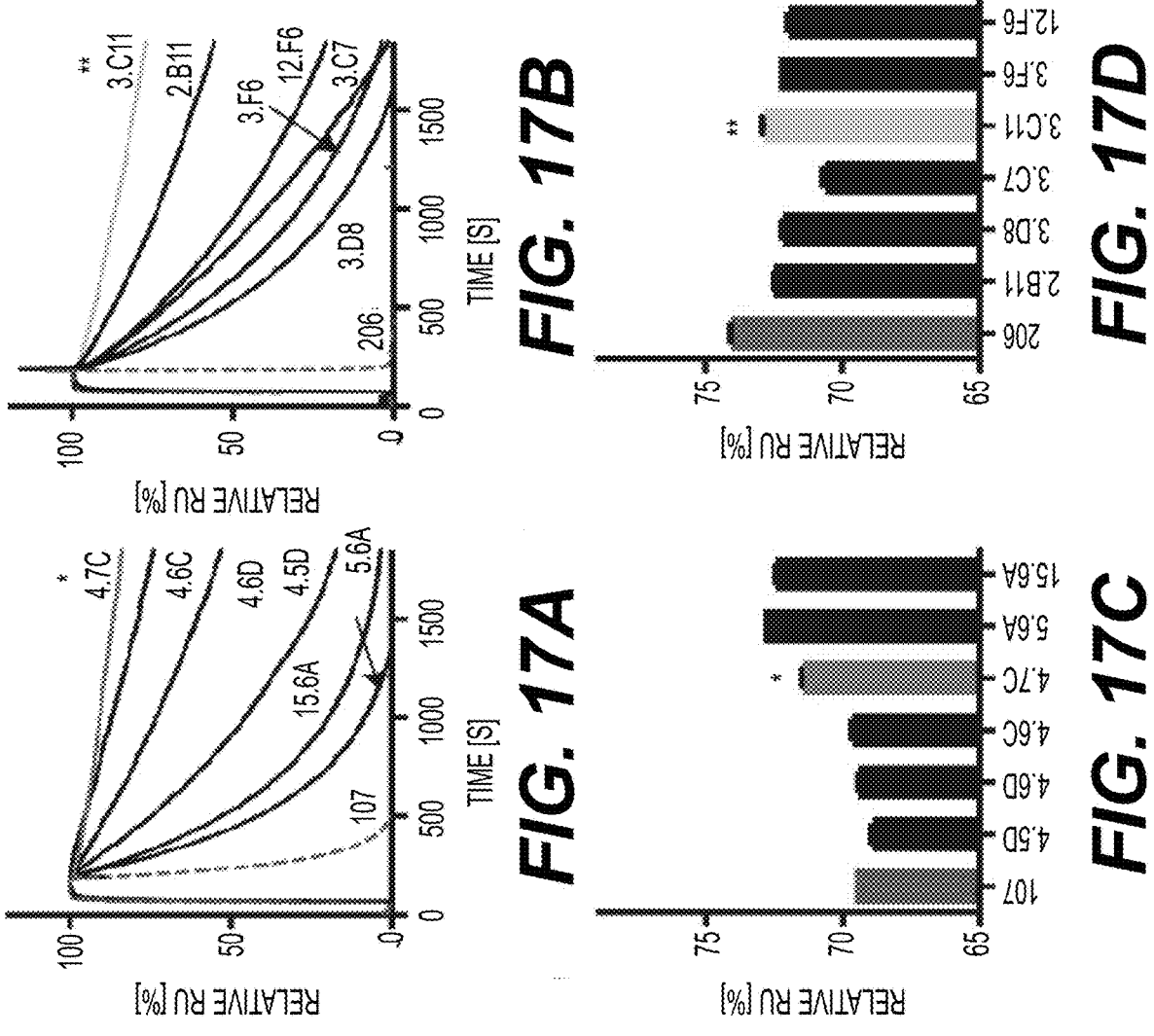
Figure 17E:
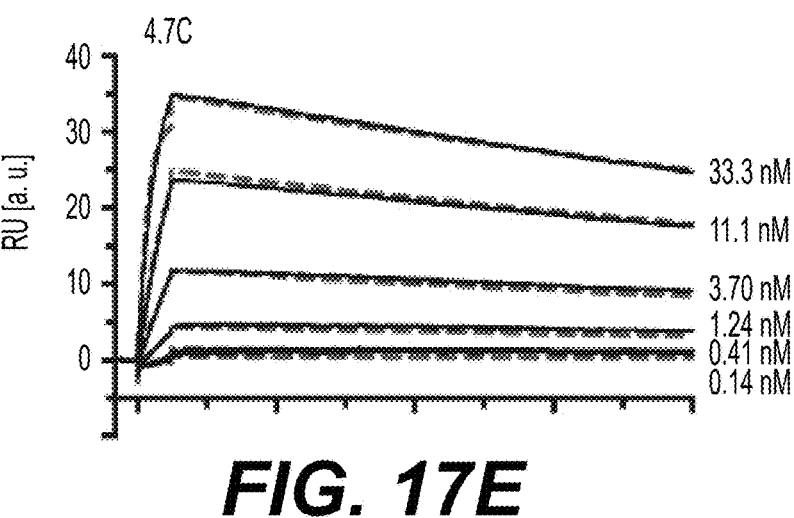
Figure 17F:
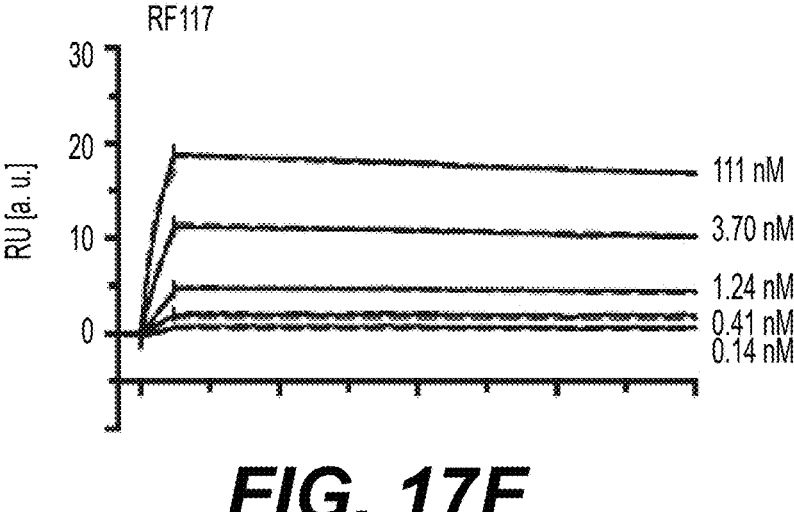
Figure 17G:
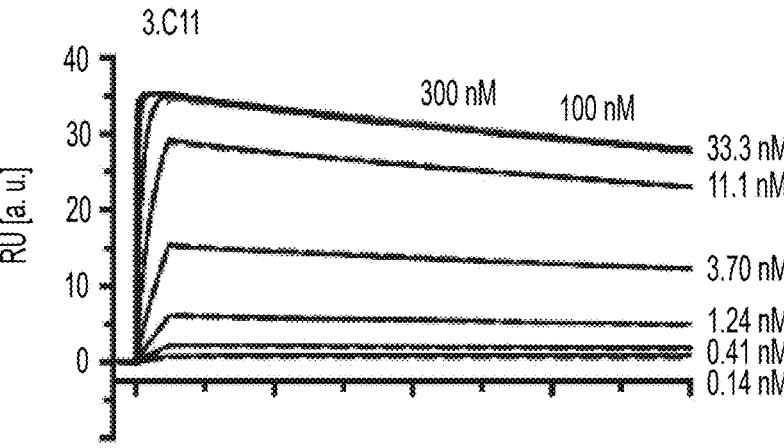
Figure 17H:
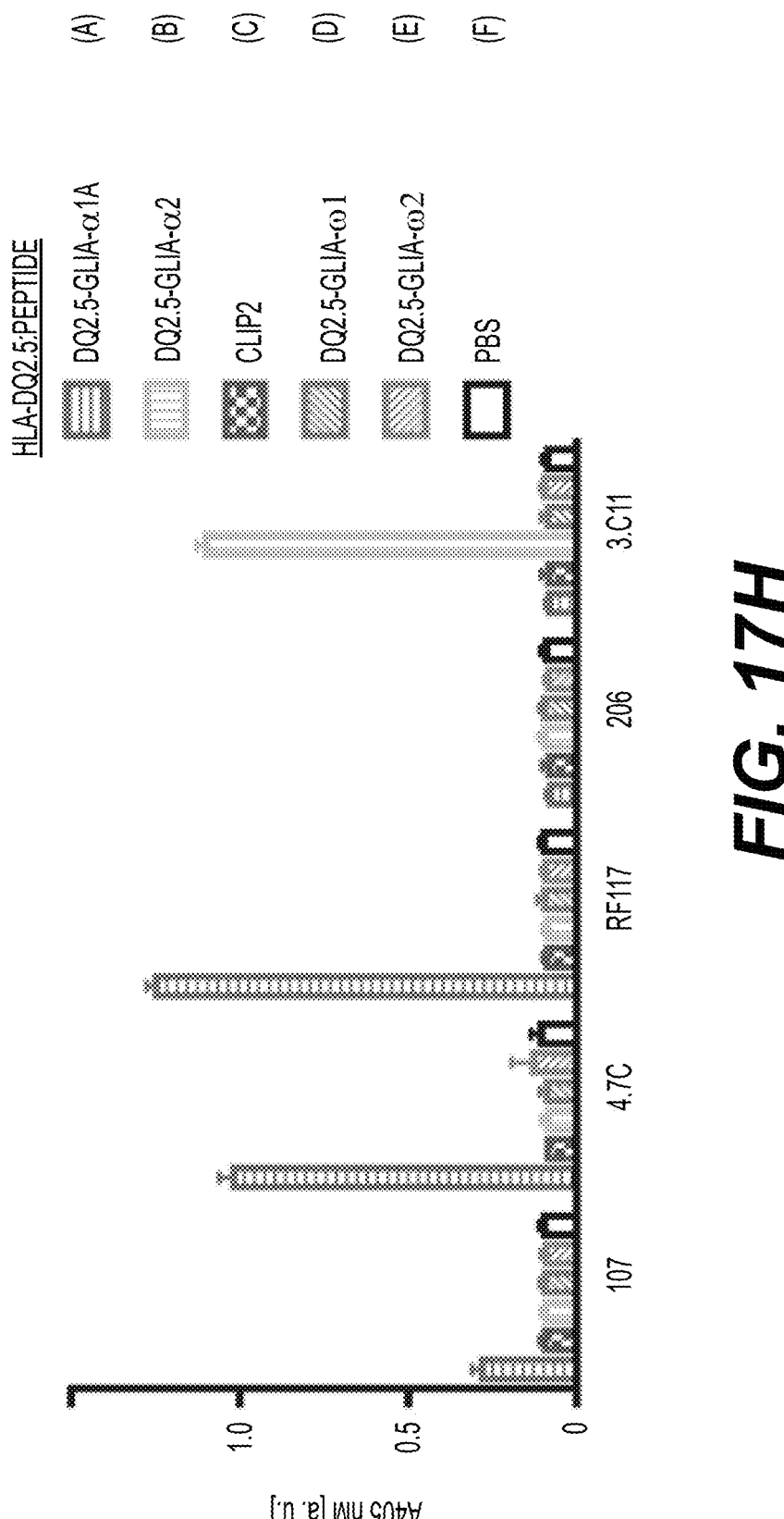

FIGS. 17A-17H. Biophysical characterization of antibodies. FIGS. 17A+B: Fab fragments were ranked based on off-rates in SPR, with the clone 4.7C marked with a single asterisk (*) and the clone 3.C11 marked with a double asterisk () (FIG. 17A: binding to HLA-DQ2.5:DQ2.5-glia-α1a, FIG. 17B: binding to HLA-DQ2.5:DQ2.5-glia-α2). FIGS. 17C+D**: Melting temperatures of the mother clones and the affinity matured Fab fragments with the clone 4.7C marked with a single asterisk (*) and the 3.C11 clone marked by a double asterisk () (FIG. 17C: HLA-DQ2.5:DQ2.5-glia-α1a, FIG. 17D: HLA-DQ2.5:DQ2.5-glia-α2). FIGS. 17E-G: Representative sensorgrams of 4.7C (FIG. 17E), and RF117 (FIG. 17F) binding to HLA-DQ2.5:DQ2.5-glia-α1a, and 3.C11 binding to HLA-DQ2.5:DQ2.5-glia-α2 (FIG. 17G) (n≥2). RF117 denotes a mutant combining the sequence of 5.6A with the CDR H3 of 4.7C. FIG. 17H**: The leads were reformatted to full-length hIgG1 and analyzed in ELISA against a panel of related soluble peptide:HLA-DQ2.5 complexes. In each set of 6 bars, from left to right, bar 1 is (a), bar 2 is (c), bar 3 is (b), bar 4 is (d), bar 5 is (e) and bar 6 is (f).

Figures 18A, 18B:
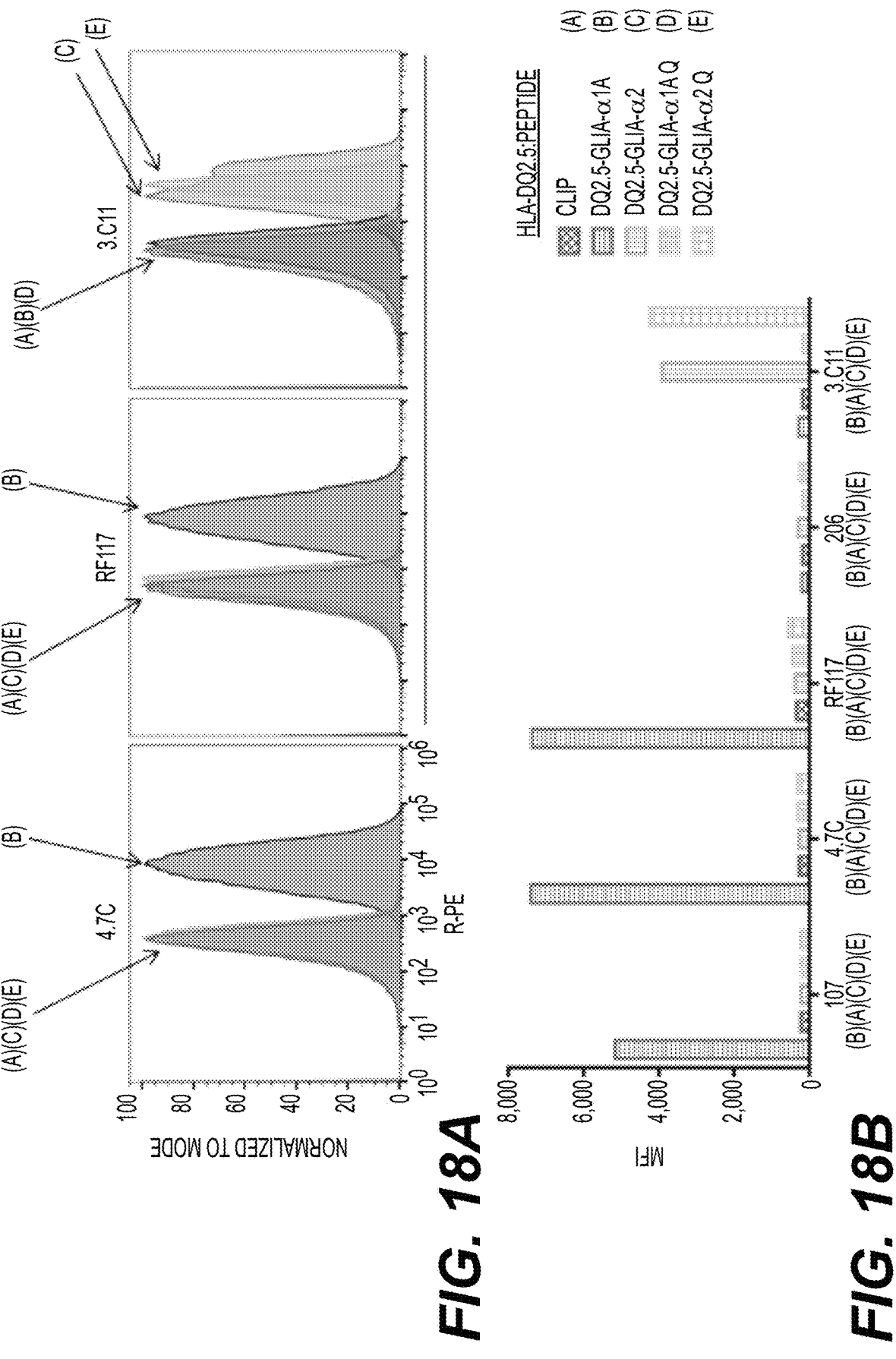

FIGS. 18A-18B. Antibodies stain engineered A20 mouse B cells. A20 cells were engineered to express HLA-DQ2.5 with covalently linked peptide. They were stained with the mother clones and the high affinity variants (n=2). FIG. 18A: Representative histograms are shown for the high affinity variants. FIG. 18B: Median fluorescence intensities are shown for all antibodies.

Figure 19A:
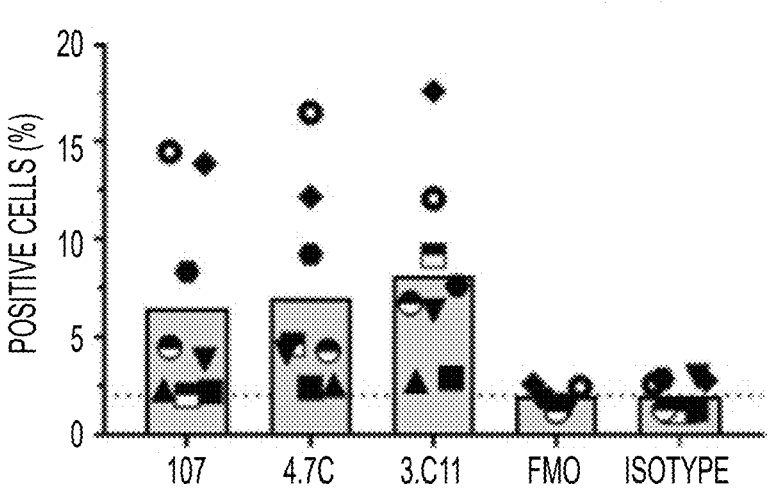
Figure 19B:
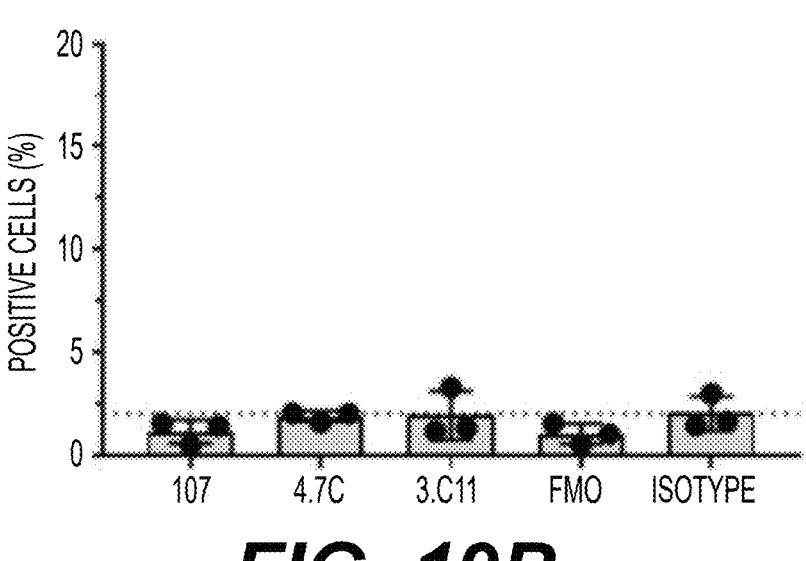

FIGS. 19A-19B. Antibodies stain plasma cells from celiac disease small intestinal biopsies. Single cell suspensions were prepared from either untreated HLA-DQ2.5+ celiac disease patients (i.e. on a gluten-containing diet, n=8) or controls with a healthy mucosal histology (n=3). (A and B) Cells were gated as live, large lymphocytes, CD3−, CD11c−, CD14−, CD38+, CD27+, CD19+, CD45+ plasma cells in (FIG. 19A) celiac patients and (FIG. 19B) controls. Bound mIgG2b antibodies were detected with an Alexa-546-conjugated secondary antibody and the frequency of positive cells was calculated and compared to use of an isotype control antibody (isotype). The secondary antibody only (FMO) is also shown. Each celiac disease patient is shown in a unique symbol.

Figure 20A:
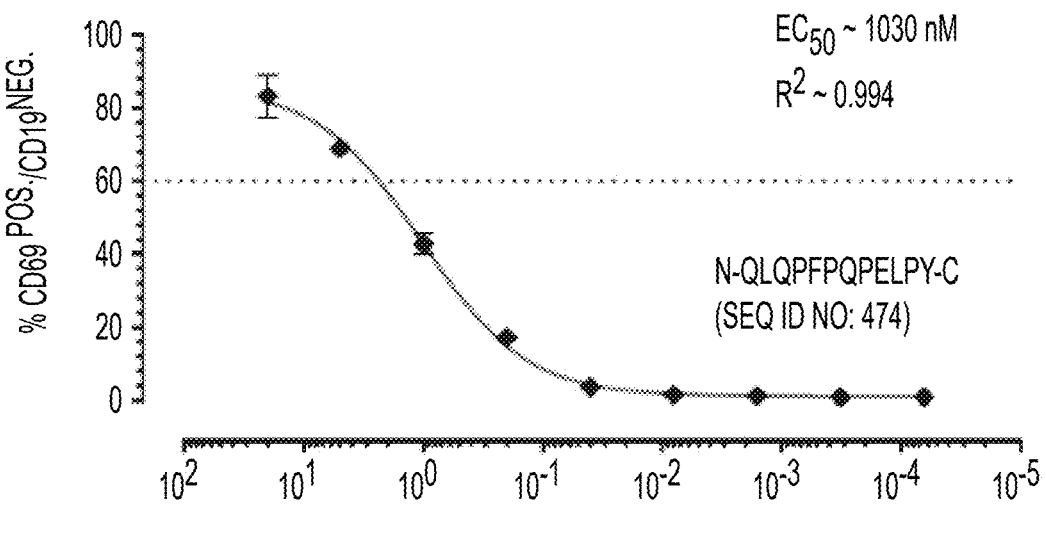
Figure 20B:
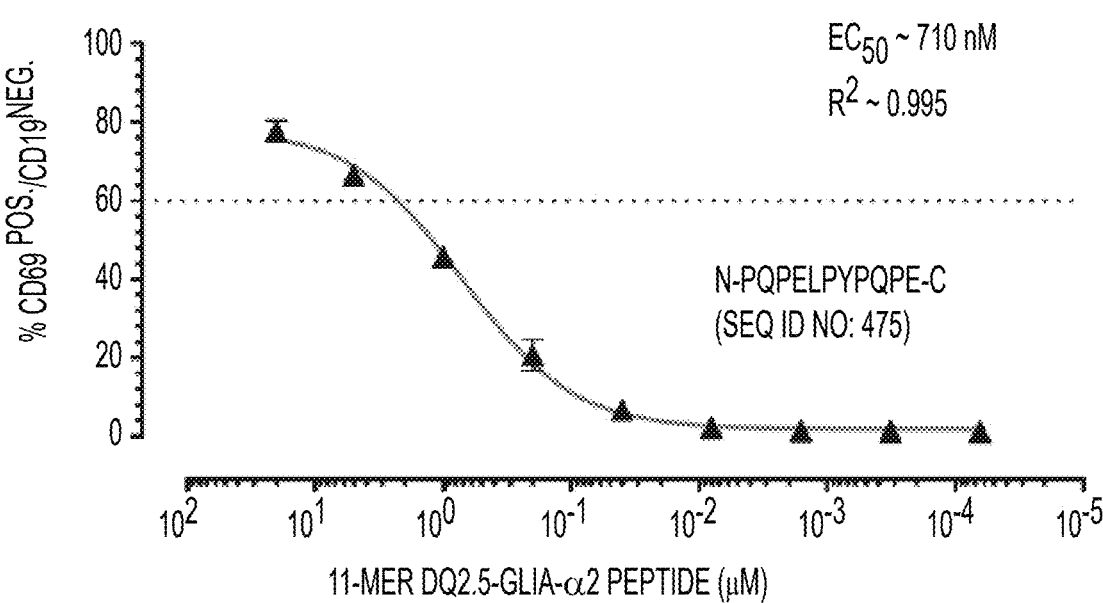
Figure 20C:
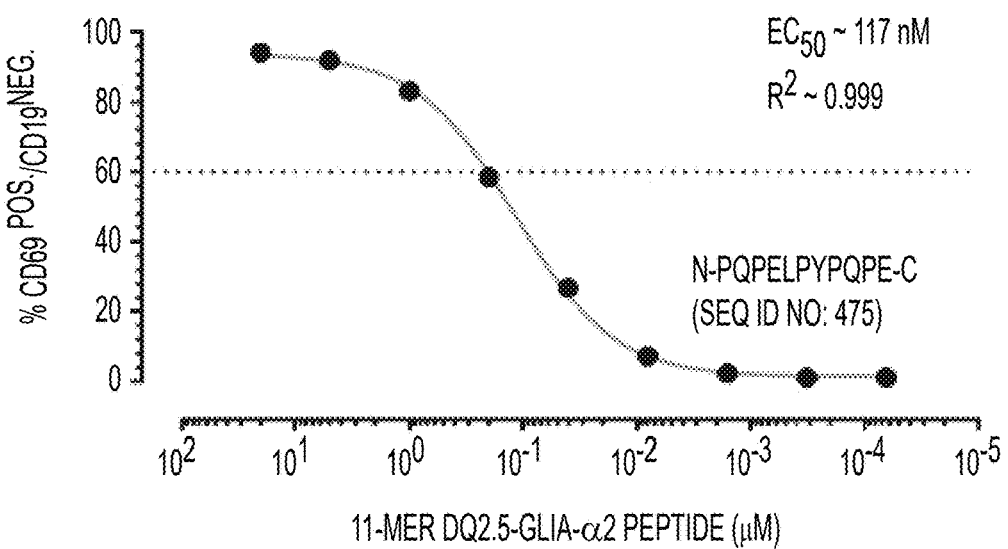

FIGS. 20A-20B. Determination of TCR-reconstructed SKW3 T cell peptide sensitivity and assessment of anti-pMHC mAb inhibition capacity. (FIGS. 20A-20C) Representative dose-response curves (n=2) of T cell activation measured as % CD69-positive cells following co-cultivation of peptide-pulsed B cells (dump gated on CD19 expression)

and the SKW3 T cells 380 (FIG. 20A), S16 (FIG. 20B) and 364 (FIG. 20C). Error bars illustrate mean±SD of duplicates from one of two independent assays, and estimated EC50, quality of fit ($R^2$) values and the peptide used in pulsing are given within each graph. Based on the dose-response curves for each individual T cell, peptide concentrations of the indicated peptides resulting in about 60% activation were chosen baseline for an Ab inhibition assay (FIGS. 20D-20F), where the SKW3-380 (FIG. 20D), SKW3-S16 (FIG. 20F) and SKW3-364 (FIG. 20F) were treated as indicated with either 1 μM of the anti-pMHC mAbs, or 0.1 μM pan anti-HLA mAbs. The presented data are given as the % activation normalized to the absolute T cell activation in the absence of Ab, which was set to 100%. Error bars illustrate mean±SD of duplicates.

EXAMPLES

Example 1

Identification of Antibodies that Specifically Bind to HLA-DQ2.5:DQ2.5-Glia-α1a

Results

Phage Selection of Recombinant Antibodies to HLA-DQ2.5 with Bound DQ2.5-Glia-α1a To isolate HLA-DQ2.5:DQ2.5-glia-α1a specific binders, we performed phage selections using a naïve, fully-human scFv-phage library [Loset, G. A., et al., 2005]. We performed four rounds (R1-R4) of selection using recombinant soluble, biotinylated pMHC (peptide MHC complex) with covalently linked peptide. After R3, the polyclonal library outputs showed preferential HLA-DQ2.5:DQ2.5-glia-α1a reactivity compared to HLA-DQ2.5:CLIP2, with a large increase in antigen reactivity from R2 to R3 (FIG. 1A). To remove low affinity clones, we performed a stringent R4 before single-clone scFv binding analysis of R2, R3 and R4 outputs. A total of 75 independent clones reacted preferentially with HLA-DQ2.5:DQ2.5-glia-α1a (Table S1), representing 11 unique clones, with a preferential usage of IGHV6-1, as well as IGKV1-9 and IGKV1-39 (FIG. 1B).

We next expressed and purified all 11 unique scFv clones in *E. coli*(FIGS. 7A and B, data not shown) and performed SPR to analyze binding affinity and specificity using HLA-DQ2.5 with DQ2.5-glia-α1a or the control peptides, DQ2.5-glia-α2 and CLIP2. Several scFvs bound pMHC, and three (R2A1-8E, R3A2-9F (also referred to as 106) and R4A1-3A (also referred to as 107)) bound specifically to HLA-DQ2.5:DQ2.5-glia-α1a with a monomeric affinity ranging in the nanomolar range (FIG. 1C, FIG. 7C-E, Table S2). R3A2-9F was highly enriched, constituting 60 out of 75 binding clones in the soluble scFv screen. Although R3A2-9F and R4A1-3A were found to differ by only one amino acid, R4A1-3A appeared only once among the screened clones (Table S1).

The Selected Antibodies are Highly Specific Towards HLA-DQ2.5:DQ2.5-Glia-α1a

To increase the functional affinity of the interaction, we reformatted and expressed the three binders as human IgG1 (hIgG1) mAbs (FIG. 8A). SPR confirmed pMHC-specific binding and a substantial gain in avidity, resulting in approximately 160-fold increase in half-life (FIG. 8B). To confirm a requirement for DQ2.5-glia-α1a peptide recognition strictly in the context of HLA-DQ2.5, we performed competition ELISA using soluble pMHC and free peptide. Indeed, only soluble HLA-DQ2.5:DQ2.5-glia-α1a, and not peptide alone, competed with the plate-bound complex for binding to the mAbs (FIG. 2A). Of note, DQ2.5-glia-α1a provided as part of a 33mer peptide fragment which binds efficiently to HLA-DQ2.5 [Shan, L., et al., 2002], was not able to inhibit mAb binding to pMHC (FIG. 2B).

Next, we extended the specificity analysis with 7 HLA-DQ2.5-gluten-peptide complexes in ELISA. This panel included common epitopes from γ- and ω-gliadin to which CD patients mount T-cell responses. None of the mAbs bound any of the complexes other than HLA-DQ2.5:DQ2.5-glia-α1a (FIG. 2C), not even the highly similar DQ2.5-glia-ω1, which differs from DQ2.5-glia-α1a in p7 and p9 only. Taken together, these results show that the mAbs exclusively recognize DQ2.5-glia-α1a bound to HLA-DQ2.5 and are not cross-reactive with HLA-DQ2.5 in complex with the other gluten peptides tested.

Mapping Fine-Specificity of the Candidate mAbs

To validate mAb binding to pMHC on cells, we utilized murine A20 B cells transduced with HLA-DQ2.5 with covalently linked DQ2.5-glia-α1a or CLIP2 peptides. When assessed for binding, all mAbs bound specifically to cells displaying the DQ2.5-glia-α1a epitope, while none bound CLIP2 (FIG. 3A and FIG. 9A).

Figure 3C:
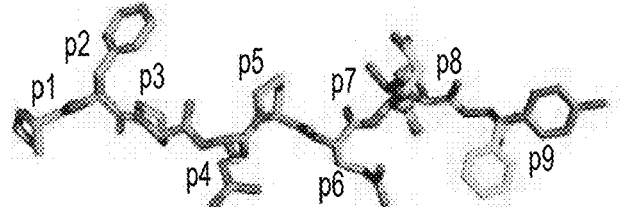
Figure 3D:
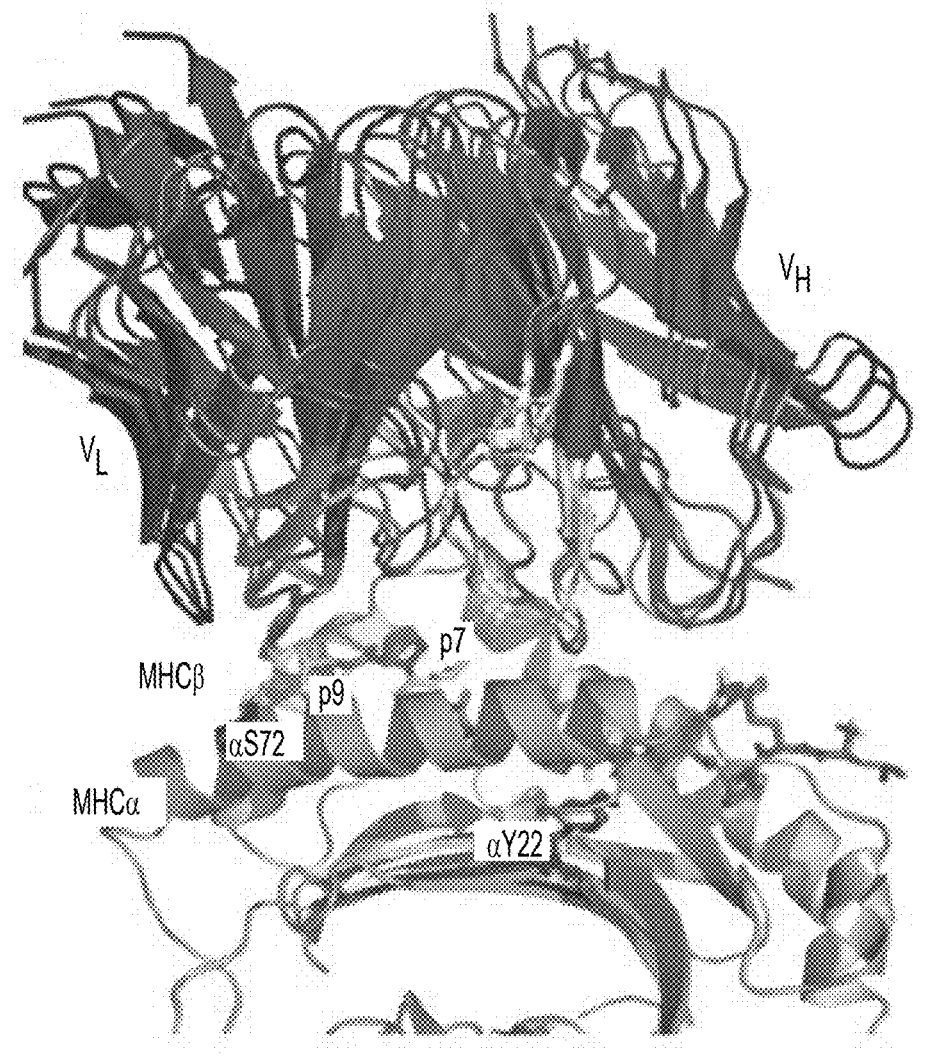
Figures 9A, 9B:
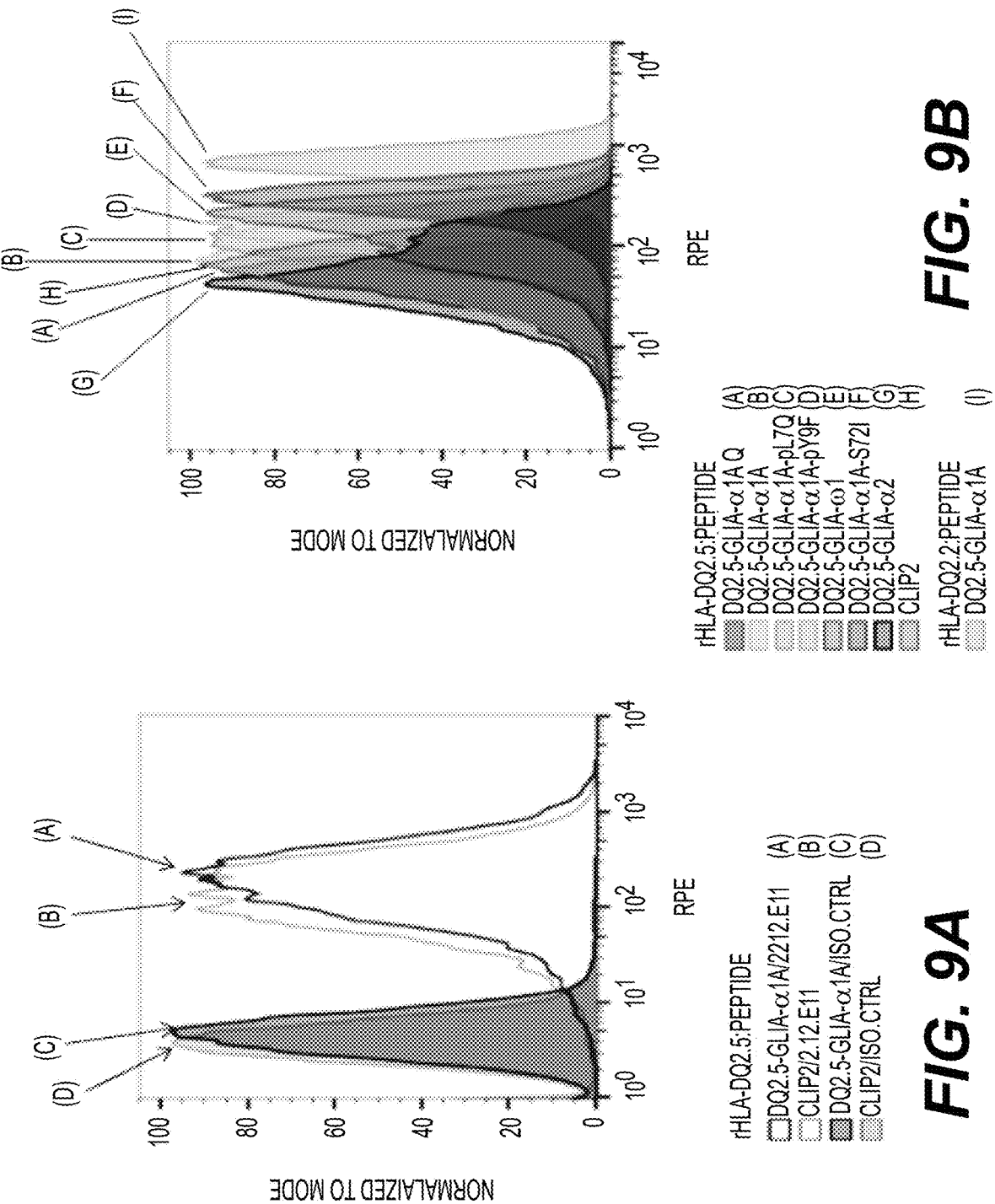
Figures 9C, 9D, 9E:
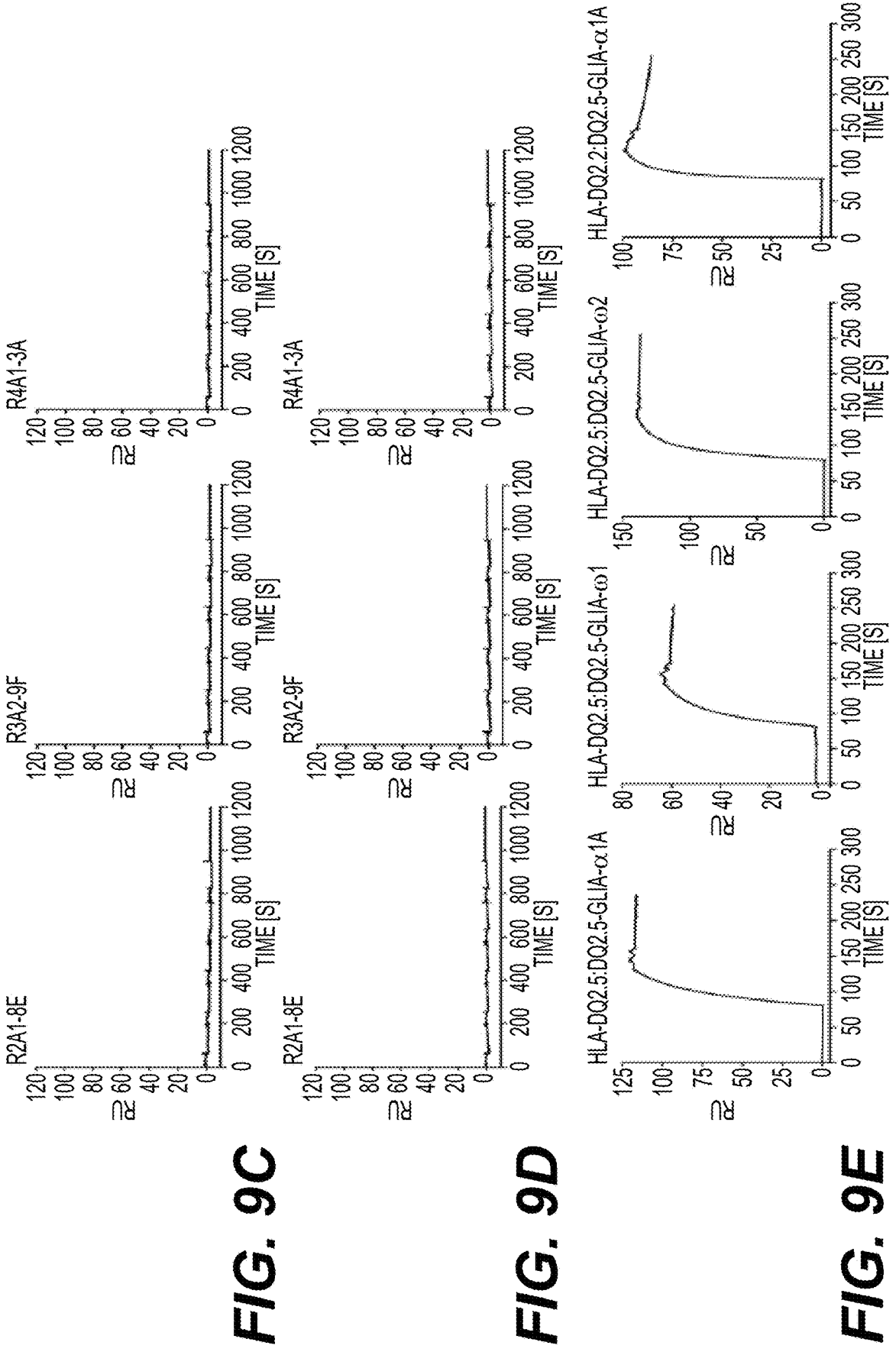

To further map fine-specificity, we screened for binding against a panel HLA-DQ2.5:peptide or HLA-DQ2.2:peptide expressing A20 B cells (FIG. 9B). Covalent attachment of the peptides to MHC largely eliminates effects of differences in peptide off-rates, enabling comparative assessment of binding. None of the mAbs bound the highly similar DQ2.5-glia-ω1 epitope or HLA-DQ2.2 with DQ2.5-glia-α1a (FIG. 3B). We also corroborated this finding with SPR using the mAbs and soluble, recombinant pMHCs (FIG. 9C-E). DQ2.5-glia-α1a and DQ2.5-glia-ω1 differ in p7 and p9 only (FIG. 3C). Thus, we constructed pL7Q and pY9F variants of DQ2.5-glia-α1a to resemble DQ2.5-glia-ω1 in these positions. All three mAbs bound the pL7Q variant, albeit not as strongly as DQ2.5-glia-α1a (FIG. 3B). However, while mAb R2A1-8E bound the pY9F variant, mAbs R3A2-9F and R4A1-3A did not (FIG. 3B). Of the polymorphic residues that differ between HLA-DQ2.5 and HLA-DQ2.2, the α72 residue is the only one in position for direct interactions (FIG. 3D). To map a potential effect of the HLA-DQ2.5 residue, we constructed the HLA-DQ2.5:DQ2.5-glia-α1a αS72I mutant (S in HLA-DQ2.5 and I in HLA-DQ2.2). The mAb R2A1-8E was the only one to bind the αS72I variant. As before, we did not observe binding to CLIP2 or DQ2.5-glia-α2 (FIG. 3B). Furthermore, the native, non-deamidated DQ2.5-glia-α1a (DQ2.5-glia-α1a-Q) was not recognized.

To understand the molecular basis for the observed specificity of the mAbs, we built Fv homology models using the V region sequence of mAb R4A1-3A. These models represent the highly similar mAbs R3A2-9F and R4A1-3A, but not mAb R2A1-8E, which differs in sequence and thus cannot be rationalized based on the models. We then docked the models to the available crystal structure of HLA-DQ2.5:DQ2.5-glia-α1a [Kim, C. Y., et al., 2004]. The top three lowest-energy models were highly similar and positioned the scFv in a diagonal manner across the pMHC (FIG. 3D). In all three models, the CDR-H3 was positioned close to p7, with residues W111.1 and H112.1 within 5 Λ of the L in p7 (FIG. 3E). Although no direct interactions are indicated in the models, the pL7Q substitution could indirectly be sensed causing the small reduction in MFI as observed (FIG. 3B). Similarly, both CDR-L1 and CDR-L3 are in close proximity to p9 (FIG. 3F). Three residues are close enough to interact with the Y, and one of these residues, D28, potentially forms a H-bond with αS72 of the MHC, giving a molecular explanation to the lost binding of the highly similar mAbs R2A3-9F and R4A1-3A (FIG. 3G). Taken together, fine-specificity analysis using single mutants revealed that the mAbs utilized distinct binding modes, and that mAbs R3A2-9F and R4A1-3A exhibited a greater specificity for DQ2.5-glia-α1a compared to mAb R2A1-8E.

Detection of Cell Surface HLA-DQ2.5:DQ2.5-Glia-α1a Complexes

As all efforts to characterize specificity and affinity of the antibodies were conducted using recombinant HLA-DQ2.5 with covalently coupled peptide, either soluble or cell-bound, we next examined if the mAbs could bind HLA-DQ2.5$^+$ cells loaded with soluble peptide. For this purpose, we isolated monocytes using PBMCs from a healthy HLA-DQ2.5$^+$ donor and in vitro differentiated to monocyte-derived DCs and loaded the cells with peptide. Using mAb R3A2-9F, we specifically detected cells presenting DQ2.5-glia-α1a (FIG. 4A).

B Cells and CD19$^+$ PCs are the Major DQ2.5-Glia-α1a Presenting Subsets in the Intestinal Mucosa of CD Patients Encouraged by the ability of the mAb R3A2-9F to specifically stain cells exogenously loaded with DQ2.5-glia-α1a peptide, we generated single-cell suspensions of intestinal biopsies from HLA-DQ2.5$^+$ untreated CD patients, and co-stained the freshly isolated cells with mouse IgG2b (mIgG2b) versions of mAb R3A2-9F together with antibodies specific for other APC surface markers (FIG. 4B and FIGS. 10A and B). Unexpectedly, we observed binding of mAb R3A2-9F almost exclusively to PCs (large, viable, CD19$^{+/-}$CD27$^+$CD38$^+$) and B cells (smaller, viable, CD19$^+$ CD38$^-$), whereas very few CD11c$^+$CD14$^-$ DCs and CD11c$^+$ CD14$^+$ or CD11c$^-$CD14$^+$ macrophages stained positive (FIG. 4B). Analysis of three patients analyzed in parallel showed an average of 27.4% and 35.4% mAb R3A2-9F positive PCs and B cells, respectively. Importantly, pre-blocking of FcγRs did not affect staining (FIG. 10C).

Figure 5C:
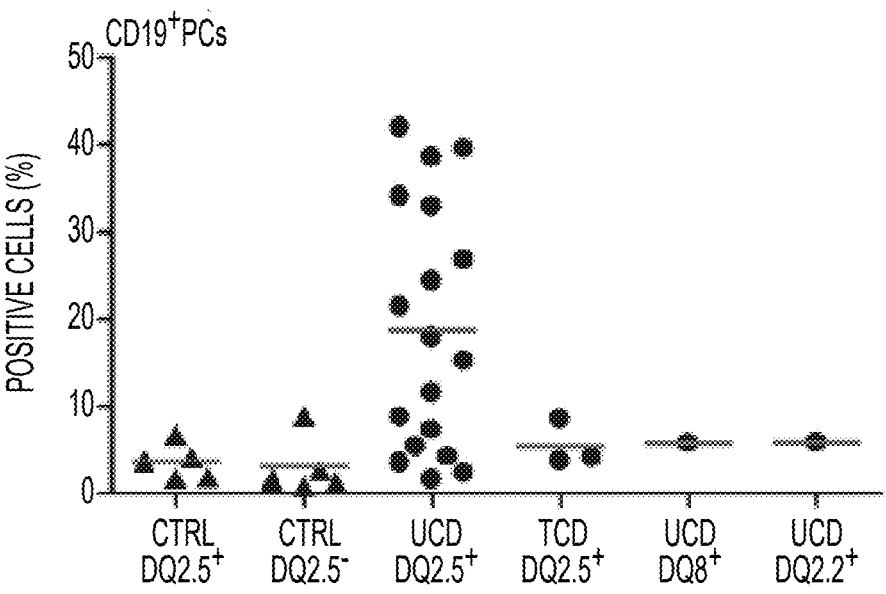
Figure 5D:
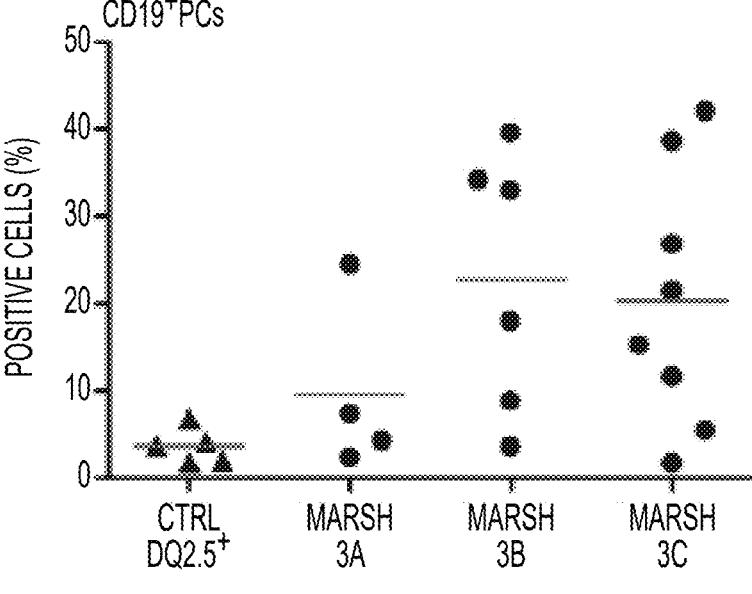

We then compared the level of peptide presentation by B cells and PCs as detected by mAb R3A2-9F or R4A1-3A staining of both untreated CD and treated CD patients (i.e. on gluten-free diet) and matched with non-CD healthy controls. Notably, these mAbs stained cells similarly. Small intestinal PCs can be separated into 3 major subsets with distinguished longevity based on CD19 and CD45 expression; CD19$^+$CD45$^+$ PCs which are dynamically exchanged, and CD19$^-$CD45$^+$ PCs and CD19$^-$CD45$^-$ PCs which are long-lived subsets and exhibits little and no replacement, respectively (herein these subsets are referred to as CD19$^+$, CD45$^+$, and CD45$^-$ PCs, respectively; FIG. 11A). Of these PC subsets, we found the CD19$^+$ PCs to display most HLA-DQ2.5:DQ2.5-glia-α1a complexes, followed by the CD45$^+$ and the CD45 PCs, with an average of 19%, 11% and 7% positive cells among HLA-DQ2.5$^+$ untreated CD patients, respectively (FIGS. 5A and B). An average of 16% of the B cells were positive (FIG. 5B). Further analysis of patients revealed that all PC subsets and the B cells of treated CD patients stained negative, comparable to both HLA-DQ2.5$^+$ and HLA-DQ2.5 healthy controls (FIG. 5C and FIG. 11B). Additionally, both HLA-DQ8$^+$ and HLA-DQ2.2$^+$ CD patients with active disease were negative. Possibly, there were a higher number of positive PCs from patients with high Marsh scores (FIG. 5D). In summary, we found PCs and B cells to be the main cell types presenting DQ2.5-glia-α1a on HLA-DQ2.5, with the highest level of staining in the CD19$^+$ PC subset.

DQ2.5-Glia-α1a Presenting PCs Express TG2-Specific IgA

To further validate our observations, we sorted four populations of PCs by use of mAb R4A1-3A and TG2-antigen multimers; bulk PCs, bulk TG2$^+$ PCs, R4A1-3A$^+$ TG2$^+$ PCs and R4A1-3A$^+$TG2$^-$ PCs. All groups of sorted cells were microscopically confirmed to be PCs, with the typical PC morphology characterized by large nuclei and little cytoplasm (FIG. 6A). This further strengthens our observations from flow cytometry, largely excluding unspecific mAb binding by cells such as macrophages and DCs. Moreover, culturing and subsequent TG2-specific ELISPOT using the sorted PCs verified that the cells secrete IgA antibodies specific for TG2 (FIG. 6B). Importantly, within the TG2+ PC and the R4A1-3A+TG2+ PC populations spots were clearly visible, while none were found in the R4A1-3A+TG2− sorted PC population, nor in the T-cell negative control. Among bulk PCs spots were only visible when using many cells, in line with the approximately 10% TG2-specific PCs in the inflamed mucosa of CD patients.

Intestinal PCs Express MHC Class II

Despite the fact that intestinal PCs appear to have a functional BCR, and thus Ag capturing capacity, they are thought to lack APC properties by virtue of transcriptional silencing of the MHC class II loci. The specific detection of gluten peptide presentation on HLA-DQ2.5 requires MHC class II expression in human intestinal PCs in CD patients. To experimentally verify this, we performed flow cytometric staining showing that the CD19+, CD45+ and CD45− PCs all indeed express MHC class II, albeit to a lower level as compared to DCs, monocytes and macrophages or B cells (FIG. 6C and FIG. 12).

DISCUSSION

In this study, we report the generation of mAbs highly specific for HLA-DQ2.5 in complex with one of the immunodominant T-cell epitopes in CD, DQ2.5-glia-α1a. By utilizing these mAbs, we identify B cells and PCs as the main APCs presenting gluten peptides in the inflamed intestine of CD patients.

TCR and TCR-like mAb binding to the same pMHC complex have been compared before, usually revealing distinct fine-specificities with mAb binding modes ranging from highly tilted to TCR-like docking. For the HLA-DQ2.5:DQ2.5-glia-α1a complex, binding experiments using 11 T-cell clones showed a striking dependence on p7, as a pL7A mutation completely abrogated binding for all clones, whereas alternations of all other positions resulted in clone-dependent effects. In the case of a model TCR clone, a pL7Q mutation reduced binding, while a pY9F mutation increased binding, presumably translating into HLA-DQ2.5:DQ2.5-glia-ω1 cross-reactivity. Among the three HLA-DQ2.5:DQ2.5-glia-α1a-specific mAbs described in this paper, R3A2-9F and R4A1-3A behaved similarly, while mAb R2A1-8E showed a distinct recognition pattern. All mAbs bound irrespective of p7 mutation, while p9 mutation abrogated binding for mAbs R3A2-9F and R4A1-3A, explaining the lack of binding to the DQ2.5-glia-ω1 epitope.

TABLE S1

Table S1. Overview of selection and candidate clones.

| Selection round/strategy[a] | Input (cfu) | Output (cfu) | Enrichment factor[b] | # positive clones[c] | # unique clones[d] | # specific clones[e] |
|---|---|---|---|---|---|---|
| R1 | $1.32 \times 10^{11}$ | $2.73 \times 10^{6}$ | ND | ND | ND | ND |
| R2A1 | $6.50 \times 10^{11}$ | $5.11 \times 10^{5}$ | 0.38 | 5/188 | 1 | R2A1-8E |
| R2A2 | $6.50 \times 10^{11}$ | $1.04 \times 10^{6}$ | 7.73 | 3/188 | 3 | 0 |
| R3A1 | $7.35 \times 10^{11}$ | $1.78 \times 10^{6}$ | 3.08 | 41/188 | 1 | * |
| R3A2 | $8.00 \times 10^{10}$ | $4.95 \times 10^{5}$ | 3.87 | 9/188 | 2 | R3A2-9F |
| R4A1 | $3.83 \times 10^{11}$ | $3.09 \times 10^{5}$ | 0.33 | 6/188 | 2 | R4A1-3A/* |
| R4A2 | $4.83 \times 10^{10}$ | $1.71 \times 10^{5}$ | 0.57 | 11/188 | 5 | 0/* |
| Total | — | — | — | 75/1128 | 11 | 3 |

[a]Selection was performed using two parallel strategies from R2-R4; A1 without soluble competitor and A2 with soluble competitor. In both cases the selection stringency was increased for each round.
[b]Enrichment factor was determined using the ratio from the current selection round divided by the ratio from the previous round. The ratio was obtained by dividing the phage output (cfu$^{ampR}$) on the phage input (cfu$^{ampR}$) in a selection round.
[c]Determined by ELISA after scoring clones with a signal/background ratio above background level (set by empty E. coli XL1-Blue) as positive.
[d]Determined by sequencing of single clones. Some clones are not included due to out-of-frame mutations or unattainable sequence.
[e]Determined by SPR binding analysis.
*Same clone as R3A2-9F
ND, not determined
Note;
$V_H$ of clone R4A1-3A contains the recognition sequence of one of the enzymes used to sub-clone the scFv cassette from the phagemid to the vector for soluble expression. As the cloning step was performed prior to screening of the libraries, clones with this particular sequence may have been lost. Thus, its frequency may be under-estimated in the selection output.

TABLE S2

Table S2. Kinetics of the scFv-HLA-DQ2.5:DQ2.5-glia-α1a interaction.

| Clone | Single cycle kinetics[a] | | | | Steady state | |
|---|---|---|---|---|---|---|
| | $k_{on}$ (M$^{-1}$s$^{-1}$) | $k_{off}$ (s$^{-1}$) | $K_D$ (M) | SE $K_D$ (M) | $K_D$ (M) | SE $K_D$ (M) |
| R2A1-8E | NA | NA | NA | NA | $2.03 \times 10^{-7}$ | $1.20 \times 10^{-8}$ |
| R3A2-9F | $1.29 \times 10^{5}$ | 0.01262 | $9.79 \times 10^{-8}$ | $5.63 \times 10^{-8}$ | $1.42 \times 10^{-7}$ | $2.20 \times 10^{-8}$ |
| R4A1-3A | $2.89 \times 10^{5}$ | 0.02151 | $7.43 \times 10^{-8}$ | $7.14 \times 10^{-8}$ | $6.70 \times 10^{-8}$ | $1.30 \times 10^{-8}$ |

[a]Kinetics were determined by fitting data to a 1:1 Langmuir binding model.
[b]Steady state $K_D$ was derived from the single cycle kinetics runs.
NA, not available.

R3A2-9F and R4A1-3A differ by one amino acid in the framework of $V_L$, while mAb R2A1-8E shares $V_H$ with the two former mAbs, but utilizes a different $V_L$. While p7 appears solvent exposed and the pL7Q mutation reduced mAb binding, p9 is generally considered a buried anchor residue. However, crystallographic analysis of HLA-DQ2.5 in complex with DQ2.5-glia-α1a has shown that the p9 residue can either act as an anchor or be positioned outside of the pocket. Docked models of mAb R4A1-3A and HLA-DQ2.5:DQ2.5-glia-α showed that the CDR-L1 and CDR-L3 loops are in close proximity to p9 and αS72. Although there are no direct interactions with p9, D28 of CDR-L1 interacts with αS72, an interaction that would be disrupted after mutation to the αI72 found in HLA-DQ2.2, possibly explaining the lack of binding to HLA-DQ2.2 with DQ2.5-glia-α1a. The molecular basis for the lack of mAb binding to the DQ2.5-glia-α1a epitope with the corresponding native sequence remains unclear. The p6E is generated by TG2 mediated deamidation and acts as an anchor residue involved in an extensive H-bond network with both the peptide and MHC. It is conceivable that this H-bond network will rearrange in the presence of the native Q, which may then directly or indirectly influence the ability of the mAb to bind.

HLA-DQ2.5 is largely resistant to HLA-DM-mediated peptide exchange, resulting in an extraordinarily high level of CLIP peptides presented by HLA-DQ2.5$^+$ APCs. As a consequence, the relative proportion of HLA-DQ2.5 loaded with other peptides is assumed to be low. Cross-reactivity to CLIP2 would limit the utility of the mAbs as specific reagents. As seen in both binding experiments using recombinant molecules in ELISA and SPR, as well as in flow cytometry after staining of DQ2.5$^+$ cells with covalently coupled CLIP2 peptide, CLIP2 is not detected. Each naturally processed antigenic pMHC complex has been estimated to occur in numbers of 10-1000 per cell. This contrasts the high density of TCR on T cells, estimated to about 50.000 molecules per cell, thus, in comparison with tetramer detection of a TCR, the use of TCR-like mAbs is challenging, particularly for detection of inefficiently loaded antigens. Still, we were able to detect both in vitro loaded cells and pMHC complexes generated in vivo after gluten consumption by CD patients.

The intestinal compartment of conventional APC is dominated by macrophages, with smaller populations of DCs, naïve and memory B cells. DCs have been suggested to participate in priming of T cells in CD. We detect very few DCs, which might in part be explained by their low density in the intestine, and by migration to the mesenteric lymph node after antigen uptake. Although the affinities of mAbs R3A2-9F and R4A1-3A are in line with those reported for other TCR-like mAbs isolated from naïve libraries, it might be too low to detect scarce cell populations.

B cells and PCs expressing Ig specific for gliadin and TG2 are characteristics of CD. The dominant B-cell lineage in the lamina propria is PCs, which are found at high densities, constituting 25-35% of the total mononuclear cell population, whereas there is only a minor population of memory B cells and very few naïve B cells. In CD, 1% and 10% of the PCs are specific for gliadin and TG2, respectively. The role of these cells and the antibodies they produce in disease development and maintenance has been unclear. Our findings indicate their involvement as APCs for gluten-reactive CD4$^+$ T cells. Comparing the 3 major subsets of small intestinal PCs, we found the CD19$^+$ subset to present DQ2.5-glia-α1a most efficiently. This subset is highly dynamic and undergoes constant renewal, whereas the CD45$^+$ and CD45$^-$ PCs are long-lived and more static, in particular the CD45–$^-$ PCs where we detected the lowest level of peptide presentation. The observed lack of correlation between DQ2.5-glia-α1a presentation and serum anti-TG2 IgA titer is in line with the previous observation that the frequency of TG2-specific PCs does not correlate with serum Ab titers.

Although the conventional view is that B cells are not efficient activators of naïve T cells, B cells have been shown to be efficient APCs when they recognize the same antigen as the responding T cell. In a murine model of systemic lupus erythematosus (SLE), activation of naïve self-reactive T cells was shown to depend on B cells. In CD, a hapten-carrier model has been suggested for efficient presentation of gluten peptides by TG2-specific B cells, whereby BCR-bound TG2 is itself associated with the gluten peptide, or has catalyzed the coupling of the peptide to neighboring molecules. The presence of DQ2.5-glia-α1a-presenting B cells builds on these observations and strengthens the hapten-carrier hypothesis in activation of T cells. The phenotype of the CD19$^+$CD38$^-$ B cells we identified has been thoroughly investigated. This population was found to constitute mostly memory B cells (CD27$^+$IgD$^-$IgA$^+$) with a minor population of naïve-mature B cells (CD27$^-$IgD$^+$IgM$^+$), most likely representing a variable contribution from isolated lymphoid follicles.

The ability of PCs to act as APCs is controversial, and conflicting results have been reported from human and murine studies. Murine PCs have been shown to process antigen and activate naïve T cells. This has proven much more difficult to verify for human PCs, despite the observation that IgA and IgM PCs in the bone marrow and lamina propria have functional BCR that is able to transmit intracellular signals and internalize antigen. Nevertheless, MHC expression and an ability to activate T cells have been demonstrated for human myelomas. Additionally, human bone marrow and splenic PCs have been shown to express MHC class II. Expression from the MHC class II locus is believed to be controlled by CIITA. Upon PC maturation, CIITA expression is lost, leading to silencing of MHC class II expression. However, epigenetic mechanisms as well as carcinogenesis have been shown to induce class II expression in PCs, both by reactivation of CIITA and in its absence. We have shown that the PCs present gluten peptides on HLA-DQ2.5, which indicates that PCs function as APCs.

In summary, we have isolated highly specific HLA-DQ2.5:DQ2.5-glia-α1a-specific mAbs, and we found PCs and B cells to be the main cell types presenting DQ2.5-glia-α1a in the intestinal lesion of CD patients. The mAbs are highly specific, detecting DQ2.5-glia-α1a solely in the context of HLA-DQ2.5. The lack of detection in HLA-DQ2.2$^+$ and HLA-DQ8$^+$ untreated CD patients strongly implies that our clear staining of HLA-DQ2.5$^+$ untreated CD patients is not an artifact caused by a highly inflamed tissue. The treatment for CD is to completely abstain from gluten. However, for a fraction of CD patients, this is not curative and this group is in need of novel therapeutic intervention. Up to 50% of the gluten-reactive CD4$^+$ T$_H$ cells in the active CD lesion may be focused on either of the immunodominant DQ2.5-glia-α1a and DQ2.5-glia-α2 epitopes. Importantly, selective blocking of dominating epitopes in HLA-driven diseases has been shown to ameliorate disease. The previously unappreciated ability of PCs to act as APCs, and the observed importance of B cells in gluten peptide presentation may also offer instructive clues for understanding of other T-cell driven autoimmune diseases.

Materials and Methods

Human and Animal Material

Duodenal biopsy material was obtained according to approved protocols (Regional Ethics Committee of South-Eastern Norway approval 2010/2720 S-97201), and all subjects gave informed written consent. CD diagnosis was given according to the British Society for Gastroenterology guidelines including clinical history, anti-TG2 serological testing, HLA typing and histological analysis of small intestinal biopsies obtained by esophagogastroduodenoscopy and forceps sampling from the duodenum.

Recombinant pMHC Expression and Purification

Recombinant HLA-DQ2.5 or HLA-DQ2.2 with covalently coupled gluten-derived peptides containing the T-cell epitopes DQ2.5-glia-α1a (QLQPFPQPELPY, underlined 9mer core sequence) (SEQ ID NO: 474), DQ2.5-glia-α2 (PQPELPYPQPE) (SEQ ID NO: 475), DQ2.5-glia-ω1 (QQPFPQPEQPFP) (SEQ ID NO: 497), DQ2.5-glia-ω2 (FPQPEQPFPWQP) (SEQ ID NO: 480), DQ2.5-glia-γ1 (PEQPQQSFPEQERP) (SEQ ID NO: 482), DQ2.5-glia-γ2 (QGIIQPEQPAQL) (SEQ ID NO: 484), DQ2.5-glia-γ3 (TE-QPEQPYPQP) (SEQ ID NO: 486), DQ2.5-glia-γ4c (TE-QPEQPFPQP) (SEQ ID NO: 488) and CLIP2 (MATPLL-MQALPMMGAL) (SEQ ID NO: 490) were generated as previously described [Fallang, L. E., et al., 2008, Quarsten, H., et al., 2001]. Briefly, insect cell produced soluble, recombinant pMHC was affinity purified using mAb 2.12.E11 [Viken, H. D., et al., 1995] specific for DQ2 and occasionally by size exclusion using Superdex 200, followed by site-specific biotinylation using BirA (Avidity). Recombinant pMHC used for SPR was further purified by size exclusion using Superdex 200 after biotinylation.

Selection and Rescue of scFv Phage Libraries

HLA-DQ2.5:DQ2.5-glia-α1a-specific binders were isolated from a naïve human scFv library (described in Loset, G. A., et al., 2005). Dynabeads MyOne Streptavidin T1 beads (Invitrogen) and phages ($1.32 \times 10^{11}$ cfu$^{ampR}$ in R1) were blocked 1 h using either 4% non-fat skim milk powder or 2% BSA (essentially fatty acid free) in PBS, alternating the blocking reagent for each selection round. 1 ml pre-blocked phage samples were incubated 1 h with 80 nM biotinylated HLA-DQ2.5:CLIP2 for negative selection (R1, R2, R3), before transfer to tubes containing beads and further incubated for 30 min. Beads containing captured HLA-DQ2.5:CLIP2 with bound phage were absorbed on a magnet and supernatant containing unbound phage was transferred to new tubes and incubated 1 h with 80 nM biotinylated HLA-DQ2.5:DQ2.5-glia-α1a for positive selection, before transfer to beads as before. After 5 washes with PBS with 0.05% Tween-20 (PBST) and 5 washes with PBS (a brief vortex between each wash), bound phages were eluted by 30 min incubation with 0.5 ml trypsin/EDTA. In subsequent rounds, all samples were selected using two strategies; alterative 1 as in R1, and alternative 2, by addition of 16.6 nM non-biotinylated HLA-DQ2.5:DQ2.5-glia-α1a competitor in solution [Zahnd, C., et al., 2010]. All incubations were performed using rotation at room temperature (RT). The selection stringency was increased for each round; washing 10+10 in R2, 20+20 in R3 and R4, decreasing antigen amount 10 times for each round, and 100 times for R4. The eluted output was used to infect 9.5 ml E. coli XL1-Blue (Stratagene) at OD$_{600nm}$ 0.6 in 2×YT-TG (30 pg/ml tetracycline and 0.1 M glucose). Additional 0.05 M glucose was added to the cultures immediately before infection to ensure complete shutdown of the lac promoter. Infection was allowed for 30 min/80 rpm/37° C., followed by 30 min/220 rpm/37° C. incubation. Cultures were harvested by centrifugation, plated onto Bio-Assay dishes (NUNC) containing 2×-YT-TAG (30 pg/ml tetracycline, 100 μg/ml ampicillin, and 0.1 M glucose) and incubated overnight at 30° C. Cells were scraped and re-inoculated to OD$_{600nm}$ 0.05 in 50 ml 2×YT-TAG. M13K07 (GE Healthcare) at MOI 20 was added at OD$_{600nm}$ 0.1-0.2 and allowed to infect as before, followed by medium replacement to 2×YT-AK (100 μg/ml ampicillin and 50 μg/ml kanamycin), and incubated overnight at 30° C. Cultures were centrifuged and supernatants were filtrated using 0.22 μm filters. Virions were purified and concentrated by PEG precipitation as described [Marks, J. D., et al., 1991]. Phage was spot-titrated onto nitrocellulose filters essentially as before [Koch, J. et al., 2000]. Antigen-specific clones identified after selection were sequenced by GATC Biotech.

Reformatting from Phage to Soluble Expression scFv cassettes encoding selected clones were retrieved either by batch-cloning a midi-prepped library glycerol stock (for R3 screening) or by PCR amplification directly from the phage stocks (for R2 and R4 screening). Briefly, the scFv cassette was cloned as NcoI/NotI fragment from the phagemid pSEX81 pL-NBLκ into pFKPEN [Gunnarsen, K. S., et al., 2010], placing the scFv in-frame with c-myc and his-tags, and transformed into E. coli XL1-Blue. Alternatively, the scFv cassette was retrieved directly from the PEG precipitated phages stocks by PCR using Phusion HotStart DNA polymerase (Thermo Scientific). 1 μl phage stocks were used with 0.5 μM primers scTCR_fw 5'-CTCAGCCGGCCATGGCC-3' (SEQ ID NO: 516) and scTCR_rv 5'-TTTGGATCCAGCGGCCGC-3' (SEQ ID NO:517), 0.2 mM dNTPs, annealing temperature 60° C. The PCR was purified from agarose gel and the scFv cassette cloned as NcoI/NotI fragment into pFKPEN.

Soluble Prokaryotic Protein Expression and Purification

Soluble prokaryotic expression both for library screening and large-scale single-clone production was performed essentially as before [Gunnarsen, K. S., et al., 2010]. For single clone screening in 96-deep well plates, single colonies were picked and inoculated into 400 μl LB-AG, sealed with AirPore Tape Sheet (QIAGEN) and incubated with shaking at 750 rpm/37° C. overnight using Titramax (Heidolph). 50 μl of the cultures were transferred to plates containing fresh LB-AG and incubated with shaking at 600 rpm/4 h/37° C. before medium replacement to 450 μl LB-A supplemented with 0.1 mM IPTG. The plates were incubated with shaking at 600 rpm/30° C. overnight. For large-scale scFv expression, the cells were inoculated into 1 L 2×YT-AG in baffled shaker flasks, and incubated at 37° C./220 rpm overnight. The cultures were then re-inoculated to OD$_{600nm}$ 0.025 using 1 L 2×YT-AG. Medium was replaced to 2×-YT-A when the cultures reached OD$_{600nm}$ 0.6 and incubation continued overnight at 30° C./250 rpm. Periplasmic fractions containing expressed scFv were harvested by resuspension of cell pellets in ice-cold periplasmic extraction solution (50 mM Tris-HCl, 20% sucrose, 1 mM EDTA, pH 8) supplemented with 1 mg/ml lysozyme and 0.1 mg/ml RNase A, using 300 μl for 96-well cultures and 80 ml for 1 L cultures, and incubate for 1 h/rotation/4° C. Periplasmic fraction were harvested by centrifugation and protein either used directly in screening or filtered (0.22 μm filters) and purified by IMAC (HiTrap, GE Healthcare) followed by size exclusion using HiLoad Superdex 200 (GE Healthcare) run in PBS supplemented with 150 mM NaCl and pH adjusted according to the pI of the proteins. Superdex 200 3.2/300 was used for analytical size exclusion.

SDS-PAGE

To visualize purified protein, 2 μg was mixed with BOLT™ LDS sample buffer, heated 5 min at 95° C. before separation on 12% NUPAGE BT gels in BOLT™ MES SDS running buffer (reagents from Novex) at 165 V/35 min along with Spectra prestained multicolor broad-range ladder (Thermo Scientific). Gels were stained with coomassie gel stain. Samples were in some cases reduced using DTT.

ELISA 96-well MaxiSorp microtiter plates (Nunc) were coated overnight at 4° C. with NeutrAvidin™ (Avidity, 10 μg/ml in PBS), before blocking with 4% skim milk powder in PBS (w/v). Biotinylated pMHC was captured onto the NeutrAvidin™. Due to variations in biotinylation levels, different pMHCs were normalized to give the same signal as 63 ng/well of HLA-DQ2.5:DQ2.5-glia-α1a in ELISA with mAb 2.12.E.11 detection. Phage, periplasmic fractions containing scFvs, or 0.5 pg/ml hIgG1 diluted in PBS with 0.05% Tween-20 (PBST) were added to the wells, and detected with either anti-M13-HRP (Amersham Biosciences, 1:5000), anti-His-tag-HRP (AbD Serotech, 1:5000), or polyclonal anti-human IgG Fc-ALP (Sigma, 1:2000) in PBST, respectively. 0.2 pg/ml mAb 2.12.E11 [Viken, H. D., et al., 1995] was detected using polyclonal anti-mouse IgG Fc-ALP (Sigma, 1:2000). HRP ELISAs were developed by addition of TMB solution (Calbiochem), while ALP ELISAs were developed with 1 mg/ml phosphatase substrate in diethanolamine buffer before absorbance reading at 620 nm (450 nm in the case of HCl addition) or 405 nm, respectively. Assays were performed at RT with duplicate wells, except for single clone screenings with only one well per sample. Between each layer, the plates were washed 3× with PBST. In competition ELISAs, 0.1 pg/ml hIgG1 was pre-incubated 30 min with non-biotinylated pMHC or peptides 2-fold diluted from 1 μM. Deamidated gliadin peptides used were 12mer DQ2.5-glia-α1a (QLQPFPQPELPY) (SEQ ID NO: 474), 12mer DQ2.5-glia-α2 (PQPELPYPQPQL) (SEQ ID NO: 524) and 33mer (LQLQPFPQPELPYPQPELPYPQPELPYPQPQPF) (SEQ ID NO: 476).

Binding Analysis by SPR

Binding specificity, affinity, and kinetics was determined on Biacore™ T100 (T200 sensitivity enhanced) (GE Healthcare). 1000 RU of NeutrAvidin™ (Avidity) diluted in acetate buffer pH 4.5 was immobilized on CM3 sensor chips (GE Healthcare) by amine coupling, before capture of 150-300 RU biotinylated pMHC. Samples were 3-fold diluted from 2 μM in PBS supplemented with 150 mM NaCl and 0.05% surfactant P20 for estimation of scFv affinity and binding kinetics. Data were acquired at 30 ul/min using the single cycle kinetics method (data collection rate 10 Hz), with an association time 120 sec and a final dissociation of 600 sec. Alternatively, a kinetic/affinity method was employed using the same conditions as above, with association times as indicated in the figure panels. For half-life comparisons of scFv and hIgG1 variants, 0.25 μM was used of each protein, with association time 120 sec and dissociation of at least 600 sec. All experiments were performed at 25° C. The surface was regenerated by a 10 sec injection of Glycine-HCl pH 2.2 at 10 ul/min. Presence of functionally folded pMHC was verified after running samples by injection of 0.2 μM mAb SPV-L3, binding only correctly folded DQ2. NeutrAvidin™ reference flow cell values were subtracted before data analysis using Biacore™ T200 Evaluation Software, version 1.0 and RI set to constant. A 1:1

Langmuir binding model was used for determination of $K_D$. Figures were prepared using GraphPad Prism 7.

IgG Cloning and Eukaryotic Protein Expression and Purification

Synthetic gene fragments encoding $V_H$ and $V_L$ from the selected scFvs together with intronic splice donor sites (Genscript) were cloned as BsmI-BsiWi fragment into the IgG genomic expression vectors pLNOH2$_{NIP}$ and pLNOk$_{NIP}$ [Norderhaug, L., et al., 1997], encoding constant human gamma1 with N297G mutation and constant human kappa domains, respectively, exchanging the existing specificity for the hapten NIP [Neuberger, M. S., 1983]. Alternatively, synthetic gene fragments encoding $V_H$ and $V_L$ were ordered together with codon optimized mouse gamma2b or mouse kappa cDNA, respectively, and cloned as BsmI-BamHI fragments into the vectors described above. E. coli Top10F (Life Technologies) were transformed with the resulting plasmids before preparation of DNA. HEK293E cells (ATCC) were co-transfected with the expression vectors encoding Ig H and L chains using Lipofectamine 2000 (Invitrogen) and grown in DMEM supplemented with 10% fetal calf serum, 2 mM L-glutamine, 50 U/ml Streptomycin and 50 U/ml Penicillin. Medium was collected and replaced every day/every second day for two weeks, followed by filtration (0.22 μm) and purification on either HiTrap protein L (GE Healthcare) or a NIP-coupled column (in-house prepared) using 0.2 M glycine-HCl pH 3.0 for elution followed by rapid neutralization using 1 Tris-HCl pH 8. Protein containing fractions were further purified by size exclusion on HiLoad Superdex 200 (GE Healthcare) run in PBS supplemented with 150 mM NaCl and pH adjusted according to the pI of the proteins.

Retroviral Transduction of A20 Murine B Cells and Flow Cytometry

A20 B cells expressing HLA-DQ2.5 with the covalently attached DQ2.5-glia-α1a (deamidated=E, native=Q, pL7Q and pY9F variants), DQ2.5-glia-ω1, DQ2.5-glia-α2 as well as HLA-DQ2.5:CLIP2 have been described. The construct encoding HLA-DQ2.5:DQ2.5-glia-α1a-Sα72I was generated by cloning a BgIII/BamHI codon-optimized synthetic DNA fragment (Genscript) encoding the HLA-DQ2.5 α-chain (DQA1*05:01) with the Sα72I mutation into the pMIG-II-eGFP retroviral plasmid (Holst J, Vignali KM, Burton A R, Vignali D A., Nat Methods. 2006; 3(3):191-197) already encoding HLA-DQ2.5:DQ2.5-glia-α1a. HLA-DQ2.2:DQ2.5-glia-α1a was generated by exchange of the HLA-DQ2.5 α-chain (DQA1*05:01) with a BgIII/BamHI codon-optimized synthetic DNA fragment encoding the HLA-DQ2.2 α-chain (DQA1*02:01). The constructs were made to have identical ectodomains as in the soluble, recombinant pMHCs. The resulting pMIG-II-eGFP-rDQ2.5: peptide plasmids and the pAmpho plasmid were then co-transfected (Lipofectamine 2000, Invitrogen) into GP2-293 packaging cells (Clontech), before virus-containing supernatants were collected 48 and 72 h after transduction and cell debris removed by centrifugation and filtration (0.45 μm). Fifty thousand A20 cells were incubated with 1.3 ml of virus-containing supernatant supplemented with 10 μg/ml polybrene and centrifuged 3000 g at 32° C. for 90 min. The supernatant was then discarded and the cells cultured in RPMI with 10% FCS for 5 days, before cells were sorted using FACSAria II (BD Biosciences) based on eGFP expression level. The A20 B cells were cultivated in RPMI-10% FCS. Data was analyzed using FlowJo™ software V10.

Differentiation and Flow Cytometric Detection of Peptide-Loaded Monocyte-Derived DCs Monocyte-derived DCs were prepared from PBMCs from DR3/DQ2-positive blood donors [Qiao, S. W., et al., 2004]. Briefly, monocytes were positively selected from PBMCs using anti-CD14 MicroBeads (Miltenyi Biotec) and cultured in RPMI 1640 with 10% FCS containing 1000 U/ml GM-CSF and 500 U/ml IL-4 (both from R&D Systems). On day 6, DCs were matured using 150 ng/ml LPS for 48 h, supplemented with 40 µM deamidated DQ2.5-glia-α1a peptide (QLQPFPQPELPY) (SEQ ID NO: 474) after 24 h. For flow cytometry, cells were washed twice with flow buffer buffer (PBS with 2% FCS) in V-bottomed 96-well plates, incubated for 45 min on ice with 10 µg/ml of mAb R3A2-9F or isotype control mAb. After washing, the cells were incubated as before with 2 µg/ml F(ab')2 anti-human IgG-biotin (Southern Biotech), followed by 30 min incubation with streptavidin-RPE (Invitrogen). After staining, cells were washed once with flow buffer and immediately analyzed on FACSCalibur (BD Biosciences), and data were analyzed with FlowJo™ 10.0.7 software (Tree Star). All antibodies were diluted in flow buffer.

Isolation of Single-Cell Suspensions from Duodenal Biopsies and Flow Cytometry

To obtain single-cell suspensions from duodenal biopsies, epithelial cells were removed by three washing steps with PBS containing 2 mM EDTA and 1% FCS for 15 min at 37° C. The remaining lamina propria was minced and digested in RPMI containing 2.5 mg/ml liberase and 20 U/ml DNase I (both from Roche) at 37° C. for 1 h. Cells were passed through 100 µM cell strainers (Falcon) and washed three times in PBS. Single-cell suspensions from lamina propria were stained in V-bottomed 96-well plates with either 10 µg/ml mIgG2b mAb R3A2-9F and R4A1-3A or isotype control mAb (mIgG2b/K, Sigma) for 30 min, followed by staining with 1 µg/ml secondary antibody goat anti-mouse IgG2b conjugated to either Alexa-488 or FITC (Southern Biotech). Cells were subsequently stained with the following fluorochrome-conjugated mAbs targeting human cell-surface markers for 30 min on ice; CD14-APC-Cy7 (clone HCD14), CD45-v510 (clone H130), HLA-DR-bv605 (clone L243) (all Biolegend) and CD11c-v450 (clone B-Ly6); or CD3-APC (clone OKT3, eBioscience), CD11c-APC (clone S-HCl-3), CD14-APC (clone HCD14), CD45-BV510 (clone HI30), HLA-DR-BV605 (clone L243), CD19-PE-Cy7 (clone HIB19), CD38-APC-Cy7 (clone HIT2) and CD27-BV421 ((clone 0323) all from Biolegend). For panHLA detection single-cell suspensions were stained with 10 µg/ml anti-human DR/DQ/DP/Dx (clone CR3/43, Santa Cruz Biotechnology) or isotype control mAb (mouse IgG1/κ, clone MOPC-21,BD Pharmingen; or clone AD1.1.10, AbD Serotec) followed by 1 µg/ml secondary mAb anti-mouse IgG1-PE (clone A85-1, BD Biosceinces) or Ab anti-mouse-PE (BD Pharmingen), before staining with the following fluorochrome-conjugated mAbs targeting human cell-surface markers; CD3-FITC (clone OKT3, Biolegend), CD11c-BV450 (clone Bly-6, BD Horizon), CD14-Pacific Blue (clone M5E2, BD Pharmingen), CD45-BV510, CD19-PE-Cy7, CD38-APC-Cy7. Additionally, cells were occasionally stained with fluorescent TG2 multimers where prepared by preincubation of biotinylated TG2 with either streptavidin-RPE (Life Technologies) or Strep-tactin-APC (iba solutions for life sciences). Propidium iodide was used to exclude dead cells and FcRs were blocked using human FcR Blocking Reagent (Miltenyi Biotec). All antibodies and reagents were diluted in PBS containing 5% FCS and 0.1% sodium azide and incubations were performed on ice. Cells were washed between each staining layer. After staining, cells were washed once and immediately acquired on LSR Fortessa cytometer (BD Biosciences), and data were analyzed with FlowJo™ 10.0.7 software (Tree Star).

Sorting of PCs, Validation of Morphology by Light Microscopy and TG2 ELISPOT

Single-cells suspensions from duodenal biopsies were stained with Alexa-488-conjugated hIgG1 R3A2-9F or hIgG1 anti-RSV as isotype controls mAbs (both in-house conjugated) together with the following antibodies against cell-surface markers; CD4, CD8 and CD14-Pacific Blue (Biolegend), CD11c-BV450 (BD Biosciences), CD27-PE-Cy7 (eBioscience), IgA-PE (Southern Biotech), and multi-merised TG2 (Strep-tactin-APC, iba solutions for life sciences). PCs were sorted using FACSAriaII (BD Biosciences) directly into RPMI1640 without phenol red using a 100 µM nozzle. Sorted cells were spun down, resuspended in fresh medium and kept in culture at 37° C., 5% $CO_2$ over night before imaging live cells in culture using a 40×NA 0.5 objective on an inverted Leica DM IL microscope equipped with a Axiocam MRc camera (Zeiss).

MultiScreenHTS IP Filter Plate (0.45 µm) ELISPOT plates (Millipore) were activate with a 1 min incubation with 20 µl 35% ethanol, solution discarded and wells washed 3× with 200 µl PBS before coating with 100 µl 5 µg/ml TG2 (Phadia) in PBS or PBS only to negative control wells and incubated overnight at 4° C. Wells were 3× washed with 200 µl PBS and block with 200 µl 1% w/v BSA in PBS for 2 h at RT. Sorted cells were added in a total volume of 100 µl and plates incubated at 37° C., 5% $CO_2$ for 3 days. Cell were aspired and wells washed 3× with 200 µl PBS and 6× with 200 µl PBST before incubation with AP-conjugated goat anti-human IgA (Sigma, 1:2000) in 100 µl 1% BSA in PBST for 1.5 h at RT. Wells were wash 6× with 200 µl PBST, 3× with 200 µl PBS, 2× with 200 µl $dH_2O$, followed by detection of spots by addition of 100 µl BCIP/NBT solution (AP Conjugate Substrate Kit, Bio-Rad). The reaction was stopped with extensively washing under running water. Plates were dried and read by ImmunoSpot Analyzer. Spots were counted manually. The BW58α⁻ ρ⁻, human CD4 T cell hybridoma transduced with TCR364 was used as negative control.

Antibody Modeling

Antibody homology models were generated essentially as described in [Weitzner, B. D., et al., 2017]. The sequences of the light and heavy variable regions were saved in fasta format, aligned to homologs with known structure, and grafted together into models using RosettaAntibody. Multiple templates of the $V_L$-$V_H$ orientation [Marze, N. A., et al., 2016] were used, resulting in 10 grafted models. The grafted models were further refined by de novo CDR H3 loop modeling and the $V_L$-$V_H$ docking. During modeling, the CDR H3 was constrained to the kinked conformation with a harmonic potential [Weitzner, B. D. and J. J. Gray, 2017]. We obtained a total of 2,800 Fv models. Models for docking were selected based on low Rosetta™ energy and good $V_L$-$V_H$ orientation. To keep some of the diversity generated by the multi-template grafting, we considered models from at least three different $V_L$-$V_H$ orientation templates. In the end, 10 Fv models were docked to the pMHC complex, using SnugDock [Sircar, A. and J. J. Gray, 2010].

Antibody Docking to pMHC

A crystal structure of unliganded HLA-DQ2.5:DQ2.5-glia-α1a is available in the PDB (1S9V, [Kim, C. Y., et al., 2004]) and was used as the docking partner for the antibody models. To alleviate pre-existing steric clashes, the structure was "relaxed" in the Rosetta™ energy function [Conway et al., 2014]. The top 10 Fv models and the relaxed pMHC structure were prepared for docking by running the ensemble prepack protocol as described in [Weitzner, B. D., et al., 2017]. The initial orientation was chosen based on the solved TCR:pMHC interaction (4OZI, [Petersen, J., et al., 2014]). Docking consisted of an initial spin around the Ab-Ag center-of-mass axis and uniformly sampled from 0 to 360°, and additional random perturbations consisting of small translations and rotations, with values sampled from Gaussian distributions centered at 3 Å and 8°, respectively. During docking, the flexible CDR H2 and H3 loops were refined by kinematic loop closure and the $V_L$-$V_H$ orientation was refined by $V_L$-$V_H$ docking. A total of 1,000 models were generated using SnugDock. The final models were picked based on low Rosetta™ energy, reasonable orientation relative to the pMHC, and agreement with experimentally observed specificities.

REFERENCES

Shan, L., et al., *Structural basis for gluten intolerance in celiac sprue*. Science, 2002. 297(5590): p. 2275-9.

Loset, G. A., et al., *Construction, evaluation and refinement of a large human antibody phage library based on the IgD and IgM variable gene repertoire. J Immunol Methods*, 2005. 299(1-2): p. 47-62.

Kim, C. Y., et al., *Structural basis for HLA-DQ2-mediated presentation of gluten epitopes in celiac disease*. Proc Natl Acad Sci USA, 2004. 101(12): p. 4175-9.

Petersen, J., et al., *T-cell receptor recognition of HLA-DQ2-gliadin complexes associated with celiac disease*. Nat Struct Mol Biol, 2014. 21(5): p. 480-8.

Quarsten, H., et al., *Staining of celiac disease-relevant T cells by peptide-DQ2 multimers*. J Immunol, 2001. 167(9): p. 4861-8.

Viken, H. D., et al., *Characterization of an HLA-DQ2-specific monoclonal antibody. Influence of amino acid substitutions in DQ beta 1*0202. Hum Immunol, 1995. 42(4): p. 319-27.

Zahnd, C., C. A. Sarkar, and A. Pluckthun, *Computational analysis of off-rate selection experiments to optimize affinity maturation by directed evolution*. Protein Engineering Design and Selection, 2010. 23(4): p. 175-184.

Marks, J. D., et al., *By-passing immunization. Human antibodies from V-gene libraries displayed on phage*. J Mol Biol, 1991. 222(3): p. 581-97.

Koch, J., F. Breitling, and S. Dubel, *Rapid titration of multiple samples of filamentous bacteriophage (M13) on nitrocellulose filters*. Biotechniques, 2000. 29(6): p. 1196-8, 2002.

Gunnarsen, K. S., et al. *Periplasmic expression of soluble single chain T cell receptors is rescued by the chaperone FkpA*. BMC Biotechnol, 2010. 10, 8 DOI: 10.1186/1472-6750-10-8.

Norderhaug, L., et al., *Versatile vectors for transient and stable expression of recombinant antibody molecules in mammalian cells*. J Immunol Methods, 1997. 204(1): p. 77-87.

Neuberger, M. S., *Expression and regulation of immunoglobulin heavy chain gene transfected into lymphoid cells*. EMBO J, 1983. 2(8): p. 1373-8.

Mach, N., et al., *Differences in dendritic cells stimulated in vivo by tumors engineered to secrete granulocyte-macrophage colony-stimulating factor or Flt3-ligand*. Cancer Res, 2000. 60(12): p. 3239-46.

Qiao, S. W., et al., *Dependence of antibody-mediated presentation of antigen on FcRn*. Proc Natl Acad Sci USA, 2008. 105(27): p. 9337-42.

Qiao, S. W., et al., *Antigen presentation to celiac lesion-derived T cells of a 33-mer gliadin peptide naturally formed by gastrointestinal digestion*. J Immunol, 2004. 173(3): p. 1757-62.

Weitzner, B. D., et al., *Modeling and docking of antibody structures with Rosetta*. Nat Protoc, 2017. 12(2): p. 401-416.

Marze, N. A., S. Lyskov, and J. J. Gray, *Improved prediction of antibody VL-VH orientation*. Protein Eng Des Sel, 2016. 29(10): p. 409-18.

Weitzner, B. D. and J. J. Gray, *Accurate Structure Prediction of CDR H3 Loops Enabled by a Novel Structure-Based C-Terminal Constraint*. J Immunol, 2017. 198(1): p. 505-515.

Sircar, A. and J. J. Gray, *SnugDock: paratope structural optimization during antibody-antigen docking compensates for errors in antibody homology models*. PLoS Comput Biol, 2010. 6(1): p. e1000644.

Conway, et al. Protein Sci. 2014 January; 23(1):47-55.

Example 2

Identification of Antibodies that Specifically Bind to HLA-DQ2.5:DQ2.5-glia-α2

Antibodies with specificity for HLA-DQ2.5:DQ2.5-glia-α2 were isolated by use of phage display. Three rounds of selection against the target complex were performed using a large, naïve human single chain fragment variable (scFv) library and different display formats (high valence vs. low valence display, pill fusions vs. pIX fusions). Single clones were isolated from the selection output and screened for target binding and cross-reactivity to related pMHC complexes. All the scFv identified that bind specifically to HLA-DQ2.5:DQ2.5-glia-α2 use a VH1 gene segment.

The sequences of identified clones 6 (also referred to as 206), 17 (also referred to herein as 217), 18 (also referred to herein as 218), 20 (also referred to herein as 220), 21 (also referred to herein as 221), 23 (also referred to herein as 223), 26 (also referred to herein as 226 or 261) and 28 (also referred to herein as 228) are set forth elsewhere herein.

These clones in the scFv format, were tested for their specificity and affinity for HLA-DQ2.5:DQ2.5-glia-α2 using surface plasmon resonance (SPR) experiments.

First the target antigen was immobilized on a NeutrAvidin™ coated chip and binding of candidates (scFv clones) was tested briefly. The above mentioned clones demonstrated binding to the target antigen.

The clones were analyzed in single cycle kinetics experiments regarding their binding to HLA-DQ2.5:DQ2.5-glia-α2, HLA-DQ2.5:DQ2.5-glia-α1a, HLA-DQ2.5:DQ2.5-glia-ω2 (FIG. 13). Binding to HLA-DQ2.5:DQ2.5-glia-α2 was observed for the above clones and dissociation constants Kd were calculated from two independent experiments with different ligand concentrations. The same single cycle kinetics method was used to analyze binding to HLA-DQ2.5:DQ2.5-glia-α1a and HLA-DQ2.5:DQ2.5-glia-ω2.

The clones demonstrated specificity for the HLA-DQ2.5:DQ2.5-glia-α2 (FIG. 13) In particular, none of the clones, demonstrated significant cross-reactivity to HLA-DQ2.5:DQ2.5-glia-α1a.

The affinities of the scFvs for HLA-DQ2.5:DQ2.5-glia-α2 were in the range of approximately 10 nM to 5 μM (Table Y).

TABLE Y

| (dissociation constants ($K_D$)) | | |
| --- | --- | --- |
| | KD* (affinity ) | KD (kinetics*) |
| scFv 6 | (20 ± 10) nM | (12.6 ± 0.9) nM |
| scFv 17 | (4,900 ± 200) nM | (5,080 ± 20) nM |
| scFv 18 | (2,700 ± 800) nM | (2,400 ± 600) nM |
| scFv20 | (900 ± 200) nM | (730 ± 70) nM |
| scFv 21 | (700 ± 100) nM | (590 ± 70) nM |
| scFv23 | (2,300 ± 300) nM | (2,200 ± 300) nM |
| scFv 26 | (300 ± 100) nM | (170 ± 50) nM |
| scFv 28 | (240 ± 80) nM | (110 ± 70) nM |

*Dissociation constants KD were determined as mean values from two separate single cycle kinetics experiments with different scFv concentrations. Errors were calculated as standard deviations.
** KD was determined by using a fit to the responses for different concentrations.
***KD was also determined by estimating the on- and off-rates. For all candidates the dissociation constants estimated with the two methods have overlapping errors.

The ELISA was performed as essentially as per the method in Example 1. Briefly, 96-well MaxiSorp microtiter plates (Nunc) were coated overnight at 4° C. with NeutrA-vidin™ (Avidity, 10 μg/ml in PBS), before blocking with 4% skim milk (SM) powder in PBS (w/v). Biotinylated pMHC was captured onto the NeutrAvidin™.

The biotinylated pMHCs captured were:

HLA-DQ2.5:DQ2.5-glia-α2 (native (P4Q))
HLA-DQ2.5:DQ2.5-glia-α2 (deamidated P4E)
HLA-DQ2.5:DQ2.5-glia-ω2
HLA-DQ2.5:DQ2.5-α1a
HLA-DQ2.5:DQ2.5-hor3
HLA-DQ2.5:DQ2.5-glia-γ2
HLA-DQ2.5:CLIP2

Due to variations in biotinylation levels, the different pMHCs were normalized to give the same signal as 63 ng/well of HLA-DQ2.5:DQ2.5-glia-α1a in ELISA with mAb 2.12.E.11 detection (2.12.E.11 is a monoclonal antibody specific for the DQ2 β-chain). 0.5 pg/ml hIgG1 (antibodies 206, 220 and 228) was diluted in PBS with 0.05% (v/v) Tween-20 (PBST) were added to the wells, and detected with polyclonal anti-human IgG Fc-AP (Sigma, 1:2000) in PBST. mAb 2.12.E11 (0.2 pg/ml) was detected using polyclonal anti-mouse IgG Fc-AP (Sigma, 1:2000). AP ELISAs were developed with 1 mg/ml phosphatase substrate in diethanolamine buffer before absorbance reading at 405 nm. Assays were performed at RT with duplicate wells. Between each layer, the plates were washed 3× with PBST.

The ELISA results (FIG. 14A) indicate that the antibodies show preferential binding to the HLA-DQ2.5:DQ2.5-glia-α2 molecules as compared to the other tested pMHCs.

FIG. 14B is a control experiment which demonstrates that the 107 antibody (hIgG1), which specifically binds to HLA-DQ2.5:DQ2.5-glia-α1a, does not bind to any of the other tested pMHCs, and also that an isotype control does not bind to any of the tested pMHCs. FIG. 14C is a control experiment which shows consistent pMHC immobilization levels.

Example 3

Affinity Matured Antibodies

Affinity matured antibodies that specifically bind to HLA-DQ2.5:DQ2.5-glia-α1a or that specifically bind to HLA-DQ2.5:DQ2.5-glia-α2 were generated.

Starting from the 107 (R4A1-3A) "mother clone" that specifically binds HLA-DQ2.5:DQ2.5-glia-α1a, affinity matured second generation clones were generated. The sequences of six such clones are set forth elsewhere herein, 4.5D (or 107-4.5D), 4.6D (or 107-4.6D), 4.6C (or 107-4.6C), 4.7C (or 107-4.7C), 5.6A (or 107-5.6A) and 15.6A (107-15.6A).

Starting from the 206 "mother clone" that specifically binds HLA-DQ2.5:DQ2.5-glia-α2, affinity matured second generation clones were generated. The sequences of six such clones are set forth elsewhere herein, 2.B11 (or 206-2B11), 3D.8 (or 206-3D.8), 3.C7 (or 206-3.C7), 3.C11 (or 206-3.C11), 3.F6 (or 206-3.F6) and 12.F6 (206-12.F6).

ELISA

To assess the specificity of the affinity matured clones ELISA experiments were performed. ELISA wells were coated with NeutrAvidin™ (10 pg/mL), blocked with PBS supplemented with 0.05% tween and 5% skim milk powder, biotinylated forms of HLA-DQ2.5:CLIP, HLA-DQ2.5:DQ2.5-glia-α1a, and HLA-DQ2.5:DQ2.5-glia-α2 molecules were immobilised and the scFv were added (10 pg/mL in PBS). The scFv were detected with a mouse anti-myc antibody and a secondary anti-mouse antibody coupled to horseradish peroxidase (HRP). The reaction was stopped by adding 1 M HCl to the wells. Absorbance was read at 450 nm.

As shown in this ELISA experiment (FIG. 15), all tested affinity matured scFvs are specific to the relevant HLA-DQ2.5:DQ2.5-peptide antigen (pMHC) and do not cross-react to HLA-DQ2.5 with the other α-gliadin or CLIP bound.

Surface Plasmon Resonance (SPR)

To assess the affinity improvement, we performed Surface Plasmon Resonance (SPR) experiments (FIG. 16). We immobilized NeutrAvidin™ on a CM3 sensor chip and captured biotinylated pMHC (HLA-DQ2.5:DQ2.5-glia-α1a or HLA-DQ2.5:DQ2.5-glia-α2). The different scFv were run over the pMHC molecules. We confirmed that there is no cross-reactivity between the two targets.

All of the affinity matured antibodies showed improved affinity relative to their respective mother clone. The affinity matured scFv bound their targets and showed different off-rates. All of them showed improved off-rates compared to the mother clone. None of them was cross-reactive to the other α-gliadin pMHC complex (only depicted in FIG. 16 for 12.F6, 3.F6, 15. A6, and 4.7C).

Based on the rate of the decaying signal, we ranked the antibodies and chose 4.7C and 2.B111 as lead candidates for high affinity binding to HLA-DQ2.5:DQ2.5-glia-α1a and HLA-DQ2.5:DQ2.5-glia-α2, respectively. This also matches the results obtained in ELISA experiments where these candidates showed the highest signals.

Example 4

Antibody Modelling/Docking

To assess the "footprint" (or "recognition motif" or "codon") to which antibodies of the present invention may bind, antibody modelling was done using the 107 antibody that specifically binds to HLA-DQ2.5:DQ2.5-glia-α1a and the 206 antibody that specifically binds to HLA-DQ2.5:DQ2.5-glia-α2.

Methods

We chose to use the RosettaAntibody and SnugDock applications (software) to generate models of the docked complexes of the antibodies with their pMHC targets. Both applications belong to the Rosetta™ software suite for macromolecular structure prediction and design.

RosettaAntibody's performance was tested in the antibody modeling assessment II (AMA-II) [B. D. Weitzner, et al. 2014]. It predicted all framework regions and 76% of non-H3 CDR loops at sub-Ångström accuracy. RosettaAntibody further produced the best H3 models for 4 out of 11 targets compared to competitors. It can be regarded as among the best available computational methods for prediction of antibody structures.

SnugDock's ability to correctly predict antibody:antigen complexes was benchmarked on 15 solved structures when the software was first published [A. Sircar and J. J. Gray, 2010]. When analyzing the top10 lowest energy models produced by SnugDock in combination with a method called EsembleDock (Chaudhury and Gray, 2008), a model of at least acceptable quality was found in 14 out of the 15 candidates.

Antibody homology models were obtained essentially as described in [B. D. Weitzner, 2016a]. The amino acid sequences of the light and heavy variable regions in fasta format were aligned to homologs with solved crystal structure, and grafted together into models using RosettaAntibody. To improve the accuracy we used multiple templates of the $V_L$-$V_H$ orientation [N. A. Marze and J. J. Gray, 2016], resulting in 10 grafted models. The grafted models were refined by de novo CDR H3 loop modeling and $V_L$-$V_H$ docking. The CDR3 loop of the heavy chain was constrained to the kinked conformation with a harmonic potential [B. D. Weitzner and J. J. Gray, 2016b]. We obtained 2,800 Fv models. We selected models for docking based on low Rosetta™ energy and $V_L$-$V_H$ orientations within the ranges that are observed in solved antibody structures. In order to maintain structural diversity generated by the multi-template grafting, we considered models from at least three different $V_L$-$V_H$ orientation templates. 10 Fv models were docked to the pMHC complex, using SnugDock [A. Sircar and J. J. Gray, 2010].

We used the crystal structure of the binary complex of HLA-DQ2.5:DQ2.5-glia-α1a (PDB ID 1S9V [C.-Y. Kim, 2004]) and the crystal structure of HLA-DQ2.5:DQ2.5-glia-α2 in complex with T cell receptor JR5.1 (PDB ID 4OZF [Petersen et al., 2014]) as docking partners.

The pMHC structures were first "relaxed" in the Rosetta™ energy function [Conway et al., 2014] to remove pre-existing steric clashes. The top 10 Fv models and the relaxed pMHC structure were prepared for docking by running the ensemble prepack protocol as described in [Weitzner et al, 2016a]. The initial orientation was selected based on the solved TCR:pMHC interaction (4OZ1 and 4OZF [J. Petersen, 2014]). Docking consisted of an initial spin around the Ab-Ag center-of-mass axis uniformly sampled from 0 to 360°, and additional random perturbations consisting of small translations and rotations, with values sampled from Gaussian distributions centered at 3 Å and 8°, respectively. The flexible CDR2 and CDR3 loops of the heavy chain were refined by kinematic loop closure and the $V_L$-$V_H$ orientation was refined by $V_L$-$V_H$ docking. For each antibody, 1,000 models were generated using SnugDock. The final models were picked based on low Rosetta™ energy, reasonable TCR-like orientation relative to the pMHC, as well as agreement with experimentally observed specificities.

The recognition motif was identified by visual inspection of the three and four lead docking models of 107 (0063, 0158, 0195) and 206 (0064, 0083, 0107, 0265), respectively.

Results

A diagonal binding mode of the antibodies across the pMHC groove, similar to the one observed for TCRs. This has been observed for TCR like antibodies before and is supported by our docking models.

The docking models predict the variable light chain of 107 and 206 to be positioned mostly over MHC and the C terminal end of the peptide. The variable heavy chain is positioned over both MHC and peptide.

Based on the strong enrichment of different IGVH gene families during the phage display selections (IGVH6-1 for the α1a selection and IGVH1-69 for the α2 selection) it is likely that the heavy chains contribute strongly to peptide specificity.

The models of 107 and 206 in complex with pMHC predict CDR3 loop of the light chain to be oriented to the DQB1*02 chain of MHC. CDR1 loop of the light chain is oriented towards to DQA1*05 chain.

Because of the sequence conservation and the closely related IGKV-1 genes used by 107 and 206, we think that IGKV-1 drives binding to the MHC, HLA-DQ2.5.

This is exemplified by IGKV1-9 and IGKV1-12 gene usage for the 107 and 206 antibodies, respectively.

The models show VH6-1 (for antibody 107) and VH1-69 (for antibody 206) to be supporting binding to DQB 02:05 (MHC contacts) and additionally harboring peptide specificity.

Based on the antibody modelling, the recognition motif in the conserved stretches of the antibody light chain is predicted to be comprised of a set of residues including but not limited to an N at position 92 of the VL chain of the 107 or 206 antibodies (which is in CDR3), an S at position 93 of the light chain of the 107 or 206 antibodies (which is in CDR3), and a Y at position 94 of the light chain of the 107 and 206 antibodies (which is in CDR3), a D at position 28 of the of the VL chain of the 107 or 206 antibodies (which is in CDR1), and an S at position 30 of the VL chain of the 107 and 206 antibodies (which is in CDR1).

These light chain residues are predicted to interact with a set of MHC residues including a Y at position 60 of the MHC beta chain, a Q at position 64 of the MHC beta chain, a D at position 66 of the MHC beta chain, an R at position 70 of the MHC beta chain, an H at position 68 in the MHC alpha chain, an S at position 72 of the MHC alpha chain, and an R at position 76 of the MHC alpha chain.

Thus, this antibody modeling study indicates that, surprisingly, the 107 antibody that specifically binds to HLA-DQ2.5:DQ2.5-glia-α1a and the 206 antibody that specifically binds to HLA-DQ2.5:DQ2.5-glia-α2, despite having different antigen specificities, share a common recognition motif which recognises the HLA-DQ2.5 MHC molecule. This recognition motif involves residues found in the variable light chain of the antibodies, as discussed above.

REFERENCES

B. D. Weitzner, D. Kuroda, N. Marze, J. Xu, and J. J. Gray, "Blind prediction performance of RosettaAntibody 3.0: Grafting, relaxation, kinematic loop modeling, and full CDR optimization," *Proteins Struct. Funct. Bioinforma.*, vol. 82, no. 8, pp. 1611-1623, 2014.

A. Sircar and J. J. Gray, "SnugDock: Paratope Structural Optimization during Antibody-Antigen Docking Compensates for Errors in Antibody Homology Models," *PLoS Comput. Biol.*, vol. 6, no. 1, p. e1000644, January 2010.

B. D. Weitzner, J. R. Jeliazkov, S. Lyskov, N. Marze, D. Kuroda, R. Frick, N. Biswas, and J. J. Gray, "Modeling and docking antibody structures with Rosetta," *Nat. Publ. Gr.*, vol. 12, no. D, pp. 1-28, 2016a.

N. A. Marze and J. J. Gray, "Improved prediction of antibody VL-VH orientation," *Protein Eng. Des. Sel.*, no. 2011, pp. 1-9, 2016.

B. D. Weitzner and J. J. Gray, "Accurate structure prediction of CDR H3 loops enabled by a novel structure-based C-terminal 'kink' constraint," *J. Immunol.*, vol. 2017, 2016b.

C.-Y. Kim, H. Quarsten, E. Bergseng, C. Khosla, and L. M. Sollid, "Structural basis for HLA-DQ2-mediated presentation of gluten epitopes in celiac disease.," *Proc. Natl. Acad. Sci. U.S.A*, vol. 101, no. 12, pp. 4175-4179, 2004.

J. Petersen, V. Montserrat, J. R. Mujico, K. L. Loh, D. X. Beringer, M. van Lummel, A. Thompson, M. L. Mearin, J. Schweizer, Y. Kooy-Winkelaar, J. van Bergen, J. W. Drijfhout, W.-T. Kan, N. L. La Gruta, R. P. Anderson, H. H. Reid, F. Koning, and J. Rossjohn, "T-cell receptor recognition of HLA-DQ2-gliadin complexes associated with celiac disease.," *Nat. Struct. Mol. Biol.*, vol. 21, no. 5, pp. 480-8, May 2014.

P. Conway, M. D. Tyka, F. DiMaio, D. E. Konerding, and D. Baker, "Relaxation of backbone bond geometry improves protein energy landscape modeling," *Protein Sci.*, vol. 23, no. 1, pp. 47-55, 2014.

Chaudhury and Gray, "Conformer Selection and Induced Fit in Flexible Backbone Protein-Protein Docking Using Computation and NMR Ensembles", J Mol Biol. 2008 Sep. 12; 381(4):1068-87.

Example 5

Biophysical Characterization of Affinity Matured pMHC-Specific Antibodies

In order to assess improvements in binding strength of the 107 and 206 derived binders and to choose lead clones, we performed SPR (surface plasmon resonance) and ranked the antibodies based on off-rates (FIG. 17A+B and Table Z). Strongly improved off-rates were observed for all clones tested. As expected, the 107-derived clones 5.6A and 15.6A, both from the random, error-prone library (i.e. clones derived from a random library made by error prone PCR across the entire scFv), had less pronounced improvements in off-rate compared to the CDR3 mutants (i.e. mutants derived from a library of CDR3 mutated clones). Based on these results, we chose 4.7C and 3.C11 as leads for binding to HLA-DQ2.5:DQ2.5-glia-α1a and HLA-DQ2.5:DQ2.5-glia-α2, respectively.

We next assessed the thermostability of all Fab fragments by determining their melting temperatures by nanoDSF (nano differential scanning fluorimetry) (FIG. 17C+D). Whereas most HLA-DQ2.5:DQ2.5-glia-α1a binders had improved thermostability compared to 107, the HLA-DQ2.5:DQ2.5-glia-α2 binders surprisingly had slightly lower melting temperatures than the 206 mother clone. The lead clones 4.7C and 3.C11 had the highest thermostabilities among the selected clones from the targeted libraries (i.e. from the library of CDR3 mutated clones). In line with the rational for generating the random mutagenesis libraries, the mutants 5.6A and 15.6A had the highest improvements in thermostability, with 5.6A being the highest with a melting temperature 3.3° C. higher than 107.

To harness both the improved off-rate and improved thermostability of the HLA-DQ2.5:DQ2.5-glia-α1a binders, a combination mutant, RF117, was generated, combining the lowest off-rate CDR3 loop (4.7C) with the most stable clone (5.6A). Affinities of the lead antibodies were determined in SPR (FIG. 17E-G). In concordance with the improved (lower) off-rates, all candidates had a strong improvement in affinity, with 4.7C, and 3C11 having $K_D$s of 170±40 pM and 88±11 pM, respectively (Table Z). This is a 400-fold improvement for 4.7C and a 2,600-fold improvement for 3.C11. The combination mutant RF117 had a $K_D$ of 20±17 pM, an approximately 3,600-fold improvement. To our knowledge, RF117 has the highest reported monomeric affinity of a pMHC-specific antibody in any human system.

The 2nd generation antibodies were then expressed as full-length hIgG1 and tested for specific binding in ELISA (FIG. 17H). In agreement with previous results, both 4.7C and RF117 bound exclusively to the target complex HLA-DQ2.5:DQ2.5-glia-α1a and 3.C11 was specific for HLA-DQ2.5:DQ2.5-glia-α2.

TABLE Z

Kinetics and affinity of affinity matured variants.

| Clone | $k_{on}$ (M$^{-1}$s$^{-1}$) | $k_{off}$ (s$^{-1}$) | $K_D$ (M) | SE $K_D$ (M) | $K_D$ (M) | SE $K_D$ (M) |
|---|---|---|---|---|---|---|
| | | Kinetics and affinity | | | Steady state[c] | |
| | | HLA-DQ2.5:DQ2.5-glia-α1a binders | | | | |
| scFv 107[a] | $2.89 \times 10^5$ | 0.02151 | $7.43 \times 10^{-8}$ | $7.44 \times 10^{-8}$ | $6.70 \times 10^{-8}$ | $1.30 \times 10^{-8}$ |
| Fab 107[a] | $2.24 \times 10^5$ | 0.01601 | $7.14 \times 10^{-8}$ | $5.54 \times 10^{-8}$ | $7.41 \times 10^{-8}$ | $1.20 \times 10^{-9}$ |
| Fab 107[b] | $2.377 \times 10^5$ | 0.01698 | $7.145 \times 10^{-8}$ | | NA | NA |
| Fab 4.7C[b] | $3.776 \times 10^5$ | $9.819 \times 10^{-5}$ | $2.600 \times 10^{-10}$ | | NA | NA |
| Fab 4.5D[b] | $3.830 \times 10^5$ | $1.657 \times 10^{-3}$ | $4.327 \times 10^{-9}$ | | NA | NA |
| Fab 4.6C[b] | $6.972 \times 10^5$ | $2.617 \times 10^{-4}$ | $3.754 \times 10^{-10}$ | | NA | NA |
| Fab 4.6D[b] | $4.638 \times 10^5$ | $5.413 \times 10^{-4}$ | $1.167 \times 10^{-9}$ | | NA | NA |
| Fab 5.6A[b] | $1.002 \times 10^6$ | $3.442 \times 10^{-3}$ | $3.436 \times 10^{-9}$ | | NA | NA |
| Fab 15.6A[b] | $5.883 \times 10^5$ | $2.209 \times 10^{-3}$ | $3.755 \times 10^{-9}$ | | NA | NA |
| Fab 4.7C | $9.007 \times 10^5$ | $1.770 \times 10^{-4}$ | $1.966 \times 10^{-10}$ | $5.40 \times 10^{-7}$ | NA | NA |
| Fab 4.7C | $6.697 \times 10^5$ | $9.685 \times 10^{-5}$ | $1.446 \times 10^{-10}$ | $5.60 \times 10^{-7}$ | NA | NA |
| Fab RF117 | $1.829 \times 10^6$ | $5.861 \times 10^{-5}$ | $3.024 \times 10^{-11}$ | $3.70 \times 10^{-7}$ | NA | NA |
| Fab RF117 | $2.048 \times 10^6$ | $1.550 \times 10^{-5}$ | $7.569 \times 10^{-12}$ | $5.60 \times 10^{-7}$ | NA | NA |
| | | HLA-DQ2.5:DQ2.5-glia-α2 binders | | | | |
| Fab 206[a] | $1.02 \times 10^6$ | 0.2291 | $2.24 \times 10^{-7}$ | $2.25 \times 10^{-7}$ | $2.54 \times 10^{-7}$ | $2.70 \times 10^{-9}$ |
| Fab 206[b] | $1.077 \times 10^6$ | 0.2462 | $2.280 \times 10^{-7}$ | | NA | NA |
| Fab 2.B11[b] | $2.208 \times 10^6$ | $3.285 \times 10^{-4}$ | $1.488 \times 10^{-10}$ | | NA | NA |
| Fab 3.C11[b] | $1.669 \times 10^6$ | $6.967 \times 10^{-6}$ | $4.174 \times 10^{-11}$ | | NA | NA |
| Fab 3.C7[b] | $2.006 \times 10^6$ | $7.111 \times 10^{-4}$ | $3.544 \times 10^{-10}$ | | NA | NA |

TABLE Z-continued

| | Kinetics and affinity | | | | Steady state[c] | |
|---|---|---|---|---|---|---|
| Clone | $k_{on}$ (M$^{-1}$s$^{-1}$) | $k_{off}$ (s$^{-1}$) | $K_D$ (M) | SE $K_D$ (M) | $K_D$ (M) | SE $K_D$ (M) |
| Fab 3.D8[b] | $1.545 \times 10^6$ | $1.729 \times 10^{-3}$ | $1.119 \times 10^{-9}$ | | NA | NA |
| Fab 3.F6[b] | $8.096 \times 10^5$ | $1.225 \times 10^{-3}$ | $1.513 \times 10^{-9}$ | | NA | NA |
| Fab 12.F6[b] | $8.039 \times 10^5$ | $7.456 \times 10^{-4}$ | $9.275 \times 10^{-10}$ | | NA | NA |
| Fab 3.C11 | $1.190 \times 10^6$ | $1.126 \times 10^{-4}$ | $9.462 \times 10^{-11}$ | $3.10 \times 10^{-7}$ | NA | NA |
| Fab 3.C11 | $1.387 \times 10^6$ | $1.118 \times 10^{-4}$ | $8.064 \times 10^{-11}$ | $1.30 \times 10^{-7}$ | NA | NA |
| Fab 3.C11 | $1.335 \times 10^6$ | $1.206 \times 10^{-4}$ | $9.039 \times 10^{-11}$ | $1.20 \times 10^{-7}$ | NA | NA |

Kinetics were determined by fitting data to a 1:1 Langmuir binding model.
[a]Determined from single cycle kinetics.
[b]Determined from one concentration of protein in off-rate screening.
[c]Steady state $K_D$ was derived from the single cycle kinetics runs.
NA, not available.

Materials and Methods

ELISA

EIA/RIA plates were coated with 10 µg/ml NeutrAvidin™ in PBS (100 µl/well) and incubate overnight at 4° C. Plates were blocked with 5% skim milk powder in PBS-T (300 µl/well) for 1 h/RT with agitation. Biotinylated pMHCs were prepared as per in Example 1 herein. Equal amounts of biotinylated pMHC (normalized to 300 ng/ml) were captured for 1 h/RT and followed by addition of 0.5 pg/ml purified pMHC-specific antibodies. hIgG1 were detected with anti-hIgG-ALP (Sigma Aldrich, 1:3,000). All antibodies were diluted in PBS-T. Plates were developed with TMB solution (Calbiochem) and the enzymatic reaction stopped by addition of 1 M HCl and read at 450 nm or developed with 1 mg/ml phosphatase substrate (Sigma Aldrich) in dietanolamine buffer and read at 405 nm using a microplate reader (Tecan sunrise).

SPR

Kinetics of antibody binding to pMHC were determined using a Biacore™ T200 (GE Healthcare). Briefly, NeutrAvidin™ (10 µg/ml in 10 mM sodium acetate, pH 4.5) was coupled onto a CM3 sensor chip to 1000 response units (RU) by amine coupling. Biotinylated pMHCs were prepared as per in Example 1 herein. Soluble, recombinant, biotinylated pMHC (1 pg/ml) was then captured at approximately 80-90 RU by passing over the flow cells at 10 µl/min. Antibody samples (scFv or Fab fragments) in PBS supplemented with 150 mM NaCl and 0.05% (v/v) surfactant P20 were run over the surface at various concentrations using either single cycle kinetics or a multi cycle method. For off-rate ranking, all samples were used at 0.5 µM. Binding experiments were performed at 25° C. with a flow-rate of 30 µl/min. The surface was regenerated using either Glycine-HCl pH 2.2 or Diethylamine pH 11 when necessary. Binding data were buffer subtracted and NeutrAvidin™-reference-cell subtracted using the T200 Evaluation Software v1.0. Kinetic constants were determined by fitting the data to a 1:1 Langmuir binding model.

Example 6

Structural Basis for Improved Affinity

In an effort to visualize the interaction interfaces, docking models of the two leads, 4.7C and 3.C11, were generated. Interestingly, the mutations responsible for the increased affinity of 4.7C, are not seen to be directly involved in binding to the pMHC, but rather to stabilize the CDR H3 loop with additional hydrogen bonds. The overall docking geometry does not appear to be changed. In contrast, 3.C11 is predicted to form several new interactions with pMHC via the CDR H1 loop as a result of the increased loop length (2 amino acids). In the model, the mutated CDR H1 loop is positioned where the CDR H3 loop was in the mother clone. This suggests that it takes over the function of the CDR H3 loop, which is displaced to the periphery of the interface. The interfaces were further analyzed using Rosetta™'s InterfaceAnalyzer. The solvent accessible surface area (SASA) of the interface increased from the mother clones to the high affinity variants in both cases, and Rosetta™ further estimated lower binding energies for the improved variants. The binding energies are also improved when normalized to the interface SASA, meaning that the gained affinity is likely both due to a larger interface surface and to improved interactions across the interface.

Materials and Methods

Antibody Modeling

Structural models of Fv fragments were generated as described (Weitzner et al. 2017 and supra). CDR loops and framework regions were separately aligned to homologs with known structures and grafted together using RosettaAntibody. We used 10 templates for the $V_L/V_H$ orientation (Marze and Gray 2016, supra) resulting in 10 grafted models. The grafted relaxed models were further improved by de novo CDR H3 modeling and VL/VH docking. The CDR H3 was constrained to a kinked conformation (Weitzner and Gray 2016, supra) and a total of 2,800 Fv models were generated. The 10 final models were selected based on low Rosetta™ energy and $V_L/V_H$ orientations within the natural distribution. Models were taken from at least three initial grafted templates to maintain diversity.

Antibody Docking to pMHC

Crystal structures of HLA-DQ2.5:DQ2.5-glia-α1a (1S9V) (Kim et al. 2004) and HLA-DQ2.5:DQ2.5:glia-α2 (4OZF) (Petersen et al. 2014, supra) were retrieved from the PDB and "relaxed" into the Rosetta™ energy function. We used the cocrystal structure with the T-cell receptor (4OZI) (Petersen et al. 2014, supra) as a template for an initial orientation of the Fv models relative to the pMHC. We used SnugDock+EnsembleDock starting with 10 antibody Fv models (Sircar and Gray 2010, supra) to generate 1,000 docking models for each antibody. Random moves during docking consisted of a spin around the antibody:antigen center-of-mass axis sampled from 0-360°, and additional random translations and rotations, sampled from Gaussian distributions centered a 3 Å and 8°, respectively. CDRs H2 and H3 were refined by kinematic loop closure and $V_L/V_H$ orientations were improved by $V_L/V_H$ docking. The final models were ranked and selected based on low Rosetta™ energy, occurrence of "energy funnels", and an orientation relative to the pMHC that agrees with the observed specificities. Rosetta™s InterfaceAnalyzer application was used to obtain information about binding energies and interfaces.

Example 7

Detection of Cell-Surface pMHC

Having demonstrated specificity and improved affinity to soluble, recombinant, biotinylated pMHC molecules, we tested whether the antibodies would stain pMHC complexes on the surface of cells. To this end, A20 mouse B cells were engineered to express variants of covalently linked pMHC complexes. Functional cell-surface pMHC expression was verified and the A20 cells were stained with the engineered hIgG1 variants (FIG. 18A+B). 107 and its offspring 4.7C and RF117 bound the deamidated target specifically. The high affinity clone 3.C11 bound to both native and deamidated HLA-DQ2.5:DQ2.5-glia-α2.

Materials and Methods

B Cell Lines

The murine A20 B cell lymphoma had previously been engineered to express HLA-DQ2.5 or HLA-DQ2.2 with different peptide variants covalently linked to the MHC β-chain (Kristin Støen Gunnarsen et al. 2017, JCI Insight 2 (17) doi:10.1172/jci.insight95193). Notably, the ectodomains are identical as in the soluble pMHC molecules used for selection, screening and characterization of antibody binding by SPR and ELISA. All cells were cultured under standard conditions in RPMI 1650 supplemented with 10% FCS, 0.1 mg/ml Streptomycin and 100 U/ml Penicillin.
Flow Cytometry A20 murine B cells were stained for flow cytometry experiments using the pMHC-specific antibodies. For staining A20 B cells, pMHC-specific hIgG1 antibodies were used at 5 µg/mL together with rat anti-mouse CD16/CD32 block (BD, 1:200). Bound hIgG1 were detected with biotinylated goat F(ab')2 anti-human IgG (Southern Biotech, 2 µg/ml) followed by streptavidin R-PE (Invitrogen, 2 µg/ml). All stainings were performed on ice using V-bottom shaped 96-well plates and an equal number of cells were used in each staining (at least 100,000).all PBS supplemented with 2% FCS was used to wash cells and for dilution of antibodies and streptavidin.

Data was acquired using an Attune NxT flow cytometer and analyzed using FlowJo™ software v10.4.1.

Example 8

Staining Human Small Intestinal Biopsy Material

We generated fresh single-cell suspensions of intestinal biopsies from either untreated HLA-DQ2.5+ celiac disease patients or control patients and stained them with the pMHC specific mIgG2b antibodies as well as antibodies against different APC surface markers (FIGS. 19A-19B). We have previously detected the highest levels of DQ2.5-glia-α1a presentation on CD19+CD45+ plasma cells (see Example 1 herein). These cells have been characterized in the small intestinal mucosa and were found to be dynamically exchanged (Landsverk et al. 2017, Journal of Experimental Medicine, 214(2):309-317). The high affinity variants also stain CD19+CD45+ plasma cells and confirm that these cells present gliadin peptides in celiac disease patients. 4.7C stains a similar percentage of cells as the 107 mother clone, while 3.C11 appears to stain a slightly higher number of cells. Two out of six samples are consistently negative for pMHC using all three antibodies. Only one sample (#5) is negative for staining with the mother clone but has a positive population when stained with 4.7C and especially 3.C11. The two control subjects confirm that there is little background staining with all antibodies used.

Materials and Methods

Human Material

Duodenal biopsy material was obtained according to approved protocols (Regional Ethics Committee of South-Eastern Norway approval 2010/2720 S-97201), and all subjects gave informed written consent. CD (celiac disease) diagnosis was given according to the British Society for Gastroenterology guidelines including clinical history, anti-TG2 serological testing, HLA typing and histological analysis of small intestinal biopsies obtained by esophagogastroduodenoscopy and forceps sampling from the duodenum (Ludvigsson et al. 2014, Gut, 63 (8):1210-28). Small intestinal resections (duodenum-proximal jejunum tissue) were obtained from nonpathological small intestine during Whipple procedure (pancreatoduodenectomy) of pancreatic cancer patients who gave informed written consent (approval 2010/2720 S-97201). Only material with confirmed normal histology was included.
Isolation of Single-Cell Suspensions from Duodenal Biopsies and Small Intestinal Resections and Flow Cytometry Single-cell suspensions from duodenal biopsies or from small intestinal resection were prepared as described (Landsverk et al. 2017, supra) and analyzed by flow cytometry as detailed in the Table below.
Antibodies Used for Staining of pMHC on APCs in Human Biopsy Material and Analysis by Flow Cytometry:

| Antigen | Conjugate | Clone | Supplier | Dilution |
|---|---|---|---|---|
| mIgG2b 107/4.7C/3.C11 | — | 107, 4.7C, 3.C11 | In-house | 10 µg/ml |
| Isotype control | — | OMV | In-house | 10 µg/ml |
| mIgG | Alexa-546 | Polyclonal | Invitrogen | 1 µg/ml |
| CD3 | FITC | OKT3 | Biolegend | 1:20 |
| CD11c | APC | S-HCl-3 | BD Biosciences | 1:20 |
| CD14 | APC | HCD14 | Biolegend | 1:20 |
| CD14 | APC-Cy7 | HCD14 | Biolegend | 1:20 |
| HLA-DR | BV605 | L243 | Biolegend | 1:20 |
| CD45 | BV510 | H130 | Biolegend | 1:20 |
| CD19 | PE-Cy7 | HIB19 | Biolegend | 1:20 |
| CD38 | APC-Cy7 | HIT2 | Biolegend | 1:20 |
| CD27 | BV421 | O323 | Biolegend | 1:20 |

Example 9

Figure 20D:
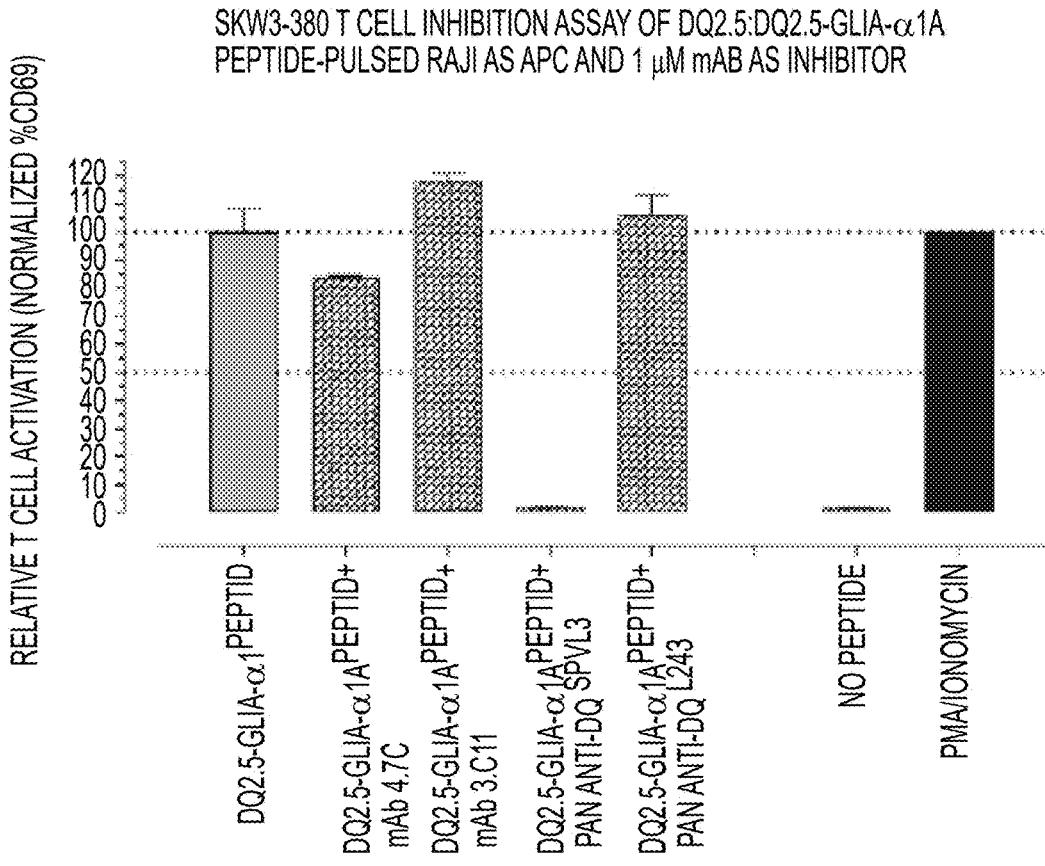
Figure 20E:
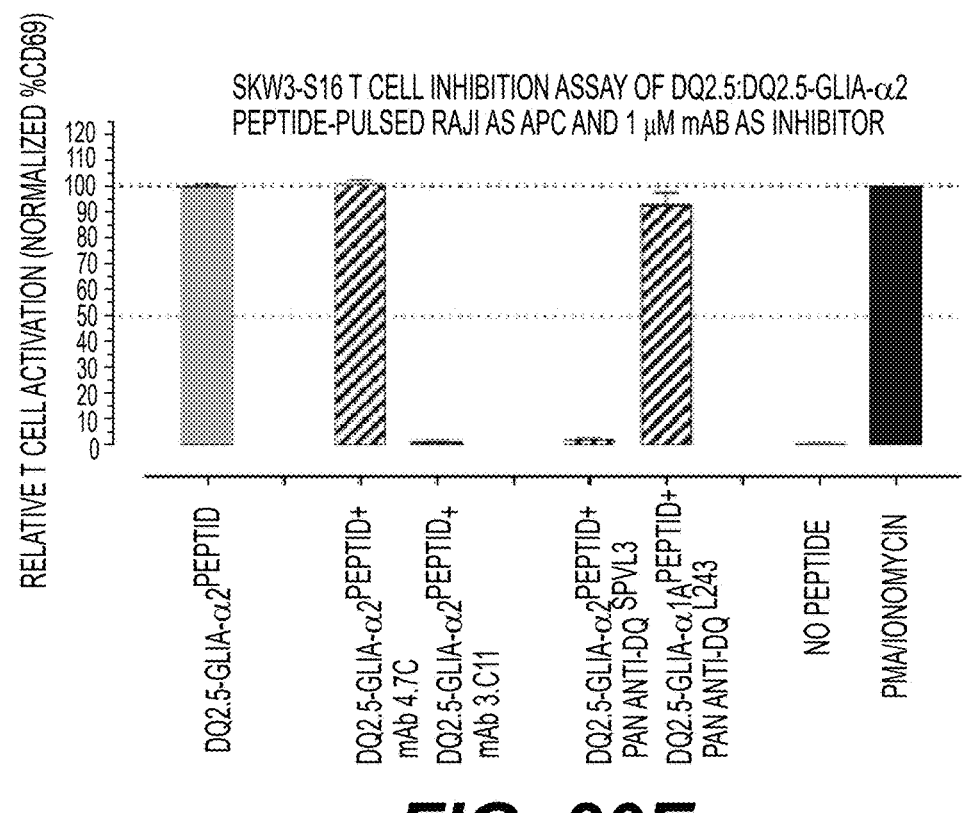
Figure 20F:
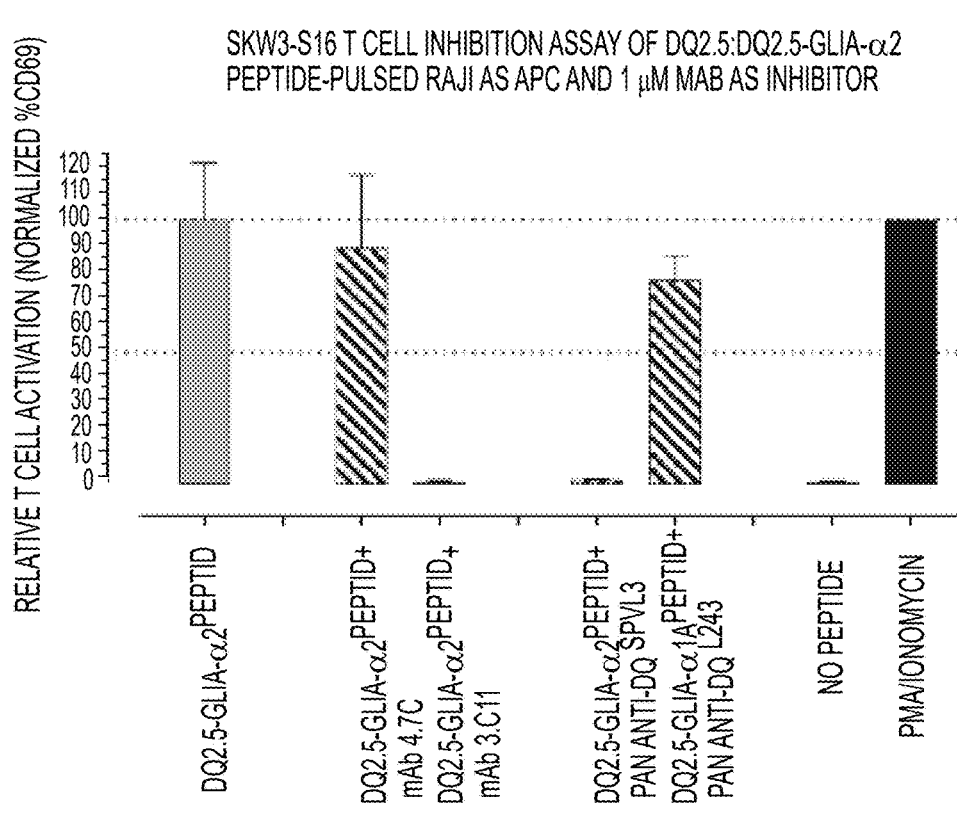

Inhibition of T Cell Activation Using Affinity Maturated mAbs 4.7C and 3.C11
Results The anti-pMHC specific mAbs 4.7C (also referred to herein as 107-4.7C) and 3.C11 (also referred to herein as 206-3.C11) exhibit strong HLA and peptide dependent in vitro inhibitory capacity of T cell activation To assess whether or not the affinity maturated lead candidate mAb clones 4.7C and 3.C11 have relevant T cell inhibitory capacity, and thus might function as disease (e.g. celiac disease) modifying agents, we generated T cell receptor (TCR) reconstructed SKW3 T cells clones expressing three different human TCRs derived from celiac patients. Two of these TCRs are specific for DQ2.5:DQ2.5-glia-α2 (clone S16 and 364), whereas the last TCR is specific for DQ2.5: DQ2.5-glia-α1a (clone 380). We then characterized the peptide dose-response of T cell activation using a human HLA-DQ2.5 positive B cells line (Raji) as antigen presenting cells (APCs) loaded with exogenous peptide. For the subsequent T cell inhibition, we fixed the amount of exogenous specific peptide to the concentration resulting in about 60% of full T cell activation (FIGS. 20A-20C). After having loaded the APC with peptide, we then added the pMHC-specific and control Abs followed by adding T cells and continue incubation ON (overnight). When measuring the resulting T cell activation, indeed we observed an interference of T cell activation directly conferred by the Abs (FIGS. 20D-20F). In the case of the mAb 4.7C, there was an about 20% reduction in T cell activation, but only where the APC was loaded with the peptide containing the correct epitope (FIG. 20, D). Correspondingly, the pan anti-DQ Ab (clone SPVL3) exhibited a close to complete inhibition, whereas the pan anti-DR Ab (clone L243) had no apparent effect (FIG. 20D). Importantly, the mAb 3.C11 had no inhibitory effect on this SKW3-380 T cell activation underscoring the peptide specificities of these anti-pMHC mAbs. Conversely, the situation was opposite when the mAb 3.C11 was used to inhibit activation of the SKW3-S16 and 364 T cells (FIGS. 20E and 20F). Here, a complete inhibition on par with the pan anti-DQ Ab was seen in the case of both T cells, whereas the 4.7C had a negligible effect. Thus, we conclude that the observed T cell inhibitory capacity seen with mAb 4.7C and 3.C11 is both peptide and DQ dependent underscoring the high specificity and strong target binding capacity of these mAbs.

Materials and Methods

IgG Protein Expression and Purification

Purified full-length human IgG1 protein harboring the VH and VL domains of the identified affinity maturated clones 4.7C and 3.C11 were custom produced in HEK293 cells by Genscript based on the provided VH and VL domain amino acid sequences.

Retroviral Transduction of Human SKW3 T Cells and Flow Cytometry

The human T cell line SKW3 and the retroviral vector pMSCV were purchased from CLS Cell Lines Service GmbH and Clontech Laboratories, Inc, respectively. Based on the published T cell receptor (TCR) sequences (PMID: 24777060—Petersen et al., 2014, Nat. Struct. Mol. Biol. 21(5):480-8, 28878121—Gunnarsen et al., 2017, *JCI*

*Insight,* 2 (17), and 29649333—Gunnarsen et al., 2018, *PLoS One,* 13(4)e0195868), TCRs 380, 364 and s16 were reconstructed by gene synthesis as human/mouse chimeric TCRs as described (PMID: 28878121, supra), and cloned into pMSCV (performed by Genscript). Retroviral transduction of the SKW3 cells was performed using the Retro-X Universal Packaging System (Clonetech) according to the manufacturer's instructions. Stable, homogenous TCR-redirected SKW3 T cells were obtained by standard cell expansion and FACS sorting using a FACSAria II cytometer (BD Biosciences) based on their TCR expression levels assessed by H57-Alexa647 (Thermo Fisher Scientific) antibody staining. The TCRs transduced SKW3 cells were validated for peptide-specific activation using a panel of known agonistic and antagonistic peptides, essentially as described (PMID: 28878121, supra), using CD69 up-regulation as activation marker assessed by anti-hCD69-APC (BD Biosciences) antibody staining. Data was acquired on a BD Accuri C6 cytometer (BD Biosciences) and analyzed using FlowJo™ software V10 (Tree Star).

T Cell Activation and Inhibition Assays

For T cell activation assays 50,000 Raji cells, which natively express HLA-DQ2.5 (PMID: 19845894—Bentley et al., 2009, *Tissue Antigens,* 74(5):393-403), were incubated in RPMI/10% FCS at 37° C./ON with titrated amounts of peptide (as indicated in the figures), followed by washing to remove remaining free peptide and addition of 40,000 SKW3 T cells and growth 37° C./ON (overnight) before being analysed in flow. The following peptides were used (epitopes are underlined): DQ2.5-glia-α1a (QLQPFPQPELPY) (SEQ ID NO: 474) and DQ2.5-glia-α2 (PQPELPYPQPE) (SEQ ID NO: 475). As a control, Cell Stimulation Cocktail containing PMA and ionomycin (eBioscience, 1:500) was added to wells containing SKW T cells only. Data analysis (EC50 determination) and figures were prepared using GraphPad Prism 7. Based on the established dose-response in T cell activation, a peptide concentration estimated to result in about 60% T cell activation (measured as CD69 upregulation) was chosen for the inhibitory assays. Following ON (overnight) incubation with peptide as above and washing, either 1 μM (final concentration) mAb 4.7C or 3.C11 were added to the Raji cells, before T cells were added and incubation continued ON. The resulting T cell activation was measured as above. As control Abs, either 0.1 μM (final concentration) of pan-anti-DR (clone L243: Thermo Scientific) of pan-anti-DQ (clone SPVL3: BD Biosciences) was added on parallel. Relative inhibitory capacity was estimated by normalizing the data according to the T cell activation in the absence of mAb, which was set to 100% activation (gray left bar in FIGS. 20D-20F).

The invention claimed is:

1. An antibody, wherein said antibody binds to HLA-DQ2.5:DQ2.5 presenting an α2 gliadin peptide (HLA-DQ2.5:DQ2.5-glia-α2), and wherein said antibody comprises at least one heavy chain variable region that comprises three CDRs and at least one light chain variable region that comprises three CDRs;

wherein said light chain variable region comprises:
    (a) a variable light (VL) CDR1 of SEQ ID NO:368,
    (b) a VL CDR2 of SEQ ID NO:369, and
    (c) a VL CDR3 of SEQ ID NO:370; and wherein said heavy chain variable region comprises:
    (d) a variable heavy (VH) CDR1 of SEQ ID NO:365,
    (e) a VH CDR2 of SEQ ID NO:366, and
    (f) a VH CDR3 of SEQ ID NO:367.

2. A composition comprising the antibody of claim 1 and a diluent, carrier or excipient.

3. An immunoconjugate comprising the antibody of claim 1 attached to a therapeutic or diagnostic agent.

4. A nucleic acid comprising a nucleotide sequence that encodes the antibody of claim 1.

5. A method of producing the antibody of claim 1, comprising the steps of (i) culturing a host cell comprising the nucleic acid of claim 4 under conditions suitable for the expression of the encoded antibody, and (ii) isolating or obtaining the antibody from the host cell or from the growth medium/supernatant.

6. The method of claim 5, further comprising a step of formulating the antibody into a composition including at least one additional component.

7. An antigen binding protein, wherein said antigen binding protein binds to HLA-DQ2.5:DQ2.5 presenting an α2 gliadin peptide (HLA-DQ2.5:DQ2.5-glia-α2), and wherein said antigen binding protein comprises at least one heavy chain variable region that comprises three CDRs and at least one light chain variable region that comprises three CDRs;

wherein said light chain variable region comprises:
    (a) a variable light (VL) CDR1 of SEQ ID NO:368,
    (b) a VL CDR2 of SEQ ID NO:369, and
    (c) a VL CDR3 of SEQ ID NO:370; and wherein said heavy chain variable region comprises:
    (d) a variable heavy (VH) CDR1 of SEQ ID NO:365,
    (e) a VH CDR2 of SEQ ID NO:366, and
    (f) a VH CDR3 of SEQ ID NO:367; and wherein the antigen binding protein is an scFv or a Fab fragment.

8. A composition comprising the antigen binding protein of claim 7 and a diluent, carrier or excipient.

9. An immunoconjugate comprising the antigen binding protein of claim 7 attached to a therapeutic or diagnostic agent.

10. The method of claim 6, wherein the at least one additional component is a pharmaceutically acceptable carrier or excipient.

* * * * *